(12) United States Patent
Sumi et al.

(10) Patent No.: US 10,624,612 B2
(45) Date of Patent: Apr. 21, 2020

(54) BEAMFORMING METHOD, MEASUREMENT AND IMAGING INSTRUMENTS, AND COMMUNICATION INSTRUMENTS

(71) Applicant: Chikayoshi Sumi, Saitama (JP)

(72) Inventors: Chikayoshi Sumi, Saitama (JP); Naoto Yamazaki, Kanagawa-ken (JP)

(73) Assignee: CHIKAYOSHI SUMI, Saitama (JP)

( * ) Notice: Subject to any disclaimer, the term of this patent is extended or adjusted under 35 U.S.C. 154(b) by 615 days.

(21) Appl. No.: 14/730,583

(22) Filed: Jun. 4, 2015

(65) Prior Publication Data
US 2016/0157828 A1   Jun. 9, 2016

(30) Foreign Application Priority Data

Jun. 5, 2014 (JP) ................. 2014-116949
Aug. 14, 2014 (JP) ................. 2014-165284
(Continued)

(51) Int. Cl.
*A61B 8/08* (2006.01)
*G01N 29/46* (2006.01)
(Continued)

(52) U.S. Cl.
CPC .......... *A61B 8/5207* (2013.01); *A61B 8/4494* (2013.01); *G01N 29/0654* (2013.01);
(Continued)

(58) Field of Classification Search
CPC ........................................... A61B 8/08
(Continued)

(56) References Cited

U.S. PATENT DOCUMENTS

| 5,720,708 A | 2/1998 | Lu et al. |
| 6,685,641 B2 | 2/2004 | Liu |

(Continued)

FOREIGN PATENT DOCUMENTS

| JP | 5-63509 | 8/1993 |
| JP | 2005278892 | 10/2005 |

(Continued)

OTHER PUBLICATIONS

Office Action dated Oct. 30, 2018 in Japanese Patent Application No. 2014-116949, with English language translation.
(Continued)

*Primary Examiner* — John E Breene
*Assistant Examiner* — Jeffrey C Morgan
(74) *Attorney, Agent, or Firm* — Wenderoth, Lind & Ponack, LLP

(57) ABSTRACT

Beamforming method that allows a high speed and high accuracy beamforming with no approximate interpolations. This beamforming method includes step (a) that generates reception signals by receiving waves arrival from a measurement object; and step (b) that performs a beamforming with respect to the reception signals generated by step (a); and step (b) including without performing wavenumber matching including approximate interpolation processings with respect to the reception signals, and the reception signals are Fourier's transformed in the axial direction and the calculated Fourier's transform is multiplied to a complex exponential function expressed using a wavenumber of the wave and a carrier frequency to perform wavenumber matching in the lateral direction and further, the product is Fourier's transformed in the lateral direction and the calculated result is multiplied to a complex exponential function, from which an effect of the lateral wavenumber matching is
(Continued)

removed, to perform wavenumber matching in the axial direction, by which an image signal is generated.

40 Claims, 39 Drawing Sheets

(30) Foreign Application Priority Data

| Mar. 9, 2015 | (JP) | 2015-046528 |
|---|---|---|
| Apr. 22, 2015 | (JP) | 2015-087901 |
| May 26, 2015 | (JP) | 2015-106798 |

(51) Int. Cl.

| G01N 29/26 | (2006.01) |
|---|---|
| G01N 29/06 | (2006.01) |
| G01S 15/89 | (2006.01) |
| G01S 7/52 | (2006.01) |
| G10K 11/34 | (2006.01) |
| G10K 11/32 | (2006.01) |
| A61B 8/00 | (2006.01) |
| A61B 8/12 | (2006.01) |

(52) U.S. Cl.
CPC .......... *G01N 29/262* (2013.01); *G01N 29/46* (2013.01); *G01S 7/52047* (2013.01); *G01S 15/8915* (2013.01); *G01S 15/8997* (2013.01); *G10K 11/32* (2013.01); *G10K 11/341* (2013.01); *G10K 11/346* (2013.01); *A61B 8/12* (2013.01); *G01N 2291/02475* (2013.01); *G01S 15/8977* (2013.01)

(58) Field of Classification Search
USPC ........ 702/14, 42, 43, 189; 324/318; 600/440
See application file for complete search history.

(56) References Cited

U.S. PATENT DOCUMENTS

| 7,690,838 | B2 | 4/2010 | Sumi | |
|---|---|---|---|---|
| 7,775,980 | B2 | 8/2010 | Sumi | |
| 7,868,824 | B2 | 1/2011 | Sumi | |
| 7,957,609 | B2 | 6/2011 | Lu et al. | |
| 8,211,019 | B2 | 7/2012 | Sumi | |
| 9,084,559 | B2 | 7/2015 | Sumi | |
| 9,326,748 | B2 | 5/2016 | Sumi | |
| 2005/0273265 | A1* | 12/2005 | Ren | G01V 1/28 702/14 |
| 2007/0150232 | A1* | 6/2007 | Szeto | G01V 1/28 702/179 |
| 2009/0036772 | A1* | 2/2009 | Lu | G01S 7/52046 600/437 |
| 2011/0172538 | A1 | 7/2011 | Sumi | |
| 2013/0046175 | A1* | 2/2013 | Sumi | A61B 8/08 600/431 |

FOREIGN PATENT DOCUMENTS

| JP | 2007152074 | 6/2007 |
|---|---|---|
| JP | 2011-521204 | 7/2011 |
| JP | 5441292 | 3/2014 |
| WO | 2008/010375 | 1/2008 |

OTHER PUBLICATIONS

Partial Translation of Notification of Reasons for Rejection dated Aug. 7, 2018 in Japanese Patent Application No. 2014-116949.
J. W. Goodman, "Introduction to Fourier Optics" 2nd ed., McGraw-Hill Co, Inc., 1996.
L. J. Busse, "Three-Dimensional Imaging Using a Frequency-Domain Synthetic Aperture Focusing Technique", IEEE Trans. UFFC, vol. 39, No. 2, pp. 174-179, 1992.
J. Cheng, J.-y. Lu, "Extended High-Frame Rate Imaging Method with Limited-Diffraction Beams", IEEE Trans. UFFC, vol. 53, No. 5, pp. 880-899, 2006.
H. Peng, J.-y. Lu, X. Han, "High frame rate ultrasonic imaging system based on the angular spectrum principle", Ultrasonics 44, e97-e99, 2006.
P. Kruizinga et al, "Plane-Wave Ultrasound Beamforming Using a Nonuniform Fast Fourier Transform", IEEE Trans. UFFC, vol. 59, No. 12, pp. 2684-2691, 2012.
M. A. Haun, D. L. Jones, W. D. O'Brien, Jr., "Efficient Three-Dimensional Imaging from a Small Cylindrical Aperture", IEEE Trans. UFFC, vol. 49, pp. 861-870, 2002.
C. Sumi et al, "Effective Lateral Modulations With Applications to Shear Modulus Reconstruction Using Displacement Vector Measurement", IEEE Trans. on Ultrasonics, Ferroelectrics, and Frequency Control, vol. 55, No. 12, pp. 2607-2625, Dec. 2008.
C. Sumi, S. Uga, "Effective ultrasonic virtual sources which can be positioned independently of physical aperture focus positions", Rep. Med. Imag., vol. 3, pp. 45-59, 2010.
M. Soumekh, "Fourier Array Imaging", PTR Prentice Hall, Englewood Cliffs, New Jersey 07632, 1994.
S. Haykin, A. Steinhardt ed. "Adaptive Radar Detection and Estimation", John Wiley & Sons, inc. New York, 1992.
K. W. Hollman, K. W. Rigby, M. O'Donnell, "Coherence Factor of Speckle from a Multi-Row Probe", Proc. of IEEE Ultrasonics Symp, pp. 1257-1260, 1999.
D. Garcia, L. L. Tarnec, S. Muth, E. Montagnon, J. Poree, G. Cloutier, "Stolt's f-k Migration for Plane Wave Ultrasound Imaging", IEEE Trans. UFFC , vol. 60, No. 9, pp. 1853-1867, 2013.
C. Sumi, "Displacement Vector Measurement Using Instantaneous Ultrasound Signal Phase—Multidimensional Autocorrelation and Doppler Methods", IEEE Trans. on Ultrasonics, Ferroelectrics, and Frequency Control, vol. 55, No. 1, pp. 24-43, Jan. 2008.
C. Sumi, Y. Ishii, "Ultrasonic lateral modulation imaging, speckle reduction, and displacement vector measurements using simple single-beam scanning or plural crossed-beam scanning with new spectra frequency division processing methods", Rep. Med. Imag., vol. 5, pp. 57-101, 2012.
C. Sumi, "Fine Elasticity Imaging Utilizing the Iterative RF-echo Phase Matching Method", IEEE Trans. on Ultrasonics, Ferroelectrics, and Frequency Control, vol. 46, No. 1, pp. 158-166, Jan. 1999.
S. Srinivasan, F. Kallel, J. Ophir, "Estimating the Elastographic Signal-To-Noise Ratio Using Correlation Coefficients", Ultrasound Med. Biol., vol. 28, pp. 359-368, 2002.
C. Sumi, "Regularization of Tissue Shear Modulus Reconstruction Using Strain Variance", IEEE Trans. UFFC, vol. 55, pp. 297-307, 2008.
C. Sumi, K. Sato, "Regularization for Ultrasonic Measurements of Tissue Displacement Vector and Strain Tensor", IEEE Trans. UFFC, vol. 55, pp. 787-799, 2008.
C. Sumi, Y. Takanashi, K. Ichimaru, "Consideration of generated beam angles increases the accuracy of ultrasonic displacement measurements", Rep. Med. Imag., vol. 5, pp. 23-50, 2012.
C. Kasai, K. Namekawa, A. Koyano, R. Omoto, "Real-Time Two-Dimensional Blood Flow Imaging Using an Autocorrelation Technique", IEEE Trans. On Sonics and Ultrasonics, vol. 32, pp. 458-464, 1985.
J. A. Jensen, "FIELD: A Program for Simulating Ultrasound Systems," Med, Biol, Eng, Comp, 10th Nordic-Baltic Conference on Biomedical Imaging, vol. 34, Supplement 1, Part 1, pp. 351-353, 1996.
B. Schrope, V. L. Newhouse, V. Uhlendorf, "Simulated Capillary Blood Flow Measurement Using a Nonlinear Ultrasonic Contrast Agent", Ultrason. Imag., vol. 14, pp. 134-158, 1992.
P. N. Burns, S. R. Wilson, D. H. Simpson, "Pulse Inversion Imaging of Liver Blood Flow: Improved Method for Characterizing Focal Masses with Microbubble Contrast", Investigative Radiology, vol. 35, No. 1, pp. 58-71, 2000.
M. A. Averkiou, D. N. Roundhill, J. E. Powers, "A New Imaging Technique Based on the Nonlinear Properties of Tissues", 1997 IEEE Ultrasonics symp, pp. 1561-1566, 1997.

(56) References Cited

OTHER PUBLICATIONS

B. Haider, R. Y. Chiao, "Higher Order Nonlinear Ultrasonic Imaging", 1999 IEEE Ultrasonics symp., pp. 1527-1531, 1999.
A. Needles, M. Arditi, N. G. Rognin, J. Mehi, T. Coulthard, C. Bilan-Tracey, E. Gaud, P. Frinking, D. Hirson, F. S. Foster, "Nonlinear Contrast Imaging With an Array-Based Micro-Ultrasound System", Ultrasound Med. Biol., vol. 36, No. 12, pp. 2097-2106, 2010.
J. R. Doherty, G. E. Trahey, K. R. Nightingale, M. L. Palmeri, "Acoustic Radiation Force Elasticity Imaging in Diagnostic Ultrasound", IEEE Trans. on UFFC, vol. 60, No. 4, pp. 685-701, Apr. 2013.
K. Hynynen, "Demonstration of Enhanced Temperature Elevation Due to Nonlinear Propagation of Focussed Ultrasound in Dog's Thigh In Vivo", Ultrasound Med. Biol. vol. 13, No. 2, pp. 85-91, 1987.
Y. Huang, N. I. Vykhodtseva, K. Hynynen, "Creating Brain Lesions With Low-Intensity Focused Ultrasound With Microbubbles: A Rat Study at Half a Megahertz", Ultrasound Med. Biol., vol. 39, No. 8, pp. 1420-1428, 2013.
C. Sumi, "Utilization of an ultrasound beam steering angle for measurements of tissue displacement vector and lateral displacement", Rep. In Med. Imag., vol. 3, pp. 61-81, 2010.
A. K. Katsaggelos, K. T. Lay, "Maximum Likelihood Blur Identification and Image Restoration Using the EM Algorithm", IEEE Trans. Signal Processing, vol. 39, No. 3, pp. 729-733, 1991.
R. Molina, A. K. Katsaggelos, J. Mateos, "Bayesian and Regularization Methods for Hyperparameter Estimation in Image Restoration", IEEE Trans. Image Processing, vol. 8, No. 2, pp. 231-246, 1999.
M. Nikolova, "Markovian Reconstruction Using a GNC Approach", IEEE Trans. Image Processing, vol. 8, No. 9, pp. 1204-1220, 1999.
R. Molina, J. Mateos, A. K. Katsaggelos, M. Vega, "Bayesian Multichannel Image Restoration Using Compound Gauss-Markov Random Fields", IEEE Trans. Image Processing, vol. 12, No. 12, pp. 1642-1654, 2003.
H. Kokubo, S. Yagi, K. Nakayama, "High resolution ultrasonic imaging using 2-D echo filtering", Journal of Acoustical Society of Japan, vol. 47, No. 7, pp. 443-450, 1991.
T. Morohoshi, K. Nakayama, S. Yagi, A. Suzuki, "High Resolution Ultrasonic Imaging Utilizing AR-Estimated Point Spread Function", Journal of the Institute of Electronics, Information and Communication Engineers, vol. J76-D-II, No. 2, pp. 233-240, 1993.
C. L. Chan, A. K. Katsaggelos, "Iterative Maximum Likelihood Displacement Field Estimation in Quantum-Limited Image Sequences", IEEE Trans. Image Processing, vol. 4, No. 6, pp. 743-751, 1995.
J. C. Brailean, A. K. Katsaggelos, "Simultaneous Recursive Displacement Estimation and Restoration of Noisy-Blurred Image Sequences", IEEE Trans. Image Processing, vol. 4, No. 9, pp. 1236-1251, 1995.
Y.-L. You, M. Kaveh, "Blind Image Restoration by Anisotropic Regularization", IEEE Trans. Image Processing, vol. 8, No. 3, pp. 396-407, 1999.
T. F. Chan, C.-K. Wong, "Total Variation Blind Deconvolution", IEEE Trans. Image Processing, vol. 7, No. 3, pp. 370-375, 1998.
F. Sroubek, J. Flusser, "Multichannel Blind Iterative Image Restoration", IEEE Trans. Image Processing, vol. 12, No. 9, pp. 1094-1106, 2003.
Miles N. Wernick et al, "Fast Spatio-Temporal Image Reconstruction for Dynamic PET", IEEE Trans. on Medical Imaging, vol. 18, pp. 185-195, 1999.
A. K. Katsaggelos, J. Biemond, R. W. Schafer, R. M. Mersereau, "A Regularized Iterative Image Restoration Algorithm", IEEE Trans. Signal Processing, vol. 39, pp. 914-929, 1991.
C. Sumi, "Determination of Lateral Modulation Apodization Functions Using a Regularized, Weighted Least Squares Estimation", Int. J. Biomed. Imag, ID: 635294 (7 pages), 2010.
C. Sumi et al, "A Demonstration of Optimal Apodization Determination for Proper Lateral Modulation", Jpn, J. of Appl. Phys., vol. 48 (7B), 07GJ06, Jul. 2009.
Office Action dated May 29, 2018 in Japanese Application No. 2014-116949, with Partial Translation.
Partial Translation of Office Action dated Nov. 12, 2019 in corresponding Japanese Patent Application No. 2016-013287.

\* cited by examiner

FIG.3
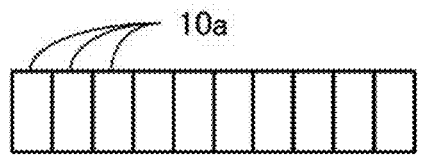
(a1) DENSE
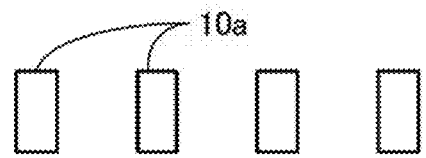
(b1) SPARSE
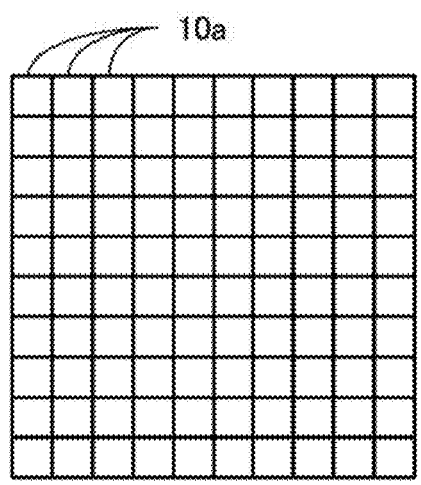
(a2) DENSE
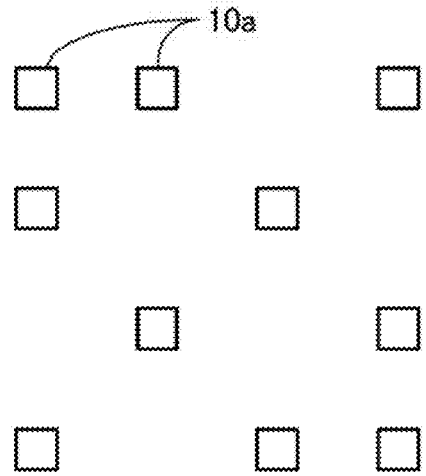
(b2) SPARSE
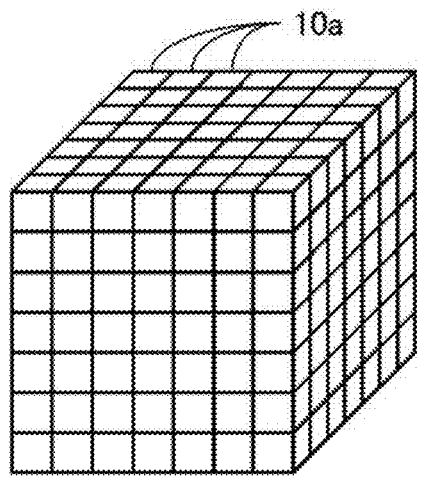
(a3) DENSE
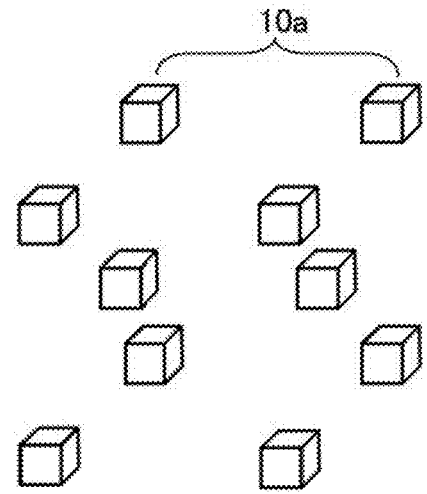
(b3) SPARSE

FIG.7
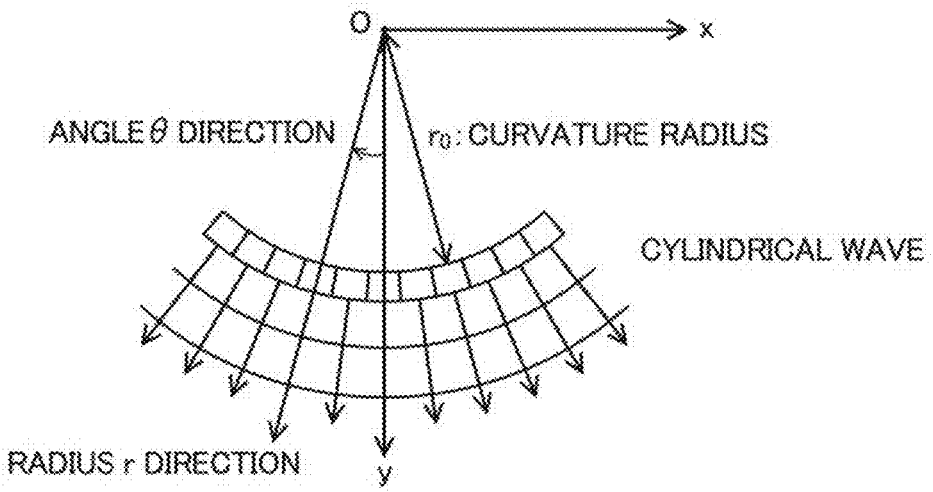
(a) CONVEX-TYPE APERTURE ELEMENT ARRAY
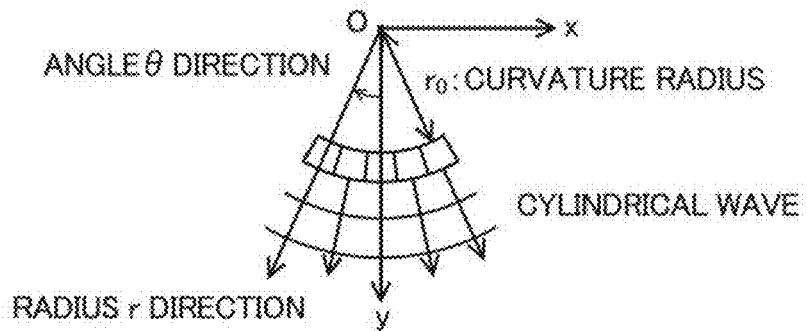
(b) SECTOR-TYPE APERTURE ELEMENT ARRAY
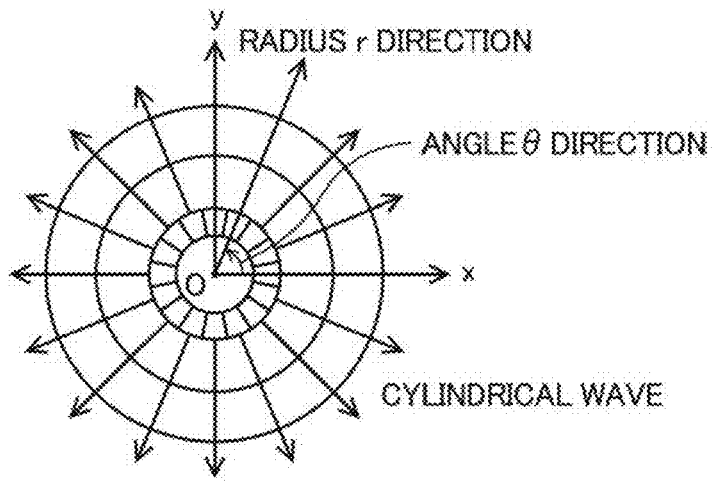
(c) IVUS(CIRCULAR-TYPE) APERTURE ELEMENT ARRAY

FIG.8A
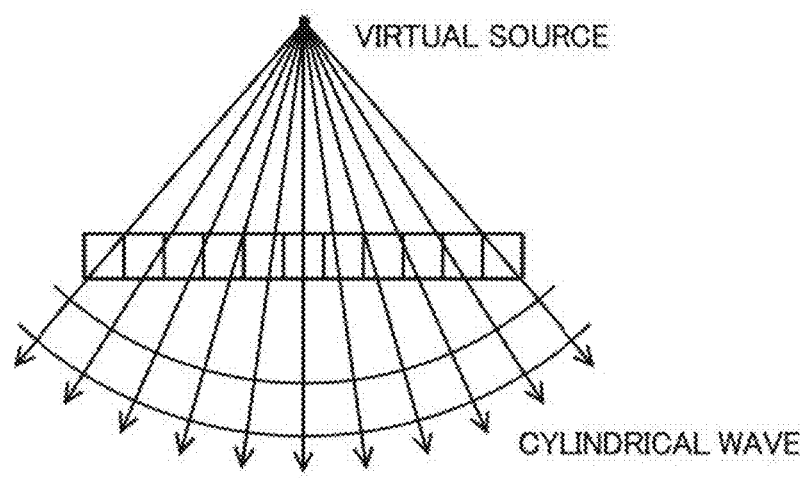
(a) LINEAR-TYPE APERTURE ELEMENT ARRAY
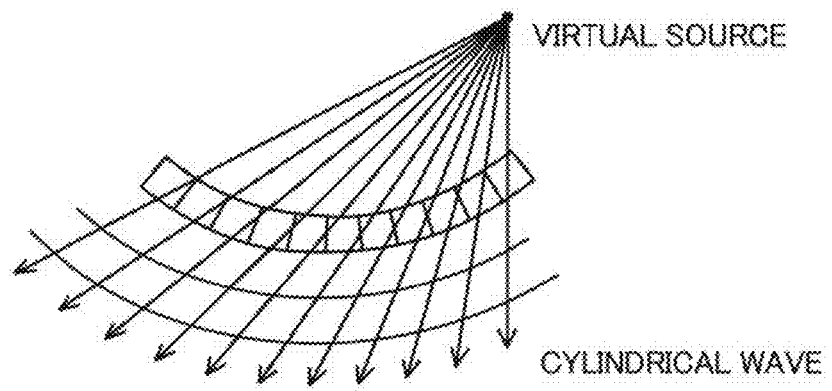
(b) CONVEX-TYPE APERTURE ELEMENT ARRAY
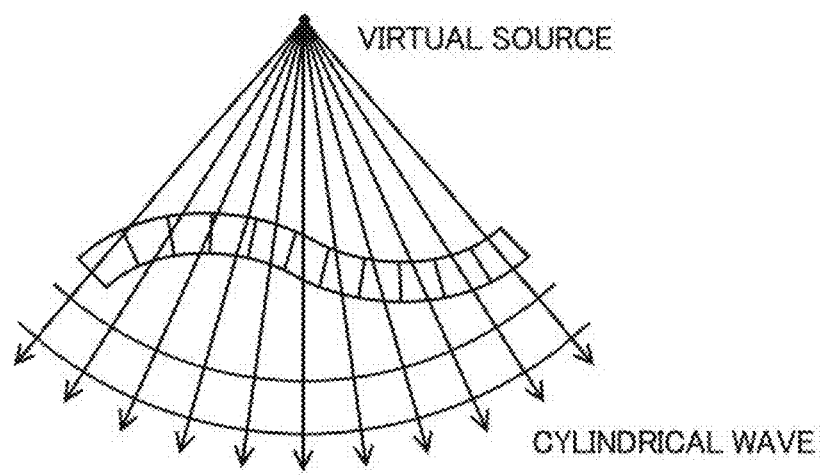
(c) ARBITRARY APERTURE ELEMENT ARRAY

FIG. 8B
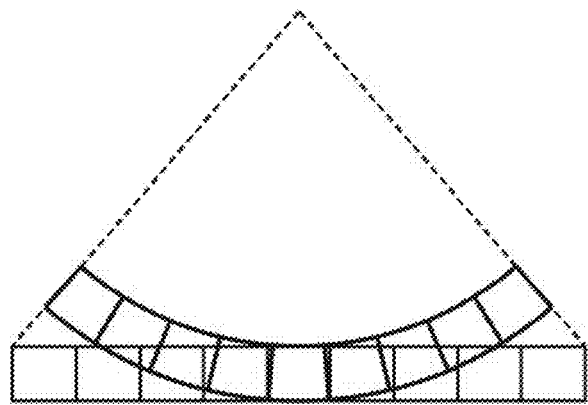
(d)
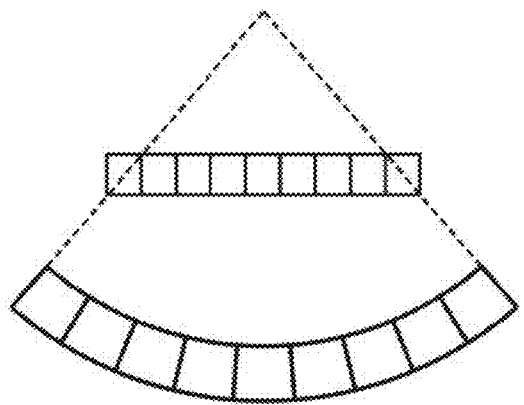
(e)
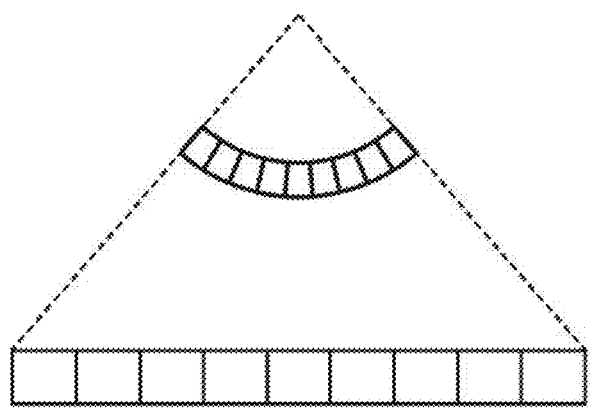
(f)
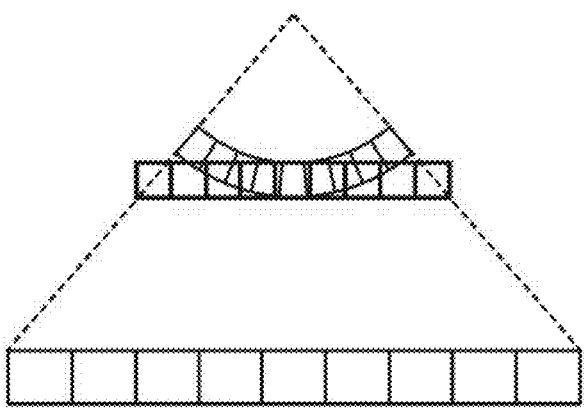
(g)

FIG.18A
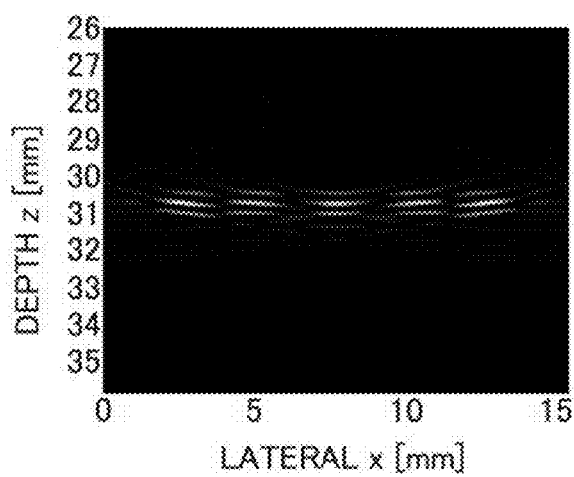
(a) θ = 0°
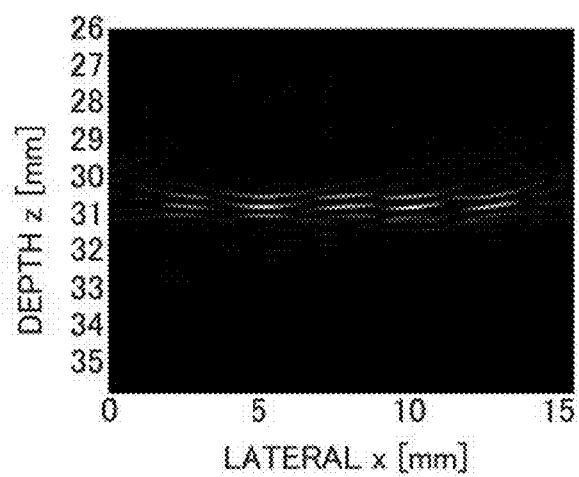
(b) θ = 5°
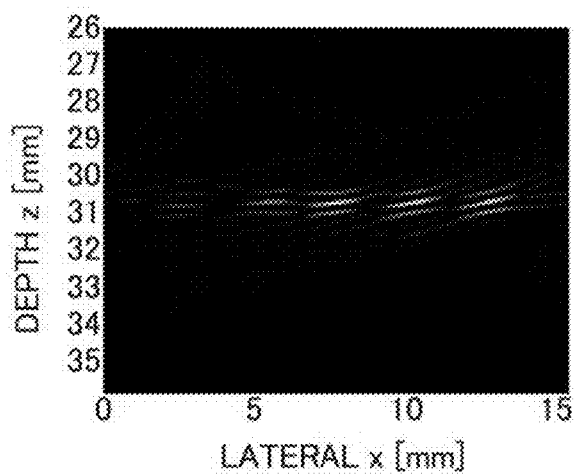
(c) θ = 10°
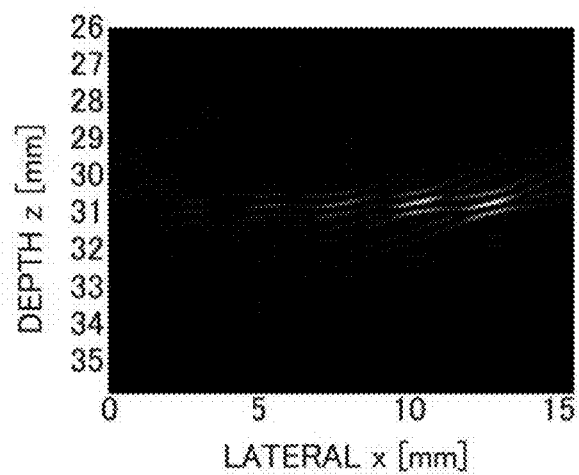
(d) θ = 15°

FIG.18B
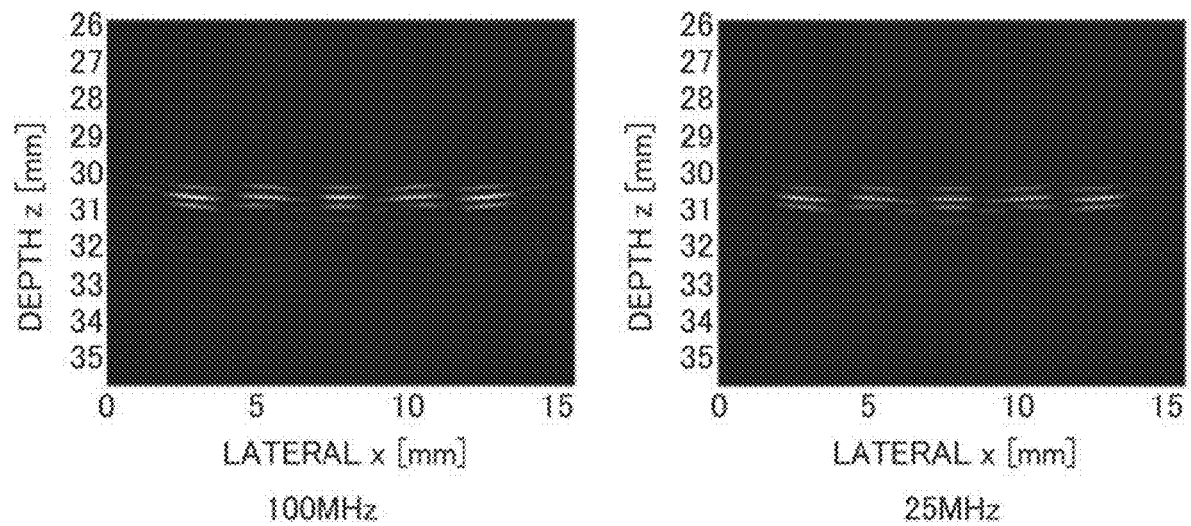
(e) $\theta = 0°$, APPROXIMATE INTERPOLATIONS USING NEIGHBORING SPECTRA
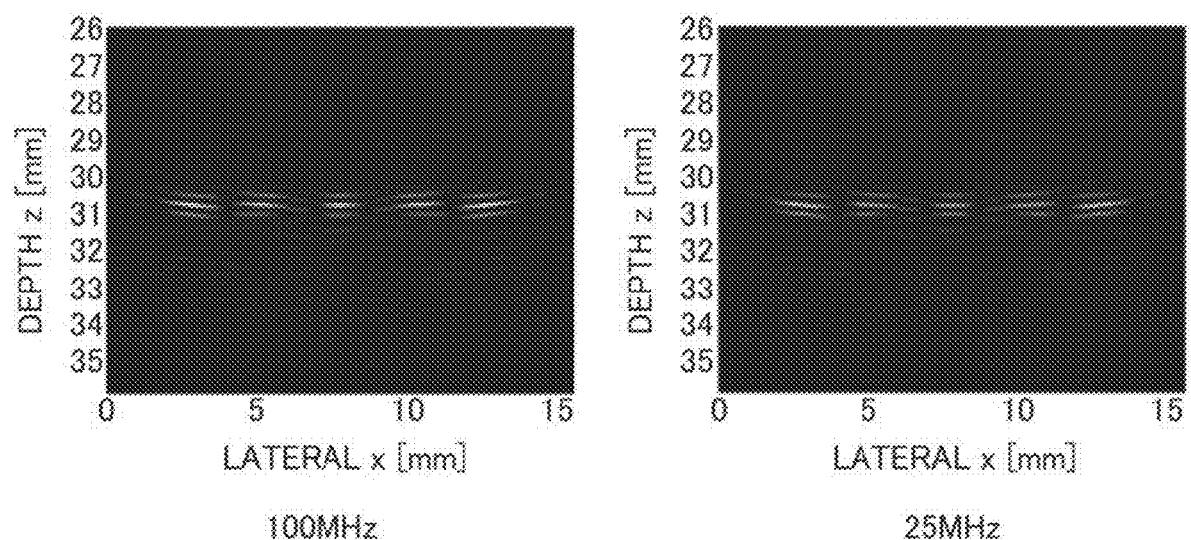
(f) $\theta = 0°$, LINEAR APPROXIMATE INTERPOLATIONS

| SET ANGLE (DEGREE) | 0 | 5 | 10 | 15 | 20 |
|---|---|---|---|---|---|
| OBTAINED STEERING ANGLE (DEGREE) | −0.7853 | 5.6048 | 9.4149 | 14.5036 | 19.1852 |
| ERROR (DEGREE) | −0.7853 | 0.6048 | −0.5851 | −0.4964 | −0.8148 |

FIG.21
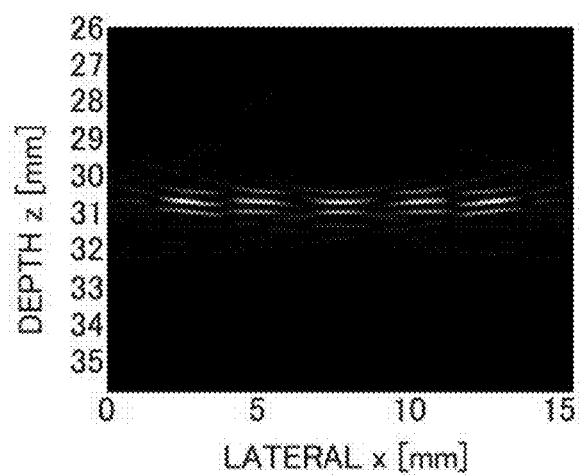
(a) 1 WAVE (0°)
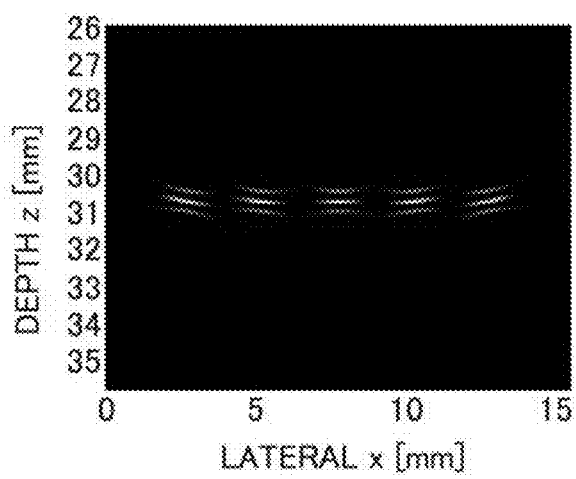
(b) 11 WAVES (−5° TO 5°)
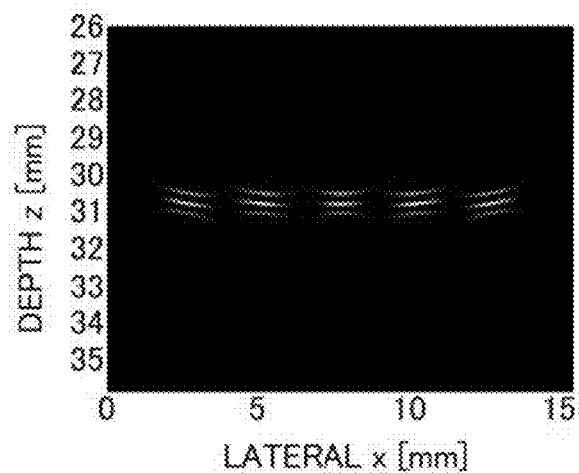
(c) 21 WAVES (−10° TO 10°)
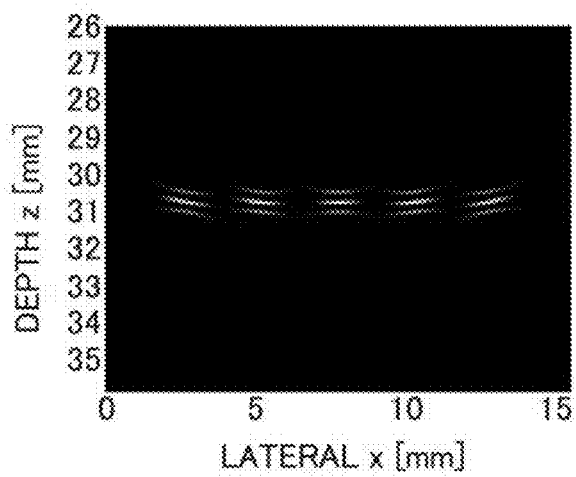
(d) 41 WAVES (−20° TO 20°)

FIG.23
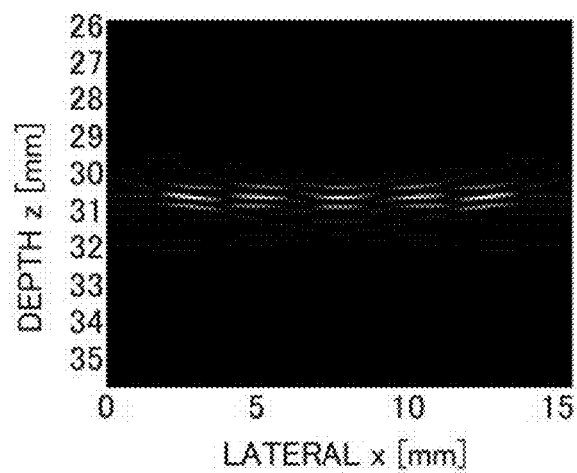
(a) $\theta = 0°$
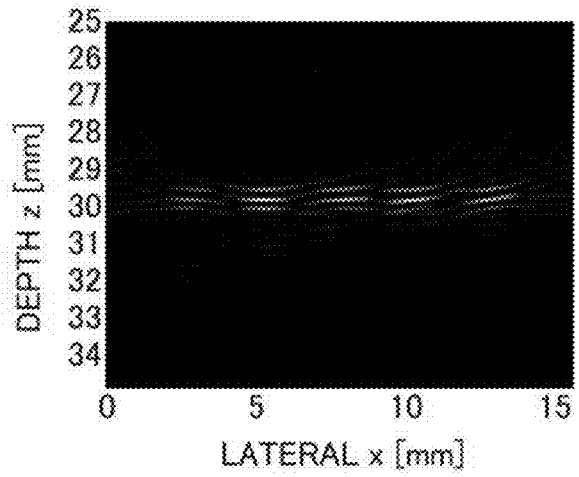
(b) $\theta = 5°$
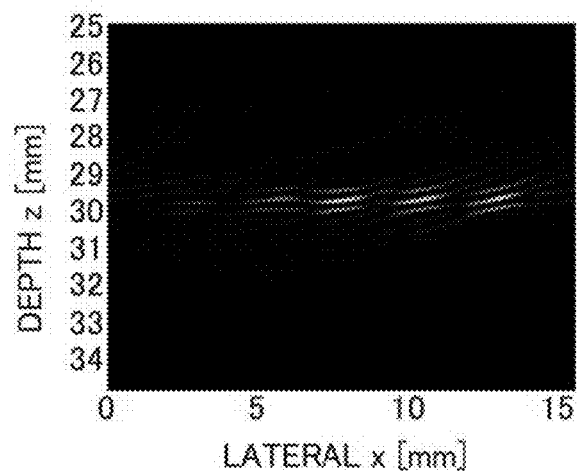
(c) $\theta = 10°$
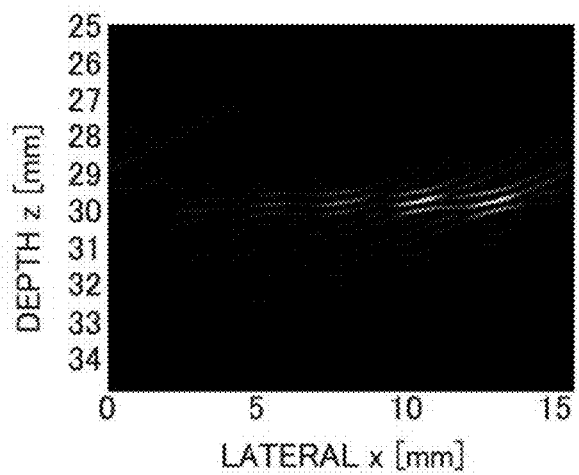
(d) $\theta = 15°$

*FIG. 24*
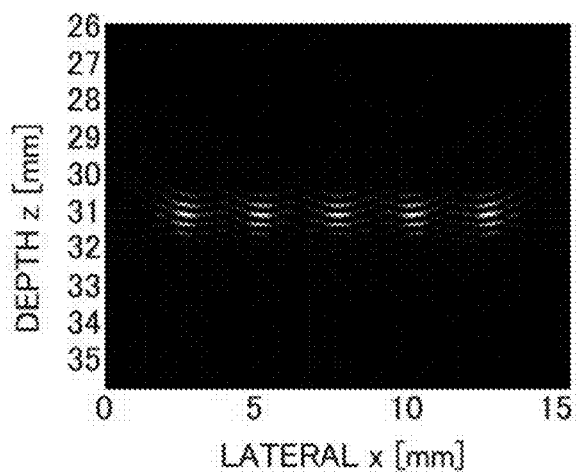
(a) $\theta = 0°$
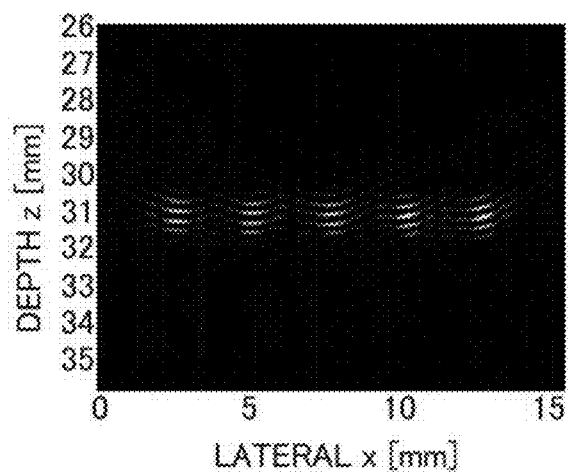
(b) $\theta = 5°$
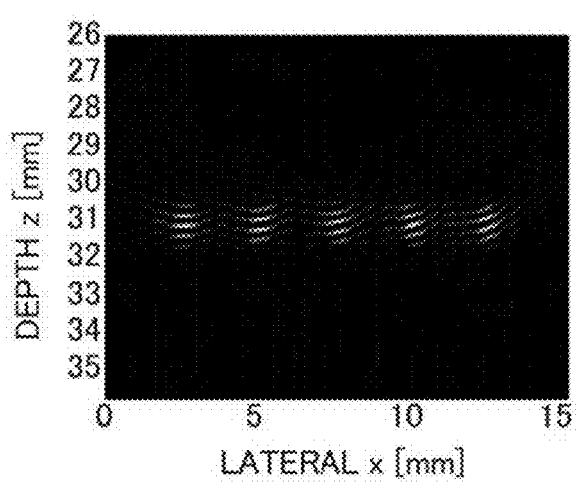
(c) $\theta = 10°$
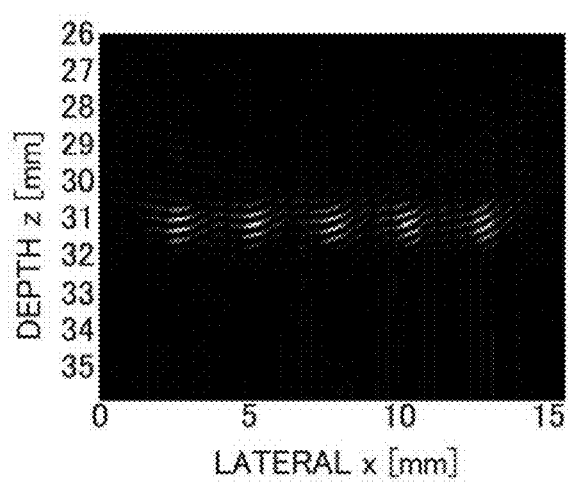
(d) $\theta = 15°$

FIG. 25
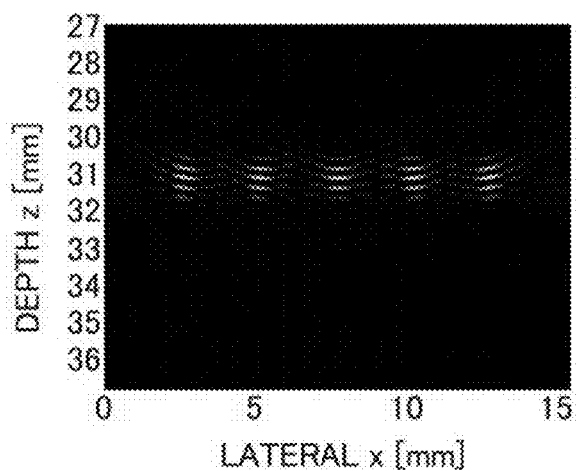
(a) 1 ELEMENT
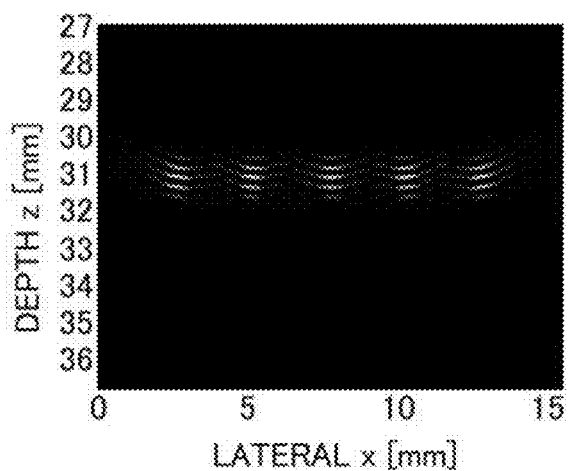
(b) 33 ELEMENTS
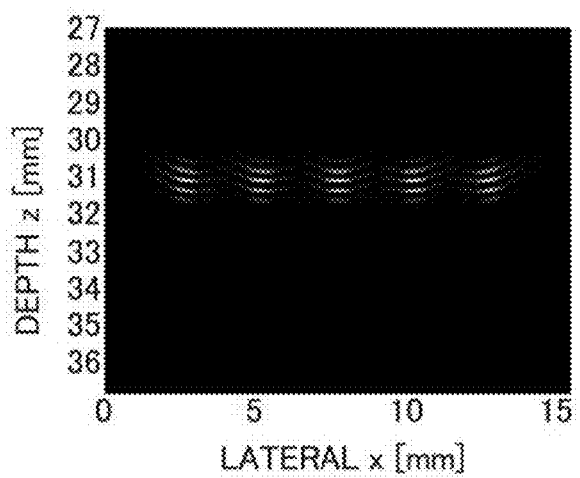
(c) 65 ELEMENTS
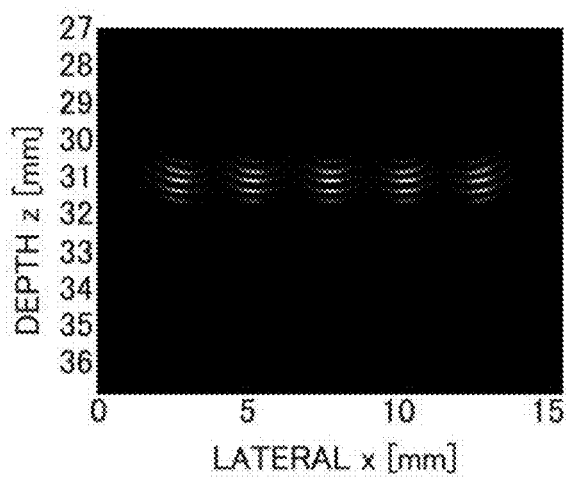
(d) 129 ELEMENTS FIG.27
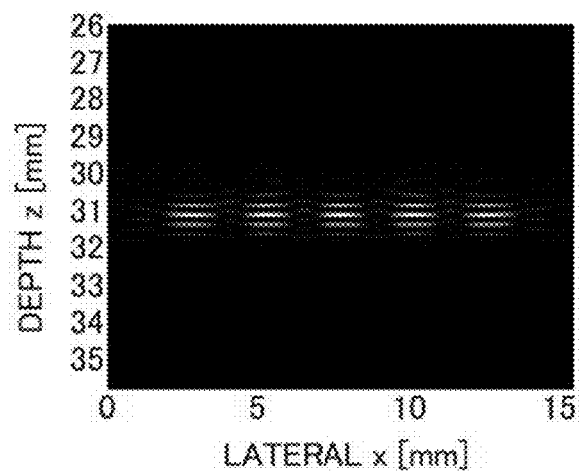
(a) METHOD(1)
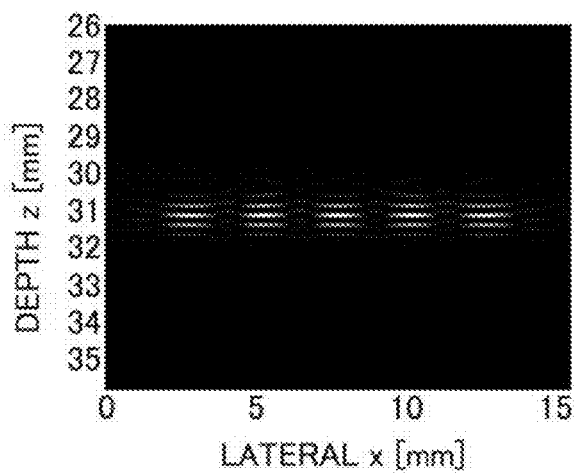
(b) METHOD(2)
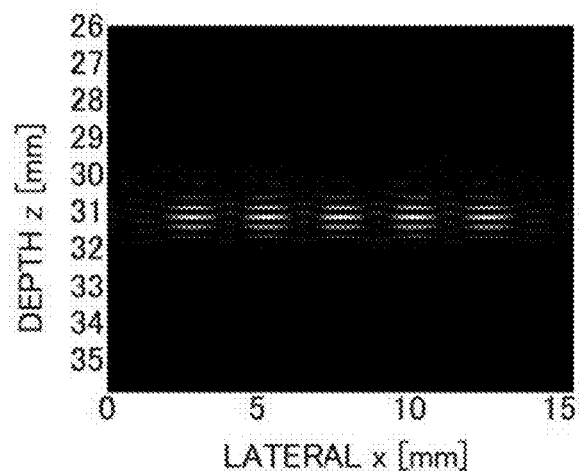
(c) METHOD(3)

FIG.28
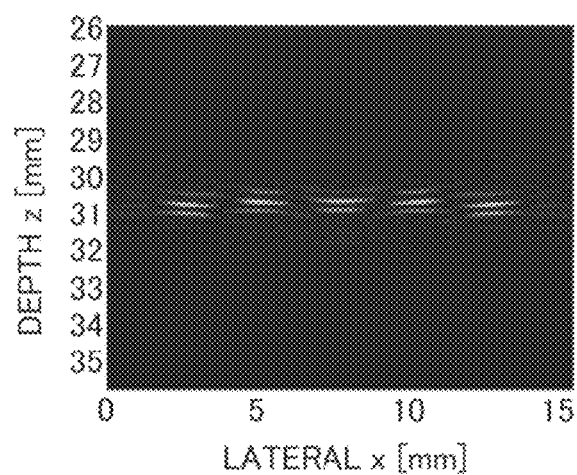
(a)
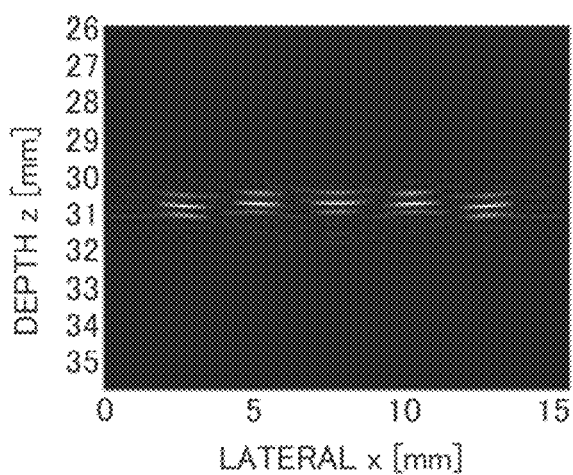
(b)
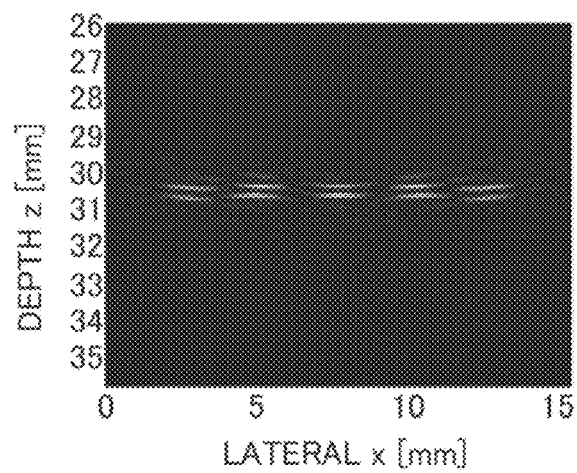
(c)
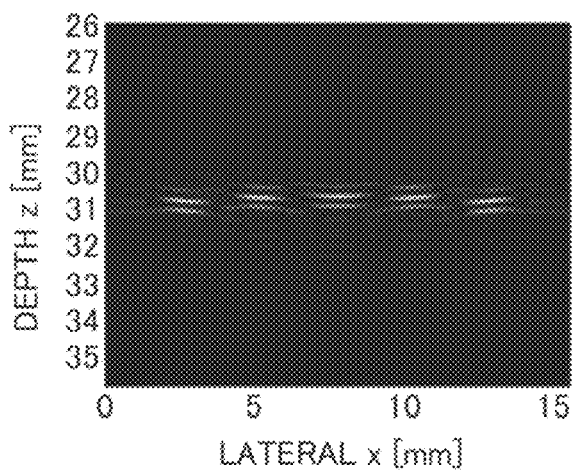
(d)

FIG. 29
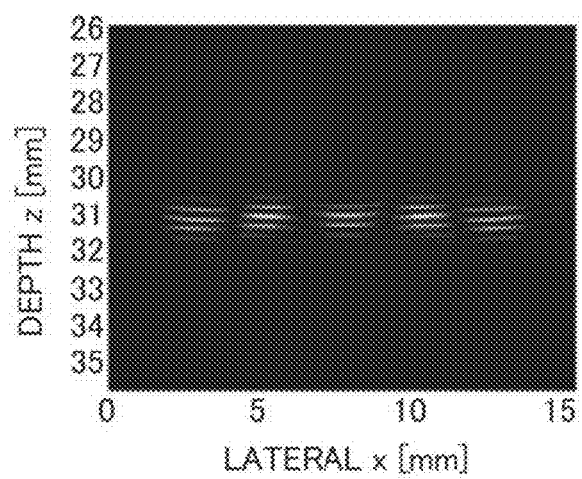
(a)
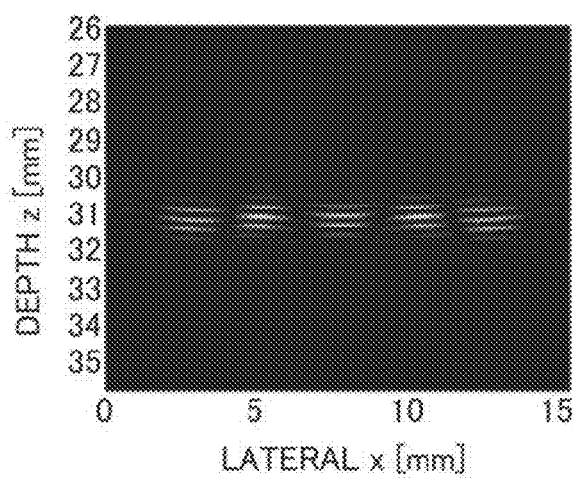
(b)
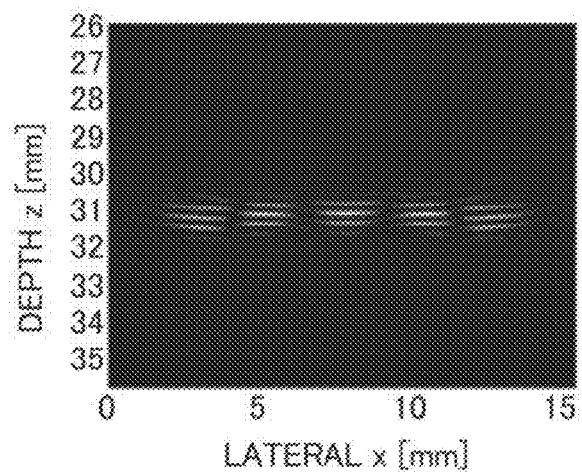
(c)

FIG.32
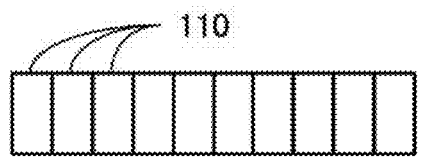
(a1) DENSE
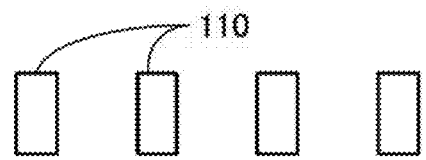
(b1) SPARSE
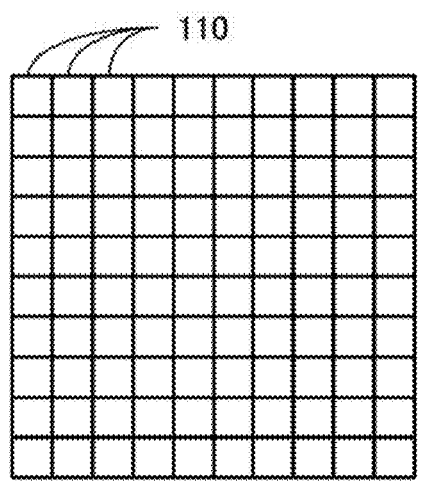
(a2) DENSE
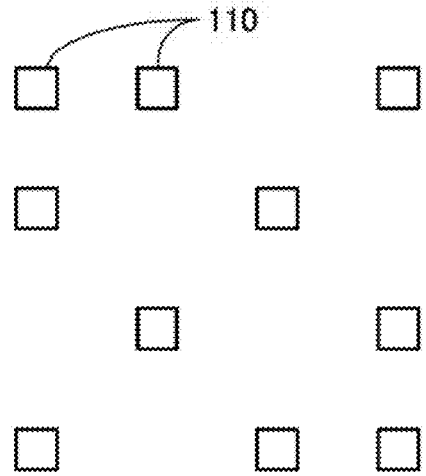
(b2) SPARSE
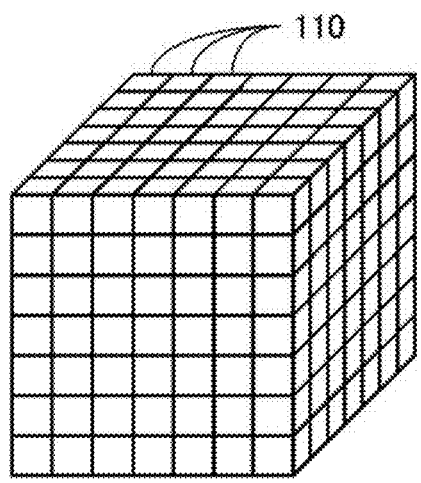
(a3) DENSE
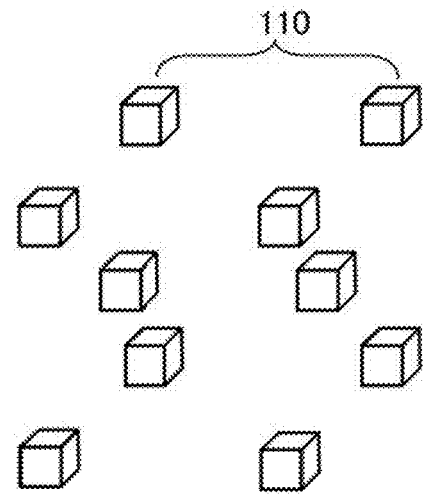
(b3) SPARSE

FIG.33
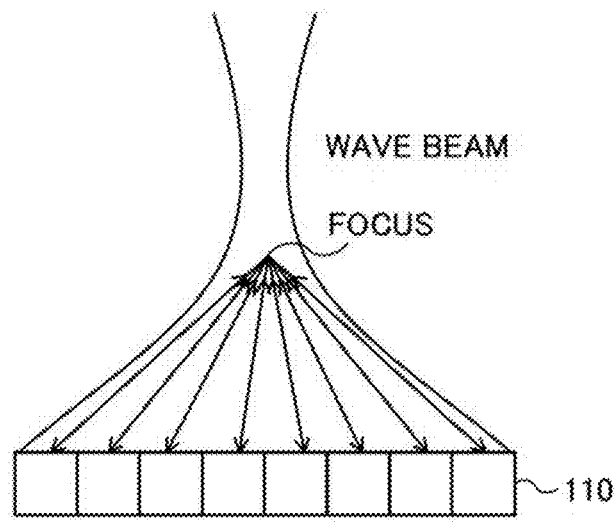
(a) TRANSMISSION OR RECEPTION FOCUSING
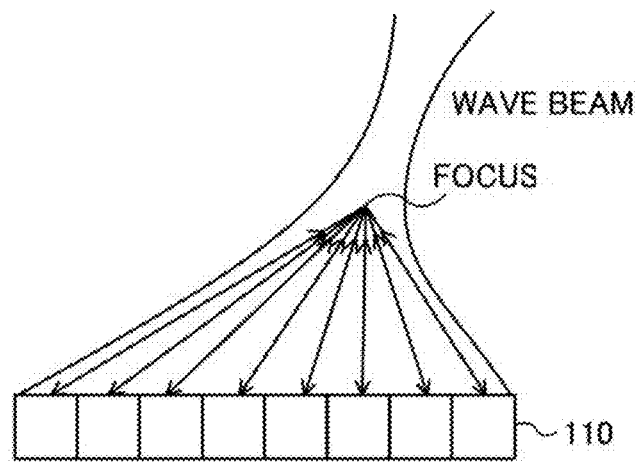
(b) TRANSMISSION OR RECEPTION STEERING
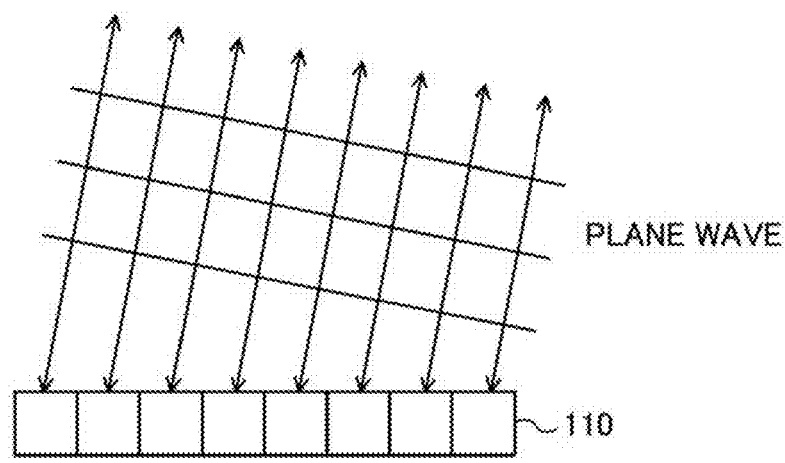
(c) TRANSMISSION OR RECEPTION OF PLANE WAVE

FIG.34
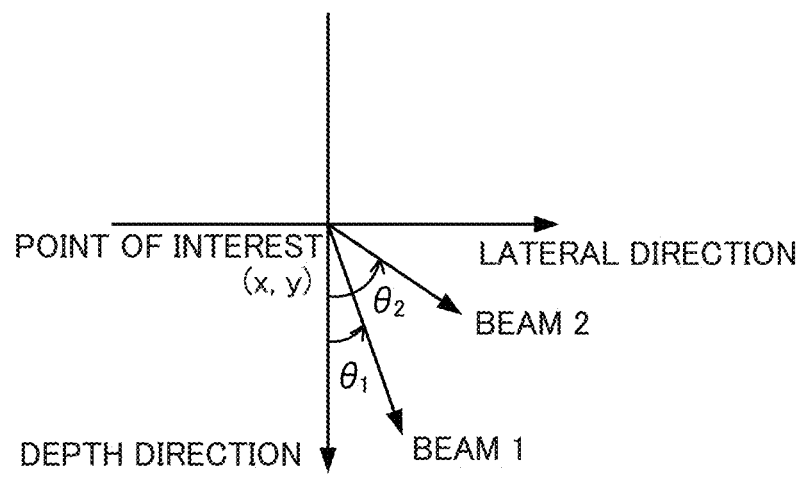
(a) SPATIAL DOMAIN
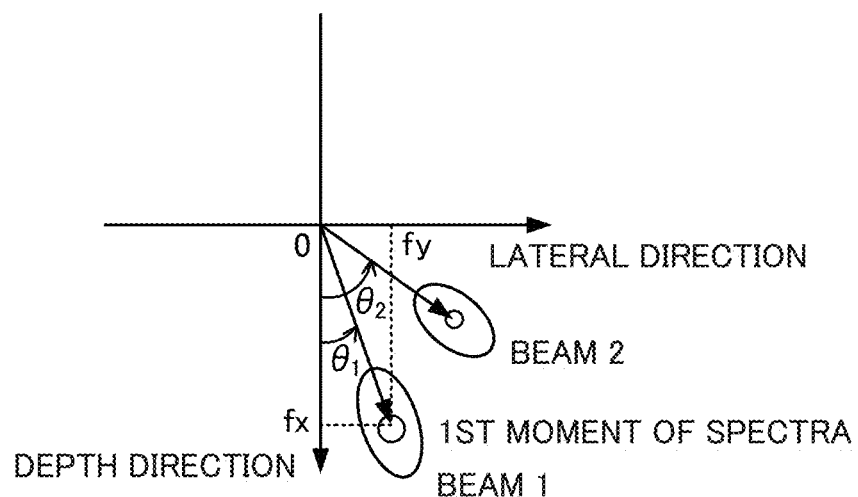
(b) FREQUENCY DOMAIN

FIG.38
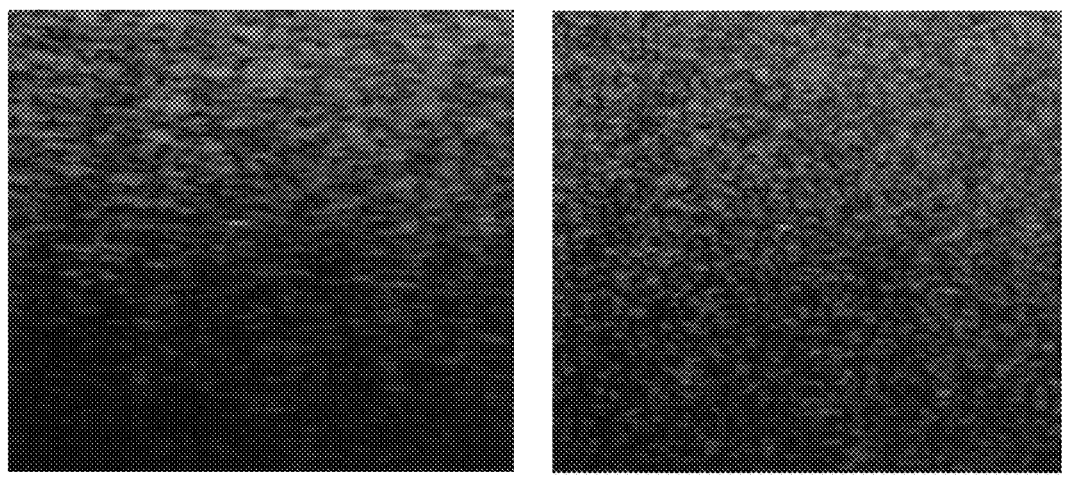
(a1) ENVELOPE DETECTION AND SQUARE DETECTION
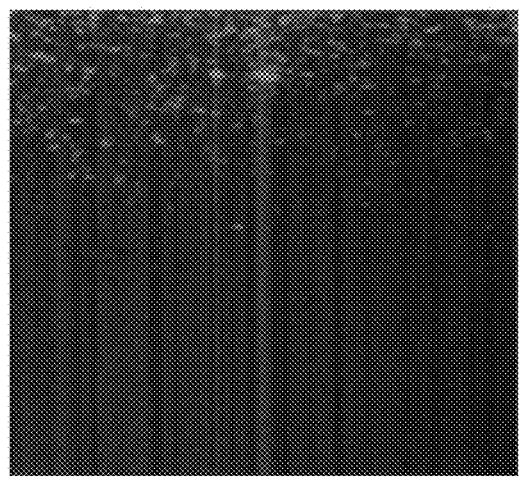
(a2) ENVELOPE DETECTION
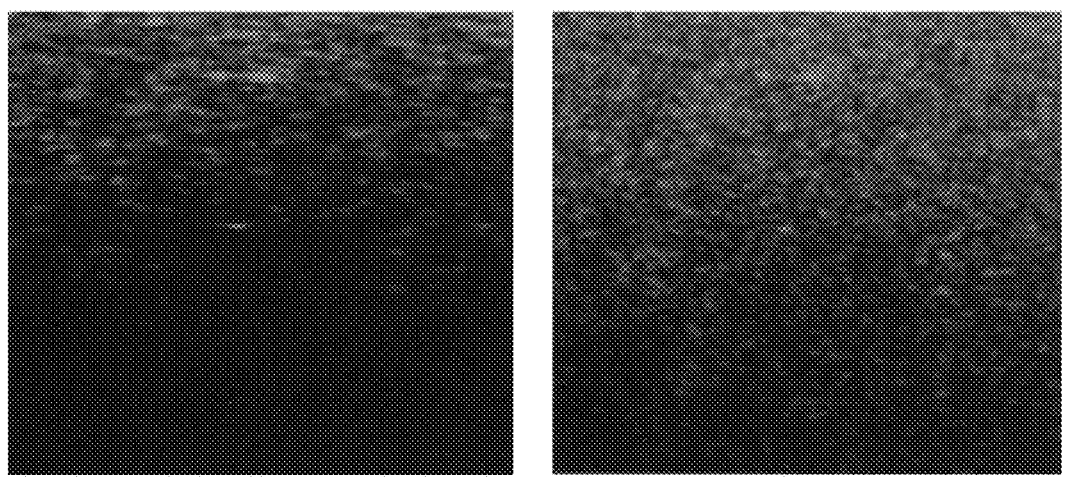
(a3) ENVELOPE DETECTION AND SQUARE DETECTION

FIG.39
(b1) ENVELOPE DETECTION AND SQUARE DETECTION
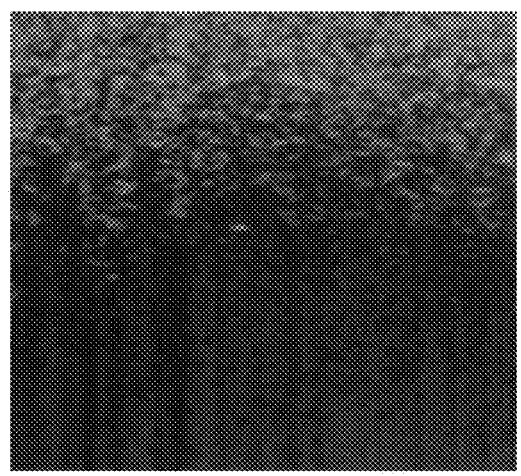
(b2) ENVELOPE DETECTION

(b3) ENVELOPE DETECTION AND SQUARE DETECTION

FIG.40
(b4) SQUARE DETECTION
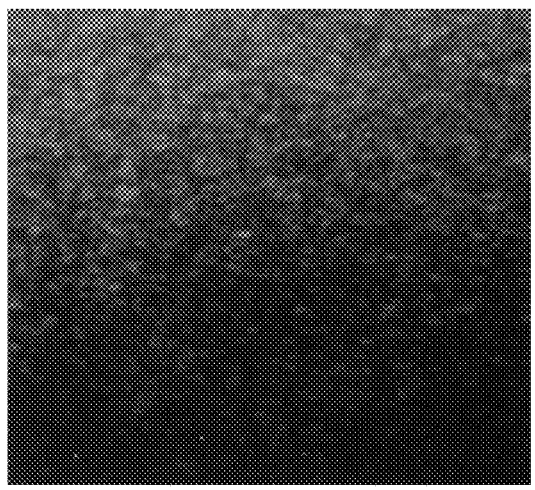
(b5) SQUARE DETECTION
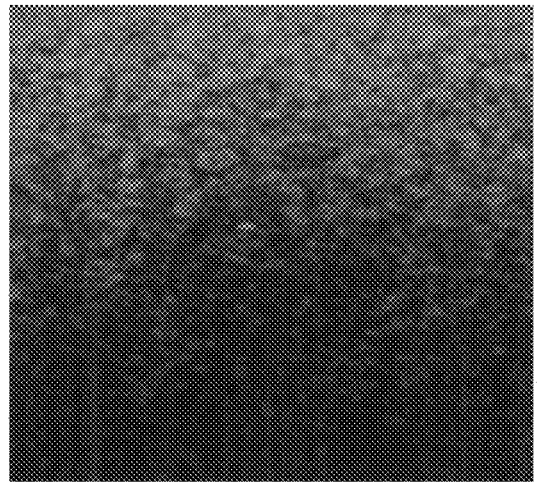
(c1) SQUARE DETECTION
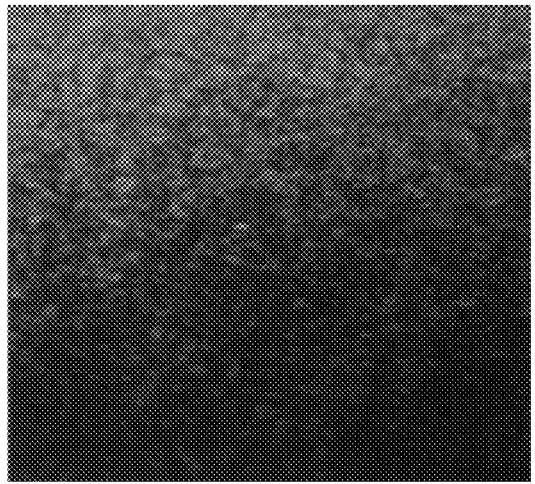
(c2) SQUARE DETECTION

FIG. 42
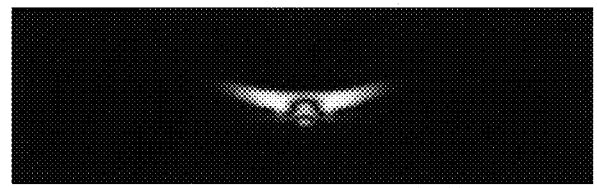
(a1)
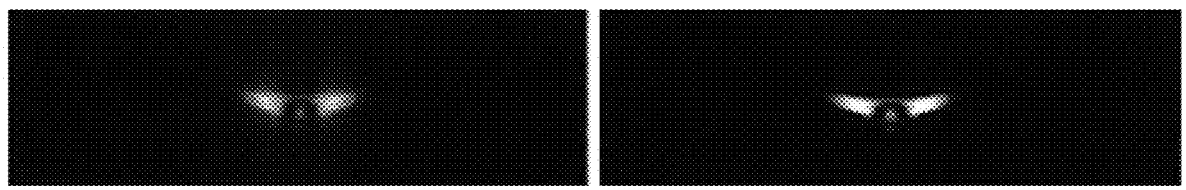
(a2)
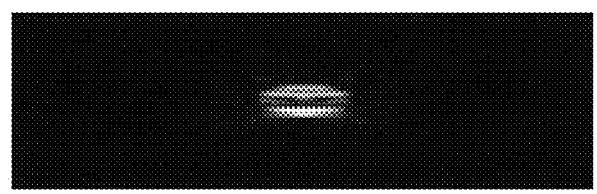
(b1)
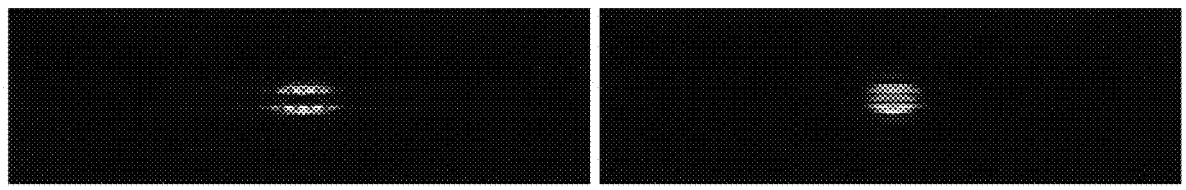
(b2)

BEAMFORMING METHOD, MEASUREMENT AND IMAGING INSTRUMENTS, AND COMMUNICATION INSTRUMENTS

CROSS-REFERENCE TO RELATED APPLICATION

The present application claims priority from Japanese Patent Applications No. 2014-116949 filed on Jun. 5, 2014 (inventor: Dr. Chikayoshi Sumi, an associate professor at Sophia University, Tokyo Japan), No. 2014-165284 filed on Aug. 14, 2014 (inventors: Dr. Chikayoshi Sumi and Mr. Naoto Yamazaki, a master degree student at Sophia University, Tokyo Japan), No. 2015-046528 filed on Mar. 9, 2015 (Dr. Chikayoshi Sumi), No. 2015-087901 filed on Apr. 22, 2015 (Dr. Chikayoshi Sumi), and No. 2015-106798 filed on May 26, 2015 (Dr. Chikayoshi Sumi), the contents of which are incorporated herein by reference in their entirety.

BACKGROUND OF THE INVENTION

Field of the Invention

The present invention relates to beamforming methods that are used for beamforming on arbitrary waves that arrive from measurement objects. The present invention also relates to measurement and imaging instruments, and communication instruments using such beamforming methods.

Particularly, the present invention relates to digital beamforming methods used in instruments that perform, on the basis of arbitrary waves such as electromagnetic waves, lights, mechanical vibrations, acoustic waves, thermal waves etc. that arrive from measurement objects, imaging of the objects, or nondestructively measuring and imaging of physical quantities such as temperatures, displacements etc., compositions and structures etc. of the objects. The measurement objects are various such as organic and inorganic substances or matters, solids, liquids, gases, rheology matters, living things, celestial objects, an earth, environments etc., and the application range is prominently widespread.

The present invention relates to nondestructive evaluations, diagnoses, resource explorations, growth and manufacturing of substances and structures, monitoring of physical and chemical restorations and treatments, applications of clarified functions and physical properties etc., where a high measurement accuracy can be required to be achieved without generating turbulences under the conditions of a noninvasiveness, a low invasiveness, no observable blood etc. Ideally, the measurement objects should be observed at their original positions in situ.

Measurement objects can also be treated or restored owing to the actions of the waves themselves. Simultaneously, the processes can also be observed by performing the beamforming using the responses from the objects. Beamforming is also performed on satellite communications, radars, sonars etc. to perform accurate communications under saving energies by realizing informationally safe environments. In ad hoc communication instruments and mobile instruments, beamforming has also been used. When the objects are dynamic, real time characteristics is demanded and therefore, the beamforming is required to be completed in a short time.

Description of a Related Art

Behaviors of waves such as electromagnetic waves, lights, mechanical vibrations, acoustic waves, thermal waves etc. are different on their frequencies, bandwidths, intensities, modes etc. Many transducers of various waves are developed so far, and imaging with the transmission waves, reflection waves, refracted waves or scattered waves (forward or back scattered waves) etc. is performed.

For instance, it is well known that a higher frequency acoustic wave categorized into an ultrasound is used for non-destructive evaluations, a medicine and sonars. For radars, proper frequency electromagnetic waves such as a radio wave, an FM wave, a micro wave, a terahertz wave, an infrared wave, a visible wave, a violet wave, a radioactive ray such as an X-ray etc. are used. Also for other waves, the behavior is different and dependent on the frequency and therefore it has a specific name, which is used for various sensing and communications properly with respect to measurement objects, media and bandwidths (polarization can also be performed on electromagnetic waves).

By those applications, the measurement objects are often scanned with a transducer mechanically. Also the same transducer is often used plural times, or plural transducers aligned in an array form beforehand are often used to perform beamforming processing. It is well known that when the earth and land, the ocean, weather are observed by the radar of a satellite and an airplane, a synthetic aperture processing etc. is performed. When imaging of the measurement objects in particular, an appropriate directivity is kept, and the beamforming is often intended that a high spatial resolution and a high contrast are achieved in a region of interest or at a point of interest.

As a result, a reflection and transmission generated by a spatial change of the impedance, various scattering (Rayleigh scattering, Mie scattering, and others), attenuation or those frequency variance etc. acting on a wave in the measurement object can be observed, and the inside and surface structures and compositions can be observed in addition to what the measurement object is. The measurement object can also be observed in a various spatial resolution. At various levels of the structure and composition (e.g., an individual level, a molecular level, an atom level, a nuclear level etc.), characteristic evaluations (characterization) can be performed.

For the purpose of highly accuracy, high-spatial resolution imaging, the signal compression technique such as a charp technology and an encoding technique have been representatively used for a long time. In ISAR (inverse synthetic aperture radar) etc., the inversion of beam properties is implemented on an observed signal to generate a super-resolution (e.g., when performing SA or others). Alternatively, a spatial resolution may also be reduced positively. For their processing, the singular value decomposition (SVD), the regularization, the Wiener filtering etc. are effective.

In addition, the encoding technology is also used for separating the simultaneously received signals into the respective signals, e.g., for a reception signal with respect to plural transmitted signals with different transmission positions. The waves to come from the different directions can be separated, and a signal source can be separated or identified. In such cases, matched filtering that achieves a high signal detection is great. However, when signal energy is obtained, but on the other hand, the object movement with the deformation, and the object displacement and strain etc. decrease the spatial resolution of signals, and therefore, the measurement accuracy is decreased as well. For the separation of waves and signals, the use of frequency and bandwidth or multidimensional spectra is also useful.

For imagings with the waves mentioned above, the distribution of amplitude data provided through quadrature detection and envelope detection or square detection is displayed as a gray image and a color image in one dimension, two dimensions or three dimensions, and the imaging often provides morphologic images. In addition, the functional observation is also possible, and for instance, a raw coherent signal is processed in the Doppler measurement using those waves (ultrasound Doppler, Radar Doppler, Laser Doppler etc.).

In addition, for instance, there is no information of a tissue displacement direction, but the power Doppler used in the medical ultrasound field can detect a tissue with the movement, which is a useful technique. In addition, when using a microwave, a terahertz wave or far infrared rays, the temperature distribution of object can be observed. Those measured physical quantities can be displayed with superposing them on morphologic images. In the field of the image measurement, observation of the movement can also be performed using the incoherent signal obtained through detection of a coherent signal (cross-correlation processing or optical flow etc.). On a medical ultrasound and a sonar, imaging using harmonic waves, and chord and different tone waves generated physically are also carried out. Particularly when a measurement object is dynamic, real time characteristics are demanded for beamforming processing.

In addition, in satellite communications, radars, sonars etc., beamforming is also performed to realize an informationally safe environment under the energy saving, and accurate communication is performed. In the ad hoc communication instruments and for mobile communications, beamforming has also been applied. Beamforming is also effective for an authorized person and a specific signal outbreak source, the specific communication with the position. In communications, information is put on a wave at the transmission side and sent to the reception side from the transmission side, which can be a purpose, the reception side can also reply to the transmission side by a result of the communication, and can also reply for the transmitted information and communicate again, but, of course, communications are not limited to these examples. When contents are dynamic, depending on a communication object and an observation object, real time characteristics are demanded, and it is demanded that the beamforming in that case is completed in a short time.

In such communication and medical fields, for instance, the present inventor develops ultrasonic imaging techniques for a differential diagnosis of lesions such as cancerous diseases, sclerosis etc. of human tissues. The present inventor increases a spatial resolution in echo imaging and an accuracy in measurement and imaging of a tissue displacement; and the present inventor also increases a spatial resolution and an efficiency of HIFU (High Intensity Focus Ultrasound) treatment; and the present inventor also promotes those imagings based on the reception of the echo with respect to the HIFU radiation. Those imagings are based on performing appropriate beamforming at high speed and therefore, the present inventor develops and discloses appropriate, high speed detection methods, tissue displacement measurement methods and shear wave propagation measurement methods etc.

The medical ultrasound diagnosis imaging instrument passed more than 20 years after it was digitized. In old times, mechanical scanning was performed using a single aperture transducer (a single element); and subsequently electronic scanning using plural transducers (elements) and the array type devices consisting of them was performed, and the device which processed a signal changed from an analog device to a digital device afterwards. Actually, the classical synthetic aperture processing itself has been digital beamforming since those days when it came to be used in a radar carried by a satellite and an airborne, but it was rare to be used in a medical ultrasound instrument by the reason of the strength of the reception signal (echo intensity) being weak.

In contrast, in late years the present inventor invented the multidirectional synthetic aperture method and achieved multidirectional beamforming by using a reception echo data set for a conventional synthetic aperture method. As a result, lateral modulation imaging with a carrier frequency in the lateral direction orthogonal to an axial direction and with a higher spatial resolution than conventional imaging was enabled by becoming able to obtain multidirectionally steered image signals at the frame rate that was the same as that by the conventional electronic scanning, and the coherent superposition (compounding). Besides, a real time measurement was enabled for the displacement vector distribution by using the multidimensional autocorrelation method that the present inventor invented together. In addition, speckle reduction was also enabled by performing incoherent superposition (compounding). Although conventionally transmission beams in different directions were used for the speckle reduction, the invented multidirectional synthetic aperture achieved a higher frame rate speckle reduction. In other sensing devices which use the waves such as a microwave, a terahertz wave, radioactive rays such as an X-ray etc., other electromagnetic waves, vibration waves including a sound, a thermal wave etc. for non-destructive evaluations other than those in ultrasound fields, digitization is pushed forward.

For instance, the synthetic aperture performed in those sensing instruments is an active beamforming, and the wave to be targeted for processing is a transmission wave, a reflection wave, a refracted wave or a scattered wave (forward or backward scattered wave etc.) with respect to those waves generated by a transducer. On the other hand, for instance, in a passive beamforming, a transmission wave, a reflection wave, a refracted wave or a scattered wave (forward or backward scattered wave etc.) become targets under the assumption that all the waves are generated from a wave emitted from the signal source which is by oneself a divergence targeted for a measurement (self-emanating), so that a case to measure a temperature distribution based on the far infrared observation mentioned above and an electrical activity source by the brain magnetic field of the creature is also. The examples corresponding to them exist much elsewhere. But recently photoacoustics is also targeted for a measurement of living things, and a laser is irradiated to an ultrasound creature as a measurement object (ultrasound source), i.e., a volume change caused by heat absorption with the laser frequency dependence generates an ultrasound, by which peripheral blood vessels can be distinguished as a result of reception beamforming, i.e., arteries or veins, for instance.

The digital instrument needs a lot of processing time in comparison with an analog instrument, but there are many advantages such as it being easy to implement high level calculation processing, being cheap and downsized including data storage medium, which improves calculation processing capacity and flexibility markedly. Actually, the high-speed analog processing performed immediately after having a received signal is extremely important, and it should be implemented with digital processing after AD conversion (Analogue-to-Digital conversion) relatively considered to be in around of the sensing device appropriately even if the instrument is called as a digital system.

In the analog instrument, the beamformings of the transmission and reception are carried out by analog processing. On the other hand, in the digital instrument, the transmission beamforming can be carried out by analog processing or digital processing, and the reception beamforming is carried out by digital processing. Thus, in the present invention, a beamformer performing reception beamforming by digital processing by all means is referred to as a digital beamformer.

After having received the waves from a measurement object through plural transducers (elements), an array type device consisting of them or mechanical scanning with one or more transducers (elements); DAS (Delay and Summation: phasing and summing) that is so-called synthetic aperture processing is carried out. For transmission, plural elements are excited to perform transmission beamforming, or a classical synthetic aperture processing is perform on the basis of one element transmission, whereas for reception beamforming, the DAS processing is performed commonly.

In other words, the transmission beamforming is carried out by analog processing or digital processing. On the other hand, in the reception beamforming, a reception signal is generated by each element in the array or by each element of the different position; and is AD converted into a digital reception signal after level adjustment of signal amplitude by the analogue amplification or attenuation, or analog filtering etc.; and the digital reception signal of each element is stored into a storage. Afterwards a device or computer, PLD (Programmable Logic Device), FPGA (Field-Programmable Gate Array), DSP (Digital Signal Processor), GPU (Graphical processing Unit) or microprocessor etc. with the general-purpose calculation processing capacity, or a dedicated computer, a dedicated digital circuit or a dedicated device, the digital processing is performed on the stored reception signals.

The device performing these digital processing can comprise those analog devices or AD converter, memory etc. The device or computer with computing capacity can be multi-cores. These make it possible to carry out a dynamic focusing that is almost impossible with an analog device at the reception. The parallel computations can also be carried out. A transmission line (e.g., multilayer circuit etc.) or a broadband wireless line is important on speeding up the analog processing and digital processing.

The dynamic focusing improves the spatial resolutions of generated image signals in a range direction or a depth direction for a measurement object. Alternatively, it is possible to perform a transmission dynamic focusing only when performing a classical synthetic aperture using one element transmission. In order to generate energy of a transmitted wave, a fixed focus transmission is often performed using plural excited elements instead of the synthetic aperture using the one element transmission.

The present inventor developed a high frame rate echo imaging that allowed interrogating a large region using one transmission by using a lateral wide wave such as a plane wave etc. Moreover, the present inventor realized lateral modulation and increasing a lateral bandwidth (a lateral spatial resolution) by performing coherent compounding (superposition) of plural waves with different steering angles. Particularly when using the above-mentioned autocorrelation method, the following displacement vector measurements are enabled, a shear wave propagation, a rapid blood flow in a carotid, a complex flow in a heart etc. When performing the multidirectional synthetic aperture or the transmission beamforming, similarly the imaging and measurement can be achieved. Otherwise, superposing plural waves with different carrier frequencies can also realize increasing an axial bandwidth (an axial spatial resolution).

For an active beamforming, these processings are performed, whereas for a passive beamforming, a transmitter is not used. Thus, a digital beamformer is comprised of a transmitter (an active beamforming case), a receiver and a DAS processing device, which is realized by building up them. Recently, they are packaged into a small size and can be used.

Phasing in the DAS processing can performed with a high speed by implementing delays onto a received echo signals via spatial approximate interpolations in a spatial domain, whereas the delays can also be implemented with a high accuracy, but with vast time, on the basis of the Nyquist theorem via phase rotations using multiplications of complex exponential functions in a frequency domain (a present inventor's past invention). After the phasing, the received signals are summed in a spatial domain (phasing and summing). In a digital instrument, for instance, a command signal generated by a control unit and used for transmitter's generating a transmission signal sent to an element to be driven can be used as a trigger signal for digital sampling of an analogue received signal (AD conversion).

When driving plural elements with transmission delays for a beamforming, one of analogue or digital transmission delay patterns set on a transmit unit in advance can be used for realizing a transmission focus position or a direction of steering etc. to be chosen by an operator. Moreover, in a received digital processing, a command signal used for driving an element at first, at last or other can be used as a trigger signal for starting the sampling of received signals; and the digital delays can be implemented on the digitized, received signals. The command signals can be generated on the basis of a command signal used for starting beamformings for a frame.

When implementing a digital delay for a transmission delay, an error determined by a clock frequency that generates a digital control signal, which is different from when performing an analogue delay. Thus, for a transmission delay, an analogue delay should be implemented. Alternatively, because for performing a reception dynamic focusing, when implementing a digital delay on to a received signal, an error is caused by the above-mentioned interpolation approximation, the sampling frequency of an AD converter is made sufficiently high with a high cost, or the above-mentioned high accuracy digital delay (phase rotation processing) must be implemented, which leads to a low speed beamforming.

The phasing and summing performed with the interpolation approximations can be achieved by simply adding echo signals of positions including the position of which an echo signal is synthesized, or by performing interpolations such as a bi-linear or a polynomial fitting etc. to increase the accuracy of the synthesized echo signal. Such beamformings are much faster than the high accuracy phasing and summing using complex exponential functions, but, the accuracy is lower than that of the high accuracy phasing and summing. The high accuracy phasing and summing is much slower. The phasing and summing is performed under the condition that the wave propagation speed is known or under using of an assumed wave propagation speed, for instance, a constant speed in a region of interest (ROI). Alternatively, phase aberration correction can also be performed via measuring of the wave propagation speed. For instance, the phase aberration can be calculated via estimating a cross-correlation function between adjacent beam signals or beam signals with different steering angles. When the wave propagation speed is homogeneous, interferometry analysis is achieved.

When the aperture elements exist in a 2D region or a 3D space, or a 2D or 3D array is comprised of the aperture elements, the further more processings are required for the beamforming and many processors are used for parallel processing etc. than when the aperture elements exist in a 1D region or a 1D array is comprised of the aperture elements. For the beamforming performed at positions that yield less interferences of transmission waves, the transmission beamforming of plural different directions (different steering angles), a transmission beamforming solo, parallel reception beamforming can be performed.

For the control of communication, being dependent on a kind of communication data and the data amount, and medium properties, a proper wave should be generated, and an optimized communication should be performed under the observation of them. Interfered waves can also be separated using an analogue device, or analogue or digital signal processing. Waves with controlled propagation directions, encodings, frequencies and/or bandwidths are important.

The present inventor's another invent similarly to the above-mentioned multidirectional synthetic aperture processing is to perform reception beamformings with plural directions with respect to one transmission beamforming; yielding a high frame rate. Also for the beamforming, apodization can be important. For instance, the respective transmission and reception apodizations can be performed to decrease sidelobes; properly the apodizations should be performed because they have a relation of trade-off with a lateral resolution. Alternatively, a simple beamformer with no apodization can also be used not to decrease the spatial resolution. However, the present inventor has been reporting that for the steering beamforming, proper apodizations are required to yield a high lateral resolution as well as suppressed sidelobes. The present inventor's previous invents include an approach that removing the sidelobes in a frequency domain.

Agents can be used to use nonlinear properties of waves propagating in an object. For instance, in a medical ultrasound field, microbubbles can be used. The present inventor invented imaging with a high spatial resolution and a high contrast by suppressing the sidelobes via transmitting high intensity waves or waves including harmonic waves, or implementing nonlinear processing onto received coherent signals or phased and summed coherent signals. The present inventor also invented a high accuracy tissue displacement (vector) measurement on the basis of the nonlinear processing.

Also imaging signals can also be generated using virtual sources. Regarding virtual sources, a virtual source set behind a physical aperture and a virtual source set at a focus position were reported previously. The present inventor also reported a virtual detector as well as a virtual source that is set at an arbitrary position, i.e., including not a focus position, and a proper scatter and a proper diffraction grid with an arbitrary position to be used as a physical wave source or a physical detector etc. A high spatial resolution and a large field of vision (FOV) can be obtained.

For performing imaging, a quadrature detection, an envelope detection, or a square detection can be used. The present inventor makes much of the using of phase information, e.g., by displaying a waveform itself in a color or gray image. Thus, toward various purposes, various multidimensional systems using various waves are developed.

As far, several digital beamforming methods using the Fourier's transform were disclosed. One of them is the digitized, analogue processing via the Fourier's transform that is an analytic solution of a classical monostatic synthetic aperture (SA) (nonpatent document 1), i.e., the beamforming that performs the classical synthetic aperture with a high speed and a high accuracy by using the fast Fourier's transform (FFT) (nonpatent document 2). In the processing, any approximate interpolation processing is not required. However, any digital processing for steering and a multistatic SA (receptions using plural elements, generally, including a transmission element and the surrounding elements) has not been disclosed yet.

All other digital beamforming methods disclosed perform approximate interpolation processings, and then yield low accuracies. For instance, for a plane wave transmission including a steered case, in which a wavenumber matching (mapping) via the FFT (nonpatent documents 3-5) and a non-flat aperture of an array (e.g., the array aperture geometry is an arc (nonpatent document 6)), the calculation and displaying require approximate interpolation processings, and yield low accuracies. The beamformings using the FFT for a plane wave transmission is also disclosed in patent documents 1-4, all of which perform the wavenumber matching via approximate interpolations. Multidimensional spectra are calculated on a wavenumber coordinate system with constant intervals via the approximate interpolations from directly calculated angular spectra, and the beamforming is completed by implementing the inverse FFT (IFFT).

In recently published nonpatent document 5, the nonuniform IFFT to be implemented on spectra with non-constant intervals is disclosed, which is also based on an approximate interpolation processing. As mentioned above, although such digital beamforming has already had a long history, because in a case where a real-time processing up to displaying an image is made much of, approximate interpolations are often performed, the highest accuracy is not always provided. Moreover, for the popular beamformings such as a fixed focus processing and steering etc. known to be performed via the DAS processing, any processing method using the digital FFT has not been disclosed yet.

Also the migration method is also reported (for instance, nonpatent document 7), which also requires approximate interpolation on the wavenumber matching. In order to achieve a high accuracy for these processings with approximate interpolations, sufficient over-samplings are performed by setting the analogue-to-digital (AD) sampling frequency high.

PATENT DOCUMENT LIST

[PATENT DOCUMENT 1] U.S. Pat. No. 5,720,708
[PATENT DOCUMENT 2] U.S. Pat. No. 6,685,641
[PATENT DOCUMENT 3] U.S. Pat. No. 7,957,609
[PATENT DOCUMENT 4] US patent applicant publication 2009/0036772
[PATENT DOCUMENT 5] U.S. Pat. No. 8,211,019
[PATENT DOCUMENT 6] U.S. Pat. No. 7,775,980
[PATENT DOCUMENT 7] US patent applicant publication 2011/0172538

NONPATENT DOCUMENT LIST

[NONPATENT DOCUMENT 1] J. W. Goodman, "Introduction to Fourier Optics" $2^{nd}$ ed., McGraw-Hill Co, Inc., 1996

[NONPATENT DOCUMENT 2] L. J. Busse, IEEE Trans. UFFC, vol. 39, no. 2, pp. 174-179, 1992

[NONPATENT DOCUMENT 3] J. Cheng, J.-y. Lu, IEEE Trans UFFC, vol. 53, no. 5, pp. 880-899, 2006

[NONPATENT DOCUMENT 4] H. Peng, J.-y. Lu, X. Han, Ultrasonics, 44, e97-e99, 2006

[NONPATENT DOCUMENT 5] P. Kruizinga et al, IEEE Trans. UFFC, vol. 59, no. 12, pp. 2684-2691, 2012

[NONPATENT DOCUMENT 6] M. A. Haun, D. L. Jones, W. D. O'Brien, Jr., IEEE Trans. UFFC, vol. 49, pp. 861-870, 2002

[NONPATENT DOCUMENT 7] C. Sumi, IEEE Trans. UFFC, vol. 55, pp. 2607-2625, 2008

[NONPATENT DOCUMENT 8] C. Sumi, S. Uga, "Effective ultrasonic virtual sources which can be positioned independently of physical aperture focus positions," Rep. Med. Imag., vol. 3, pp. 45-59, 2010

[NONPATENT DOCUMENT 9] M. Soumekh, "Fourier array imaging," PTR Prentice-Hall, Englewood Cliffs, N.J. 07632, 1994

[NONPATENT DOCUMENT 10] S. Haykin, A. Steinhardt ed. "Adaptive radar detection and estimation," John Wiley & Sons, inc. New York. 1992

[NONPATENT DOCUMENT 11] K. W. Hollman, K. W. Rigby, M. O'Donnell, "Coherence Factor of Speckle from a Multi-Row Probe," Proc. of IEEE Ultrasonics Symp, pp. 1257-1260, 1999

[NONPATENT DOCUMENT 12] D. Garcia, L. L. Tarnec, S. Muth, E. Montagnon, J. Poree, G. Cloutier, IEEE Trans. UFFC vol. 60, no. 9, pp. 1853-1867, 2013

[NONPATENT DOCUMENT 13] C. Sumi, IEEE Trans. UFFC, vol. 55, pp. 24-43, 2008

[NONPATENT DOCUMENT 14] C. Sumi, Rep. Med. Imag., vol. 5, pp. 57-101, 2012

[NONPATENT DOCUMENT 15] C. Sumi, IEEE Trans. UFFC, vol. 46, pp. 158-166, 1999

[NONPATENT DOCUMENT 16] S. Srinivasan, F. Kallel, and J. Ophir, Ultrasound Med. Biol., vol. 28, pp. 359-368, 2002

[NONPATENT DOCUMENT 17] C. Sumi, IEEE Trans. UFFC, vol. 55, pp. 297-307, 2008

[NONPATENT DOCUMENT 18] C. Sumi and K. Sato, IEEE Trans. UFFC, vol. 55, pp. 787-799, 2008

[NONPATENT DOCUMENT 19] C. Sumi, Y. Takanashi, K. Ichimaru, Rep. Med. Imag., vol. 5, pp. 23-50, 2012

[NONPATENT DOCUMENT 20] J. A. Jensen, "Field: A program for simulating ultrasound systems," Med, Biol, Eng, Comp, $10^{th}$ Nordic-Baltic Conference on Biomedical Imaging, Vol. 4, Supplemental, Part 1: 351-353, 1996

[NONPATENT DOCUMENT 21] B. Schrope, V. L. Newhouse, V. Uhlendorf, "Simulated capillary blood flow measurement using a nonlinear ultrasonic contrast agent," Ultrason. Imag., vol. 14, pp. 134-158, 1992

[NONPATENT DOCUMENT 22] P. N. Burns, S. R. Wilson, D. H. Simpson, "Pulse Inversion Imaging of Liver Blood Flow: Improved Method for Characterizing Focal Masses with microbubble Contrast," Investigative Radiology, vol. 35, no. 1, p. 58, 2000

[NONPATENT DOCUMENT 23] M. A. Averkiou, D. N. Roundhill, J. E. Powers, "A new imaging technique based on the nonlinear properties of tissues," 1997 IEEE Ultrasonics symp, pp. 1561-1566, 1997

[NONPATENT DOCUMENT 24] B. Haider, R. Y. Chiao, "Higher order nonlinear ultrasonic imaging," 1999 IEEE Ultrasonics symp., pp. 1527-1531, 1999

[NONPATENT DOCUMENT 25] A. Needles, M. Arditi, N. G. Rognin, J. Mehi, T. Coulthhard, C. Bilan-Tracey, E. Gaud, P. Frinking, D. Hirson, F. S. Foster, "Nonlinear contrast imaging with an array-based micro-ultrasound system," Ultrasound Med. Biol., vol. 36, no. 12, pp. 2097-2106, 2010

[NONPATENT DOCUMENT 26] J. R. Doherty, G. E. Trahey, K. R. Nightingale, M. L. Palmeri, "Acoustic Radiation Force Elasticity Imaging in Diagnostic Ultrasound," IEEE Trans. on UFFC, vol. 60, no. 4, pp. 685-701, April 2013

[NONPATENT DOCUMENT 27] K. Hynynen, "Demonstration of enhanced temperature elevation due to nonlinear propagation of focused ultrasound in dog's thigh in vivo," Ultrasound Med. Biol. vol. 13, no. 2, pp. 85-91, 1987

[NONPATENT DOCUMENT 28] Y. Huang, N. I. Vykhodtseva, K. Hynynen, "Creating brain lesions with low-intensity focused ultrasound with mcrobubbles: A rat study at half a megahertz," Ultrasound Med. Biol., vol. 39, no. 8, pp. 1420-1428, 2013

[NONPATENT DOCUMENT 29] C. Sumi, "Utilization of an ultrasound beam steering angle for measurements of tissue displacement vector and lateral displacement," Reports in Medical Imaging, vol. 3, pp. 61-81, 2010

SUMMARY OF THE INVENTION

Technical Problem

As explained above, because when performing the reception dynamic focusing by implementing the digital delays at the reception, errors occurs due to the above-mentioned approximate interpolations, the AD sampling frequency is made high with a high cost, or the low speed beamforming must be performed by implementing the above-mentioned high accuracy digital delays on signals (phase rotation processing).

As far, for waves such as electromagnetic waves, vibration (mechanical) waves such as acoustic waves (compressible waves), shear waves and surface waves etc., and thermal waves etc., disclosed digital beamforming methods on waves such as reflection and transmission waves, scattering waves (forward and backward scattering etc.), refractions, surface waves, ballistic waves, or waves generated by self-emanating sources are limited to the monostatic SA with no steering, the plane wave transmission including a steering case, and the migration method as mentioned above. Also, except for the monostatic SA, all the digital beamforming methods require approximate interpolations; yielding low accuracies.

In contrast to these, when using a transmission or reception transducer array device with an arbitrary aperture geometry (the transducer can also be used for both transmission and reception; different waves can be respectively dealt with for the transmission and reception), or when using only the reception transducer for the passive beamforming, regardless the using the transmission and reception focusing or steering, and for the cases where the coordinate systems are different for the transmissions and receptions of beams and the displaying images, an arbitrary beamforming should be realized with a high speed and a high accuracy with no approximate interpolate calculations.

For the active beamforming, array-type transmission and reception transducer devices with arbitrary aperture geometries are used (one device may be used for both transmission and reception). For the passive beamforming, only an array-type reception transducer device with an arbitrary aperture geometry is used. For the beamforming, arbitrary beamforming is desired to be performed with a high speed and with a high accuracy via digital processing. In practice, arbitrary focusings and arbitrary steerings are desired to be performed using array-type transducer devices with arbitrary aperture geometries.

After beamforming with phasing and summing, linear or nonlinear signal processing is implemented on plural beams with at least one different wave parameter among a frequency, a bandwidth, a pulse shape, a beam shape etc. in each direction in order to yield a new beam with at least one different wave parameter (in various fashions such as frequency modulation, widebanding, multi-focusing etc.). In beamformings like these, focusing, steering and apodization can be performed via the DAS processing using arbitrary array-type transducer devices with arbitrary aperture geometries.

Because the propagation speed of a wave is determined by the properties of a medium under physical conditions, when the multidimensional array comprising of 2D or 3D distribution of aperture elements is used for multidimensional space imaging, due to increasing the number of beams and data required for generating one beam, it takes much longer time to complete beamforming. Thus, a real-time processing instrument or an instrument that displays results in a short time should be used by obtaining a high speediness in beamforming.

As far, regarding digital beamformings using Fourier's transform, mainly the beamformings to be achieved via approximate interpolations on the Cartesian coordinate system using a 1D or 2D linear array-type transducer is disclosed. However, including the cases where coordinate systems are different for transmission, reception and display, digital beamformings are desired to be performed not with approximate interpolations at all.

Also the methods disclosed for cases where the geometry of an array aperture is not flat (for instance, the geometry of an array aperture is an arc) requires approximate interpolations. For instance, as typical cases, for using a convex-type transducer, an electric or mechanical sector scan or an IVUS scan (intravascular ultrasound), beamformed data are required to be generated directly on arbitrary display coordinate systems such as the Cartesian coordinate system by implementing digital processings on signals received on arbitrary coordinate systems such as the polar coordinate system.

Although recently a memory and an AD convertor became remarkably cheap, by sampling a wave on the basis of the Nyquist theorem, however, without over-sampling of data, the beamforming is desired to be completed with a higher speed than the beamforming with the DAS processing. The apodization is also required to be performed properly.

By solving these problems, it is desired to achieve a high spatial resolution and a high contrast including the effects of suppressing sidelobes in image signals obtained in a real-time or in a short time. Moreover, it is desired to achieve high accuracy measurements of target's motion (displacement) or deformation, or temperature etc. from the obtained signals. For instance, recently in a medical ultrasound field, after measuring a tissue displacement or velocity by applying the Doppler method to echo signals, by applying temporal or spatial derivatives to these measurements, a tissue acceleration or strain etc. is calculated and displayed. Since the temporal or spatial derivative is a processing that amplifies high frequency measurement errors and decreases an SNR (Signal-to-Noise ratio), the displacement measurement accuracy must be made high by using the signal phase. As far, as the high accuracy beamforming, the dynamic focusing on the basis of the so-called DAS processing was used. The 3D imaging instrument using a 2D or 3D array tends to spread. Thus, it is desired to achieve arbitrary beamformings including the dynamic focusing with high speeds and high accuracies without approximate interpolations.

Recently, the present inventor realized high accuracy measurement methods of a rather high speed tissue motion or shear wave propagation on the basis of high speed beamformings using steered plane wave transmissions (high speed transmission and reception of signals from an ROI). Also for such beamformings with no focusing, it is desired to complete the beamformings with high speeds and high accuracies with no approximate interpolations. By performing high speed beamformings with changing a steering angle and coherent superposition of them, it is made possible to yield almost the same image qualities (a spatial resolution and a contrast) as those of conventional focused beamforming, however, with a higher speed. Such high speed beamformings are also effective for the multidimensional imaging using a multidimensional array.

Also it is desired to achieve the steering using a classical SA (monostatic type) on the basis of scanning with driving each one transmission element and the multistatic SA with high speeds and high accuracies without approximate interpolations. Also when using so-called migration processing, similarly it is desired to perform arbitrary beamformings on arbitrary coordinate systems with high speeds and high accuracies with no approximate interpolations. Other concrete examples of beamformings to be realized are described in other parts of the present patent document, similarly which are also desired to be performed with high speeds and high accuracies.

The first purpose of the present invention is that it is made possible, while using instruments with digital operational functions as digital beamformers, to perform arbitrary beamformings with high speeds and high accuracies with no approximate calculations. According to the invention, for instance, the below-described various applications of waves including superresolution imaging using nonlinear processing etc. can be made performable.

Solution to Problem

The present invention solves the above-mentioned technical problem at least partially. The beamforming method according to one aspect of the present invention is a method on a Cartesian coordinate system using an axial direction x determined by a direction of a aperture of a flat reception aperture element array and a lateral direction x orthogonal to the axial direction x, in a case where an arbitrary wave is transmitted form a wave source positioned in an arbitrary direction to a measurement object and a wave arrival from the measurement object is processed as a transmission or a reception beamforming is performed with a steering angle $\theta$ defined with respect to the axial direction is zero or nonzero degree, and the wave arrival from the measurement object is reception-dynamic-focused with a steering angle $\varphi$ defined with respect to the axial direction is zero or nonzero degree, and the a beamforming method includes the steps of: (a) where the wave arrival from the measurement object is received at least by a reception aperture element to generate a reception signal; and (b) where beamforming processing is performed at least by implementing Fourier's transform and wavenumber matching with respect to the reception signal generated in step (a), wherein step (b) includes without performing wavenumber matching including approximate interpolation processings in a wavenumber domain or in a frequency domain with respect to the reception signal, and the reception signal is Fourier's transformed in the axial direction y and the calculated Fourier's transform is multiplied to a complex exponential function (101) expressed using a wavenumber k of the wave and a wave number $k_0$ expressed by a carrier frequency $\omega_0$ as $k_0$ ($=\omega_0/c$) and imaginary unit i to perform wavenumber matching in the lateral direction x, $$\exp\{i(k\sin\theta + k_0\sin\phi)x\}, \quad (101)$$

and further, the product is Fourier's transformed in the lateral direction x and the calculated result is multiplied to a complex exponential (102), from which an effect of the lateral wavenumber matching is removed, to yield a spatial resolution in the axial direction y and simultaneously multiplied to a complex exponential function (103) as well to perform wavenumber matching in the axial direction y, and the lateral wavenumber is expressed as $k_x$, $$\exp(i\sqrt{k^2-(k_x-k\sin\theta-k_0\sin\phi)^2}y), \quad (102)$$

$$\exp[i\{k\cos\theta+k_0(-1+\cos\phi)\}y], \quad (103)$$

by which the wavenumber matching is performed with no approximate interpolations, and an image signal is generated on the Cartesian coordinate system directly.

The present invention includes instruments and methods that are used for performing arbitrary beamformings on arbitrary coordinate systems with a high speed and a high accuracy, and without approximate calculations required for general digital processings, on the basis of properly using the FFT, the multiplications of complex exponential functions and the Jacobi operation. In order to solve the problem, for waves such as electromagnetic waves, vibration (mechanical) waves such as acoustic waves (compressible waves), shear waves and surface waves etc., and thermal waves etc., proper digital processing algorithms implemented on digital circuits and softwares and analogue and digital hardwares are used for the waves such as reflection and transmission waves, scattering waves (forward and backward scattering etc.), refractions, surface waves, ballistic waves, or waves generated by self-emanating sources, waves transmitted from moving bodies, or waves that arrive from unknown sources etc.

The hardware includes an instrument that equips an operational function that allows digital wave signal processing as well as a phasing and summing device that is used in a general beamformer of each wave instrument, in which the softwares of the present invention can be implemented, or digital circuits that performing the operations can be used. As mentioned later, other required devices are, at least, transducers, transmitters, receivers, and storage devices of received signals etc., which are used in general. Waves such as harmonic waves can also be dealt with. Beamformings using virtual sources and virtual receives can also be performed. Parallel processing can also be performed for generating plural beams simultaneously.

The present invention uses analogue devices such as the above-mentioned analogue amplifiers or attenuators for controlling a signal level, analogue filters etc., and effective applications of analogue signal processing devices (linear and specific nonlinear devices for modifying a wave shape by such as enhancing or decreasing of wave properties of a driving signal), and for performing digital processing on stored signals, the above-mentioned devices or calculators, PLDs (Programmable Logic Devices), FPGAs (Field-Programmable Gate Arrays), DSPs (Digital Signal Processors), GPUs (Graphical Processing Units), microprocessors etc. that equip general calculation capabilities, and also special calculators and special digital circuits, or special devices.

It is important that not only such analogue devices, AD convertors, memories, devices that perform digital signal processing (multi-cores etc.) are high efficient but also the number of communication channels between devices, channel capacities, wirings, wideband wireless communications. In particular, in the present invention, it is desired that such functional devices are installed into a chip or a circuit board (the devices may be detachable), or the devices are directly implemented into a chip or a circuit board (including a multilayer type). Parallel processings are also important. When a calculator also plays a role of a controller unit, if the device is not detachable, a remarkably higher security can be achieved than that obtained under a general programmed control. In a contrary, under the existing legislation, cases where disclosing of processing contents is demanded will increase.

Advantageous Effects of Invention

According to one of viewpoints of the present invention, it is made possible, while using instruments with digital operational functions as digital beamformers, to perform arbitrary beamformings with high speeds and high accuracies with no approximate calculations. As explained later in detail, the present invention realizes, on the basis of proper using of the multiplications of complex exponential functions and the Jacobi operation, arbitrary beamformings on arbitrary orthogonal coordinate systems including a curvilinear coordinate system with high speeds and high accuracies with no approximate interpolations.

Although the DAS (Delay and Summation) processing realizes arbitrary beamformings including conventional beamformings, when using a 1D array-type physical aperture and a general PC (personal computer), at least the present invention makes the calculation speeds 100 times as high as those achieved using the DAS processing. When the aperture elements distribute in a 2D or 3D space or comprise a multidimensional array, the present invention efficiently solve the problem that it takes more processing times in the multidimensional cases than in the 1D case, i.e., the increasing the speediness of beamforming becomes more efficient.

That is, the present invention uses a transmission or reception transducer array device with an arbitrary aperture geometry (it may be used for both transmission and reception) or a sensor array device, and allows arbitrary beamformings with high speeds and high accuracies and with no approximate interpolations via digital processing. In practical, arbitrary focusings, arbitrary steerings, arbitrary apodizations can be performed with array devices with arbitrary aperture geometries.

For instance, in a field of medical ultrasound imaging, according to observation targets, a coordinate system on which physical transmission and reception and digital sampling are performed is selected such as a Cartesian coordinate system for a linear array-type transducer and a polar coordinate system popular for a convex type transducer, a sector scan, or an IVUS (intravascular ultrasound). For instance, for observing a heart dynamics between ribs, the sector scan is performed generally. An aperture of not a transducer with an array-type aperture geometry but a PVFD (polyvinylidene fluoride) based transducer may be deformable. That is, the present invention allows obtaining signals directly beamformed on arbitrary coordinate systems such as image displays etc. with no approximate interpolations by processing digital signals obtained from waves transmitted and received on arbitrary coordinate systems.

For the multistatic SA, echo data frames with the number of reception elements are made from echo signals received at a same position within plural reception positions with respect to a transmission position, each of which echo data frame are processed by the monostatic SA of the present invention and finally the IFFT is implemented on the superposition of all the monostatic SA results. That is, echo data can be generated by performing the monostatic SA processings with the same number as that of received channels. Thus, it takes shorter time to complete the beamforming (a higher speed) than the DAS method, known as the general multistatic type method, that yields high spatial resolution image signals by generating low spatial resolution image signals to be superposed.

And on the basis of the multistatic processing of the present invention, the reception dynamic focusing and steering can also be performed, with respect to the popular fixed transmission focusing, with a high speed and a high accuracy. All the beamformings can be achieved by implementing the proper phase rotation processings using the multiplications of complex exponential functions.

Also regarding a coordinate system, the present invention also allows, on the basis of performing the Jacobi operation on the Fourier's transform, generating echo data directly on a Cartesian coordinate system used for the display with a high speed and a high accuracy with no approximate interpolations, for instance, for performing the signal processing on the convex or sector scan, IVUS.

Using the present invention, when using the so-called migration processing, similarly arbitrary beamformings can be performed on arbitrary coordinate systems with high speeds and high accuracies with no approximate interpolations. The present invention also allows the uses of virtual sources for performing high SNR and high spatial resolution imagings with high speeds. Moreover, the present invention also allows with high speeds and high accuracies, on the basis of digital signal processing, frequency modulating and widebanding of beams via linear or nonlinear processing, multi-focusing, parallel processing, virtual sources or receivers etc. The present invention is also effective for optimizing beamformings that require much calculations.

As mentioned above, regardless performing the transmission and reception focusing, and transmission and reception apodizations or not, the present invention allows, for waves such as electromagnetic waves, vibration (mechanical) waves such as acoustic waves (compressible waves), shear waves, ballistic waves, surface waves etc., thermal waves etc., arbitrary beamformings with high accuracies and high speeds on the basis of digital processings, even if the coordinate systems of transmissions/receptions and generations of beamformed signals are different each other.

Thus, not only the frame rates for displaying the images of beamformed signals increase but also, regarding image qualities, high spatial resolutions and high contrasts can be yielded. Moreover, using the beamformed signals, measurement accuracies on displacements, deformations, temperatures etc. can also increase. The increase in a processing speediness yields a remarkable effect on the multidimensional imaging using a multidimensional array. The present invention relates to mathematical algorithms regarding wave propagations, which was obtained as products by leading to solutions with no approximate calculations even via performing the digital processings. These cannot be achieved simply.

BRIEF DESCRIPTION OF THE DRAWINGS

FIG. 3 shows illustrations of configurations of plural transmission aperture elements used in a transmission transducer;

FIG. 7 shows illustrations of cylindrical wave transmissions on polar coordinate system $(r,\theta)$ (transmissions of waves, in a radial (r) direction, widely spread in an angle direction ($\theta$));

FIG. 8A shows illustrations of cylindrical wave transmissions on polar coordinate system $(r,\theta)$ (transmissions of waves, in a radial (r) direction, widely spread in an angle direction ($\theta$)) from virtual sources set behind physical apertures with arbitrary aperture geometries, and FIG. 8B shows illustrations of positions of physical apertures with arbitrary aperture geometries, or other apertures or waves generated in front of or behind the physical apertures;

FIGS. 18A and 18B show images obtained using method (1) for steered plane wave transmissions;

FIG. 21 shows images obtained for steered plane wave transmissions with method (1) together with a compounding method;

FIG. 23 shows images obtained for steered plane wave transmissions with method (6), i.e., the migration method;

FIG. 24 shows images obtained using method (2), i.e., monostatic SA;

FIG. 25 shows images obtained using method (3), i.e., multistatic SA;

FIG. 27 shows images obtained using method (4), i.e., fixed focusing transmissions;

FIG. 28 shows images obtained for a cylindrical wave transmission using a convex-type array with method (5-1), and for a cylindrical wave transmission using a linear-type array with method (5-1').

FIG. 29 shows images obtained using a convex-type array with method (5-2), i.e., fixed focusing transmissions.

FIG. 32 shows illustrations of configurations of plural transducers;

FIG. 33 shows figures that explain various wave formations obtained using 1D transducer array;

FIG. 34 shows illustrations of a beam direction, an angle of a direction of arriving wave and the first moments of spectra in spatial and frequency domains in a 2D measurement case;

FIG. 38 shows varieties of B-mode echo images obtained via an embodiment of the present invention;

FIG. 39 shows varieties of B-mode echo images obtained via an embodiment of the present invention;

FIG. 40 shows varieties of B-mode echo images obtained via an embodiment of the present invention;

FIG. 42 shows varieties of acoustic pressures obtained using a concave HIFU applicator via an embodiment of the present invention.

DESCRIPTION OF THE PREFERRED EMBODIMENTS

Below, embodiments of the present invention will be explained in detail with referring to figures. The same compositions of instruments are referred to using the same codes or numbers by which overlapped explains are omitted. The instruments related to the present invention can be used as a measurement and imaging instrument as well as a communication instrument. Below explained are mainly about generations of image signals of transmission waves, refraction waves, reflection waves, scattering waves (forward and backward scatterings etc.) such as of an acoustic pressure and a particle (medium) velocity for an acoustic wave such as an ultrasound etc., a stress wave or a strain wave for a compressible wave (longitudinal wave) or a shear wave (transverse wave), a ballistic wave, a surface wave etc., an electric field wave or a magnetic wave for an electromagnetic wave, a temperature or a thermal flux for a thermal wave.

The 1st Embodiment

Figure 1:
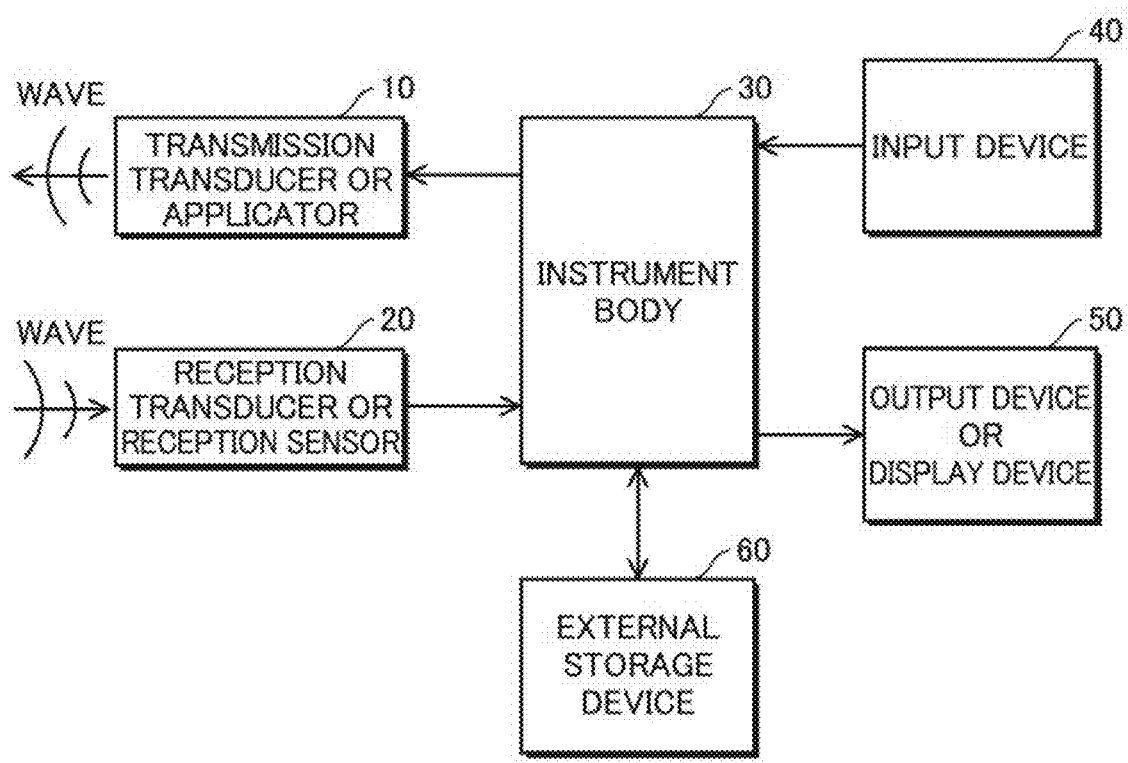
FIG. 1 shows schematic representation (block map) of compositions of a measurement and imaging instrument or a communication instrument related to the first embodiment of the present invention.

At first, the compositions of the measurement and imaging instrument or the communication instrument related to the first embodiment of the present invention are explained. FIG. 1 shows a schematic representation (block map) of compositions of the measurement and imaging instrument or the communication instrument related to the first embodiment of the present invention. As shown in FIG. 1, the measurement and imaging instrument (or communication instrument) is equipped with a transmission transducer (or an applicator) 10, a reception transducer (or a reception sensor) 20, an instrument body 30, an input device 40, an output device (or a display device) 50, and an external storage (memory) device 60.

Figure 2:
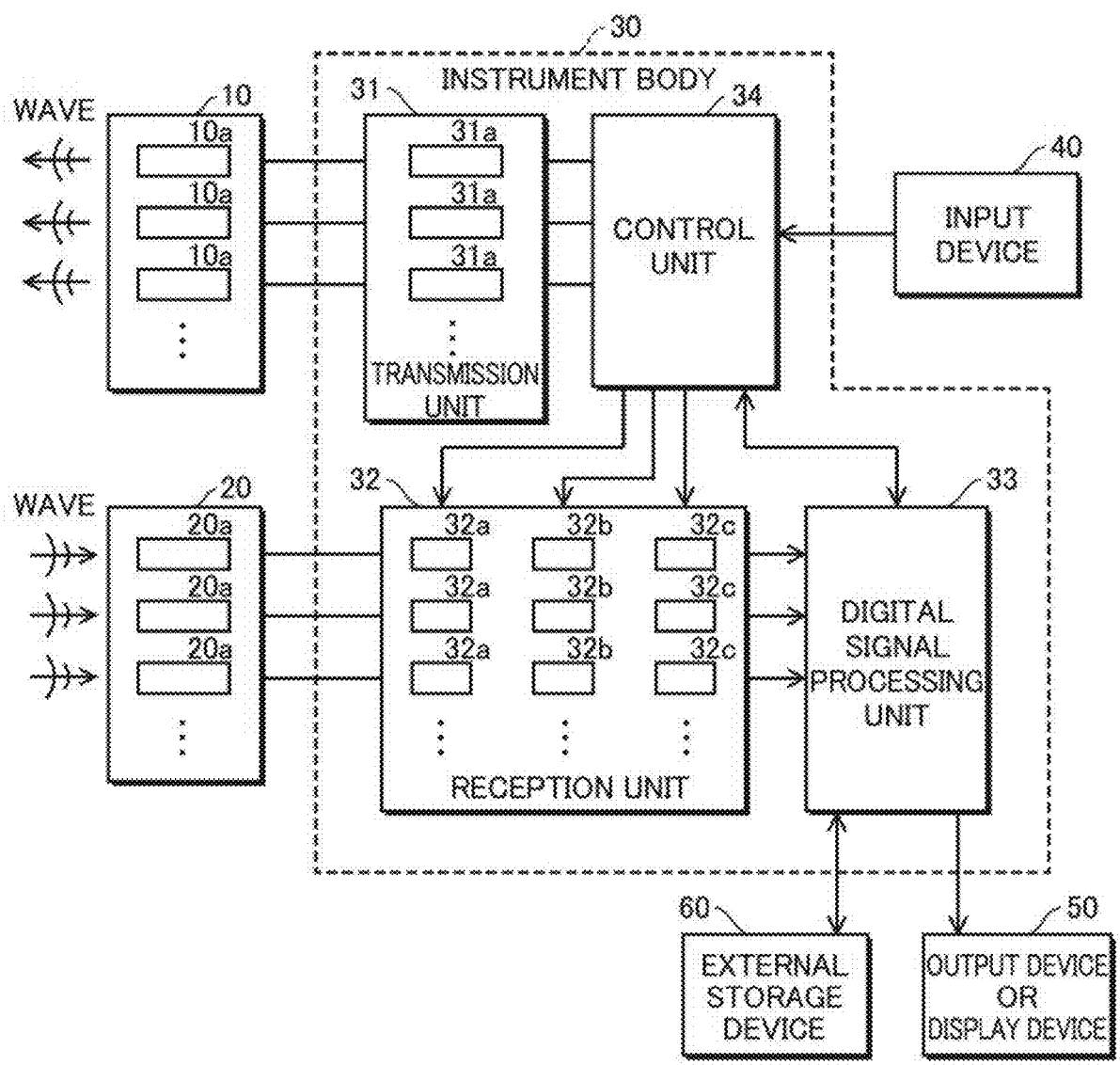
FIG. 2 shows the specific schematic representation (block map) of compositions of a body of instrument shown in FIG. 1.

FIG. 2 shows the specific schematic representation (block map) of compositions of a body of instrument shown in FIG. 1. Mainly, the body of instrument 30 is equipped with a transmission unit 31, a reception unit 32, a digital signal processing unit 33 and a control unit 34. Here, the reception unit 32 can include the digital signal processing unit 33. FIG. 1 and FIG. 2 show a properly simplified block map to the last, to which the present embodiment is not limited and the detail of the present embodiment is explain below. For instance, communications between the instruments, or between the units or in units are properly performed on the basis of a wire or wireless technology, and they can also be set at different positions. The body of instrument 30 is conventionally referred to one comprised of such plural units.

<Transmission Transducers>

The transmission transducer (or the applicator) 10 shown in FIG. 2 generates and transmits waves using drive signals provided from the transmission unit 31 in the body of instrument 30. On the present embodiment, plural transmission aperture elements 10a of the transmission transducer 10 comprise an array.

FIG. 3 shows illustrations of configurations of plural transmission aperture elements used in a transmission transducer. FIG. 3($a1$) shows plural transmission aperture elements 10a arrayed densely in a 1D array state; FIG. 3($b1$) shows plural transmission aperture elements 10a arrayed sparsely in a 1D array state; FIG. 3($a2$) shows plural transmission aperture elements 10a arrayed densely in a 2D array state; FIG. 3($b2$) shows plural transmission aperture elements 10a arrayed sparsely in a 2D array state; FIG. 3($a3$) shows plural transmission aperture elements 10a arrayed densely in a 3D array state; FIG. 3($b3$) shows plural transmission aperture elements 10a arrayed sparsely in a 3D array state.

The respective transmission aperture elements 10a have shapes of a rectangular, a circle, a hexagon or others, and a flat, a concave or a convex etc., and an array is 1D, 2D or 3D state. The directivity of a transmission aperture element 10a is determined by the frequency or bandwidth of a generated wave, and the geometry of transmission aperture element 10a. Generally, the directivity is exhibited in a 2D or 3D space. When the element is comprised of two apertures that respectively have directivities in orthogonal two directions, or three apertures that respectively have directivities in orthogonal three directions, the element can also be counted to be one. Also an element can also be comprised of larger than three apertures that have directivities in larger than three directions. The number of apertures in an element may be different at positions and also they can be mixed in with.

Although the transmission aperture element 10a can exist spatially densely or sparsely (at far positions), the present embodiment is explained with no distinguish with 1D to 3D array types. According to objects (communication) in which the waves propagate or the observation is performed, the aperture element arrays have various formations such as a linear type (the alignment of elements is flat), a convex type (a convex, an arc alignment), a focus type (a concave, an arc alignment), a circular type (for instance, an IVUS in a medical ultrasound etc.), a spherical type, a convex or concave spherical kernel type, a convex or concave other geometry types etc. The types are not limited to these. Proper driving these aperture element arrays generates the above-mentioned waves that widely spread in a lateral direction such as plane waves, the steering, the synthetic aperture, fixed transmission focusing etc., i.e., a transmission beam or a transmission wave with a wave-front.

For electric scanning, as mentioned in detail later, in order to a transmission beam or a transmission wave with a wave-front, by using independent drive signals generated by plural transmission channels equipped in the transmission unit 31 shown in FIG. 2, the transmission aperture elements 10a with the same number as that of the drive signals are independently driven. The transmission aperture element array that is used for generating a transmission beam or a transmission wave with a wave-front is referred to as a transmission effective aperture. Otherwise, all the aperture elements are totally referred to as a physical aperture element array, from which the transmission aperture that is realized by the transmission aperture element 10a driven simultaneously is referred to as a transmission subaperture element array or simply a transmission subaperture.

When the object in which waves propagate (communication object) are large or over a region of interest (ROI) is observed at once, the instrument may have transmission channels with the same number as that of the aperture elements existing in a physical aperture element array, and all the channels may always be used. However, in order to make the instrument cheaper, by translating the transmission subaperture element array by switching the transmission channels electrically, or by performing a mechanical scan with a physical aperture element array, waves can be transmitted to over the ROI with the minimum number of transmission channels. When the object in which waves propagate (communication object) is large or the size of object to be observed is large, both the electric and mechanical scanning can also be performed.

When performing sector scanning, a spatially fixed aperture element array of the above-mentioned type can be electrically driven to perform the scanning (electric scanning), or the aperture element array itself can be used to perform the mechanically scanning, or both can be performed together. As classical SAs, there are two types using electric scanning in which the respective elements in an aperture element array are individually driven or using mechanical scanning using one aperture element. That is, a transmission aperture array is composed by performing transmissions at different positions. For the electric scanning, the transmission unit 31 is equipped with transmission channels with the same number as that of transmission elements in a physical aperture array and then, the transmission channel number can be decreased by using a switching device and at least one channel is required similarly to the mechanical scanning. For transmitting polarized waves, at least the channel number expressed by the multiplication of the element number to be driven simultaneously and the number of polarized waves is required for the transmission unit 31.

<Reception Transducers>

The reception transducer (or the reception sensor) shown in FIG. 2 can also be used as the transmission transducer 10 or an exclusive reception array-type sensor another one from the transmission transducer 10. Thus, the reception transducer 20 can also be set at a different position from that of the transmission transducer 10. Otherwise, the reception transducer 20 can be one that allows detecting a different type wave from that generated by the transmission transducer 10. Such a reception transducer 20 can be set at the same position as that of the transmission transducer 10 and can also be installed into a body.

The reception transducer 20 used in the present embodiment has an array comprised of at least one reception aperture element 20a, and the signals received by the respective elements are independently transmitted to the reception unit 32 (FIG. 2) in the body of instrument. The respective reception aperture elements 20a have shapes of a rectangular, a circle, a hexagon or others, and a flat, a concave or a convex etc., and an array is 1D, 2D or 3D state. The directivity of a reception aperture element 20a is determined by the frequency or bandwidth of a received wave, and the geometry of reception aperture element 20a. When the element comprised of plural apertures can also be counted to be one. The number of apertures in such an element may be different at positions and also they can be mixed in with.

According to objects (communication) in which the waves propagate or the observation is performed, similarly to the transmission transducer 10, the aperture element arrays have various formations such as a linear type (the alignment of elements is flat), a convex type (a convex, an arc alignment), a focus type (a concave, an arc alignment), a circular type (for instance, an IVUS in a medical ultrasound etc.), a spherical type, a convex or concave spherical kernel type, a convex or concave other geometry types etc. The types are not limited to these. Receiving waves using these aperture element arrays, the above-mentioned waves that widely spread in a lateral direction such as plane waves, the steering, the synthetic aperture, fixed transmission focusing, dynamic focusing etc. are performed, i.e., a reception beam or a reception wave with a wave-front is generated.

The transducer aperture (element) can also spatially exist not densely but sparsely (at far positions); or transmission and reception can also be performed by mechanically scanning the measurement object; or no array-type transducer generally referred to as can also be used to perform almost same processings of received signals; and the present embodiment is explained with no distinguish about them particularly by mentioning mainly about cases using array-type devices. For instance, when radar apertures exist at different positions of lands, the respective apertures can be comprised as arrays or not.

Not only for radars carried by a satellite or an airborne but also a transducer to be used for performing mechanical scanning of a measurement target, also in such cases, the transducers can also have an array or not; transmissions and receptions of signals can also be performed at spatially continuously or densely, or at far positions or sparsely. Thus, not only the classical SAs (transmission from one element) but also receptions of signals with respect to transmission beamformings are performed. The aperture element can exist in a 1D, 2D or 3D state. In addition to electric scanning, mechanical scanning can also be performed together.

Regarding with the electric scanning, as mentioned later, in order to realize a reception beam or a received wave with a generated wave-front, received signals can be detected simultaneously via aperture elements with the same number as that of reception channels equipped with the reception unit 32 (a reception effective aperture). The reception effective aperture can be different from the transmission effective aperture. Such a reception effective aperture is distinguished with the total aperture elements referred to as the physical aperture element array, and the reception aperture realized by the reception aperture elements 20a simultaneously used is referred to as a reception subaperture element array or only a reception subaperture.

When the object in which waves propagate (communication object) are large or over a region of interest (ROI) is observed at once, the reception unit 32 may have reception channels with the same number as that of the aperture elements existing in a physical aperture element array, and all the channels may always be used. However, in order to make the instrument cheaper, by translating the reception subaperture element array by switching the reception channels electrically (electric scanning), or by performing a mechanical scan with a physical aperture element array, waves can be received from over the ROI with the minimum number of reception channels.

When the object in which waves propagate (communication object) is large or the size of object to be observed is large, both the electric and mechanical scanning can also be performed. When performing sector scanning, a spatially fixed aperture element array of the above-mentioned type can be electrically driven to perform the scanning (electric scanning), or the aperture element array itself can be used to perform the mechanically scanning, or both can be performed together. As classical SAs, there are two types using electric scanning in which the respective elements in an aperture element array are individually driven or using mechanical scanning using one aperture element. That is, a transmission aperture array is composed by performing transmissions at different positions. For the electric scanning, the transmission unit 31 is equipped with transmission channels with the same number as that of transmission elements in a physical aperture array and then, the transmission channel number can be decreased by using a switching device and at least one channel is required similarly to the mechanical scanning.

Alternatively, regarding the reception in the case, in a monostatic type where the receptions are performed by the same elements as those of the active transmission elements, the reception unit 32 is equipped with the reception channels with the same number as that of the transmission channels at least. Alternatively, in a multistatic type where plural elements around the active transmission elements to be used in almost cases, for electric scanning, the reception unit 32 is equipped with reception channels with the same number as that of reception elements in a physical aperture array, whereas both for electric and mechanical scanning, the reception unit 32 is equipped with the reception channels with the same number as that of the elements of a reception effective aperture at least. For receiving polarized waves, at least the channel number expressed by the multiplication of the element number to be used for the receiving simultaneously and the number of polarized waves is required for the reception unit 32.

<Concrete Examples of Transducers>

Transducers 10 or 20 to be used include various ones that allow generating or receiving arbitrary waves such as electromagnetic waves, lights, mechanical waves, acoustic waves or thermal waves etc. For instance, there are transducers 10 that allow transmitting arbitrary waves to the measurement target and receiving reflected waves or backscattered waves generated in the measurement target (also used as the transducers 20). For instance, when the arbitrary wave is an ultrasound, an ultrasound transducer can be used, which allows transmitting ultrasounds using drive signals provided and generating received signals by receiving ultrasounds. It is well known that according to the applications, ultrasound elements (PZT (Pb (lead) zirconate titanate), PVDF (polyvinylidene fluoride) piezoelectric element etc.) are different as well as the structures of the transducers.

In the medical applications, for blood flow measurement, a narrowband ultrasound is used historically. First in the world, the inventor of present invention has been realizing to use a wideband echo imaging transducer for measurements of soft tissues' displacement or strain (including static cases), shear wave propagation (speed) etc. Also for HIFU treatment, although a continuous wave can be used, in order to realize a high spatial resolution treatment, the inventor of the present patent has been developing new applicators using devices in a high frequency type or in a wideband type. As one of applications of a high intensity ultrasound, as mentioned above, tissues are stimulated by generating mechanical sources in measurement targets with no thermal effects, for which echo imaging transducer can also be used. In addition to the thermal treatments and generations of mechanical sources, echo imagings can also be performed simultaneously. This is also for using of other wave sources and transducers.

The digital signal processing unit 33 allows controlling the shear wave propagation direction by superposing plural shear waves generated by respective mechanical sources generated temporally or spatially, by which anisotropies of a visco-shear modulus or a shear wave propagation speed. Because shear waves generated almost simultaneously are superposed physically, after observing the shear waves via ultrasonic displacement measurement, the shear waves can be separated. When the shear waves are not superposed physically, after shear waves generated by respective mechanical sources are observed by analyzing and observing ultrasound signals, the results are superposed in order to calculate regarding the synthesized shear wave (superposed shear waves), the propagation direction, the propagation velocity, the visco-shear modulus in the propagation direction. Alternatively, ultrasounds obtained when the respective mechanical sources are generated are superposed, and the synthesized shear wave (superposed shear waves respectively generated by the respectively mechanical sources) is observed to calculate them similarly. These are also in cases where thermal waves generated by thermal sources are observed to calculate thermal properties. As mentioned below, other various processings are performed.

It is possible to realize a desired thermal source and a desired mechanical source by performing optimizations of transmission and reception apodizations or delays, and a radiation intensity that control the shapes of a thermal source or a mechanical source, and a sound pressure by detecting a transmission wave or a reflection wave. The wave shapes can also be observed with a high sensitivity using a hydrophone, or the shapes can also be estimated by calculating the autocorrelation functions of the signals detected by sensors etc.; on the basis of such processings, linear or nonlinear optimization is performed. The propagation directions of shear waves and thermal waves can also be optimized. In the respective cases, estimation results of mechanical properties and thermal properties are desired to be used.

For instance, when using a concave applicator, it is possible to focus at a focus position an ultrasound with a high intensity and thus, a wide bandwidth is yielded in a lateral direction. But, the sound pressure shape has feet growing from the focus position. Then, processings such as filtering, weighting etc. are performed on spectra calculated after receiving reflection or reflection waves to shaping the shape to be an ellipse (nonpatent document 7). The fact that the spectra of waves or beams propagating in the respective directions exist in the same directions in a frequency domain can be used. Consequently, an image quality as well as the accuracy of displacement measurement increases.

Such processing can also be perform to yield the same effects in cases where beams or waves with new properties that cannot be generated by generation of one wave or one beamforming on the basis of one transmission and one reception (for instance, cases where lateral modulation or increasing a lateral bandwidth is performed by superposing crossed waves or beams, multi-focusing is performed, etc.) are yielded by superposing plural reception signals respectively generated by performing plural transmissions, plural receptions or the both with at least a different wave or beamforming parameter, i.e., one of a transmission focus position when transmission focusing is performed, a plane wave, a cylindrical wave, a spherical wave etc. when transmission focusing is not performed, a steering angle (including zero degree with no steering), using or not of apodization, an F-number, a transmission ultrasound frequency or a transmission bandwidth, a reception frequency or a reception bandwidth, a pulse shape, a beam geometry etc. The superposition can also be performed in a real-time (at the same time with the transmissions and receptions), or regarding with the received signals at the measurement objects' same phase, however, at different times. The respective signals to be superposed can also be reception-beamformed ones, or the superposed raw signals can also be reception-beamformed.

The received signals obtained from the single wave or beam, or the superposed waves or beams can be weighted in a frequency domain to increase a bandwidth and perform superresolution (increasing a spatial resolution). Also the methods etc. described in the paragraph 0009, the observed waves are multiplied by the conjugate or reciprocal of a frequency response of beam properties as the inversion of beam properties. Alternatively, the conjugate of observed wave or the frequency response can also be implemented (These are detection processings, i.e., the former yields a square of envelope; the later yields autospectra or an autocorrelation function). The beamformed (SA), received signals can also be superresolution-processed, and received signals non-reception-beamformed or not beamformed at all (received signals for SA) can also be beamformed after performing superresolution processings.

Regarding displacement (vector) measurement, in order to increase the accuracies of displacement components, the frequency in the direction of displacement components can be increased. If increasing a spatial resolution is also required, increasing a bandwidth is also performed. For instance, by increasing the frequency via decreasing low spectra, the displacement measurement accuracy can be increased. The calculation amounts can also be decreased. High accuracy displacement measurement etc. can also be performed by generating over-determined systems via generating plural waves or beams physically or dividing spectra on the basis of signal processing. For performing imaging, envelop detection, square detection or absolute detection is implemented, and by superposing the detected waves or beams, speckles can be decreased and specular reflections can be enhanced.

Similarly, these processings can be performed in various fields using electromagnetic waves as well as using ultrasound or in the medical field. For instance, audible sounds can be observed using ultrasounds (Doppler effect), acoustic sounds or thermal waves can be observed using electromagnetic waves or lights, or earthquake waves can be observed using such waves. In conjunction, physical properties (distributions) related to the waves can also be observed.

For a transducer, there are contact and contactless types. Every time, impedance matching is properly performed with respect to each measurement object by putting an impedance matcher such as a gel or water etc. for an ultrasound between the measurement target and the transducer. Such an impedance matcher can also be installed into the transducer in advance (impedance layers for an ultrasound). Thus, impedances of waves are performed properly with respect to measurement targets. A power or a carrier frequency, a bandwidth (wide or narrow ones that determines the axial resolution etc.), a wave shape, a size of element (determining a lateral resolution), a directivity etc. designed on the basis of both the aperture element level and the array capability (detail omitted) are used. As an ultrasonic transducer, there is a combined type using layered PZTs and PVDFs, which is equipped with both a transmission acoustic power and a wideband When performing forcedly vibrating using a drive signal, by controlling the drive signal, the generated ultrasound frequency or bandwidth can be adjusted or the ultrasound can be encoded (On reception, a bandwidth is selected from signal with a bandwidth determined by the used transducer using an analogue or digital filter). Occasionally, aperture elements with different properties such as a frequency and a sensitivity etc. can be arrayed. Originally, the ultrasound transducer is a handy type and with a favorable usability. Recently, a non-cable type transducer can be used with a handy body of instrument. For a low frequency sound such as an audible sound, there as a speaker and a microphone. With a viewpoint similarly to the ultrasound, transducers for other waves can be realized and however, they are not limited to the case.

Alternatively, as a transducer 10, transmission transducers that generate arbitrary waves, and as a transducer 20, reception transducers (sensors) that receive arbitrary waves can be used. In the cases, the transmission transducers allows transmitting arbitrary waves to the measurement targets and the sensors allows receiving reflected or backscattered waves generated in the measurement targets, or transmitted, refracted or forwardly scattered waves etc. in the measurement targets.

For instance, when the arbitrary wave is a thermal wave, a sunlight or illumination, a metabolism etc. that is a thermal source not made intentionally, and alternatively, an infrared warmer or heater etc. that is rather stationary, or an ultrasound transducer that transmits an ultrasound for heating (that may also be used for generating a mechanical source in the measurement object) or an electromagnetic wave transducer, laser etc. can also be used, which are controlled according to drive signals. For receptions of thermal waves for generating reception signals, an infrared sensor, a pyroelectric sensor, detectors of a microwave or a terahertz wave, a temperature sensor such as an optical fiber, an ultrasound transducer (detection of a temperature change using the dependency of a sound speed and a volume change on a temperature), a magnetic resonance signal detector (detection of a temperature using a chemical shift of magnetic resonance frequency) etc. can be used. For the respective waves, transducers that properly performing the receptions can be used.

For an optical digital camera or a digital mammography, the Charge-Coupled Device (CCD) technology is used, and an integrated circuit (IC) and a sensor can be installed into one body. The same technology is also used in an ultrasound 2D array, and a real-time 3D imaging can be made possible. For detection of an X-ray, the combination of a scintillator and a photocoupler is used, and observation of the X-ray wave has been able to be made possible. When performing digital sampling of high frequency signals, it is effective to perform analogue detection or modulation as preprocessings, i.e., it is effective to store signals into a memory or storage device (storage media) via AD conversion after reception signals is made the low frequency signals. Otherwise, digital detection can also be performed. These can be installed into one body, a chip or a circuit board together with a transmitter or a receiver.

Otherwise, for instance, when radars exist at far positions etc., the respective apertures can be comprised of array elements, and there are also other cases. A wide directivity can also be obtained by performing mechanical scanning with various apertures. Apertures can exist spatially continuously or densely, or at far positions or sparsely, or with some regularity such as an equal interval, or with an irregularity under physical limitations. For instance, in sea or building, indoor etc., apertures to be used can be spatially fixed with respect to objects in which waves propagate (communication object) or positions to be observed. Otherwise, the respective apertures can also be used for transmissions and receptions, which can receive waves that are responses with respect to transmission from other apertures as well as the reception apertures themselves. In a medicine or biology, ultrasounds generated by radiating lasers to objects can be observed, referred to as photoacoustics (plural wave transducers can be installed into one body). The present invention allows performing photoacoustics that is realized by combining an ultrasound diagnosis instrument and OCT, for instance, for differentiating an artery and a vein, and measuring the respective blood flow velocity (The superresolutions can also be performed). Otherwise, by applying vibrations or ultrasounds to cancerously diseased parts after performing intravenous injection of magnetic substrates having an affinity for the cancerous diseases, generated electromagnetic waves can also be observed. It is possible to use electromagnetic waves to perform communications with various moving bodies.

Transducers (arrays) used for passive observations such as earthquakes (seismograph), brain waves (EEG, electroencephalograph), MEGs (magnetoencephalograph), biological neural networks (electrode array), electromagnetic waves (antenna), radars etc. are also various, and they can also be used for observing the wave sources. It is possible to estimate the directions of arriving waves on the basis of spectra analysis (one of past achievements of the present patent's inventor). Moreover, when information regarding propagation times cannot also be obtained (generally, positions of wave sources are calculated using times of observed waves at plural positions), particularly using the instruments of the present invention with plural transducers equipped with different positions or reception effective apertures, positions of wave sources etc. can be calculated geometrically. Even if the waves are not pulsed waves nor burst waves, continuous waves can also be used to observe such wave sources. Via any processings, at once the directions of arriving waves are known, the wave sources can be observed in detail by steering or focusing plural types of beams. In the processings, transmissions are steered and receptions are selectively performed in very probable directions, and the image, spatial resolution, contrast, signal intensity etc. are observed, or the directions of wave sources are specified via spectral analysis. Thus, the transducer used in the instrument of the present invention is used for steering, with which the mechanisms of electric scanning, mechanical scanning, or both scannings can be equipped with.

As the transducers that allows demonstrating the effectiveness of the present invention, typical transducers being rather familiar with or some special transducers are enumerated and, however, the transducers used or applied in the present patent are not limited to them and include various transducers that allow generating and receiving arbitrary waves such as electromagnetic waves, lights, mechanical vibrations, sound waves, or thermal waves.

<Beamformings>

At the same time, the same phase of the observation objects in which waves are propagated (communication object) or conditions being identical or almost identical, other time or other phase, plural beamformings, transmissions or receptions can be performed using each aperture. Similarly, plural beamformings, transmissions or receptions can be performed at a pair of apertures. Similarly, plural beamformings, transmissions or receptions can be performed at respective pairs of apertures. In cases including the cases where plural results of beamformings and receptions are obtained using such apertures, new data can also be generated via linear or nonlinear operations. The reception signals to be processed can be superposed ones originally or processed to be superposed.

For radars etc. carried by spatially moving bodies such as a satellite or an airborne, the arrays can have an array or not, and mechanical scannings can also be performed to obtain wide directivities. Transmissions and receptions of signals can also be performed at spatially continuously or densely, or at far positions or sparsely, or with some regularity such as an equal interval, or with an irregularity if necessary. The moving bodies are various and also include cars, ships, electric trains, submarines, moving robots etc. Others are circulation goods etc., living things etc., bodies moving regularly or randomly etc. In such cases, mobile communication instruments can be used. RFID (Radio Frequency Identification) tag or IC card etc. can also be used.

In such cases, reception beamformings can be performed with performing transmission beamformings in addition to classical SA (SA on the basis of transmission of each element). Mechanical scannings can also be performed in a regular fashion or irregularly with performing electric scannings to properly propagate waves in spatially large regions (communications) or properly observe large regions. Needless to say that using a multidimensional array allows properly propagating waves in spatially large regions (communications) or properly observing large regions (permitting multi-directional steering as well as increasing the size of physical aperture).

Apertures carried can also be used for both transmission and reception apertures, only transmission apertures, or only reception apertures that receive responses not with respect to the transmissions by the reception apertures themselves but with respect to the transmissions by other apertures. Plural moving bodies can be equipped with apertures. At the same time, the same phase of the observation objects in which waves are propagated (communication object) or conditions being identical or almost identical, other time or other phase, plural beamformings, transmissions or receptions can be performed using each aperture.

Similarly, plural beamformings, transmissions or receptions can be performed at a pair of apertures. Similarly, plural beamformings, transmissions or receptions can be performed at respective pairs of apertures. In cases including the cases where plural results of beamformings and receptions are obtained using such apertures, new data can also be generated via linear or nonlinear operations. In applications mentioned above, according to the objects in which waves are propagated (communication objects) or observation objects, combinations of the apertures of moving bodies and the fixed apertures can also be used.

Thus, in the present embodiment, using plural transmission aperture elements 10a and plural reception aperture elements 20a (respective elements can work as both the transmission aperture elements 10a and the reception aperture elements 20a), active beamformings are performed. In the active beamformings, arbitrary beamformings can be performed via digital processing including FFT with high speeds and with no approximate interpolations. In practical, arbitrary focusings and arbitrary steerings can be performed using transducer array devices with arbitrary aperture geometries.

Since the directions of the faces of respective aperture elements are made much account of, generally orthogonal coordinate systems determined by the geometries of physical aperture element arrays (virtual sources are explained separately) are used. The features of the present invention are to generate signals expressing waves directly on the coordinate systems used for displaying the signals mainly via performing reception digital beamformings with no approximate interpolations; and also to perform the reception beamformings on the coordinate systems used for performing transmission beamformings derivatively. Virtual sources or virtual receptors etc. can also be used, and the beamformings can be performed similarly to using the physical aperture element arrays.

<Transmission Unit>

Next, the transmission unit 31 (FIG. 2) equipped with the bogy of instrument 30 is explained. The transmission unit 31 includes the transmitters 31a with plural transmission channels. The transmission channel number is the number of communication lines that are used for performing one beamforming, to send different drive signals to the respective aperture elements. For instance, as mentioned below, the formations of transmission channels are various. The generated waves on the respective transmission aperture elements 10a have frequencies, bandwidths, wave shapes, and directivities that are determined by the transmission aperture elements 10a and the transmission unit 31.

Applying impulse signals to the transmission aperture elements 10a generates waves determined by the geometries of the transmission aperture elements 10a (thickness or aperture size and shape) and materials (a single crystal is representative type of ultrasound element), and additionally using drive signals with frequencies, bandwidths and wave shapes (including an encoded case), generated at the transmission unit 31, can also be used for performing forcedly vibrating the transmission aperture elements 10a to control the frequencies, bandwidths, wave shapes and directivities of the waves to be generated. The properties of drive signals to be generated are set as parameters under the control by the control unit 34. Desired parameters can also be set automatically via the control unit 34's distinguishing the transducers set on, and the parameter settings or adjustings can also be performed using the input device 40.

Generally, in order to perform one beamforming every time, plural aperture elements are excited using drive signals with different delays. That is, the transmission unit 31 is equipped with analogue or digital delay patterns, and for instance, delay patterns that realize transmission focusings or steering directions etc. can be used according to the operator's selection using the input device 40. The patterns can be programmable and according to the purposes, the pattern to be used or selective can also be installed via various media such as CD-ROMs, floppy disks, or MOs etc. After running programs, using the input device 40, the patterns can also be selected interactively, and the delays (patterns) can also be directly input. Otherwise, there various cases including the case where the patterns are set by reading out files in which data are recorded etc. Particularly, when the delays to be used are analogue, the delays can also be changed in an analogue or digital manner, the delay circuit or the delay patterns themselves are exchanged by others or switched to others.

In the body of instrument 30 (FIG. 2), the command signals are sent to the transmitters 31a with plural channels from the control unit 34 to generate drive signals (including an encoded case) for exciting the corresponding transmission aperture elements 10a. Such command signals can be generated on the basis of the command signals for starting the beamformings for generating one frame. When the transmission delays are digital, for instance, digital delays can be implemented on the respective command signals sent to the plural transmitters 31a using, as the trigger signal, the command signal for the transmission aperture element to be excited first. For implementing the digital delays, digital devices to be used in a digital circuit can also be used.

Otherwise, after a drive signal generated in the transmitter 31a for exciting an element first is implemented with analogue delays for exciting the respective aperture elements, drive signals are sent to the respective aperture elements. When such analogue delays are used, synchronizations required for using digital circuits are not required, and at least a transmitter 31a can be used to excite transmission aperture elements 10a. Thus, transmission analogue delays can be set at several timings, i.e., in front of, behind or in the transmitters 31a, or in the control unit 34, whereas transmission digital delays can be set at in front of or in the transmitters 31a, or in the control unit 34.

The delay patterns can also be selected by switching analogue circuits or analogue devices and digital circuits or digital devices, and the delays set on the delay devices can be changed under the controls by the control unit 34 or programmable via installing or setting using inputting etc. Delay devices can also be set in the control unit 34. Moreover, when the control unit 34 is made using a calculator etc. as mentioned below, the control unit 34 can directly output command signals that are delayed under software controls.

The control unit 34 or digital delay can be realized using devices, calculators, PLD (Programmable Logic Device), FPGA (Field-Programmable Gate Array), DSP (Digital Signal Processor), GPU (Graphical Processing Unit), microprocessor etc. with general calculation capabilities, or an exclusive digital circuit and an exclusive device. The devices are desired to exhibit high performance (multi-cores etc.), and also devices used for analogue devices, AD convertors 32b, memories 32c and/or digital signal processing unit 33 performing transmission or reception beamforming processings.

Important are the number of communication channels between devices, channel capacities, wirings, wideband wireless communications. In particular, in the present invention, it is desirable that such functional devices are installed into a chip or a circuit board (the devices may be detachable), or the devices are directly implemented into a chip or a circuit board (including a multilayer type). Parallel processings are also important. When the calculator also plays a role of the controller unit 34, if the device is not detachable, a remarkably higher security can be achieved than that obtained under a general programmed control. In a contrary, under the existing legislation, cases where disclosing of processing contents is demanded will increase.

The control software or delays can also be directly encoded, input or installed. The ways how to implementing digital delays are not limited to these. When implementing digital delays for transmission delays, being different from implementing analogue delays, errors determined by the clock frequency for generating the digital control signals occurs; thus in the viewpoints of an accuracy, the analogue delay had better be implemented for the transmission delays. Basically, the errors can be reduced by using a high clock frequency with a high cost. Alternatively, the analogue delays can also be changed in an analogue manner, the delay can also be programmable and the digital control can be made possible. However, the analogue processing has a lower degree of freedom than the digital delay processing, and if the cost is required to decrease, the delay pattern realized using an analogue circuit can also be switched.

Transmission apodizations are performed using energies of drive signals provided to the respective aperture elements, or temporal changes of magnitudes, i.e., temporal changes in wave shapes (including an encoded case). On the basis of calibration data regarding the aperture elements' conversion efficiencies from the drive signals to waves, the drive signals are controlled. For other purposes such as calibrations, adjustments of the drive signals can also be performed. The command signals from the control unit 34 to the transmitters 31a can be signals that express, as temporal series, the information of wave shapes or phases of drive signals to be generated by the transmitters 31a, encoded signals which the transmitters 31a recognize to generate pre-determined drive signals, or only signals that convey commands to the transmitter 31 that generate pre-determined drive signals with respect to the respective aperture elements existing in an effective aperture.

Similarly to the delay setting, the transmitters 31a can be programmable such that pre-determined drive signals are generated with respect to the respective aperture elements in an effective aperture, and various formations can be generated. To generate drive signals, an electric power supplier or an amplifier can be used; electric power suppliers that can provide different electric powers or energies, or amplifiers with different amplification degrees can be switched or simultaneously used to generate a drive signal. Similarly to the transmission delay patterns, as mentioned above, the transmission apodizations are directly set or programmable. The delays and apodizations can be implemented in the transmission unit, which are realized at the same hierarchy level or at different hierarchy levels, and in the same or different formations.

The transmission channels used for driving aperture elements in an transmission effective aperture are switched using switching devices such as a shift-register, a multiplexer etc., beamformings can be performed using other positioned effective apertures to scan the ROI. The delays of delay elements can also be changeable, the delay pattern (delay elements) can also be switched. Moreover, steering in plural directions can also be performed using an effective aperture, and occasionally the aperture position or the effective aperture width can also be changed. Moreover, steering directions can also be changed.

When switching high voltage signals, exclusive switching devices can be used. Apodizations set on apodization elements can be changeable in a temporal transmission direction or an array direction of aperture elements, or apodization patterns (apodization elements) can be switched on. Being dependent on the aperture position, range direction, or steering direction, the beam geometry can be controlled. Specifically, an apodization (value), zero, means the corresponding transmission element is not active and off. Thus, the apodization can also work as a switch of effective element, and can also determine the effective aperture width (when apodization function in the aperture element array direction is a rectangular window, the switches of the effective elements are on; and when the apodization function is not constant, the switches are weighted on).

Regarding the delay pattern or apodization pattern, the body of instrument 30 can be equipped with plural patterns, or can be programmable. Then, on the basis of the responses from the object or the results of beamformings performed by the reception unit 32 explained next, the digital signal processing unit 33 (FIG. 2), explained later, in the body of instrument 30 calculates waves' attenuations, scatterings (forward or back scatterings etc.), transmissions, reflections, refractions or sound's frequency variances or spatial distributions etc., optimizations regarding the delays or intensities of waves transmitted from the respective apertures, steering directions of beams or wave-fronts, apodization patterns etc. can be performed.

For classical SA, there are monostatic and multistatic types performed using transmissions from respective aperture elements (i.e., each 1 element), the active transmission aperture elements 10a are switched or switched using apodizations as mentioned above. There is a case where all the transmission elements are equipped with transmission channels including transmitters 31a. For SAs, it is required to generate waves with sufficient intensities or energies, and the transmission apodization functions are not always important themselves. In practical, generally, SAs are performed simultaneously with reception apodizations using the phasing and summation device. In the present invention, the digital signal processing unit 33 often performs SAs together with the reception apodization. Representative transmission units used in the present embodiment are above-explained, all allowing transmission beamforming can be arbitrarily used and they are not limited to the units above-explained.

<Reception Unit and Digital Signal Processing Unit>

Explained next is about the reception unit 32 and the digital signal processing unit 33 (FIG. 2) equipped with the body of instrument 30. The reception unit 32 includes the receivers 32a with plural channels, AD convertors 32b, and memories (or storage devices, storage media) 32c. The frequencies, bandwidths, wave shapes, directivities of the received signals generated by the respective reception elements are determined by the reception aperture elements 20a and reception unit 32. Arriving of waves to the reception aperture elements 20a generates the reception signals determined by the geometries of the reception aperture elements 20a (thickness or aperture size and shape) and materials (a single crystal is representative type of ultrasound element), and additionally performing filtering processings (analogue amplifiers can also work as the filters), the frequencies, bandwidths, wave shapes and directivities of the received signals to be generated are controlled. The properties of received signals to be generated are set on the basis of filter parameters (frequency properties such as a frequency, a bandwidth) under the control by the control unit 34. Desired parameters can also be set automatically via the control unit 34's distinguishing the transducers set on, and the parameter settings or adjustings can also be performed using the input device 40.

The general digital reception unit or digital reception device are equipped with the phasing and summing function in addition to like these functions. That is, the DAS processings performed in the digital reception unit or digital reception device perform phasing processings on plural reception signals and also sum the plural phased reception signals. As the phasing processings, the respective reception channels for plural reception apertures implement the AD conversions on the received signals and store the digitized signals in memories, storage devices or storage media etc. that can be written and read out in high speeds basically. In order to perform the phasings at the respective positions of interest in an ROI, reception delays can be implemented on the received signals read out from the storages with high speeds with approximate interpolations in a spatial domain. Otherwise, the reception delays can also be implemented on the received signals read out from the storages, with high accuracies on the basis of the Nyquist theorem, by performing the phase rotations with multiplications of complex exponential functions (the present inventor's past invention), however, it takes much time to complete the processings. The respective signals received by reception apertures can be stored in the positions (addresses) in storages according to the reception delays, and the received signals can be read out and summed, or summed after performing the above-mentioned processings as well.

Figure 4:
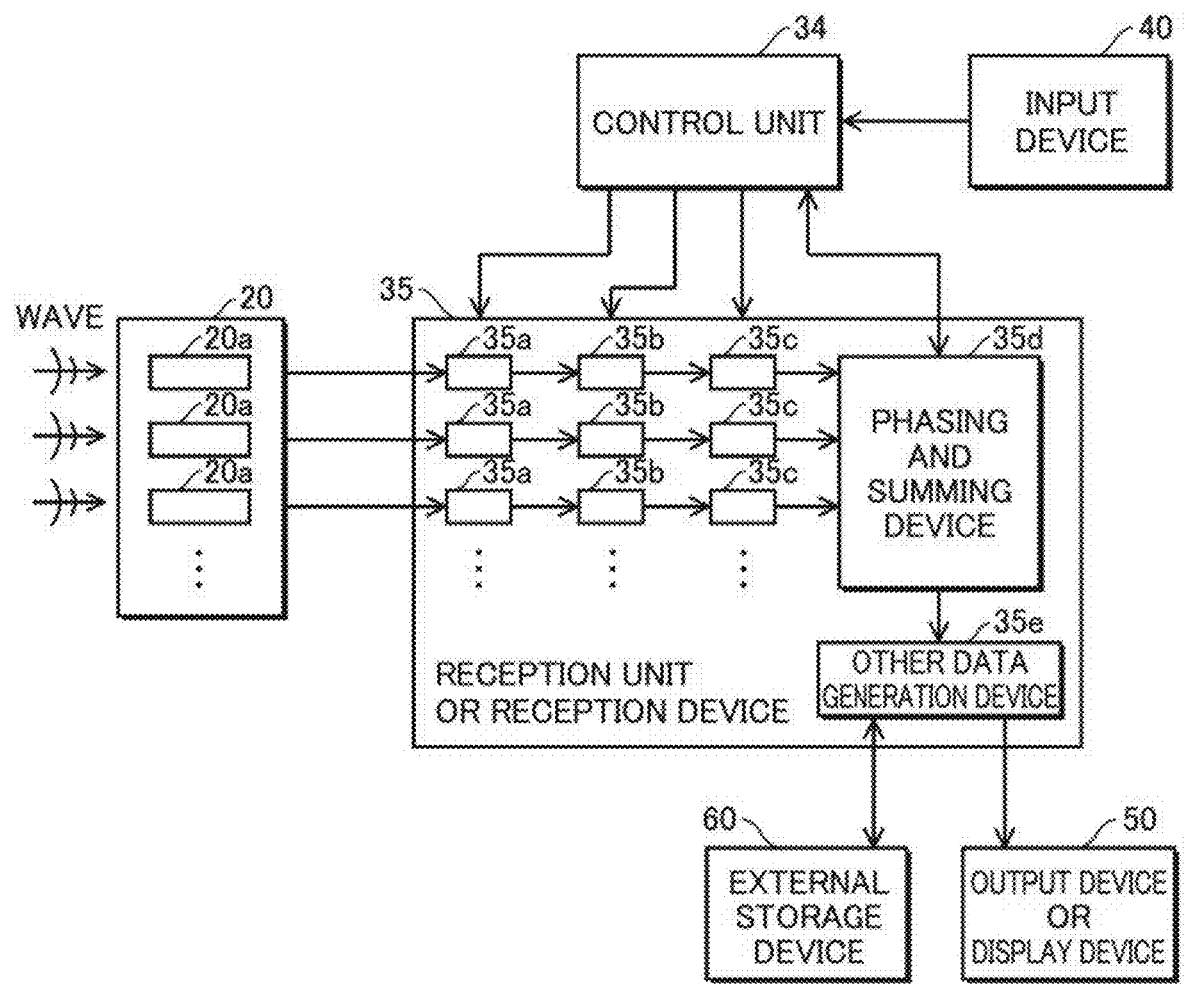
FIG. 4 shows illustrations of compositions of a reception unit including a phasing and summing device, and the peripheral devices.

FIG. 4 shows illustrations of compositions of the reception unit or reception device including the phasing and summing device that realizes the phasing and summing processings, and the peripheral devices. FIG. 4 shows the reception unit (or the reception device) 35 which is equipped with the phasing and summing device 35$d$ that performs the phasing and summing processings, and other data generation device 35$e$ that implements the digital signal processings on generated image signals, in addition to the receivers 35$a$ with plural reception channels, AD convertors 35$b$ and memories (or storage devices or storage media) 35$c$. For instance, "other data generation device 35$e$" generates image display data, and via high order calculations, for instance, "other data generation device 35$e$" performs the measurements of displacements on the basis of the Doppler method or temperatures, and performs analyses about the object.

By performing the phasing and summing processings at the respective positions in an ROI, the dynamic focusing is performed. Originally, the dynamic focusing is a term that is used for the range direction with respect to the reception by an effective aperture. In practical, however, the reception digital beamformings performed by the present invention are not limited to this. The reception unit 32 used in the embodiment of the present invention shown in FIG. 2 allows performing high accuracy digital beamformings with high speeds and with no approximate processings, calculation processes of which DAS processings are different from the above-mentioned calculation processes which the term expresses. Thus, in the embodiment of the present invention, the digital signal processing unit 33 shown in FIG. 2 is used instead of the phasing and summing device 35$d$ shown in FIG. 4. In the digital signal processing unit 33, the above-mentioned various other data can be generated on the basis of the image signals.

The general phasing and summing device can also be realized in the digital signal processing unit 33 used in the embodiment of the present invention. Particularly, the features of the reception unit 32 are that in order to realize high speed and high accuracy processings, preserving the signal intensities or reducing the noises is performed using analogue devices such as analogue amplifiers or attenuators, for signal level controls, of the received signals generated by the reception aperture elements 20$a$ or analogue filters (programmable and works under frequency properties and parameters set via the control unit 34) etc. In addition, by considering an advantage that analogue signal processings are faster than digital signal processings, effective uses of devices for linear or particularly, nonlinear single processings, if required, are also features. The analogue signals obtained through such processings are digitized (AD-converted) and the generated digital signals are stored into memories (or memory devices, memory media) 32$c$ that can be written or read out with high speeds.

The digital signal processing unit 33 equipped with can be realized using devices, calculators, PLD (Programmable Logic Device), FPGA (Field-Programmable Gate Array), DSP (Digital Signal Processor), GPU (Graphical Processing Unit), microprocessor etc. with general calculation capabilities, or an exclusive calculator, an exclusive digital circuit and an exclusive device, and the digital wave signal processings of the present invention are performed on the stored digital signals.

The devices are desired to exhibit high performances, and also devices used for analogue devices, AD convertors 32$b$, memories (or stored devices, stored media) 32$c$, and digital signal processing unit 33 (multi-cores etc.). Also important are the number of communication channels between devices, channel capacities, wirings, wideband wireless communications. In particular, in the present invention, it is desirable that such functional devices are installed into a chip or a circuit board (the devices may be detachable), or the devices are directly implemented into a chip or a circuit board (including a multilayer type). Parallel processings are also important.

When the calculator also plays a role of the controller unit 34, if the device is not detachable, a remarkably higher security can be achieved than that obtained under a general programmed control. In a contrary, under the existing legislation, cases where disclosing of processing contents is demanded will increase. The digital signal processing unit 33 can also work as the control unit 34 that controls other units by sending command signals.

In the reception unit 32 used in the present invention, the trigger signals for making the AD convertors 32$b$ to start the samplings of the received signals generated by the reception transducer (or the reception sensor) 20 (i.e., command signals for starting the AD conversions and storings of the digital signals into memories, stored devices or stored media 32$c$) are the same as those used for a general reception unit. For instance, ones of the command signals, generated by the control unit 34, for making the transmitters 31 to generate transmission signals to the transmission aperture elements 10$a$ to be excited, can be used. When performing receiving waves suing plural reception aperture elements 20$a$ in an effective aperture, the command signal to be sent to the transmission element to be excited first, last or other elements can be used, and occasionally the predetermined digital delays can be implemented on the trigger signals for staring the AD conversions.

The command signals can be generated on the basis of a command signal used for starting beamformings for a frame. In other words, the generations of the transmission trigger signals are counted, and if the hardware or control program confirms that the counted number reaches to the predetermined number, or the number, to be a programmable parameter, set by inputting using the input device 40 etc., a command signal is generated to start beamformings for the next frame. Similarly to other parameters, the number can be installed via various media such as CD-ROMs, floppy disks, MOs etc. After running programs, using the input device 40, the number can also be selected interactively, and numeric data can also be directly input. Otherwise, there various cases including the case where the number is set by reading out files in which data are recorded etc. The number can also be set using dipswitches etc. Not so many reception delay patterns are not required, analogue delay patterns can also be implemented on the received signals, after which AD conversions can be performed on the delayed, received signals.

In order to perform the reception dynamic focusing with high speeds, performing not the present patent's inventor's past invention that multiplications of complex exponential functions are performed on signals in a frequency domain on the basis of the Nyquist theorem but general high speed implementations of reception delays leads to errors determined by the sampling interval of an AD convertor. Thus, the AD converter's (32b's) sampling frequency is made high with a high cost, or the low speed beamforming must be performed by implementing the high accuracy digital delays on signals (phase rotation processing). In contrast, the present invention allows that the received signals are digital-sampled with synchronizations as mentioned above, such types of approximate errors do not occur. Moreover, high speed reception digital beamformings can be performed. The reception digital beamformings are remarkably faster than the present patent's inventor's past invention that performs the multiplications of the complex exponential functions in a frequency domain.

In the present patent, and also generally, the reception channel number is the number of communication lines that are used for performing one beamforming, to send waves (signals) received by the respective reception aperture elements 20a to the reception unit 32. Thus, the reception unit 32 can be explained as below. The formations of reception channels are various. Generally, in order to perform one beamforming every time, received signals generated by plural reception aperture elements 20a are applied with different delays. That is, the reception unit 32 is equipped with analogue or digital delay patterns as mentioned above, and the delay patterns that realize reception focusings or steering directions etc. can be used according to the operator's selection using the input device 40.

The patterns can be programmable and according to the purposes, the pattern to be used or selective can also be installed via various media such as CD-ROMs, floppy disks, or MOs etc. After running programs, using the input device 40, the patterns can also be selected interactively, and the delays (patterns) can also be directly input. Otherwise, there various cases including the case where the patterns are set by reading out files in which data are recorded etc. Particularly, when the delays to be used are analogue, the delays can also be changed in an analogue or digital manner, the delay circuit or the delay patterns themselves are exchanged by others or switched to others.

When the reception delay is digital, the received signals stored in the memories (or storage devices, storage media) 32c are read out to perform the phasing and summing the signals. In the instrument of the embodiment, the digital signal processing unit can implement the reception delays on the digital received signals, the digital received signals can be passed into the delay devices of digital circuit, or the control signals for starting the acquisitions of received signals generated by the control unit 34 (i.e., signals for switching on AD convertors 32b and memories, storage devices, or storage media 32c) can be delayed. Thus, the digital delays can be implemented at arbitrary positions including the AD convertors 32b and the post-devices, or the control unit 34.

Also the analogue delays can also be implemented on the received signals at arbitrary positions following the generating of the received signals at the reception aperture elements 20a, or at the control unit 34. When using the analogue delay patterns, plural aperture elements' generated received signals can be received at least by one receiver 32a. Thus, in the storages of the received signals, the respective received signals of reception apertures can be stored at positions (addresses) according to the reception delays, or when the received signals cannot be delayed at all, the stored received signals are read out and the digital wave signal processings mentioned later can be performed by the digital signal processing unit 33 (the digital signal processing unit 33 can also perform general phasing and summing processings).

The delay patterns can also be selected by switching analogue circuits or analogue devices and digital circuits or digital devices, and the delays set on the delay devices can be changed under the controls by the control unit 34 or programmable via installing or setting using inputting etc. Delay devices can also be set in the control unit 34. Moreover, when the control unit 34 is made using a calculator etc. as mentioned above, the control unit 34 can directly output command signals that are delayed under software controls.

The control unit 34 or digital delay can be realized using devices, calculators, PLD (Programmable Logic Device), FPGA (Field-Programmable Gate Array), DSP (Digital Signal Processor), GPU (Graphical Processing Unit), microprocessor etc. with general calculation capabilities, or an exclusive digital circuit and an exclusive device. The devices are desired to exhibit high performance (multi-cores etc.), and also devices used for analogue devices, AD convertors 32b, memories 32c and/or digital signal processing unit 33 performing transmission or reception beamforming processings.

Important are the number of communication channels between devices, channel capacities, wirings, wideband wireless communications. In particular, in the present invention, it is desirable that such functional devices are installed into a chip or a circuit board (the devices may be detachable), or the devices are directly implemented into a chip or a circuit board (including a multilayer type). Parallel processings are also important. When the calculator also plays a role of the controller unit 34, if the device is not detachable, a remarkably higher security can be achieved than that obtained under a general programmed control. In a contrary, under the existing legislation, cases where disclosing of processing contents is demanded will increase. The control software or delays can also be directly encoded, input or installed. The ways how to implementing digital delays are not limited to these.

In the present embodiment, on the basis of the above-mentioned trigger signals sent form the control unit 34 (FIG. 2) in the body of instrument 30, the respective trigger signals that are commands for staring the AD conversions are provided to the AD convertors 32b of the respective channels. According to the command signals, the AD conversions of analogue signals of respective channels and the storings of the digitized signals into the memories, storage devices or storage media 32c are started. Till one frame of received signals are stored, with changing the transmission aperture position, the transmission effective aperture width, or the transmission steering directions etc. and every the transmissions of waves or beams, with changing the reception aperture position, the reception effective aperture width or the reception steering directions, the transmission unit 31, the reception unit 32 and the digital signal processing unit 33 iteratively perform the processings from the transmission to the storing under the controls by the control unit 34. Moreover, every one frame of received signals is stored, coherent signals are generated by performing the digital wave signal processing method (digital beamforming method) of the present invention on the received signals.

Thus, if the instrument of the present invention is equipped with the above-mentioned analogue or digital delays, the delays are not always used directly for the DAS beamformings, the delays can also be used for implementing the delays on the timing for starting AD conversions of the received signals and storings the signals into memories (or storage devices, storage media) 32c to save and effectively use the memories, storage devices or storage media, and shorten the access times. The implementation of reception delays used for the beamformings are mainly the digital wave signal processings performed in the digital signal processing unit 33 absolutely and then, the saving and shortening the access time are very meaningful. When performing the classical SA that does not perform the physical beamformings at the transmissions (for instance, physical processings such as using calculators, exclusive devices etc. that are different form the software beamformings such as using calculators, exclusive devices etc.: the transmission or reception focusings or steerings, or the apodizations etc.), the transmission delays are implemented at the same timing as that for implementing the reception delays by the digital wave signal processings.

Thus, the reception unit 32 is absolutely equipped with independent devices with respect to the respective reception channels, i.e., analogue or digital delays, the receivers 32a, the AD convertors 32b and memories (or the storage devices, storage media) 32c. If required, level controls using analogue amplifiers or attenuators, filters and other analogue operational devices are equipped with. That is, in the present invention's instrument, when the delays are implemented by using the reception delays, if delays for the beamformings are not implemented, errors dependent on a clock frequency do not occur similarly to the implementation of analogue delays.

That is, since the transmission digital delays causes the errors determined by the clock frequency absolutely, it is required to use an expensive, high clock frequency for decreasing the errors. However, it is not required for implementing the reception digital delays. By implementing the digital delays for the reception delays, no decreasing the accuracy and a high degree of freedom about the settings of delay patterns can be obtained, and by further using the analogue delays for the transmission delays, a high accuracy can be obtained as well as the required clock can be made low. The analogue delays can also be possible for changing the delays in an analogue fashion, and can also be made programmable and digital controllable. However, the analogue delays have a lower degree of freedom than the digital delays, and for decreasing the cost, the delay patterns implemented by an analogue circuit can be switched and used, or exchangeable with proper ones. If a high degree of freedom is required for the transmission delay patterns, the digital delays must work with a high clock frequency.

As mentioned below, the coherent signals generated by the present invention's beamformings are referred to as "image signals." The reception effective aperture elements or their positions are controlled similarly to the transmission effective aperture elements (mentioned later). The digital beamformings are not always performed every one frame reception signals are stored. For instance, every the received signals with the number of hardware's channels or a programmable parameter determined or set by the effective aperture width, other numbers predetermined or input by the input devices 40 etc. are stored, the digital beamformings can also be performed (there exists various means of input as mentioned above). Also image signals partially beamformed can also be synthesized, to generate one frame image signals.

In the cases, the received signals to be processed at adjacent positions can also be overlapped, and for the synthesizing the received signals, simple superpositions can also be performed (spectra superposed in a frequency domain can also be Inverse Fourier's transformed), properly weighted superposition can also be performed, or simple connections can also be performed. The number of stored reception signals can also be confirmed by counting the trigger signals for storing reception signals (command signals sent from the control unit 34) in a hardware or a control program, and as mentioned above the command signal, generated by the control unit 34 every one frame, for starting the digital wave signal processings for the one frame can also be confirmed similarly, and then the one frame image signals are properly generated.

The highest frame rate realizable depends on the beamforming formation to be implemented, and basically determined by the wave propagation speed. In practical applications, it is determined by the time required for performing the digital calculations of one frame image signals. Thus, it is useful that the above-mentioned partial generations of image signals are performed in a parallel fashion. As mentioned above, it is also useful to perform the multidirectional synthetic aperture (SA) that the inventor of present invention previously developed, to generate reception beams at plural positions or in plural directions with respect to one transmission beam or to perform multi-focusings. In order to perform such beamformings with high speeds, parallel processings are useful. For all the beamformings, on the basis of the transmissions and receptions mentioned above, after storing the received signals for one frame beamforming or partially, the present invention's digital wave signal processings below-mentioned in detail can be performed. When the image signals cannot be generated in a real-time, the frame rate can also be decreased, or off-line processings can also be performed.

The reception apodizations performs the weighting on the received signals on the respective reception channels of aperture elements, and can be changeable in a range direction. Although it is not impossible to be changeable in an analogue fashion, it is simple to be changeable in a digital fashion. For almost general reception units, the apodizations are changeable at respective positions or respective range positions etc. at the timings of the phasing and summing, whereas in the instrument of the present invention the apodizations can be performed in the digital signal processing unit 33. Alternatively, it is rare that nonchangeable apodizations are performed, in which the apodizations are performed at the timings of level controls of received signals, generated by aperture elements, by analogue amplifications or attenuations.

Being different from apodizations, on the basis of calibration data about conversion efficiencies of drive signals to waves, at least the calibrations of signal levels can be performed, and also the apodizations can be simultaneously performed together with the level calibrations. The processings can also be objects, the dynamic ranges of wave shapes of received analogue signals can also be nonlinearly extended or compressed, and other analogue devices such as nonlinear elements etc. can also be used in respective reception channels. Including the amplifiers etc., the analogue devices to be used can be programmable, and the setting methods can be various formations. Similarly to other parameters, they can be directly set using the various types of input devices. Generally, the delays and apodizations can be implemented in the reception unit 32, which are realized at the same hierarchy level or at different hierarchy levels, and in the same or different formations, and then the phasing and summing devices can be used. In the digital signal processing unit 33 of the present invention, they can be carried out with a high degree of freedom.

The reception channels used for driving aperture elements in a reception effective aperture are switched using switching devices such as a shift-register, a multiplexer etc., beamformings can be performed using other positioned effective apertures to scan the ROI. The delays of delay elements can also be changeable, the delay pattern (delay elements) can also be switched. Moreover, steering in plural directions can also be performed using an effective aperture, and occasionally the aperture position or the effective aperture width can also be changed. Moreover, steering directions can also be changed. Simple memories, storage devices, or storage media can be saved, and the access time can also be shorten. It is effective that the data to be frequently used are stored into small size memories that are simply written and read out.

In the present invention, the saving and shortening the access time are meaningful. The apodization patterns comprised of apodization elements can also be switched. Depending on the aperture position, the range direction and the steering direction, the beam shape can also be controlled. Specifically, an apodization (value), zero, means the corresponding reception element is not active and off. Thus, the apodization can also work as a switch of effective element, and can also determine the effective aperture width (when apodization function in the aperture element array direction is a rectangular window, the switches of the effective elements are on; and when the apodization function is not constant, the switches are weighted on). Thus, the apodization elements are the same levels as those of switches.

When the delays or apodization patterns are equipped with plural patterns or programmable, the digital signal processing unit 33 in the body of instrument 30 calculates for waves propagating in media, on the basis of the responses from the transmission objects or the results of beamformings, the attenuations, scatterings (forward scattering or backscattering), transmissions, reflections, refractions or acoustic sound's frequency variances or the spatial distributions etc., and the delays or intensities of waves transmitted from or received by respective apertures, steering directions of beams or waves, or apodization patterns etc. can also be optimized.

In the classical synthetic aperture (SA), all the reception elements can be equipped with the reception channels including the receivers 32a. Generally, SA can be performed, in the phasing and summing device, together with the reception apodizations, and in the present invention, SA can be implemented, in the digital signal processing unit 33, together with the reception apodizations.

The parameters used in the transmission unit 31 or reception unit 32 mentioned above can effective by installing the parameters into respective functional devices in the units via various media such as CD-ROMs, DVDs, floppy disks, or MOs etc., i.e., an ultrasound frequency, a bandwidth, a code, a delay pattern, an apodization pattern, an analogue device used for the signal processing, an effective aperture, a focus position, a steering angle, and times to perform the transmissions and receptions required.

After running programs, using the input device 40, the number can also be selected interactively, and numeric data can also be directly input. Otherwise, there various cases including the case where the number is set by reading out files in which data are recorded etc. The number can also be set using dipswitches etc. The units can also be exchanged or switched. By selecting the measurement objects, or setting the transducers on the instrument, the instrument can recognize them and can automatically operate under the desired parameters. It is possible to post-control the parameters. In addition, by installing the functional devices of a general reception unit, the comparison between the image signals obtained using the present invention's instrument and those obtained using the general phasings and summings, particularly including approximate interpolations, can be performed.

<Input Devices>

The input devices 40 are used, for instance, for setting various types of parameters as mentioned above. The input devices are various devices such as a keyboard, a mouse, buttons, panel switches, a touch command screen, a footswitch or a tacking ball etc., and not limited to these. Using storage media such as general memories, USB memories, hard disks, flexible disks, CD-ROMs, DVD-ROMs, floppy disks or MOs etc., the operation system (OS) or the device software can be installed or versioned up, various types of parameters can be set up or updated. The input devices 40 are equipped with various types of devices that can read out data from the storage media, or the input devices 40 are equipped with interfaces such that various type devices are installed to be used, if required.

The input device 40 can be used for setting the parameters of various types of operational modes related to the present embodiment as well as controlling and switching of the operational modes. When the operator is a human, the input device 40 is a so-called man-machine interface, and however the input device 40 is not always controlled by a human. The same inputting operation can also be achieved by receiving the parameters, data, or control signals from other devices via various types of communication standards and connectors, or by using wire or wireless communication (at least communication devices equipped with reception functions) and not limited to the above-mentioned examples. Exclusive or general networks can be used.

The input data are stored into the internal or external memories with respect to the instrument, stored devices, or stored media, and the functional devices equipped in the instrument operate with referring to the stored data. Otherwise, when the functional devices in the instrument are equipped with the exclusive memories, the data are written into the memories or updated to determine the operational setting in a software fashion, or set or updated in a hardware fashion. Operation of the calculation function considers the resource of the instrument occasionally on the basis of the input data, and the optimized setting parameters can be calculated to be used. The operation modes can also be set by commands. Additional information about the waves of measurement objects (kinds, features and properties of waves, intensities, frequencies, bandwidths or codes etc.) or objects or media in which waves propagate (propagation velocities, physical properties related to waves, attenuations, forward scatterings, backward scatterings, transmissions, reflections, refractions etc. or their frequency variances etc.) are given, the instrument can also perform analogue or digital processings properly.

<Output Devices>

As a representative output device 50 is a display device, which can display the generated image signals, and others such as various results measured on the basis of the image signals as numeric data or images etc. The image signals can be converted to display images, or dynamic images or static images in formats (scan converted) and graphic-accelerators can be also used. The images are displayed in a gray (brightness) or color scale, and the means of the brightness or color can be displayed with a scale or a logo. Otherwise, the results can also be displayed using a bird'-eye view, graphs, and not limited to these.

When the results are displayed, the respective operation modes and various types of parameters or patterns (patterns' names) can also be displayed simultaneously using logos and characters. Also complementary information or various types of data about the measurement objects input by operators or other instruments can be displayed. The display instrument can also be used for displaying the GUI (Graphical User Interface) to be used for setting the respective parameters or patterns using the input instrument 40, or by using an attach command screen, drawn images of arbitrary positions or of arbitrary areas specified can be extended to be displayed largely, and can be used to display the respective numeric data for partially working as an input device 40.

As the display devices, various ones such as a CRT, a liquid crystal or an LED can be used. Exclusive 3D display devices etc. can also be used etc., and not limited to these. The output data are not always interpreted or read directly, and the body of instrument (calculator) interprets, on the basis of the predetermined calibration data or calculations, the output data and displays the results (for instance, the measurement objects' compositions and structures are understood form the spectral analysis of received signals etc.). The output data can also be output on other instruments, of which output data can also be interpreted. Moreover, the same instruments (for instance, robots etc.) or other instruments can put the output data to practical use.

One instrument can receive plural waves and can generate image signals, and further the data mining or unification (fusion) etc. can also be performed. Other instruments can also be used to perform processings of the kind. The properties or features of generated image signals (intensities, frequencies, bandwidths, or codes etc.) can also be analyzed. Thus, the data acquired by the instruments related to the present embodiment can also be used in other instruments, and in practical the communication instruments with a transmission function at least can also be used as one of the output devices 50. Exclusive or general networks can also be used.

<Storage Devices>

The generated image signals or the various results (numeric data or images etc.) measured on the basis of image signals are stored into internal or external memories with respect to the instruments, storage instruments or storage media that can become the out devices 50. Here, these are distinguished with the display devices, and referred to as "storage devices." In FIG. 2 etc., the external storage device 60 is also shown. When storing the image signals, the operation modes or parameters set, complementary information or various types of data about the measurement objects input by operators or other instruments can be stored together with the image signals. As the storage devices, general or special memories, USB memories, hard disks, flexible disks, CD-R (W), DVD-R (W), a video recorder, or image data storage devices etc. can be used, and not limited to these. The storage devices are properly used according to the applications, data amount to be stored or times required for writing in or reading out etc.

Past stored image signals or other data are read out from the storage devices and replayed. The storage devices are important in that an OS or a device software, or parameters set are stored mainly. The respective functional devices can also be equipped with exclusive storage devices. Detachable storage devices can also be used in other instruments.

The body of instrument 30 reads out image signals stored in the storage devices and implements the high order digital signal processings. Resynthesized image signals (frequency modulations, increasing bandwidths or multi-focusings etc. performed by linear or nonlinear processings) can be generated, image analyses of image signals (superresolutions, enhancings, smoothings, separations, extractings, or CGs etc.) can be performed, various types of measurements such as displacements and deformations of objects or other various temporal changes etc. can be performed; and images or measurement results can be output and can also be displayed onto display devices.

The measurement results to be stored include the wave's attenuations, scatterings (forward scatterings, backscatterings etc.), transmissions, reflections, refractions. The stored results are read out and used to optimize various types of parameters for generating image signals. Thus, the storing results can be used. The optimizations can be performed using the calculation functions equipped with the control unit 34 or the digital signal processing unit 33.

<Control Unit>

The control unit 34 controls all the operations of the instrument. The control unit 34 can be comprised of various types of calculators or exclusive digital circuits etc., and can work as the digital signal processing unit 33. Basically, according to various types of demands input via the input device 40, the control unit 34 controls, on the basis of various types of control programs or various types of data read out from the storage devices, the transmission unit 31, the reception unit 32 and the digital signal processing unit 33 such that the image signals are generated by performing the transmissions and receptions of waves and performing the wave digital signal processings.

When the control unit 34 is comprised of the exclusive digital circuits, the parameters can be changeable and however, only the determined operations can be realized even including the cases where the operations are switched. When the control unit 34 uses the calculators, including performing the version up, the degree of freedom is high. In addition to the controls for the realizing the above-mentioned various types of operations, the basis of the control unit 34 is to perform the controls of scannings and image signal generations by providing a repetition frequency or information about the transmission and reception positions etc. to the transmission unit 31 and the reception unit 32 according to the transmission and reception aperture number to be used (the respective channels) or the beam number to be generated, the frame number to be generated (the operations may be continued unless the number is not set or not stopped), the frame rate to be realized. Various interfaces are equipped with and various devices can also be used simultaneously.

The instrument related to the present embodiment can be used as one of devices used for general networks or sensor networks etc., and may be controlled by the controller of the network systems or may be used as a controller for controlling locally comprised networks. For the uses, interfaces can also be equipped with.

<Beamforming Methods>

Next, effective and fast digital beamforming methods using digital Fourier's transforms, performed by the digital signal processing unit 33 in the body of instrument 30, for plural transmission and reception aperture elements (including arrayed elements) are explained. In the digital signal processings, occasionally, the middle of data generated in the calculation process or data to be iteratively used can be stored into the memories equipped with or storage devices. For generating plural image signals with the same phases of the objects, the storage devices can be used effectively. The small size memories can also be useful.

The generated image signals can also be displayed as a static image by the output device 50 such as a display device etc., or can also be stored into the external storage devices 60 using storage media such as hard disks etc. When the digital signal processing unit 33 is a calculator, various programming languages can be used. Although the assembler is useful, when the calculator is run using high-level language programs such as C-language or Fortran etc., high speed operations can also be performed by implementing the optimizations or parallel processings at the compiling the languages. Softwares for performing general operations such as MatLab or various types of control softwares, ones with graphic interfaces etc. can also be used, or special ones can also be used.

Below, by using cases where the waves are ultrasounds, the beamfoming methods for used for the present invention's instruments are explained. The beamforming methods used for the present embodiments are the following methods (1) to (7). On the methods (7), in addition to various types of beamforming methods, the representative observation data generated by the digital signal processing unit 33 are disclosed.

The method (1) is a method used for the reception beamformings with respect to transmissions and/or receptions of plane waves including cases where the transmission direction is steered, in which wavenumber matching (mapping) is performed in a Fourier's domain with no approximate interpolation required for the past Fourier beamforming methods. The method (1) includes an invention performed on the wavenumber matching when the steering is performed, i.e., performing multiplications of the complex exponential functions related to the respective cosine and sine of a steering angle to received signals to perform the wavenumber matchings in the axial and lateral directions. Similarly to the classical monostatic SA, the accuracies of measurement results are increased. Moreover, the method (2) is also disclosed, i.e., a high speed digital processing method about steered dynamic focusings to be performed on the basis of the monostatic SA.

Moreover, the method (3) is also disclosed, i.e., a high speed digital processing method on the basis of the multistatic SA. The method (2) performing the digital monostatic SA with steering can be achieved with a high accuracy such that the 1st moments of multidimensional spectra or the instantaneous frequencies of generated image signals can be expressed ideally using the steering angle and the carrier frequency (as mentioned later, a wavenumber vector has components expressed by the multiplications of sine and cosine of the steering angle with respect to the carrier frequency) by performing wavenumber matching with no approximate interpolations similarly to the method (1). Alternatively, the method (3) performing the multistatic SA can be achieved by generating echo data frames, with the same number as that of reception elements, comprised of echo signals received at the same position in plural reception position with respect to the transmission position. Moreover, the above-mentioned monostatic digital SA is implemented on the respective echo data frames in a Fourier domain, and the superposed, processed results are inverse-Fourier transformed to accomplish the multistatic SA with a high accuracy. Consequently, the method (3) can generate echo data with the same number of digital SA processings as that of the reception aperture channels, and with a remarkably higher speed than the so-called conventional DAS (Delay and Summation) method generates a high spatial resolution image signal frame by superposing the generated low spatial resolution image signal frame.

By the way, the DAS method can be realized by implementing delays (phasing) onto the received signals with a high speed via performing approximate interpolations in a spatial domain or by implementing delays in a Fourier domain (a past achievement of the present invention's inventor), after which the phased, received signals are summed in a spatial domain. The former yields a high speed, but low accuracy, beamforming; the latter yields a high accuracy, but low speed beamforming.

The method (4) realized on the basis of the method (1) or (3) is also disclosed, i.e., a high accuracy digital dynamic focusing reception beamforming method for a transmission fixed focusing. Moreover, the method (5) is also disclosed, i.e., for allowing the echo data generations using the convex, sector scanning or IVUS, from echo data received on the polar coordinate system, directly on the Cartesian coordinate system used for displaying the echo data to be generated with a high accuracy with no approximate interpolations by performing processing via the Jacobi operation.

The method (6) is also disclosed, i.e., the migration method using the present inventions that allows high speed processings with high accuracies and with no approximate interpolations. All the beamforming processings of methods (1) to (5) can also be performed by using the migration method. At last, the applications on the basis of these methods (1) to (5) are disclosed as method (7). Using these methods, it is possible to demonstrate that arbitrary beamformings on the basis of focusings and steerings can be performed.

Method (1): Transmission and/or Reception Beamforming of Plane Wave (i) Echo Signal with Respect to Plane Wave Transmission (Image Signal)

Figure 5:
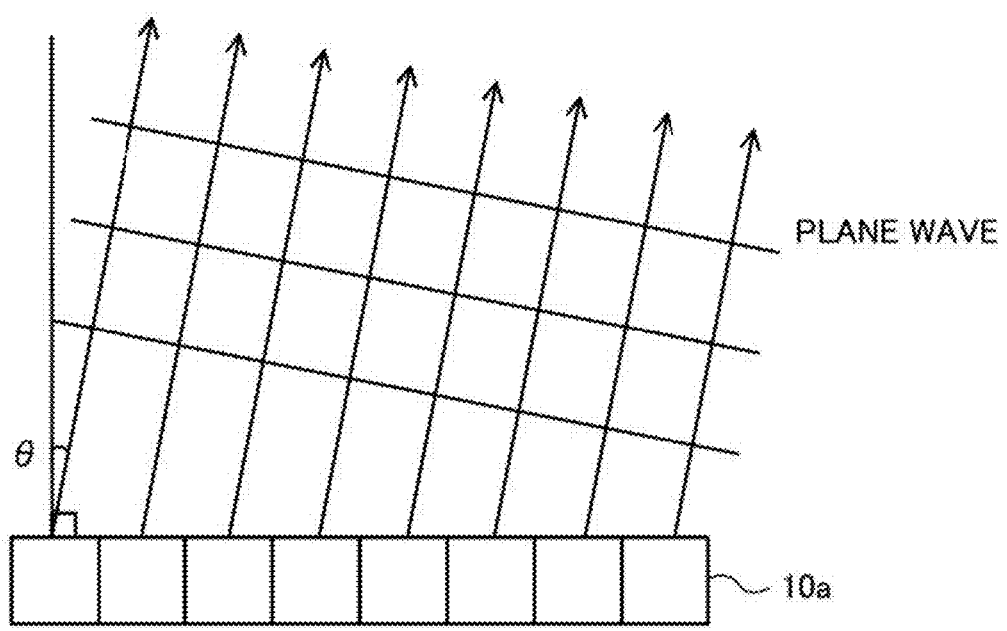
FIG. 5 shows an illustration of steered plane wave transmission.

FIG. 5 shows illustrations for a steered plane wave transmission. The plane wave transmission can be performed using a linear array-type transducer by using all the effective array elements simultaneously to transmit ultrasounds. When the wavenumber is k, and when the plane wave with the wavenumber vector expressed as eq. (0) is transmitted (x and y respectively expresses the orthogonal directions of scanning and an axial (depth) of the Cartesian coordinate system, of which zeros of y-axis exist on the position of reception effective aperture element array), the acoustic pressure of position (x,y) is expressed as eq. (1).

$$(k_x^t, k_y^t) \tag{0}$$

$$p(x,y;k) = A(k)e^{ik_x^t x + ik_y^t y} \tag{1}$$

Here, A(k) is frequency spectra of a transmitted pulse, and eq. (2) holds.

$$k_y^t = \sqrt{k^2 - (k_x^t)^2} \tag{2}$$

Each echo signal form a scatter with a reflection coefficient $f(x,y_i)$, positioned at a depth $y=y_i$, is expressed as eq. (3).

$$s(x,y_i,k)=f(x,y_i)p(x,y_i,k) \qquad (3)$$

The angular spectrum of the eq. (3) is expressed by eq. (4).

$$S(k_x, k, y_i) = \int_x s(x, y_i, k)e^{ik_x x}dx \qquad (4)$$
$$= \int_x f(x, y_i)A(k)e^{ik_x^t x + ik_y^t y_i} e^{ik_x x}dx$$

Expressing the frequency response of the transducer by $T(k)$, the angular spectra, at the aperture plane (y=0), of the echo signals from the depth $y=y_i$ are expressed by eq. (5).

$$R(k_x, k, y_i) = T(k)S(k_x, k, y_i)e^{ik_y y_i} \qquad (5)$$
$$= T(k)S(k_x, k, y_i)e^{i\sqrt{k^2-k_x^2}\, y_i}$$

Thus, adding the angular spectra from the respective depths yields the angular spectra of echo signals expressed by eq. (6).

$$R'(k_x, k) = \int_y R(k_x, k, y) dy \qquad (6)$$
$$= \int_{x,y} f(x, y)A(k)T(k)e^{ik_x'' x + ik_y'' y}dxdy$$

Thus, the echo signals (image signals) are expressed by eq. (9) by implementing IFFT on the spectra via performing the wavenumber matching expressed by eqs. (7) and (8).

$$F(k_x', k_y') = R'(k_x, k) \qquad (7)$$

$$\begin{cases} k_x' = k_x + k_x^t \\ \quad = k_x + k\sin\theta \\ k_y' = k_y + k_y^t \\ \quad = \sqrt{k^2 - k_x^2} + k\cos\theta \end{cases} \qquad (8)$$

$$f(x, y) = F^{-1}(F(k_x', k_y')) \qquad (9)$$

Considering the transmission and reception inversely, arbitrary transmission beamformings (for instance, steered plane wave, steered fixed focusing beam, steering dynamic focusing using SA, non-steered waves or beams, and various others etc.) are performed with respect to the measurement object, a wave arriving from the measurement object can be used as a received plane wave with the steering angle θ (including a case of zero degree). The way how to interpret the transmission and reception was not disclosed. Similarly, when arbitrary waves or beams transmitted with arbitrary steering angles (zero or non-zero degree) are performed, it is possible to receive the waves with the same or different steering angles θ (zero or non-zero degree). Moreover, reception beamformings can be performed on the coordinate system determined by the reception aperture with respect to arbitrary waves transmitted from arbitrary wave sources or arbitrary transmission effective aperture array (for instance, the same one as that of the reception effective aperture array or a different one with an arbitrary geometry and an arbitrary direction, other positioned one from the reception effective aperture or in the same physical aperture etc.).

When physically performing the plane wave transmission with a steering angle α (including a case of zero degree), implementing the steering with a steering angle θ (including a case of zero degree) in a software fashion yields the transmission of a steered plane wave with a steering angle (α+θ) (finally, generated transmission steering angle is the mean of α and θ). The software steering (steering angle θ) can be performed for reinforcing the physically performed steering (steering angle α) or for realizing a steering of a plane wave transmission in a software fashion purely, or can be interpret that reception steering of a plane wave is performed in a software fashion.

When performing the transmissions with a physical steering angle α, a software steering angle θ or both steerings α+θ are performed, reception dynamic focusing with a steering angle φ can be realized by performing the steering angle used in the method (2) next explained (finally, generated transmission steering angle is the mean of transmission and reception steering angles) The software steering (steering angle θ) can be performed for reinforcing the physically performed steering (steering angle α) or for realizing a steering of a plane wave transmission in a software fashion purely, or can be interpret that reception steering of a plane wave is performed in a software fashion in addition to the reception dynamic focusing (including a case where the steering angle φ is zero degree).

In these cases, the software transmission and reception beamformings can be considered inversely. Performing the exchanging of the software steered plane wave transmission (including a case where the steering angle is zero degree) and the software steered dynamic focusing reception (including a case where the steering angle is zero degree) has the same processings as those of the original beamforming (equivalent). Generated, beamformed signals can also be interpreted as ones beamformed with respect to the physically received, steered plane wave. Generally, regardless performing the steering or not, it is not reasonable to physically perform dynamic focusing transmission and however, it is also possible to interpret that a wave is physically received as a steered plane wave.

Also using this method allows performing arbitrary transmission beamformings (for instance, steered plane wave, steered fixed focusing beam, steering dynamic focusing using SA, non-steered waves or beams, and various others etc.). That is, performing the same processings as those for this plane wave transmission allows dealing with arbitrary waves or beams (for instance, the above mentioned examples etc.) generated by physical beamformings. In other words, even if arbitrary transmissions are performed, reception beamformings (dynamic focusing etc.) can be performed. Particularly when performing plural transmissions, simultaneous processings can be performed. In addition to a transmission steerings (the angles including a case of zero degree), the transmission or reception steerings of a plane wave or a dynamic focused beam can be performed (the angles including a case of zero degree). The finally generated steering angles are means of the transmission and reception angles. Also similarly to the above mentioned beamformings, the transmission and reception can be considered inversely and then, various combinations of beamformings can be performed. The respective transmission and reception beamformings are performed and plane wave processing can also be performed for both the transmission and reception in a software fashion. As explained later, these are also for the 3D beamformings using a 2D array.

On the basis of the above explained theory, the calculation method disclosed by J.-y. Lu (nonpatent documents 3 and 4) implements, in order to calculate $R(k_x,k)$, the 2D FFT on the received signals with respect to the time and space at first, the wavenumber matching using eq. (7) next, and the 2D IFFT finally (also described in paragraph 0352). The wavenumber matching is performed using approximations such as a linear interpolation or using the most neighborhood data. Thus, to increase the approximation accuracy, over sampling of received signals is required. High order approximate interpolations or a sinc function can also be used. In 3D cases, similarly, 3D FFT and 3D IFFT are performed. One of features of the present intention is to perform the wavenumber matching with no approximate interpolations and however, when the processings are applied to various beamformings as likely disclosed in paragraphs 0190 to 0194, the corresponding approximate interpolations can also be performed to yield approximate solutions with high speeds.

(ii) The Present Invention's Calculation Procedure of Echo Signal (Image Signal) with Respect to Transmission and/or Reception Beamforming of Plane Wave The case where the transmission and/or reception of a plane wave with a steering angle θ is explained. Using the present invention, the wavenumber matching is performed as follows: at first, the wavenumber matching is performed in the lateral direction x by multiplying the complex exponential function (eq. (9a)) to the received signal before performing the FFT in the lateral direction (a spatial direction), and subsequently in the depth direction by multiplying the complex exponential function (eq. (9c)) in addition to the complex exponential function (eq. (9b)) with removed the performed lateral matching processing for simultaneously yielding a spatial resolution in the depth direction y. The steering angle θ can be zero degree as well as non-zero degree. This processing is not disclosed in prior art documents.

$$\exp(ik_x'x)=\exp(ik \sin \theta x) \quad (9a)$$

$$\exp(i\sqrt{k^2-(k_x-k_x')^2}\,y)=\exp(i\sqrt{k^2-(k_x-k\sin\theta)^2}\,y) \quad (9b)$$

$$\exp(ik_y'y)=\exp(ik \cos \theta y) \quad (9c)$$

Figure 6:
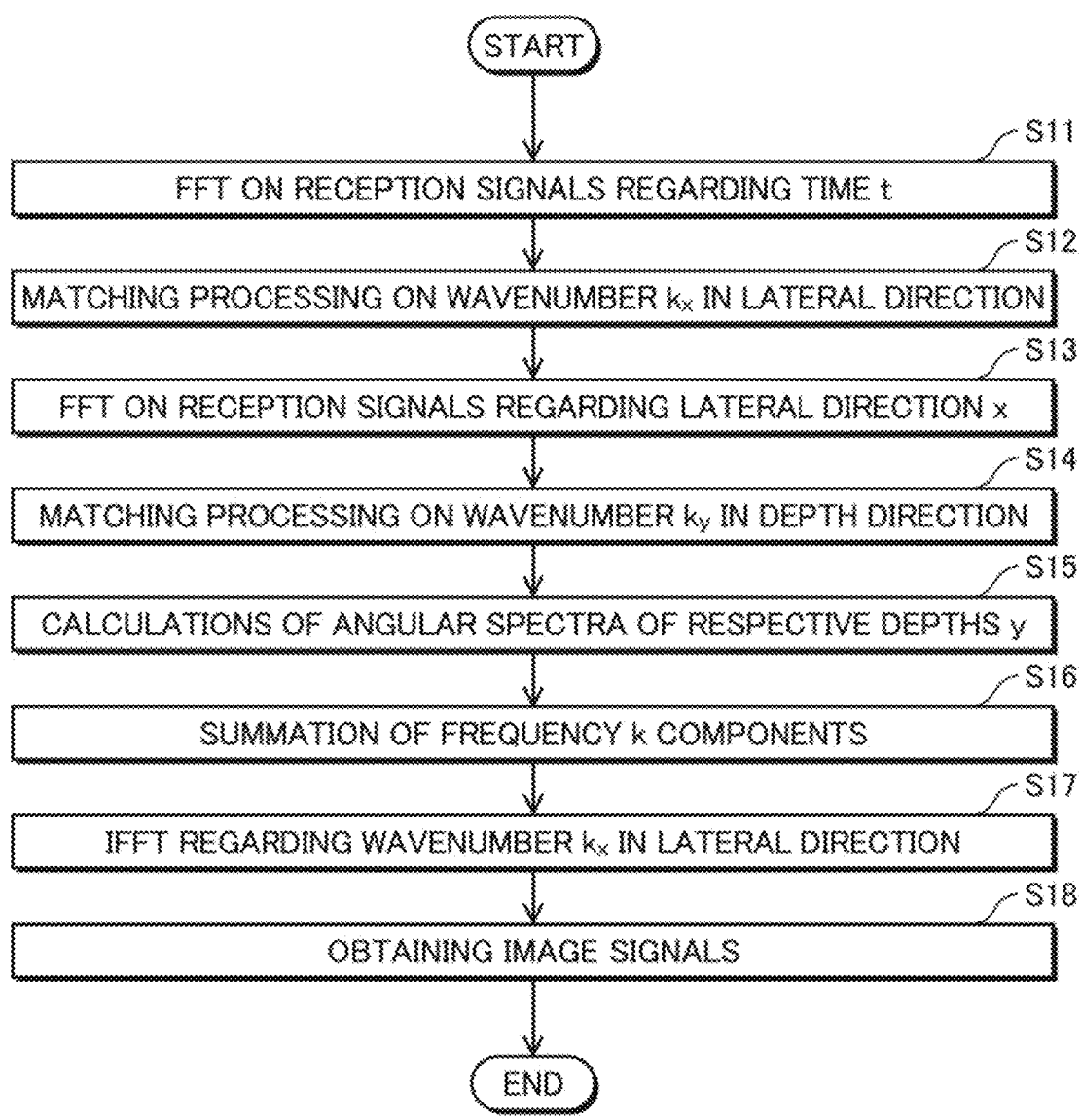
FIG. 6 shows a flowchart about the digital signal processing for steered plane wave transmission.

FIG. 6 shows the flowchart explaining the digital signal processing for the steered plane wave transmission. The calculation procedure follows. At the step S11, as shown in eq. (10), the received signals are Fourier's transformed with respect to the time t (FFT should be performed):

$$R'(x,k)=\int r(x,t)\exp(i\omega t)dt \quad (10)$$

where k is a wavenumber expressed using the angular frequency ω and an ultrasound propagation speed c as k=ω/c, form which analytic signals are obtained. Here, although according to the above-explains, the processing is performed using the plus signed kernel of the complex exponential function for the Fourier transform referred to as, according to the usual Fourier's transform, the processing can also be performed using the minus signed kernel of the complex exponential function. Anyway, when the processing to be performed later as the inverse Fourier's transformed referred to as, absolutely a kernel of which sign is inverted is used in the complex exponential function. This is also for other methods (2) to (7).

Next, at the step S12, the matching processing is performed with respect to the wavenumber $k_x$ for steering by multiplying eq. (11) to eq. (10) and at the step S13, Fourier's transform is performed on the signals in the lateral direction x (FFT should be performed) to yield signals expressed by eq. (12). When performing the multiplication of eq. (10) (the results of FFT performed on time t) and eq. (11) (the complex exponential function), exclusive FFT can also be useful to yield the multiplication results directly.

$$\exp(ik_x'x)=\exp(ik \sin \theta x) \quad (11)$$

$$R'(k_x,k)=\int R(x,k)\exp[i(k_x+k \sin \theta)x]dx \quad (12)$$

The results of eq. (12) can also be obtained by performing the calculation of eq.(12) directly.

This twice Fourier's transforms (2D Fourier's transform) analyze the received signals into plane wave components. The angular spectra of an arbitrary depth position y generated by the respective plane waves can be calculated by shifting the phase via performing of multiplication of eq. (13).

$$B(k_x, k, y) = \exp(i\sqrt{k^2-(k_x-k_x')^2}\,y) \quad (13)$$
$$= \exp(i\sqrt{k^2-(k_x-k\sin\theta)^2}\,y)$$

At the step S14, the matching processing is also performed on the wavenumber $k_y$ by simultaneously multiplying eq. (14).

$$\exp(ik_y'y)=\exp(ik \cos \theta y) \quad (14)$$

At the step S15, the angular spectra of the respective depths y are calculated. That is, by multiplying eq. (15), eq. (16) can be obtained.

$$B'(k_x,k,y)=\exp(i(\sqrt{k^2-(k_x-k\sin\theta)^2}+k \cos \theta)y) \quad (15)$$

$$R(k_x,k,y)=R'(k_x,k)B'(k_x,k,y) \quad (16)$$

The acoustic pressure field generated at a depth y by the respective plane wave components can be calculated by performing the inverse Fourier's transform (IFFT) on the lateral direction x as eq. (17).

$$f(x,y,k)=\int R(k_x,k,y)\exp(-ik_xx)dx \quad (17)$$

Finally, the image signals can be obtained by summing up the plural wavenumber k (or frequency) components.

Here, the order of integral calculations regarding the wavenumber k (or the frequency) and spatial frequency $k_x$ are exchangeable. Thus, summing up k components of angular spectra at the step S16 and performing the IFFT with respect to the wavenumber $k_x$ at the step S17 can also yield the same image signals at the step 18. In this case, the calculations can be accomplished by one time inverse Fourier's transform at each depth position and then, the high speed calculation can be achieved. This is also for all methods (1) to (6). The wavenumber matching for steering is performed on the basis of eqs. (11) and (14). Being different from the wavenumber matching method performed via approximate interpolations in a Fourier domain (nonpatent documents 3 and 4), since such approximations are not performed, the present invention allows the high accuracy calculation. Physically or mathematically, the wavenumber matching can also be performed at the first Fourier's transforms or at the last inverse Fourier's transforms. These are also for other methods (1) to (6)

Also when using a 2D aperture element array, arbitrary waves are transmitted from wave sources positioned in arbitrary directions to the measurement object and then, the waves arriving from the measurement object are received as a plane wave and processed by 3D wave digital signal processing, 3D Fourier's transform is performed regarding an axial (or depth, y) and lateral directions (x and z) on the 3D Cartesian orthogonal coordinate system (x,y,z) expressed by an axial direction y determined by the direction of a flat reception aperture element array and lateral directions x and z, for instance. When the steering angle being an angle between the reception direction as a plane wave and the axial direction (y) is expressed using zero or non-zero elevation and azimuth angles, similarly to when performing the 2D wave digital signal processing explained above, the following wavenumber matching is performed on the 3D Fourier's transform R' ($k_x$,k,$k_z$) of the received signals with no approximate interpolations.

$$F(k'_x, k'_y, k'_z) = R'(k_x, k, k_z) \quad (7')$$

$$\begin{cases} k'_x = k_x + k^t_x \\ \quad = k_x + k\sin\theta\cos\varphi \\ k'_y = k_y + k^t_y \\ \quad = \sqrt{k^2 - k_x^2 - k_z^2} + k\cos\theta \\ k'_z = k_z + k^t_z \\ \quad = k_z + k\sin\theta\sin\varphi \end{cases} \quad (8')$$

Similarly to the 2D case, when the processings are applied to various beamformings as likely disclosed in paragraphs 0190 to 0194, according to eqs. (7') and (8'), the corresponding approximate interpolations can also be performed to yield approximate solutions with high speeds and in the case, the 3D inverse Fourier's transform is performed on $F(k_x',k_y',k_z')$ When not implementing the approximate interpolations on the wavenumber matching, at first the wavenumber matching in lateral directions x and z by multiplying the complex exponential function eq. (C21) expressed by the wavenumber k and an imaginary unit i to the Fourier's transforms of the received signals in the axial direction y.

$$\exp\{ik \sin\theta(\cos\varphi x + \sin\varphi z)\} \quad (C21)$$

And the wavenumber matching is subsequently performed in the axial direction by multiplying, to the angular spectra obtained by performing Fourier's transforms on the multiplications in the lateral directions x and z (2D Fourier's transform or 2D FFT), the complex exponential function (eq. (C23)) in addition to the complex exponential function (eq. (C22)) with removed the performed lateral matching processings for simultaneously yielding a spatial resolution in the depth direction y. Here, the wavenumbers in the lateral directions are expressed as $k_x$ and $k_z$.

$$\exp(i\sqrt{k^2 - (k_x - k\sin\theta\cos\varphi)^2 - (k_z - k\sin\theta\sin\varphi)^2}\,y) \quad (C22)$$

$$\exp(ik\cos\theta y) \quad (C23)$$

The performing wavenumber matching with no approximate interpolations allows generating image signals on the Cartesian coordinate system directly. That is, the sound pressure field at each depth y generated by the respective plane waves can be obtained as image signals by performing the 2D IFFT with respect to the lateral directions x and z and summing up the plural wave number k components (or frequency components). Off course, even when the steering angle or either elevation or azimuth degree is zero, the processings can be performed.

In the above explained calculations, the bandwidth determined by the transmission signals or the SN ratio of the received signals considered is used to set the bandwidth to be processed. For instance, when generating analytic signals on the basis of eq. (10), those with the required band-limited are generated and stored (corresponding to the down-sampling). Although the method or instrument of the present invention does not perform the approximate interpolations when performing the wavenumber matching, the over-sampling of echo signals in the depth and lateral directions also yield the effects for yielding image signals robust to noises contaminated in received echo signals. These are also for other methods (1) to (6).

On eqs. (13) to (15) or eqs. (C22) and (C23), by setting the position (coordinate) y in a depth direction or the range, the interval of data in the direction, image signals with an arbitrary depth position or depth range, or an arbitrary interval or density in the depth direction can be generated with no approximate interpolations. Regardless performing the down-sampling explained in the paragraph 0206 or not, up-sampling can be performed. The down-sampling is effective within the Nyquist theorem holds. Intentionally, high frequency signal components can also be filtered out (processed to be outside the bandwidth). Regardless performing the down-sampling explained in the paragraph 0206 or not, the down-sampling can be performed within the Nyquist theorem holds. In addition, on the inverse Fourier's transform such as eq. (17) etc., by setting the lateral position (coordinate) x or the range (if required, spatial shifting is performed in an analogue fashion by using the past invention of the present invention's inventor, i.e., the phase rotation via multiplication of a complex exponential function), image signals with an arbitrary lateral position or range can be generated with no approximate interpolations; and also on the inverse Fourier's transform, by making the lateral bandwidth narrower with removed the lateral high frequency components (if required) to make the lateral density of data lower, or by making the lateral bandwidth wider with padded zero spectra in the angular spectra to make the lateral density of data higher, image signals with an arbitrary lateral interval or density can be generated with no approximate interpolations.

Thus, the image signals can be generated with the desired arbitrary positions, ranges, intervals, densities. That is, image signals with the shorter intervals than the sampling interval of the received signals and the pitch of the reception aperture elements can be generated. Otherwise, coarse intervals of image signals can also be generated in the respective directions (it is cautious that the Nyquist theorem holds). When performing the wavenumber matching with approximate interpolations, however with high accuracies, on the basis of eqs. (7) and (8) or (7') and (8'), the approximations are required to be performed with proper over-samplings of data in return an increased calculation amount. In the case, being different from in the case where image signals of arbitrary positions can be generated when no approximate interpolations are performed, it is cautious that the number of data to be used for the Fourier's transforms increases. These are also for other methods (1) to (6).

When a convex-type transducer, a sector scanning or an IVUS being used, waves spread widely in the angle direction θ (cylindrical waves) can also be transmitted or received in the radial direction r on the polar coordinate system (FIG. 7); or virtual sources set behind the apertures with arbitrary geometries being used, the same beamformings (cylindrical waves) can also be performed (see FIGS. 8A(a) to (c), patent document 7 or nonpatent document 8 etc.). In such cases, the above-explained methods can be implemented with the polar orthogonal coordinate system (r,θ) instead of the Cartesian orthogonal coordinate system (x,y) (the depth y and lateral x coordinates are replaced by r and θ, respectively) and image signals can be directly generated on the polar coordinate system (r,θ). These are also for spherical waves expressed on the spherical coordinate system. Also as shown in FIGS. 8B(d) to (f), when using the physical aperture element arrays expressed by the polar system or the physical apertures with arbitrary aperture geometries as explained above, the beamformings can also be performed similarly to generate, at an arbitrary distance position, the transmission or reception, or both of plane waves. Performing such beamformings is equivalent to make a formation of a virtual linear-type aperture array (or a plane wave) at the distance position and then, setting the distance position zero corresponds to the case where a linear-type aperture array is used at the position virtually. The distance position can be set behind as well as in the front of the physical aperture and then, the virtual linear-type aperture array (or a plane wave) can be generated at the distance positions. The virtual linear-type aperture array can also be used not as the virtual sources but the virtual receivers, or both virtual sources and receivers.

FIG. 7 shows the illustrations of cylindrical wave transmissions or receptions on the polar coordinate system (r,θ) (transmissions or receptions, in a radial (r) direction, of waves widely spread in an angle direction (θ)). FIG. 7(a) shows the cylindrical wave transmission using a convex-type aperture element array; FIG. 7(b) shows the cylindrical wave transmission using a sector-type aperture element array; FIG. 7(c) shows the cylindrical wave transmission using an IVUS (a circular-type) aperture element array. Although FIG. 7b shows an aperture of which geometry is an arc, a flat aperture can also be used for the sector scanning. Also using these apertures, focused beams can also be generated.

FIG. 8A shows the illustrations of the cylindrical wave transmissions on the polar coordinate system (r,θ) (transmissions of waves, in a radial (r) direction, widely spread in an angle direction (θ)) from virtual sources set behind physical apertures with arbitrary aperture geometries. FIG. 8A(a) shows the cylindrical wave transmission using a linear-type aperture element array; FIG. 8A(b) shows the cylindrical wave transmission using a convex-type aperture element array; FIG. 8A(c) shows the cylindrical wave transmission using an arbitrary aperture element array. Receptions can also be performed similarly. FIGS. 8B(d) to (f) show, when using the physical aperture element arrays expressed by the polar system or the physical apertures with arbitrary aperture geometries, the beamformings can also be performed to generate, at an arbitrary distance position, the transmission of a plane wave (In the figures, the cases where a convex-type aperture element array is physically used are shown). Setting the distance position zero corresponds to the case where a linear-type aperture array is used at the position virtually (FIG. 8B(d)). The distance position can be set in the front of (FIG. 8B(f)) as well as behind (FIG. 8B(e)) the physical aperture and then, the virtual linear-type aperture array (or a plane wave) can be generated at the distance positions. Reception can be also performed similarly. FIG. 8B(g) shows a special case, for instance, a case where physically using a linear-type array transducer, and a cylindrical wave is generated using a virtual source set behind the physical aperture is applied to generate, at an arbitrary distance position, a pane wave widely spread in a lateral direction or a large virtual linear-type array transducer. Reception can also be performed similarly. The virtual linear-type aperture array can also be used not as the virtual sources but the virtual receivers, or both virtual sources and receivers.

Nonpatent document 6 discloses performing of transmission focusing and similarly, the result can be obtained on the polar coordinate system (r,θ). For instance, a large FOV can be obtained. As another method from that disclosed in the nonpatent document 6, the method (1) is used for the beamformings and obtaining steered beams with steering angles on the polar coordinate system (r,θ) (one of features of the present invention). These are also when using the methods (2) to (4) and (6). For the cases, the polar coordinate system (r,θ) is used instead of the Cartesian coordinate system (x,y) (the axial x and lateral y coordinates are replaced by r and θ coordinates, respectively). However, when performing these beamformings, to obtain the signals at the positions of the discrete Cartesian coordinate system used for the display, interpolations are required to be performed. The interpolations are strictly performed in a Fourier domain by performing the phase rotations via implementing the multiplications of complex exponential functions, however, with consuming long time; or alternatively performed by approximate interpolations with consuming short time, however, with approximate errors. These are also for using the spherical coordinate system.

Also in these cases where the beamformings are performed on the polar coordinate system, the displacement measurements can also be performed, for instance, measurements of a displacement in the radial (r) or angle (θ) direction or a displacement vector comprised of both the displacements. To obtain the measurement results at the positions of the discrete Cartesian coordinate system used for the display, interpolations are required to be performed. Similarly to the interpolations for the echo signals, the interpolations are strictly performed in a Fourier domain by performing the phase rotations via implementing the multiplications of complex exponential functions, however, with consuming long time; or alternatively performed by approximate interpolations with consuming short time, however, with approximate errors. These are also for using the spherical coordinate system.

From the results of displacements, a strain (tensor) or a strain rate (tensor), a velocity (vector) or an acceleration (vector) can be calculated via calculating the partial derivatives using differential filterings and further, mechanical properties (for instance, a bulk modulus or a shear modulus (for instance, nonpatent document 7), elastic modulus tensor of an anisotropic media etc.), a temperature etc. can be calculated via numerical operations. When performing the approximate interpolations, the calculations performed on the Cartesian coordinate system with approximations allow shortening the total calculation time in many cases. Alternatively, performing the numerical operations on the polar coordinate system to obtain the results, of which approximations on the Cartesian coordinate system can be performed with small error propagations. That is, the errors generated in the processes after the displacement measurement are led to only due to the approximate interpolations for obtaining final data to be displayed (There is a case where plural data to be displayed can be obtained from same displacement data).

As mentioned above, after implementing the interpolation processings on the echo signals to express the echo data on the Cartesian coordinate system, the displacement and the subsequent measurements can also be performed. When the approximate processings are performed on the interpolation processings, errors are led to and however, the total calculation time can be shortened. When measurements are performed on the basis of other echo data processings, as mentioned above, such processings can be performed similarly. These are also when the 3D beamformings are performed using a 2D array.

For all the above-mentioned beamformings, such processings can also be performed using arbitrary orthogonal coordinate systems except for the polar coordinate system.

Alternatively, in the same way, when performing cylindrical wave transmissions or receptions on the polar coordinate system (r,θ) (transmissions or receptions, in a radial (r) direction, of waves widely spread in an angle direction (θ)) using a convex-type transducer or a sector scan, or an IVUS etc. (FIG. 7) and using virtual sources set behind physical apertures with arbitrary aperture geometries (FIGS. 8A(a) to (c)), the methods for generating image signals directly on the Cartesian coordinate system can be explained as the methods (5), (5-1), (5-1') etc. When using the physical aperture element arrays expressed by the polar system or the physical apertures with arbitrary aperture geometries as explained above, the beamformings can also be performed similarly to generate, at an arbitrary distance position, the transmission or reception, or both of plane waves (FIGS. 8B(d) to (f)). Performing such beamformings is equivalent to make a formation of a virtual linear-type aperture array (or a plane wave) at the distance position and then, setting the distance position zero corresponds to the case where a linear-type aperture array is used at the position virtually. The distance position can be set in front of as well as behind the physical aperture and then, the virtual linear-type aperture array (or a plane wave) can be generated at the distance positions. The virtual linear-type aperture array can also be used not as the virtual sources but the virtual receivers, or both virtual sources and receivers. Alternatively, in the same way, the beamforming methods can be explained as the methods (5), (5-1), (5-1') etc. In these cases, the imagings of echo signals and displacement measurements etc. can be performed on the same Cartesian coordinate system consistently. These are also for the polar coordinate system. In such cases, it is also possible to transform the echo signals or measurements on the Cartesian coordinate system to those on the polar coordinate system via interpolations. These are also when using 2D arrays for the 3D beamformings. Transmission focusings may also be performed. Alternatively, in the same way, For all the above-mentioned beamformings, such processings can also be performed using arbitrary orthogonal coordinate systems except for the polar coordinate system. As mentioned above, the virtual source or the virtual receiver are not always positioned behind the physical aperture and can also be set in front of the aperture. Regardless the geometry of a physical aperture, they can be positioned arbitrarily (patent document 7 or nonpatent document 8). Thus, the present inventions are not limited to these. On the wavenumber matching in these beamformings, approximate solutions can also be calculated with approximate interpolations. All these can be processed similarly using the methods (1) to (7).

On the present methods (1) to (7), for these received signals, apodizations for the transmission or reception, or the both can be performed at various timings, because the processings are linear. That is, the apodizations can be performed in a hardware fashion when performing the receivings or in a software fashion after performing the receivings. As mentioned above, the apodizations can also be performed at transmissions physically. These are also for the following beamformings.

It is natural that when performing the beamformings not with respect to the received echo signals but transmission waves, the coordinate y is not the half round trip distance (expressed as ct/2 using the propagation time t) but the distance (ct) from the aperture element on the coordinate system determined by the reception aperture element.

Next, the cases where synthetic apertures (SAs) are performed. Two types SAs exist, i.e., a monostatic and multistatic types.

Method (2): Monostatic Type SA

Figure 9:
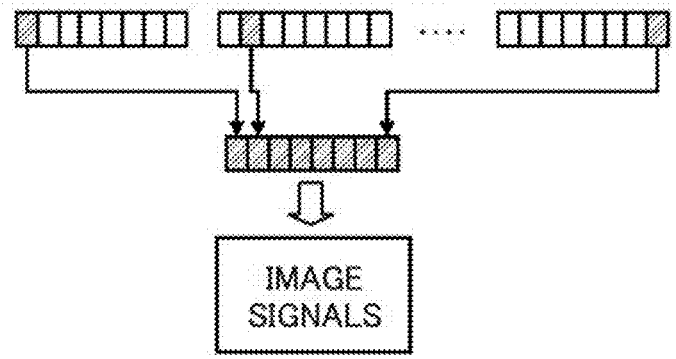
FIG. 9 shows an illustration of a monostatic synthetic aperture (SA)

FIG. 9 shows an illustration of a monostatic type SA. For the SA, an ultrasound is transmitted from one element in an array, and echo is received by the element itself. Also for the SA, by performing the wavenumber matching using the procedure shown in FIG. 6, echo signals (image signals) can be calculated.

Since the monostatic type SA performs the transmission and reception using the same elements, the propagation paths of ultrasounds to scatters at transmissions are same as those of ultrasounds from the scatters at receptions. Therefore, on the Cartesian coordinate system, of which zeros of y-axis exist on the position of reception effective aperture element array, when performing no steering (θ is zero), as shown in eq. (18a), the wavenumber matching expressed by eqs. (7) and (8) are performed with the twice wavenumber k (i.e., s=2, 2k for reflection waves). This is also for the following SAs. For transmission waves, not 2k but k is used (s=1). This is also for the following SAs.

$$\begin{cases} k'_x = k_x \\ k'_y = k_y = \sqrt{(sk)^2 - k_x^2} \end{cases} \quad (18a)$$

Figure 10:
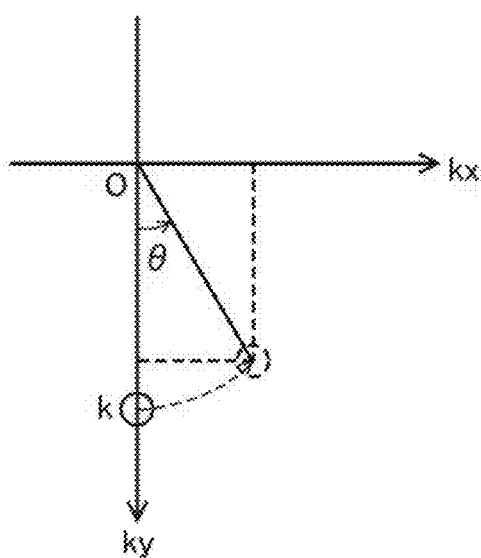
FIG. 10 shows an illustration of spectra ($\theta$, steering angle) generated by performing steering on a monostatic SA.

When the steering angle θ is not zero, image signals having the wavenumber vector $(sk_0 \sin\theta, sk_0 \cos\theta)$ expressed using the wavenumber vector $(0, k_0)$ with a wavenumber $k_0$ $(=\omega_0/c)$ expressed using the carrier frequency $\omega_0$ of ultrasound signals as the 1st moments (centers) of the multidimensional spectra or the instantaneous frequencies are generated by performing the beamforming, in which the shifting of spectra is performed (FIG. 10). That is, on eqs. (7) and (8), the wavenumber matching expressed by eq. (18b) is performed.

$$\begin{cases} k'_x = k_x + k_x^t \\ \phantom{k'_x} = k_x + sk_0\sin\theta \\ k'_y = k_y + k_y^t \\ \phantom{k'_y} = \sqrt{(sk)^2 - k_x^2} + sk_0(-1 + \cos\theta) \end{cases} \quad (18b)$$

The signal processing is performed similarly to the method (1). Particularly, the wavenumber matching is performed, at first, for the spatial (lateral) direction, by multiplying the complex exponential function eq. (19a) expressed using the carrier frequency $\omega_0$ of the ultrasound signals instead of the complex exponential function eq. (9a) prior to performing the Fourier's transform with respect the spatial (lateral) direction and next for the depth direction y, by multiplying the complex exponential function eq. (19c), instead of the complex exponential function eq. (9c), together with the complex exponential function eq. (19b)

with removed the performed lateral matching processing eq. (19a) to yield the spatial resolution in the depth direction y instead of the complex exponential function eq. (9b). This processing can be performed when the steering angle is zero degree. This processing is not disclosed in the prior art documents.

$$\exp(ik_x'x)=\exp(isk_0 \sin \theta x) \qquad (19a)$$

$$\exp(i\sqrt{(sk)^2-(k_y-k_x')^2}y)=\exp(i\sqrt{(sk)^2-(k_y-sk_0\sin\theta)^2}y) \qquad (19b)$$

$$\exp(ik_y'y)=\exp\{isk_0(-1+\cos \theta)y\} \qquad (19c)$$

For instance, when using an echo technique (a reflection method), there are cases where the steering angles of transmission and reception beams are different. When the steering angles of the transmission and reception beams are respectively $\theta_t$ and $\theta_r$, the wavenumber matching expressed by eq. (18c) with s=2 is performed on eqs. (7) and (8).

$$\begin{cases} k_x' = k_x + k_x^t \\ \quad = k_x + k_0(\sin\theta_t + \sin\theta_r) \\ k_y' = k_y + k_y^t \\ \quad = \sqrt{(sk)^2 - k_x^2} + k_0(-2 + \cos\theta_t + \cos\theta_r) \end{cases} \qquad (18c)$$

The signal processing is performed similarly to the cases where the steering angles of transmission and reception beams are same. Particularly, the wavenumber matching is performed, at first, for the spatial (lateral) direction, by multiplying the complex exponential function eq. (19d) expressed using the carrier frequency $\omega_0$ of the ultrasound signals instead of the complex exponential function eq. (19a) prior to performing the Fourier's transform with respect the spatial (lateral) direction and next for the depth direction y, by multiplying the complex exponential function eq. (19f), instead of the complex exponential function eq. (19c), together with the complex exponential function eq. (19e) with removed the performed lateral matching processing eq. (19d) to yield the spatial resolution in the depth direction y instead of the complex exponential function eq. (19b). This processing can be performed when the steering angles $\theta_t$ and $\theta_r$ are zero degree. This processing is not disclosed in the prior art documents.

$$\exp(ik_x'x)=\exp\{ik_0(\sin \theta_t+\sin \theta_r)x\} \qquad (19d)$$

$$\exp(i\sqrt{(sk)^2-(k_x-k_x')^2}y)=\exp(i\sqrt{(sk)^2-\{k_x-k_0(\sin\theta_t+\sin\theta_r)\}^2}y) \qquad (19e)$$

$$\exp(ik_y'y)=\exp\{ik_0(-2+\cos \theta_t+\cos \theta_r)y\} \qquad (19f)$$

Using the respective eqs. (19a) to (19c) and eqs. (19d) to (19f), the wavenumber matchings expressed by eqs. (18b) and (18c) can be performed on the 2D Fourier's transform R'($k_x$,k) with no approximate interpolations similarly to the combinations of eqs. (7) and (8). Alternatively, the beamformings can also be performed with approximate interpolations and with a high speed, in which F($k_x'$,$k_y'$) is 2D inverse-Fourier's transformed. Regarding eqs. (18b) and (18c), also the approximate wavenumber matching about eq (18a), corresponding to the case where steering angles are zero degree, is not disclosed in the prior art documents.

Also when performing 3D wave digital signal processing using a 2D aperture element array, the 3D Cartesian orthogonal coordinate system (x,y,z) expressed by an axial direction y determined by the direction of a flat reception aperture element array (zeros of y-axis exist on the position of reception effective aperture element array) and lateral directions x and z can be used, for instance. When the steering angle being an angle between the beam direction to be generated and the axial direction (y) is expressed using zero or non-zero elevation and azimuth angles, similarly to when performing the 2D wave digital signal processing explained above, the following wavenumber matching is performed on the 3D Fourier's transform of the received signals with respect to the depth (y) and lateral directions (x and z), where ($k_x$,$k_y$,$k_z$) is the wavenumber domain expressed using the wavenumbers $k_x$, $k_y$ and $k_z$ of the depth (y) and lateral directions (x and z).

Image signals having the wavenumber vector ($sk_0$ sin $\theta$ cos $\varphi$, $sk_0$ cos $\theta$, $sk_0$ sin $\theta$ sin $\varphi$) expressed using the wavenumber vector (0,$k_0$,0) with a wavenumber $k_0$ (=$\omega_0$/c) expressed using the carrier frequency $\omega_0$ of waves as the 1st moments (centers) of the multidimensional spectra or the instantaneous frequencies are generated by performing transmission and reception dynamic focusings, in which the shifting of spectra is performed by multiplying the complex exponential function eq. (C41), being expressed using the parameter s being 2 and 1 respectively for the y coordinates of the transmission aperture elements being zero and non-zero, the wavenumber $k_0$ and an imaginary unit i, to the Fourier's transforms of the received signals in the axial direction y to perform the wavenumber matchings in the lateral directions x and z at fast; and further by multiplying the complex exponential function eq. (C43) to 2D Fourier's transform (2D FFT) of the signals multiplied with eq. C(41) in order to perform the wavenumber matching in the axial direction together with the complex exponential function eq. (C42) with removed the wavenumber matchings performed in the lateral directions x and z. Thus, by performing the wavenumber matching with no approximate interpolations, image signals can be generated on the Cartesian coordinate system directly.

$$\exp\{isk_0 \sin \theta(\cos \varphi x+\sin \varphi z)\} \qquad (C41)$$

$$\exp(i\sqrt{(sk)^2-(k-sk_0\sin\theta\cos\varphi)^2-(k_z-sk_0\sin\theta\sin\varphi)^2}y) \qquad (C42)$$

$$\exp\{isk_0(-1+\cos \theta)y\} \qquad (C43)$$

That is, the acoustic pressure fields generated by the respective plane wave components at the depth y can also be calculated as image signals by summing, with respect to the plural wavenumber k, the 2D inverse Fourier's transform (IFFT) performed with respect to the lateral directions x and z. The calculations can also be performed for a zero steering angle (i.e., the elevation and azimuth angles are zeros) or either angle is zero at least.

By the processing, the following wavenumber matching [eq. (C44)] can be performed with respect to the 3D Fourier's transform R'($k_x$,k,$k_z$) similarly to eqs. (7') and (8'). The above-disclosed processing achieves this wavenumber matching with no approximate interpolations, whereas according to eq. (C44) the wavenumber matching can also be performed with approximate interpolations and with a high speed, in which F($k_x'$,$k_y'$,$k_z'$) is 3D inverse-Fourier's transformed. The processing is not disclosed in the prior art documents.

$$\begin{cases} k'_x = k_x + k^t_x \\ \qquad = k_x + sk_0\sin\theta\cos\varphi \\ k'_y = k_y + k^t_y \\ \qquad = \sqrt{k^2 - k_x^2 - k_z^2} + sk_0(-1 + \cos\theta) \\ k'_z = k_z + k^t_z \\ \qquad = k_z + sk_0\sin\theta\sin\varphi \end{cases} \qquad (C44)$$

For instance, when using an echo technique (a reflection method), there are cases where the steering angles of transmission and reception beams are different. When the steering angles of the transmission and reception beams are respectively (an elevation angle, an azimuth angle)=$(\theta_t, \varphi_t)$ and $(\theta_r, \varphi_r)$, the signal processing is performed with s=2 similarly to the above-mentioned cases where the angles of transmission and reception beams are same. Particularly, the wavenumber matching is performed, at first, for the spatial (lateral) directions, by multiplying the complex exponential function eq. (D41) expressed using the carrier frequency $\omega_0$ of the ultrasound signals instead of the complex exponential function eq. (C41) prior to performing the Fourier's transform with respect the spatial (lateral) directions and next for the depth direction y, by multiplying the complex exponential function eq. (D43), instead of the complex exponential function eq. (C43), together with the complex exponential function eq. (D42) with removed the performed lateral matching processing eq. (D41) to yield the spatial resolution in the depth direction y instead of the complex exponential function eq. (C42). This processing can also be performed when the steering angles of transmission and reception beams are zero degree (i.e., $\theta_t, \varphi_t, \theta_r$ and $\varphi_r$ are zero degree). This processing is not disclosed in the prior art documents.

$$\exp[ik_0\{\sin\theta_t(\cos\varphi_t x + \sin\varphi_t z) + \sin\theta_r(\cos\varphi_r x + \sin\varphi_r z)\}] \qquad (D41)$$

$$\exp\left(i\sqrt{\begin{array}{c}(sk)^2 - \{k_x - k_0(\sin\theta_t\cos\varphi_t + \sin\theta_r\cos\varphi_r)\}^2 - \\ \{k_z - k_0(\sin\theta_t\sin\varphi_t + \sin\theta_r\sin\varphi_r)\}^2\end{array}}\,y\right) \qquad (D42)$$

$$\exp(ik^t_y y) = \exp\{ik_0(-2 + \cos\theta_t + \cos\theta_r)y\} \qquad (D43)$$

For the SA that performs both the transmission and reception beamformings in a software fashion, the exchange of transmission and reception is the same processing By the processing, the following wavenumber matching [eq. (D44)] can be performed with respect to the 3D Fourier's transform $R'(k_x,k_y,k_z)$ similarly to eqs. (7') and (8'). The above-disclosed processing achieves this wavenumber matching with no approximate interpolations, whereas according to eq. (D44) the wavenumber matching can also be performed with approximate interpolations and with a high speed, in which $F(k_x',k_y',k_z')$ is 3D inverse-Fourier's transformed. The processing is not disclosed in the prior art documents.

$$\begin{cases} k'_x = k_x + k^t_x \\ \qquad = k_x + k_0(\sin\theta_t\cos\varphi_t + \sin\theta_r\cos\varphi_r) \\ k'_y = k_y + k^t_y \\ \qquad = \sqrt{k^2 - k_x^2 - k_z^2} + k_0(-2 + \cos\theta_t + \cos\theta_r) \\ k'_z = k_z + k^t_z \\ \qquad = k_z + k_0(\sin\theta_t\sin\varphi_t + \sin\theta_r\sin\varphi_r) \end{cases} \qquad (D44)$$

Using the SAs (the method (3), i.e., multistatic SA as well as the method (2), i.e., monostatic SA) with respect to the acquired echo signal data for the SAs, arbitrary beamformings can be performed (actually, the processings disclosed in the method (1) or (4) to (7) can yield image signals from the data). Also in the processings for plane wave transmissions (method (1)), by using coding, the SAs can be performed. That is, the signal data for SAs can be obtained by implementing the decoding on the received signals with respect to transmissions of encoded plane waves.

As also disclosed in the method (1), the steering can be performed on the dynamic focusing. In the method (1), when the physical steering with a steering angle α (including a case of zero degree) is performed at the transmission of plane wave, and the steering with a steering angle θ (including a case of zero degree) is performed of the method (1) is performed as well, it can be interpreted that the pane wave is steered with a transmission steering (α+θ) [the finally generated steering angle is the mean]. Therefore, in the method (1), a plane wave is steered at the transmission with the steering angle α, θ or α+θ and at the reception dynamic focusing, the steering with a reception steering angle φ (including a case of zero degree) can be achieved by performing the reception steering of the method (2); then the finally generated steering angle is a mean of all the transmission and the reception steering angles. The steering of plane wave in a software fashion (steering angle θ) is, as mentioned in the method (1), used for reinforcing the physical transmission steering (steering angle α), for purely generating the steering of plane wave in a software fashion, or for performing, in a software fashion, the steering of plane wave at the reception in addition to the reception dynamic focusing (including a case of the steering angle φ is zero degree).

That is, in a 2D case, eqs. (F41), (F42) and (F43) being respective combinations of eqs. (9a) and (19a), eqs. (9b) and (19b) and eqs. (9c) and (19c) are used to similarly perform the beamforming.

$$\exp(ik_x^t x) = \exp\{i(k\sin\theta + k_0\sin\phi)x\} \qquad (F41)$$

$$\exp(i\sqrt{k^2 - (k_x - k_x^t)^2}\,y) = \exp(i\sqrt{k^2 - (k_x - k\sin\theta - k_0\sin\phi)^2}\,y) \qquad (F42)$$

$$\exp(ik_y^t y) = \exp[i\{k\cos\theta + k_0(-1 + \cos\phi)\}y] \qquad (F43)$$

Also in a 3D case, that is, when the plane wave is physically transmitted with elevational (α) and azimuth (β) steering angles (α,β), or at least either steering angle is zero degree, to perform the steering of the plane wave with a steering angle $(\theta_1,\varphi_1)$ and the steered dynamic focusing with a steering angle $(\theta_2,\varphi_2)$ in a software fashion (including a case where at least one steering angle is zero degree), eqs. (G41), (G42) and (G43) being respective combinations of eqs. (C21) and (C41), eqs. (C22) and (C42) and eqs. (C23) and (C43) are used to similarly perform the beamforming. The finally generated steering angle is a mean of all the transmission and the reception steering angles.

$$\exp[i\{k\sin\theta_1(\cos\varphi_1 x + \sin\varphi_1 z)\} + i\{k_0\sin\theta_2(\cos\varphi_2 x + \sin\varphi_2 z)\}] \qquad (G41)$$

$$\exp\left(i\sqrt{\begin{array}{c}(k^2 - (k_x - k\sin\theta_1\cos\varphi_1 - k_0\sin\theta_2\cos\varphi_2)^2 - \\ (k_z - k\sin\theta_1\sin\varphi_1 - k_0\sin\theta_2\sin\varphi_2)^2\end{array}}\,y\right) \qquad (G42)$$

$$\exp[i\{k\cos\theta_1 + k_0(-1 + \cos\theta_2)\}y] \qquad (G43)$$

As mentioned in the method (1), performing the exchanging of the software transmission and reception has the same processings as those of the original beamforming (equivalent). That is, also in these cases, the software transmission and reception can be considered inversely. Also beamformings of various combinations can be performed in a software fashion with respect to arbitrary physical transmission beamformings (for instance, a steered plane wave, a steered fixed focusing beam, a steered dynamic focusing on the basis of SA, a non-steered wave or beam, other various ones). It is possible to perform, in a software fashion, the steerings of a plane wave or a dynamic focusing at the transmission or reception (including a case where at least one steering angle is zero degree) in addition to the physical steering of a generated arbitrary wave or beam (for instance, the above examples including a case where at least one steering angle is zero degree). Particularly, the software plane wave steering is used for reinforcing the physical transmission steering, for purely performing the steering of the physically transmitted arbitrary waves or beams or for performing, in a software fashion, the reception steering in addition to the reception dynamic focusing (including a case where the steering angle φ is zero degree). These are also for 3D beamforming using a 2D array. Others mentioned in the method (1) hold.

For the beamformings in the 2D case with eqs. (F41), (F42) and (F43) and in the 3D case with eqs. (G41), (G42) and (G43), the wavenumber matchings can also be performed with approximate interpolations and with high speeds.

In the 2D case, according to eqs. (7) and (8), the wavenumber matching expressed by eqs. (18b) and (18c) is performed with respect to the 2D Fourier's transform $R'(k_x, k)$ with approximate interpolations [eq. (F44)] and $F(kx',ky')$ is 2D inverse-Fourier's transformed. The approximate processings are not disclosed in the prior art documents.

$$\begin{cases} k'_x = k_x + k^t_x \\ \quad = k_x + k\sin\theta + k_0\sin\phi \\ k'_y = k_y + k^t_y \\ \quad = \sqrt{(sk)^2 - k_x^2} + k\cos\theta + k_0(-1 + \cos\phi) \end{cases} \quad (F44)$$

In the 3D case, according to eqs. (7') and (8'), the wavenumber matching expressed by eqs. (C44) and (D44) is performed with respect to the 3D Fourier's transform $R'(k_x, k, k_z)$ with approximate interpolations [eq. (G44)] and $F(k_x', k_y', k_z')$ is 3D inverse-Fourier's transformed. The approximate processings are not disclosed in the prior art documents.

$$\begin{cases} k'_x = k_x + k^t_x \\ \quad = k_x + k\sin\theta_1\cos\varphi_1 + k_0\sin\theta_2\cos\varphi_2 \\ k'_y = k_y + k^t_y \\ \quad = \sqrt{k^2 - k_x^2 - k_z^2} + k\cos\theta_1 + k_0(-1 + \cos\theta_2) \\ k'_z = k_z + k^t_z \\ \quad = k_z + k\sin\theta_1\sin\varphi_1 + k_0\sin\theta_2\sin\varphi_2 \end{cases} \quad (G44)$$

When performing cylindrical wave transmissions or receptions on the polar coordinate system $(r,\theta)$ (transmissions or receptions, in a radial (r) direction, of waves widely spread in an angle direction (θ)) using a convex-type transducer or a sector scan, or an IVUS etc. (FIG. 7) or using virtual sources set behind physical apertures with arbitrary aperture geometries (FIGS. 8A(a) to (c)), or acquiring echo data for the SAs on the polar coordinate system, similarly to in the method (1), the processing can also be performed with the polar orthogonal coordinate system $(r,\theta)$ instead of the Cartesian orthogonal coordinate system (x,y) (the depth y and lateral x coordinates are replaced by r and θ, respectively) and then, image signals can be directly generated on the Cartesian coordinate system (x,y) or the polar coordinate system $(r,\theta)$. When using the physical aperture element arrays expressed by the polar system or the physical apertures with arbitrary aperture geometries as explained above, the beamformings can also be performed similarly to generate, at an arbitrary distance position, the transmission or reception, or both of plane waves (FIGS. 8B(d) to (f)). Performing such beamformings is equivalent to make a formation of a virtual linear-type aperture array (or a plane wave) at the distance position and then, setting the distance position zero corresponds to the case where a linear-type aperture array is used at the position virtually. The distance position can be set in front of as well as behind the physical aperture and then, the virtual linear-type aperture array (or a plane wave) can be generated at the distance positions. The virtual linear-type aperture array can also be used not as the virtual sources but the virtual receivers, or both virtual sources and receivers. These are also when performing other transmission beamformings or performing beamformings on the spherical coordinate system. Alternatively, in the same way, when performing cylindrical wave transmissions or receptions on the polar coordinate system $(r,\theta)$ (transmissions or receptions, in a radial (r) direction, of waves widely spread in an angle direction (θ)) using a convex-type transducer or a sector scan, or an IVUS etc. (FIG. 7) and using virtual sources set behind physical apertures with arbitrary aperture geometries (FIGS. 8A(a) to (c)), image signals can be directly generated on the Cartesian coordinate system using the method (5). When using the physical aperture element arrays expressed by the polar system or the physical apertures with arbitrary aperture geometries as explained above, the beamformings can also be performed similarly to generate, at an arbitrary distance position, the transmission or reception, or both of plane waves (FIGS. 8B(d) to (f)). Performing such beamformings is equivalent to make a formation of a virtual linear-type aperture array (or a plane wave) at the distance position and then, setting the distance position zero corresponds to the case where a linear-type aperture array is used at the position virtually. The distance position can be set in front of as well as behind the physical aperture and then, the virtual linear-type aperture array (or a plane wave) can be generated at the distance positions. The virtual linear-type aperture array can also be used not as the virtual sources but the virtual receivers, or both virtual sources and receivers. In these cases, the imagings of echo signals and displacement measurements etc. can be performed on the same Cartesian coordinate system consistently. These are also for the polar coordinate system. In these cases, similarly to the method (1), it is possible to perform the processings on arbitrary orthogonal coordinate systems or via transforming the echo signals or measurements to those on other orthogonal coordinate systems. These are also when using 2D arrays for the 3D beamformings. Transmission focusings may also be performed. In these processings, transmission focusing can also be performed. As mentioned above, the virtual source or the virtual receiver are not always positioned behind the physical aperture and can also be set in front of the aperture.

Regardless the geometry of a physical aperture, they can be positioned arbitrarily (patent document 7 or nonpatent document 8). Thus, the present inventions are not limited to these. On the wavenumber matching in these beamformings, approximate solutions can also be calculated with approximate interpolations.

With respect to the received signals, apodizations for the transmission or reception, or the both can be performed at various timings, because the processings are linear. That is, the apodizations can be performed in a hardware fashion when performing the receivings or in a software fashion after performing the receivings. As mentioned above, the apodizations can also be performed at transmissions physically. When performing the wavenumber matching with approximate interpolations, however with high accuracies, on the basis of eqs. (7) and (7'), the approximations are required to be performed with proper over-samplings of data in return an increased calculation amount. In the case, being different from in the case where image signals of arbitrary positions can be generated when no approximate interpolations are performed, it is cautious that the number of data to be used for the Fourier's transforms increases. These processings can be performed similarly to the method (1), and these are also for other methods (3) to (7).

Method (3): Multistatic Type SA

Figure 11:
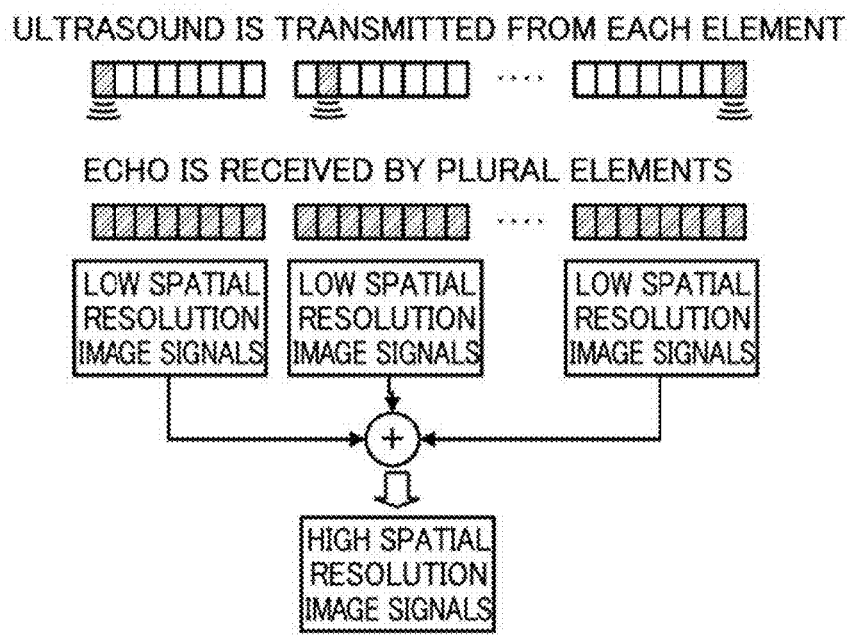
FIG. 11 shows an illustration of a multistatic SA.

FIG. 11 shows an illustration of a multistatic type SA. For the multistatic type SA, an ultrasound is transmitted from one element in an array, and echo is received by the plural elements around the transmission element (generally, including the transmission element). Low resolution image signals are generated every one transmission; and generated plural low resolution image signals are superposed to generate a high resolution image signals. To generate the low resolution image signals, the present invention can also be used.

As mentioned above, generally and traditionally the low resolution echo signals are generated from the echo signals received every the transmissions are performed by the respective transmission elements; and the generated low resolution eco signals are superposed. In contrast, the present invention generates plural sets, respective of which are comprised of signals received at the same positions with respect to the transmission positions; and respective of which are processed by the digital monostatic SA methods to generate plural low resolution image signals and superpose them. In practice, the linear superposition can be performed in a frequency domain prior to the lateral inverse Fourier's transform, which yields a high speed. Specifically, when performing the superposition in the frequency domain, the lateral positions of plural low resolution image signals are adjusted by performing the lateral shifting processings, i.e., by performing the phase rotations in the lateral direction via multiplying the complex exponential functions to data, and then with no approximate interpolations and with high speeds the image signals are generated. The inverse Fourier's transform is performed using IFFT once. To generate the respective low resolution echo signals to be superposed in a spatial domain, the multiplications of complex exponential functions for rotating the phases in the lateral direction (the lateral shifting processings) can also be performed simultaneously when performing the lateral inverse Fourier's transform. In this case, exclusive IFFT can be performed.

Important is that when using the program of monostatic type SA, if s=2, the distance of propagation path with respect to the point of interest, to which distance is y (coordinate y), between the transmission and the reception element positions, which are positioned at y=0 and have the distance between the elements Δx in the x-direction, is converted to y' and further when the steering angle is zero degree, the converted distance y' is expressed by eq. (20a). Also, if s=1, when the steering angle is zero degree, the converted distance about the point of interest, to which distance is y (coordinate y), is expressed by eq. (20b) with respect to the transmission element positioned at y=Y (non-zero) and the reception element positioned at y=0 with the element distance Δx in the x-direction. The coordinates y of the transmission and reception positions can be considered inversely.

$$y' = (y + \sqrt{y^2 + \Delta x^2}) \div 2 \quad (20a)$$

$$y' = y + \sqrt{(Y-y)^2 + \Delta x^2} \quad (20b)$$

When the steering angle is θ (including non-zero degree), the beams are generated by the multistatic SA, to which at least the reception dynamic focusing is implemented (when s=2, the transmission dynamic focusing can also be realized). Waves are transmitted from the respective transmission aperture elements in the transmission effective aperture element array and the waves arriving from the measurement object are received at least by one reception aperture element, in plural reception aperture elements, existing at a different position from that of the transmission element to generate the reception signals (even when one element is used, the instrument of the present invention can also perform the processing). To generate waves that are at least reflected or backscattered waves (s=2), or at least transmission, forward scattered or refracted waves (s=1), the transmission aperture elements are used such that the position has arbitrary x coordinates regardless the x coordinates of reception aperture elements that generate the received signals. The transmission element can also be, positioned at a constant zero y-coordinate, i.e., one of the reception aperture elements in the reception effective aperture element or different element from the reception aperture elements, or positioned at a constant non-zero y-coordinate, i.e., one of the plural transmission aperture elements in the transmission effective aperture element array faced to the reception effective aperture element array (when s=1, the y coordinates of transmission and reception can be considered inversely).

That is, when performing the steering, the above-mentioned data for the monostatic SA processing, comprised of data generated by the combination of the transmission and the reception elements with same distances, are respectively processed using the steering disclosed in the method (2) and similarly, the processing can be performed. These are also when the transmission and the reception steering angles are different. When the steering angle is non-zero and the program of the monostatic SA processing is used, similarly to the case where steering angles are zero degree, the converted distances expressed by eqs. (20a) and (20b) are respectively used for s=2 and 1 with respect to the distance y (y coordinate) to the point of interest. Thus, similarly to the methods (1) and (2), the processing can be performed using zero or non-zero steering angles on the programs that allow steerings.

For the transmission, the plane wave transmission of the method (1) can also be performed, and arbitrary transmission beamformings such as a fixed focusing etc. can also be performed etc.

As other methods, when the y coordinates of the transmission and reception elements are zero, with respect to the same sets of received signals obtained for the same distances Δx in the lateral coordinate for the positions of transmission and reception, using the half distance between the transmission and the reception aperture elements via the point of interest (eq. (20c)) expressed using the steering angle θ, the y coordinate of the point of interest and the distance Δx for s=2, or the distance between the transmission and the reception aperture elements via the point of interest (eq. (20d)) expressed using the steering angle θ, the y coordinate of the point of interest, the y coordinate of the transmission aperture element (y=Y, i.e., non-zero y) and the distance Δx for s=1 (the y coordinates of transmission and reception can also be considered inversely) for the above-disclosed monostatic SA allows generating image signals via spatial corrections of the lateral positions in a frequency domain with respect to the steered image signals and superposition of the corrected image signals, with no approximate interpolations. Although the spatial resolution in the depth direction decreases, a large steering angles can be generated.

$$y'=(y/\cos\theta+\sqrt{y^2+(y\tan\theta-\Delta x)^2})\div 2 \quad (20c)$$

$$y'=y/\cos\theta+\sqrt{(y\tan\theta-\Delta x)^2+(y-Y)^2} \quad (20d)$$

When performing the 3D wave digital signal processing is performed using the 2D aperture element array, for instance, on the Cartesian coordinate system of which y-axis is determined by the direction of a face of flat reception aperture element array and the lateral coordinates x and z are determined such that the axes are orthogonal to the y-axis, similarly to the 2D processing case, the zero or non-zero steering elevational and azimuth angles can be generated regarding the beam direction generated and the axial direction. Waves are transmitted from the respective transmission aperture elements in the transmission effective aperture element array and the waves arriving from the measurement object are received at least by one reception aperture element, in plural reception aperture elements, existing at a different position from that of the transmission element to generate the reception signals. To generate waves that are at least reflected or backscattered waves (s=2), or at least transmission, forward scattered or refracted waves (s=1), the transmission aperture elements are used such that the position has arbitrary x and z coordinates regardless the x and z coordinates of reception aperture elements that generate the received signals. The transmission element can also be, positioned at a constant zero y-coordinate (s=2), i.e., one of the reception aperture elements in the reception effective aperture element or different element from the reception aperture elements, or positioned at a constant non-zero y-coordinate (s=1), i.e., one of the plural transmission aperture elements in the transmission effective aperture element array faced to the reception effective aperture element array (when s=1, the y coordinates of transmission and reception can be considered inversely).

$$y'=(y+\sqrt{y^2+\Delta x^2+\Delta z^2})\div 2 \quad (20e)$$

$$y'=y+\sqrt{(Y-y)^2+\Delta x^2+\Delta z^2} \quad (20f)$$

For the transmission, the plane wave transmission of the method (1) can also be performed, and arbitrary transmission beamformings such as a fixed focusing etc. can also be performed etc.

As other methods, when the y coordinates of the transmission and reception elements are zero, with respect to the same sets of received signals obtained for the same distances Δx and Δz in the lateral coordinates for the positions of transmission and reception, using the half distance between the transmission and the reception aperture elements via the point of interest expressed using the steering elevational and azimuth angles θ and φ, the y coordinate of the point of interest and the distances Δx and Δz for s=2, or the distance between the transmission and the reception aperture elements via the point of interest expressed using the steering elevational and azimuth angles θ and ~, the y coordinate of the point of interest, the y coordinate of the transmission aperture element (y=Y, i.e., non-zero y) and the distances Δx and Δz for s=1 (the y coordinates of transmission and reception can also be considered inversely) for the above-disclosed monostatic SA allows generating image signals via spatial corrections of the lateral positions in a frequency domain with respect to the steered image signals and superposition of the corrected image signals, with no approximate interpolations. Although the spatial resolution in the depth direction decreases, a large steering angles can be generated.

To generate image signals that expresses unknown wave sources or the wave propagations generated by the unknown sources (passive mode), the beamformings can also be performed via setting estimates of y coordinates of the unknown sources at the y coordinates of the transmission aperture elements. It is also effective to perform the observing with changing the setting of y-coordinates of transmission elements by trial and error. For instance, it is better that the image is to be formed, the spatial resolution increases, the signal amplitude increases, the contrast increases etc., and using these as criteria for the judgement, the series of processings can also be performed automatically.

As mentioned later, as information about the wave source positions or the transmission aperture elements, the positions with respect to the reception aperture elements, the directions of positions or distances to the positions, the direction of aperture or the propagation directions of generated waves can also be given occasionally. The time when waves are generated by arbitrary wave sources can also be given. The wave sources can also be observed using other instruments. Otherwise, the received signals can also convey the information or other waves can be generated, propagating with higher speeds, and can also convey the information etc.

The beamformings can also be performed by calculating the directions of wave source positions or the wave propagation directions via estimating the 1st moment (center) frequencies of the multidimensional spectra or the instantaneous frequencies with respect to the received signals; and also by regulating the transmission or reception steering angle. Alternatively, with respect to the generated image signals, the beamformings can also be performed by calculating the directions of wave source positions or the wave propagation directions via estimating the 1st moment (center) frequencies of the multidimensional spectra or the instantaneous frequencies; and also by regulating the transmission or reception steering angle. These processings can also be performed using plural reception apertures or plural reception effective apertures, the positions and directions of the wave sources can also be calculated geometrically. These processings are useful and can also be applied to other beamformings.

As explained in the monostatic SA (method (2)), using the multistatic SA (method (3)) allows performing arbitrary beamformings by using the echo data acquired for the multistatic SA (In fact, the image signals can be generated by implementing the method (1) or (4) to (7) on the data). Although the larger amount of data to be used for the multistatic SA than that for the monostatic SA can be effective, the calculation amount increases. For plane wave processing (method (1)), the SAs can also be performed using the coding. When performing cylindrical wave transmissions or receptions on the polar coordinate system (r,θ)

(transmissions or receptions, in a radial (r) direction, of waves widely spread in an angle direction (θ)) using a convex-type transducer or a sector scan, or an IVUS etc. (FIG. 7) or using virtual sources set behind physical apertures with arbitrary aperture geometries (FIGS. 8A(a) to (c)), or acquiring echo data for the SAs on the polar coordinate system, similarly to in the method (1), the processing can also be performed with the polar orthogonal coordinate system (r,θ) instead of the Cartesian orthogonal coordinate system (x,y) (the depth y and lateral x coordinates are replaced by r and θ, respectively) and then, image signals can be directly generated on the Cartesian coordinate system (x,y) or the polar coordinate system (r,θ). These can also be performed when performing other transmission beamformings or performing beamformings on the spherical coordinate system. Alternatively, in the same way, when using a convex-type transducer or a sector scan, or an IVUS etc. and using virtual sources set behind physical apertures with arbitrary aperture geometries, image signals can be directly generated on the Cartesian coordinate system using the method (5). In the case, the imagings of echo signals and displacement measurements etc. can be performed on the same Cartesian coordinate system consistently. In these cases, similarly to the method (1), it is possible to perform the processings on arbitrary orthogonal coordinate systems or via transforming the echo signals or measurements to those on other orthogonal coordinate systems. Otherwise, the beamformings disclosed in the paragraphs 0209 to 0220 etc. in the method (1) and in the paragraphs 0238 etc. in the method (2) can be performed in the same ways and for instance, virtual sources or virtual receivers can be used at arbitrary positions regardless the geometry of physical aperture (patent document 7 and nonpatent document 8). The inventions are not also limited to these (also below).

Also as disclosed above, although the depth resolution decreases, large steering angles can also be generated using other steering methods. In the cases, different transmission and reception steerings can also be generated. The converted distances expressed using the lateral distances between the transmission and the reception elements, the transmission and reception steering angles and for the transmission cases, the distances between the transmission and the reception elements can be calculated and used.

Basically, the steerings to be performed using the method (3) are also performed in a software fashion. The apodizations can also be performed at the transmissions or are not performed. The reception apodizations are linear processings and then can be performed at various timings (in a hardware or software fashion). For instance, when performing the software apodizations, the calculation amounts being dependent on the effective aperture width etc. that determines the number of low resolution echo signals to be generated are considered to allow performing the apodizations simply at a proper timing. For instance, the apodizations can be performed with respect to the respective sets for generating the low resolution echo signals, or the generated low resolution signals in a frequency or spatial domain.

Also for the application of the monostatic SA (method (2)), the wavenumber matching can also be performed with above-disclosed approximate interpolations and with high speeds. For the approximate interpolations, the linear interpolations or using the most neighborhood data themselves approximately can also be performed, or high order approximate interpolations or using the sinc functions can also be performed. To increase the accuracies of the wavenumber matchings to be performed with approximate interpolations, proper over-samplings of data are required in return an increased calculation amount. In the case, being different from in the case where image signals of arbitrary positions can be generated when no approximate interpolations are performed, it is cautious that the number of data to be used for the Fourier's transforms increases.

Also for the adjusting the lateral positions of the low resolution image signals to be superposed (disclosed in the paragraphs 0241, 0245 and 0248), instead of the high accuracy processing that the complex exponential functions are multiplied in a frequency domain to rotate the phase in the lateral direction, spatial shifting processing can also be performed with approximate interpolations to achieve the higher speed processings. For the approximate interpolations, the linear interpolations or using the most neighborhood data themselves approximately can also be performed, or high order approximate interpolations or suing the sinc functions can also be performed. Also in the cases, to increase the accuracies of approximate interpolations, proper over-samplings of data are required in return an increased calculation amount.

Method (4); Fixed Focusing

Figure 12:
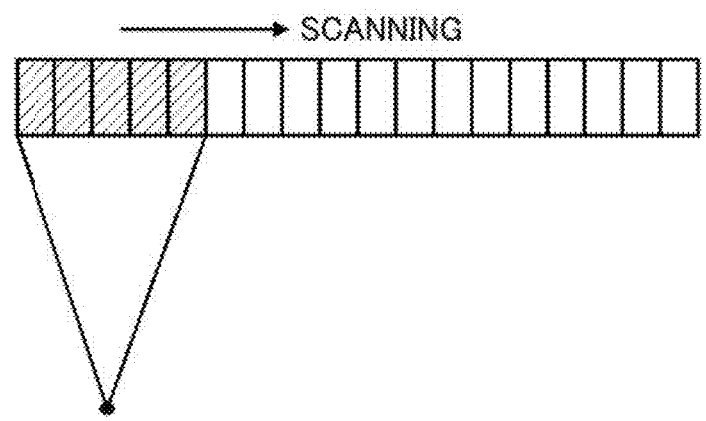
FIG. 12 shows an illustration of a fixed focusing performed using a linear array-type transducer.

FIG. 12 shows an illustration of a fixed focusing performed using a linear array-type transducer. The fixed focusing is to make ultrasound waves transmitted from the respective transmission elements to arrive at the focusing position at the same time by setting delays for the transmissions on the respective transmission elements (channels). The measurement object is scanned by receiving waves using the partial or whole physical aperture of the array type transducer as an effective aperture. Off course, the steering can also be performed. The angles of transmission and reception steerings can also be different.

The fixed focusing can be performed to generate image signals using the method (1), i.e., beamforming for plane wave transmission or the method (3), i.e., the multistatic type SA, or the combinations of the method (1) for the beamforming for plane wave transmission and the method (2) or (3) for the reception dynamic focusing. In the cases, the following three methods can be performed.

(i) Implementing image signal generation processing once on superposing of the respective reception signals obtained at the effective aperture width.

(ii) Superposing of general low resolution image signals generated using reception signals obtained with respect to the respective transmissions.

(iii) Superposing of low resolution image signals generated performing the same processings as those of the multistatic SA, i.e., the respective low resolution image signals are generated with respect to the respective data sets comprised of data with same position relationships between the transmissions and the receptions.

When performing cylindrical wave transmissions or receptions on the polar coordinate system (r,θ) using a convex-type transducer or a sector scan, or an IVUS etc. or using virtual sources set behind physical apertures with arbitrary aperture geometries, the processing can also be performed with the polar orthogonal coordinate system (r,θ) instead of the Cartesian orthogonal coordinate system (x,y) (the depth y and lateral x coordinates are replaced by r and θ, respectively) and then, image signals can be directly generated on the polar coordinate system (r,θ). As mentioned above, approximate interpolations are required after generating the image signals. These are also when performing the transmission and the reception beamformings on the spherical coordinate system. In the prior art document 6, a beamforming method for the transmission focusing with approximate processings is disclosed and similarly, the results are obtained on the polar coordinate system (r,θ). The inventor of the present invention also invented the beamforming methods (5), (5-1), (5-1') and (5-2) for generating image signals directly on the Cartesian coordinate system as the results of beamformings with respect to transmissions and receptions performed on the polar coordinate system, the spherical coordinate system or arbitrary orthogonal curvilinear coordinate systems. In the case, the imagings of transmission waves, reflected waves, scattered waves or attenuated waves etc. and displacement measurements etc. can be performed on the same Cartesian coordinate system consistently. In these cases, similarly to the method (1), it is possible to perform the processings on arbitrary orthogonal coordinate systems or via transforming the echo signals or measurements to those on other orthogonal coordinate systems. Otherwise, the beamformings disclosed in the paragraphs 0209 to 0220 etc. in the method (1) and in the paragraphs 0238 etc. in the method (2) can be performed in the same ways and for instance, virtual sources or virtual receivers can be used at arbitrary positions regardless the geometry of physical aperture (patent document 7 and nonpatent document 8). The inventions are not also limited to these (also below). Also, as mentioned above, the steering can also be performed. The cases where the steering angles of physical transmission beamforming and software reception beamforming are different can also be realized. In addition, software transmission steering can also be implemented. In the cases, the steering angle can also be different from other steering angles. For the reception, physical beamformings can also be performed. It is possible to interpret the transmission and reception inversely. The apodizations can also be performed at the transmissions and with respect to the received signals, the reception apodization processings can also be performed (in a hardware fashion at the receptions or in a software fashion after the receptions). The software apodizations can be performed according to the method (1) or (3). Similarly, the apodizations can also be performed when the combination of the method (1) for the plane wave transmission beamforming and the method (2) or (3) for the reception dynamic focusing.

Theoretically and in practice, the method (4) using the method (1) for processing the plane wave allows arbitrary physical transmissions or the reception beamformings. By performing the processings as mentioned above, various combinations of beamformings can be performed (For instance, for the plane wave transmission and the reception dynamic focusing, the proceedings such as focusings, steerings, apodizations etc. that can be performed physically, at transmissions and receptions, by using calculators or exclusive devices etc. others from those performed in software beamformings using calculators or exclusive devices etc., can be respectively performed, or both the physical and software processings can be performed. Also the transmissions and receptions can be considered inversely as mentioned above). For instance, as mentioned in the paragraphs 0107, 0110, 0363, 0365, 0366 etc., regardless the physical focuses (subaperture widths, distances or depths, positions etc.) being same or not, or the physical transmission steering angles being same or not, the above-mentioned processings mentioned in the method (4) is effective for simultaneous transmissions of plural beams including physically steered or non-steered ones, or occurrences of interferences of beams or not, such transmissions, however, at different timings, but, on the same phase of the object, or the mixed transmissions. Particularly, the method (i) that performs the processing once for generating image signals with respect to the superposition of the respective reception signals obtained at effective aperture widths yields a high frame rate. Using the method (4) does not always require beamformings to be performed at positions where the interferences of beams do not occur (mentioned in the paragraphs 0030, 0362, etc.). Even if overlapped subapertures are simultaneously used etc. or the interferences occur, the same processings realize the high frame rate. At the time, if respective the software transmission steering angles and the software reception steering angles to be implemented on the plural focused beams are same, the above-mentioned processings can be performed. When plural transmissions such as plural positioned focusings or transmission dynamic focusing are performed on the same phase of the object, the superposition of received signals can also be processed similarly. Regarding the received signals obtained at the same phase of the object, if the received signals are superposed such that the positions (time) of signals are adjusted on the basis of the transmission element position or the timing, all the cases can be processed by the method.

When either the software transmission steering angles or the software reception steering angles to be implemented on the plural focused beams include at least a different angle, the received signals are separated into those with same steering angles, and the respective separated, received signals with the same steering angles are processed, after which the processed results are superposed in a frequency domain to generate the final result. With respect to one physical transmission beam (steered or non-steered one), plural steered reception beams (a zero steering angle can be included) can also be generated and similarly processed. Also when performing plural different physical steerings, the received signals are separated into those with same steering angles, and the respective separated, received signals are processed to generate the results, or the received signals are also processed without performing the separation. When performing the separations, the superpositions can also be performed in a spatial or frequency domain.

When physically performing the transmitting in plural directions, specific transmission and reception steerings can also be implemented on the respective physical transmission steerings. In the cases, the signals generated by the respective transmitted beams can be separated in a frequency domain or the independent component analysis (many literatures exist such as a rather classical one, Te-Won Lee, Independent Component Analysis: Theory and Applications, Springer, 1998 as well as others) and the processing can be performed. Analogue devices can also be used. For instance, the same steering angles can be set on the software transmission or reception steering angle as that of the physical steering angle used. Other signal separation methods are also mentioned (for instance, the paragraph 0368).

Here, mentioned is the using of these methods on various fixed focusing processings. These methods are not limited to these and can also be used for other transmission beamformings. Similarly, the beamformings with new properties that cannot be achieved by a single beamforming by performing plural transmissions or receptions of waves or ultrasounds with different parameters such as a focusing (multi-focusings that generate plural different focusing positions with respect to the effective aperture) or a non-focusing, a steering (plural steerings with different steering angles) or a non-steering, an apodization (changeable with positions) or a non-apodization, an F-number, a transmission ultrasound frequency or a transmission bandwidth, a reception frequency or a reception bandwidth, a pulse shape, a beam shape etc. For instance, it is known that the superposing yields plural focusings or wide bandwidths in the depth and lateral directions (high spatial resolutions). These processings can be speeded up. To obtain the harmonic waves, the so-called pulse inversion method (transmissions of pulses with inverse polarities as a ultrasound parameters) etc. can be performed by superposing the received signals and similarly, the high speed processing can be performed. Off course, after performing the beamformings, the received signals can also be superposed. More than two plural beams can also be superposed.

On the basis of the considerations of the transmissions and receptions in an inverse fashion, the above-mentioned processings can also be performed simultaneously on the reception beamforming(s). Otherwise, the above-mentioned processings can also be performed on both transmission(s) and reception(s).

When the separated beamformings are performed, parallel processings can also be performed. The separations can be performed the position in an ROI as well as the above-mentioned various parameters of waves or ultrasounds such as a steering angle etc. One reception signal can also be used for various purposes such as imaging, measurement, treatment etc. via generating, by performing beamformings, informative waves (including much information) such as transmission signals, reflection signals, scattering signals, attenuation signals etc. with high accuracies and high spatial resolutions and performing post-processings such as filtering to yield signals adapted for the respective purposes. According to the respective purposes, proper beamformings can also be performed and the processings can also be performed in a parallel fashion.

The present invention allows performing beamformings for such as arbitrary beam transmissions such as fixed, focused beams etc., arbitrary wave transmissions (including non-beamformed waves), superposition of transmissions of plural beams or waves and simultaneous transmissions of plural beams or waves. That is, whenever any single or plural transmissions are performed, "the reception beamformings" (dynamic focusing etc.) can be performed at once. Plural beamformings can also be performed by using the multi-directional synthetic aperture (SA) method (past invention of the inventor of the present invention) and in the cases, similarly the processings can be performed with high speeds. The present inventions are not limited to these.

One of the features of present invention is to perform the wavenumber matchings with no approximate interpolations. However, also in the method (4) using the above-mentioned methods (1) to (3), similarly to the methods (1) to (3), approximate interpolations can be performed on the wavenumber matchings (approximate wavenumber matchings mentioned for the respective beamformings) and the beamformings can also be completed with high speeds. To increase the accuracies of the wavenumber matchings to be performed with approximate interpolations, proper over-samplings of data are required in return an increased calculation amount. In the case, being different from in the case where image signals of arbitrary positions can be generated when no approximate interpolations are performed, it is cautious that the number of data to be used for the Fourier's transforms increases.

Method (5): Image Signal Generation on Polar Coordinate System

Method (5) is used to generate image signals on the Cartesian coordinate system when performing, by using the convex-type array or sector scanning, IVUS etc., the transmissions and receptions of ultrasound cylindrical waves (or the partial waves) on the 2D polar coordinate system (r,θ) (FIG. 7). The methods (1) to (4) and (6) can be performed.

Below explained are the expression of Fourier's transform using the polar coordinate system. The 2D Fourier's transform is expressed by eq. (22).

$$F(k_x,k_y)=\iint f(r,\theta)e^{-i(k_x x+k_y y)}dxdy \quad (22)$$

The reception signals are expressed as f(r,θ) on the polar coordinate system and then, eq. (23) holds.

$$x=r\sin\theta, y=r\cos\theta \quad (23)$$

Then, eq. (24) can be obtained via the Jacobi operation. Thus, the wave expressed on the polar coordinate system can be decomposed into plane wave components ($k_x,k_y$) on the Cartesian coordinate system. Waves expressed on arbitrary orthogonal curvilinear coordinate systems can also be decomposed into the plane wave components ($k_x$, $k_y$) similarly.

$$F(k_x,k_y)=\iint f(r,\theta)|r|e^{-i(k_x r \sin\theta+k_y r\cos\theta)}drd\theta \quad (24)$$

Figure 13:
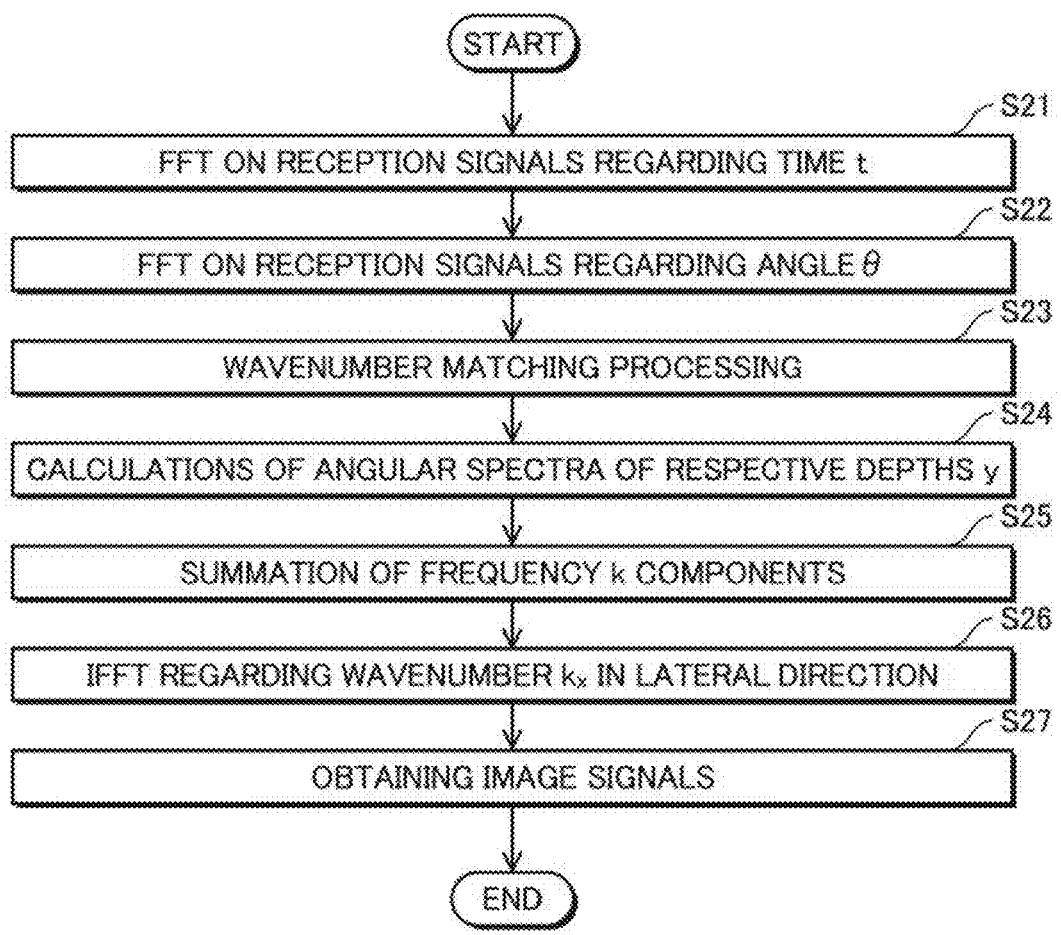
FIG. 13 shows a flowchart about the digital signal processing for a cylindrical wave transmission.

Method (5-1): Image Signal Generation of Cylindrical Wave Transmission or Reception FIG. 13 shows a flowchart about the digital signal processing for a cylindrical wave transmission. According to eq. (24), the Fourier's transform along the aperture in the angle direction θ is expressed as eq. (25).

$$U(k_x,k_y)=\int u(k,\theta)r_0 e^{-i(k_x r_0 \sin\theta+k_y r_0 \cos\theta)}d\theta \quad (25)$$

or $$U(k_x,k_y)=\int u(k,\theta)r_0 e^{-i(k_x x_0+k_y y_0)}d\theta \quad (25')$$

Here, $r_0$ is a curvature radius of the convex-type transducer; $x_0$ and $y_0$ are x and y coordinates expressing the array element positions (those of convex-type array transducer). At the step S21, the received signals are Fourier's transformed (FFT) regarding the time t and at the step S22, the received signals are Fourier's transformed (FFT) regarding the angle θ; achieving the decomposition of the signals received on the polar coordinate system into the plane wave components ($k_x,k_y$) on the Cartesian coordinate system.

Thus, for instance, the wavenumber matching expressed by eq. (26) is implemented on the spectra at the step S23 and by subsequently performing the inverse Fourier's transforms on the space (x,y), the image signals are generated.

$$U'(k_x,k_y)=U(k_x,k_y)e^{-ik(r-r_0)} \quad (26a)$$

Moreover, at the step S24, the following complex exponential function is multiplied to the 2D spectra to calculate the angular spectra at the respective depths.

$$\exp(i\sqrt{k^2-k_x^2}y) \quad (26b)$$

Otherwise, the calculations of the steps 23 and 24 can be performed inversely.

Otherwise, without using eqs. (26a) and (26b), according to the method (5), the following complex exponential function is straightforwardly multiplied to yield the angular spectra at the respective depths y as well as to perform the wavenumber matching.

$$\exp\{i(\sqrt{k^2-k_x^2}+k)y\} \quad (26c)$$

Moreover, for instance, at the step S25, summing of the angular spectra is performed with respect to the frequency (k) components and at the step S26, the inverse Fourier's transform (IFFT) is performed in the lateral direction $k_x$ and at the step S27, the image signals are generated. Purely, the 2D inverse Fourier's transform can also be implemented.

When performing the steering, according to eqs. (9a) to (9c) of the method (1), with performing the wavenumber matchings in the x and y directions, the spatial resolutions can be obtained. As mentioned later, when the calculations are performed on the polar coordinate system (r,θ), the steering angle is set on the polar coordinate system (an angle between the steered direction and the radius direction) and similarly, steering can also be performed. Similarly to the method (1) etc. and other methods, physical steering can also be performed, software steerings of transmission, reception or both the transmission and reception can also be performed, the combinations of the physical and software steerings can also be performed.

This method is used for performing beamformings to directly generate image signals on the Cartesian coordinate system (x,y) from the signals acquired on the polar coordinate system (r,θ) via no approximate wavenumber matchings and the coordinate conversion and with high speeds and with high accuracies. Similarly to the plane wave transmission performed using a linear array-type transducer, steering can also be performed with respect to the cylindrical wave on the polar coordinate system. Similarly, the cases where steering angles of the transmission and reception beamformings are different etc. can also be processed. The steerings can also be performed in a software fashion. Apodizations can also be performed. When using the cylindrical wave, at plural positions on the z axis orthogonal to the 2D polar coordinate system (i.e., the z-axis of the cylindrical coordinate system (r,θ,z)), the above-mentioned transmissions can be performed simultaneously and reception can be performed, or the above-mentioned transmissions can be performed at different times, however, at the same phase of the object, and reception performed can be superposed. For these, the above-mentioned processings can also be performed. In the z-axis, focusing can also be performed using an analogue device (lens), or arbitrary processings can also be performed using the digital signal processing of the present invention. When the wave propagation directions point to an origin of the polar coordinate system, the beamformings can be performed similarly (For instance, useful for a HIFU treatment, various type imagings using circular array-type transducers that encircles the objects or a CT etc.). Off course, in the cases, only the reception beamformings can also be performed and similarly can be processed. With respect to the received signals expressed on the polar coordinate system (r,θ), the processings mentioned in the method (1), however, with exchanging the Cartesian coordinate system by the polar coordinate system (r,θ), can also be performed to generate image signals on the polar coordinate system (r,θ) as mentioned above. When generating the image signals on the Cartesian coordinate system from the results, approximate interpolations are performed as post-processings. In these, steering can also be performed similarly. The methods (2) to (4) and (6) can also be performed similarly.

Also when the received signals are expressed as digital signals on the Cartesian coordinate system (x,y), inversely to eq. (22), f(x,y) is Fourier's transformed with respect to the radius r and the angle θ, and image signals can also be generated on the polar coordinate system (r,θ) after all. Otherwise, using the respective methods also allows generating image signals on the Cartesian coordinate system (x,y). Steering and apodization can also be performed similarly.

As shown in FIGS. 8B(d) to (f), when using the physical aperture element arrays expressed by the polar system or the physical apertures with arbitrary aperture geometries as explained above, the beamformings can also be performed similarly to generate, at an arbitrary distance position, the transmission or reception, or both of plane waves. The image signals can be generated on the Cartesian coordinate system, the polar coordinate system or orthogonal curvilinear coordinate system set according to the physical aperture geometry. Performing such beamformings are equivalent to make a formation of a virtual linear-type aperture array (or a plane wave) at the distance position and then, setting the distance position zero corresponds to the case where a linear-type aperture array is used at the position virtually. The distance position can be set in the front of as well as behind the physical aperture and then, the virtual linear-type aperture array (or a plane wave) can be generated at the distance positions. Virtually, the plane wave can also be steered or the linear-type aperture array can also be slanted (Virtually, the mechanical steering can also be performed). Off course, if required, the physical aperture can also be mechanically steered. The transmissions or the receptions of such plane waves can be performed on the basis of the transmissions and the receptions of the cylindrical waves, respectively, and occasionally, other beamformings can also be performed.

Method (5-1'): Image Signal Generation Using Virtual Source and Aperture Array with Other Arbitrary Geometries In cases where waves are transmitted from arbitrary aperture geometries such as a linear-type array transducer as well as the circular aperture arrays and specifically, generations of partial cylindrical waves using virtual sources set behind the physical apertures are explained (FIGS. 8A(a) to (c)).

(i) When using the reception signals acquired for monostatic SAs, the reception signals stored in memories etc., i.e., the reception signals received by the respective transmission elements themselves, are Fourier's transformed and if necessary, the calculated spectra are multiplied with complex exponential functions to express the responses with respect to the waves transmitted from the virtual source as the digital signals on the polar coordinate system (r,θ), and the method (5) or (5-1) can be used to generate image signals on the Cartesian coordinate system (x,y) directly. Alternatively, after the received signals are expressed as the digital signals on the polar coordinate system (r,θ) in the same way, the processings mentioned in the method (1), however, with exchanging the Cartesian coordinate system by the polar coordinate system (r,θ), can also be performed to generate image signals on the polar coordinate system (r,θ). Off course, the monostatic processings in the method (2) can be also performed on the polar coordinate system (r,θ).

(ii) When using the reception signals acquired for multistatic SAs, the reception signals stored in memories etc., i.e., the reception signals received at the surrounding reception elements of the respective transmission elements, are Fourier's transformed and if necessary, the calculated spectra are multiplied with complex exponential functions to express the responses with respect to the waves transmitted from the virtual source as the digital signals on the polar coordinate system (r,θ), and the method (3) can be used to perform the multistatic SA. Alternatively, the method (5) can be used, or after superposing the digital reception signals at the respective reception elements, the method (5-1) can be used to generate image signals on the Cartesian coordinate system (x,y) directly. Otherwise, after superposing the digital reception signals at the respective reception elements in the same way, the processings mentioned in the method (1), however, with exchanging the Cartesian coordinate system by the polar coordinate system (r,θ), can also be performed to generate image signals on the polar coordinate system (r,θ). Off course, without performing the superposition, the multistatic processings in the method (3) can also performed on the polar coordinate system (r,θ).

(iii) In these processings, to omit the processings for rewriting the reception signals, received at the physical aperture array, by the digital signals on the polar coordinate system (r,θ), delay patterns for the elements with respect to the transmissions or the receptions are used to perform the transmissions and the receptions such that the reception samplings of the received signals are performed on the polar coordinate system originally. And, using the method (2) or (3), which is on the basis of the method (5) or (5-1), can generate image signals directly on the Cartesian coordinate system (x,y). Alternatively, after obtaining the digital signals on the polar coordinate system (r,θ) in the same way, the processings mentioned in the methods (1) to (3), however, with exchanging the Cartesian coordinate system by the polar coordinate system (r,θ), can also be performed to generate image signals on the polar coordinate system (r,θ).

(iv) Also, in the same way, on the above-mentioned (i) to (iii) in the cases where the partial cylindrical wave is generated using the virtual source behind the arbitrary aperture geometry (FIGS. 8A(a) to (c)), the reception signals stored in memories etc., i.e., the reception signals received by the respective elements, are Fourier's transformed; and the calculated spectra are multiplied with complex exponential functions (times required) or approximate interpolations are performed to rewrite the reception signals by the digital signals on the Cartesian coordinate system (x,y); and f(x,y) is Fourier's transformed in the directions of a radius r and an angle θ (inversely to eq. (22) in the method (5-1)) to generate image signals on the polar coordinate system (r,θ) after all, or using the respective methods can also generate image signals on the Cartesian coordinate system (x,y). When using orthogonal curvilinear coordinate systems (curvilinear coordinate systems) set according to the aperture geometry, image signals can be generated similarly.

Otherwise, on (i) to (iv), various beamformings etc. mentioned in the method (5-1) can be performed.

As mentioned in the method (1) etc., when a cylindrical wave is transmitted (transmission delays can be used) using the virtual source set behind arbitrary aperture (one of apertures of a linear-type array transducer or other types, or quasi-array apertures generated by mechanical scanning etc.) (FIGS. 8A(a) to (c)), the transmission is encoded by implementing the coding on the signals of the respective transmission elements (channels) similarly to the cases of a plane wave transmission; and the received signals are decoded for generating the reception signals for SA processings. Then, by using the above-mentioned processings, image signals are generated directly on the Cartesian coordinate system or arbitrary orthogonal curvilinear coordinate systems such as the polar coordinate system etc. Also, not virtual sources but virtual receivers can also be set and the virtual receivers can also work as the virtual sources.

Also, as mentioned in the method (1) etc., when a cylindrical wave is transmitted (transmission delays can be used) using the virtual source set behind arbitrary aperture (one of apertures of a linear-type array transducer or other types, or quasi-array apertures generated by mechanical scanning etc.) (FIGS. 8A(a) to (c)), using the above-mentioned methods allows the following processings.

(A) With respect to the reception signals expressed on the Cartesian coordinate system (x,y), obtained using the linear-type array transducer or the mechanical scanning, the method (1) itself is used to generate image signals on the Cartesian coordinate system.

(B) With respect to the reception signals received at the reception positions by using the linear-type array transducer or the mechanical scanning, the spectra calculated by (fast) Fourier's transform in the y direction are multiplied with complex exponential functions to perform the spatial shiftings of the signals in the y direction such that on the polar coordinate system (r,θ) having the origin at the position of virtual source, the positions of signals are corrected to the r positions under θ determined by the reception positions; and the method (5) or (5-1) is implemented to the data to generate image signals on the Cartesian coordinate system (x,y) or the polar coordinate system (r,θ). Although not the spatial shiftings using the complex exponential functions but approximate spatial shiftings by zero padding in the signal values in the r coordinates can also be performed, to increase the accuracies of the approximations, proper over-samplings of the received signals are required, i.e., AD convertors with high sampling rates or many memories are required. It is cautious that the number of data to be used prior to the Fourier's transforms increases.

(C) With respect to the reception signals received by arbitrary aperture geometries except for a linear-type array transducer and quasi-linear type array apertures generated by mechanical scanning etc., the method (5) or (5-1) is implemented and in the same way, image signals are generated on the Cartesian coordinate system (x,y), the polar coordinate system (r,θ), the orthogonal curvilinear coordinate system (curvilinear coordinate system) set according to the aperture geometry.

(D) Not virtual sources but virtual receivers can also be used, or the virtual receivers can also work as the virtual sources.

As the results of these methods (5-1'), for instance, using other type transducers or other mechanical scanning such as a convex-type or sector-type transducer as shown in FIG. 7 (figures of the corresponding mechanical scanning are omitted) can also generate image signals on the Cartesian coordinate system (x,y), the polar coordinate system (r,θ), the orthogonal curvilinear coordinate system (curvilinear coordinate system) set according to the aperture geometry.

Otherwise, when the virtual linear-type array transducer is realized using the physically other type array transducers inversely (for instance, a physical convex-type array transducer is used, as shown in FIGS. 8B(d) to (f), when the virtual source or the virtual receiver is set at the position of physical aperture, or behind or in front of the physical aperture), image signals can also be generated in the same way on the Cartesian coordinate system (x,y), the polar coordinate system (r,θ), the orthogonal curvilinear coordinate system (curvilinear coordinate system) set according to the aperture geometry.

Also, in special cases, for instance, when using the linear-type array transducer physically, applications of the generations of cylindrical waves using virtual sources or virtual receivers set behind the physical aperture allows the generations of image signals in the cases where at arbitrary distance positions, a plane wave widely spread in a lateral direction or a virtual linear-type array transducer is generated (FIG. 8B(G)).

In these cases, the transmissions to be generated or wave receptions can also be steered, or the apertures can also be slanted virtually (mechanical scanning is virtually performed). Off course, if required, physical apertures can also be mechanically scanned.

Method (5-2): Image Signal Generation Using Fixed Focusing

Figure 14:
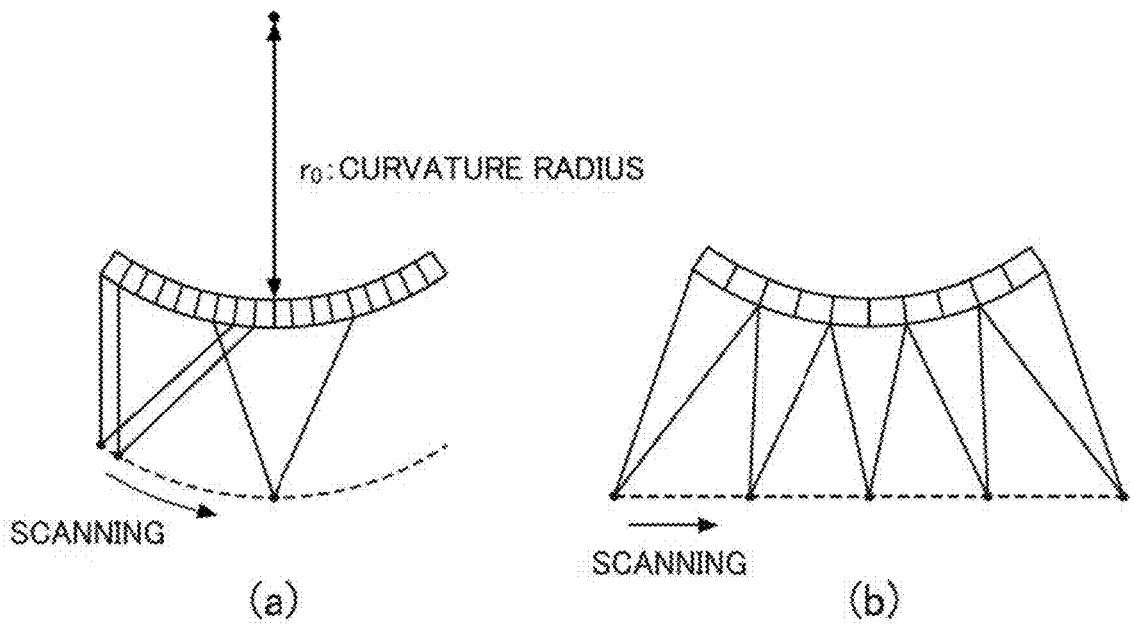
FIG. 14 shows an illustration of a fixed focusing performed using a convex-type transducer.

FIG. 14 shows an illustration of a fixed focusing performed using a convex-type transducer. Also when using a convex-type transducer, the fixed focusing can be performed. For instance, FIGS. 14(a) and (b) respectively shows cases where the fixed focus positions are equal from the respective effective aperture and arbitrarily set. Similarly to when using a linear-type array transducer (method (4)), image signals can be generated using the same calculations as those performed when the cylindrical wave is transmitted. That is, on the basis of the processings of the method (1) or (3), the following three methods can be performed.

(i) Implementing image signal generation processing once on superposing of the respective reception signals obtained at the effective aperture width.

(ii) Superposing of general low resolution image signals generated using reception signals obtained with respect to the respective transmissions.

(iii) Superposing of low resolution image signals generated performing the same processings as those of the multistatic SA, i.e., the respective low resolution image signals are generated with respect to the respective data sets comprised of data with same position relationships between the transmissions and the receptions.

By performing the above-mentioned processings, image signals can be generated directly on the Cartesian coordinate system. And, it is also possible to generate image signals on the polar coordinate system by implementing the method (4) with the axes of the polar coordinate system. Similarly, steering and apodization can also be performed. Regarding the direction of z-axis, similar processings to those of the method (5-1) can be performed.

Also when the received signals are expressed as digital signals on the Cartesian coordinate system (x,y), by implementing Fourier's transforms on f(x,y) regarding the radius r and the angle θ, image signals can be generated on the polar coordinate system (r,θ) after all or image signals can also be generated on the Cartesian coordinate system (x,y) using the respective methods. Steering, apodization and processing in the z-axis can also be performed similarly.

When performing the steering, according to the method (4), the spatial resolution can be obtained together with performing the wavenumber matchings in the x and y directions. As mentioned later, when performing the calculations on the polar coordinate system (r,θ), similarly the steering can also be performed by setting the steering angle (an angle between the steered direction and the radius direction) on the polar coordinate system similarly. Similarly to the method (1) etc. and other methods, physical steering can also be performed, software steerings of transmission, reception or both the transmission and reception can also be performed, the combinations of the physical and software steerings can also be performed.

Also, when using virtual sources or virtual receivers, by setting virtual apertures in front of or behind the physical apertures etc. mentioned in the method (5-1'), the above-mentioned, transmission fixed focusing can be performed. For instance, a linear-type array transducer can be realized virtually. Otherwise, transducers with arbitrary aperture geometries can also be realized. Image signals are generated on the Cartesian coordinate system, the polar coordinate system or the orthogonal curvilinear coordinate system. Similarly to the method (1) etc. and other methods, physical steering can also be performed, software steerings of transmission, reception or both the transmission and reception can also be performed, the combinations of the physical and software steerings can also be performed. In these cases, the transmissions to be generated or wave receptions can also be steered, or the apertures can also be slanted virtually (mechanical scanning is virtually performed). Off course, if required, physical apertures can also be mechanically scanned.

As mentioned above, the beamformings of the methods (1) to (4) can be performed, however, not limited to these. The adaptions of these approaches to arbitrary beamformings yield the same effects. Particularly, when using the method (4), the reception beamforming can be performed with respect to any transmission beams or waves in addition to the transmission fixed focusing. Off course, similarly the beamformings can also be performed on the simultaneous reception signals received with respect to the simultaneous transmissions of plural different beams or waves, or the superposition of reception signals with respect to the respective transmissions.

Method (5-3): Image Signal Generation Using Signal Reception on Spherical Coordinate System When using the wave aperture element array with a spherical kernel geometry, 3D digital wave signal processing can be performed. For instance, when using the type reception aperture element array, receptions of waves are performed on the spherical coordinate system (r,θ,φ) and then, the reception signals of received waves are expressed by f(r,θ,φ). In this case, similarly to using the 2D polar coordinate system (r,θ), various beamformings can be implemented using the Jacobi operation.

Concretely, to decompose the received waves into plane waves on the Cartesian coordinate system (x,y,z), 3D Fourier's transform is implemented on the reception signal f(r,θ,φ), expressed by eq. (27) expressed in the wavelength or frequency domain $(k_x,k_y,k_z)$ with respect to the Cartesian coordinate system (x,y,z). Moreover, the calculation of eq. (28) using the Jacobi operation using x=r sin θ cos φ, y=r cos θ and z=r sin θ sin φ on the eq. (27) can generate image signals directly on the Cartesian coordinate system with no approximate interpolations. Off course, the beamformings of the methods (1) to (4) and (6) can be performed, however, not limited to these. The adaptions of these approaches to arbitrary beamformings yield the same effects. Particularly, when using the method (4), similarly to in the 2D case, the reception beamforming can be performed with respect to any transmission beams or waves in addition to the transmission fixed focusing. Off course, similarly the beamformings can also be performed on the simultaneous reception signals received with respect to the simultaneous transmissions of plural different beams or waves, or the superposition of reception signals with respect to the respective transmissions. Also, when using the virtual sources or virtual receivers or performing the steering etc., the all can be performed similarly to in the 2D case and image signals can be generated on the Cartesian coordinate system, the polar coordinate system or the orthogonal curvilinear coordinate system set according to the physical aperture geometry.

$$F(k_x, k_y, k_z) = \int\int\int f(r, \theta, \varphi) \exp\{-i(k_x x + k_y y + k_z z)\} dx dy dz \quad (27)$$

$$F(k_x, k_y, k_z) = \int\int\int f(r, \theta, \varphi) r^2 \sin\theta \exp \quad (28)$$
$$\{-i(k_x \sin\theta\cos\varphi + k_y\cos\theta + k_z\sin\theta\sin\varphi)r\} dr d\theta d\varphi$$

Method (5"): Image Signal Generation on Arbitrary Orthogonal Curvilinear Coordinate System when Transmission or Reception is Performed on Cartesian Coordinate System Inversely to the above-mentioned series of methods, however, with the similar calculations, image signals can be generated directly on the 2D polar coordinate system or the spherical coordinate system with no approximate interpolations from reception signals obtained by performing transmissions and receptions on the Cartesian coordinate system. For instance, when the reception signals are expressed by f(x,y,z), by implementing Fourier's transforms on f(x,y,z) regarding the directions of r, θ and φ via the Jacobi operation, the reception signals f(x,y,z) are decomposed into the circular waves or spherical waves corresponding to plane waves decomposed into on the Cartesian coordinate system. These methods can also be used for changing FOV (for instance, there is a case where a larger FOV can be obtained). Using the Jacobi operation, image signals can also be obtained on arbitrary orthogonal coordinate systems similarly and whenever transmissions and receptions are performed on arbitrary coordinate systems, image signals can also be generated on arbitrary orthogonal coordinate systems. Similarly to other methods mentioned in the method (5), any transmission beams or waves can also be processed; steering can also be implemented similarly; the virtual sources or the virtual receivers can also be used.

One of the features of method (5) is to perform the beamformings on arbitrary coordinate systems with no approximate interpolations on the wavenumber matchings. However, when using the method (5) for the methods (1) to (4), the method (5), the method (6) and the method (7) to perform the beamformings with high speeds on arbitrary coordinate systems, approximate interpolations can also be performed on the wavenumber matchings (the respectively mentioned approximate wavenumber matchings). To increase the accuracies of the wavenumber matchings to be performed with approximate interpolations, proper over-samplings of data are required in return an increased calculation amount. In the case, being different from in the case where image signals of arbitrary positions can be generated when no approximate interpolations are performed, it is cautious that the number of data to be used for the Fourier's transforms increases.

Method (6): Migration Method

Using the instrument of present invention allows performing for the migration methods no approximate interpolations for the wavenumber matchings. The expression of the migration (below mentioned eq. (M6')) is well known and the derivation is also well known and then, the derivation is omitted here.

In the nonpatent document 12, the disclosed method is that the difference in a propagation time from an arbitrary transmission aperture element to the reception aperture element (i.e., the transmission aperture element itself) via an arbitrary same position of interest (i.e., the object position) with respect to the plane wave transmission and/or reception with the steering or no steering (i.e., corresponding to the method (1)) from that on the general migration using one element reception by the one element transmission (i.e., corresponding to the non-steering processing using the method (2) on the transmission and reception data for monostatic SA) is used for performing the calculation of the same type expression of the migration (eq. (M6)), of which the propagation speed and the coordinate of the position of interest (the object position) are modified (i.e., below mentioned eq. (M1))

However, regarding the processings of other methods (2) to (5), nothing is disclosed in the nonpatent document 12 (Specifically for the method (2), steering processing is not disclosed). Moreover, for calculating eq. (M6'), approximate interpolations are performed on the wavenumber matching traditionally (eqs. (M4) and (M4')). In contrast, the instrument of present invention allows performing the wavenumber matching with no approximate interpolations (eqs. (M7) and (M7')).

A 2D coordinate system is set with the lateral (x) and depth (y) directions (axes), and the temporal axis is set as t. Concretely, the propagation time required for the round trip between an arbitrary aperture element (x,0) and an arbitrary position of interest $(x_s, y_s)$ is expressed as eq. (M0).

$$\tau(x) = \frac{2}{c}\sqrt{(x_s - x)^2 + y_s^2} \tag{M0}$$

Alternatively, in the case of a plane wave transmission with a steering angle θ (it can be 0 degree), the corresponding propagation time is expressed as eq. (M0').

$$\tau(x) = \frac{1}{\alpha c}\sqrt{(x_s + \gamma y_s - x)^2 + (\beta y_s)^2}, \tag{M0'}$$

where $$\alpha = \frac{1}{\sqrt{1 + \cos\theta + \sin^2\theta}},$$

$$\beta = \frac{(1+\cos\theta)^{\frac{3}{2}}}{1 + \cos\theta + \sin^2\theta},$$

$$\gamma = \frac{\sin\theta}{2 - \cos\theta}.$$

Thus, when performing the beamforming for the steered plane wave transmission of the method (1) by using the migration method, the general migration expressions (eqs. (M4) and (M5)) are calculated by modifying the propagation speed c and the coordinate system $(x_s, y_s)$ expressing the object position by eq. (M1).

$$\hat{c} = \alpha c$$

$$(\hat{x}_s, \hat{y}_s) = (x_s + \gamma y_s, \beta y_s) \tag{M1}$$

Summarizing, all the methods (1) to (5) except for the method (2) performing the non-steering monostatic SA using the transmission and reception SA data (i.e., a general migration method) can also be performed using migration processing similarly. For instance, the migration calculation procedure is explained mainly for the steered plane wave transmission (the steering angle can be 0 degree).

Figure 15:
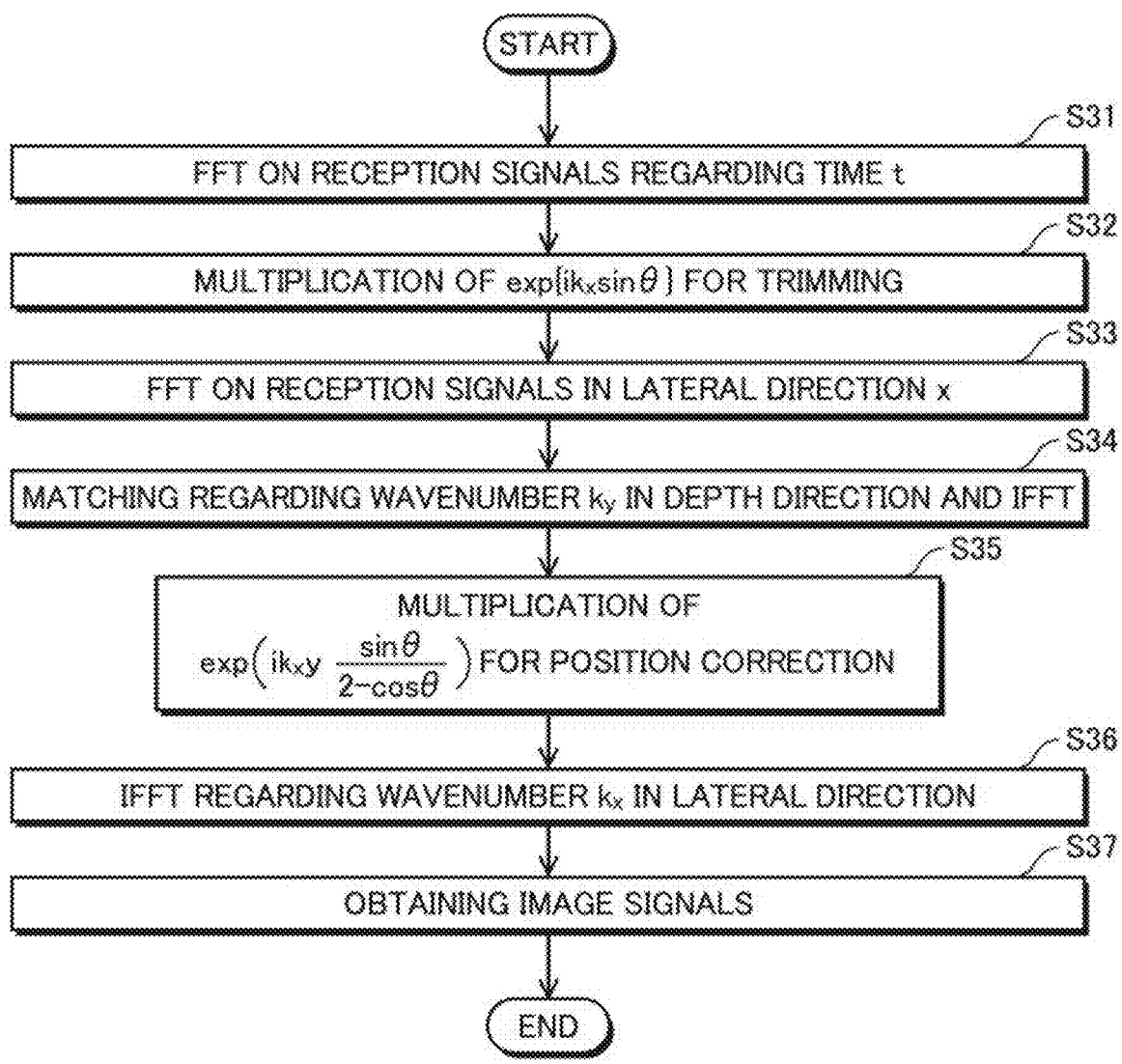
FIG. 15 shows a flowchart about the migration processing for a steered plane wave transmission.

FIG. 15 shows a flowchart about the migration processing for the steered plane wave transmission. When the received signals are expressed by r(x,y,t), the received signals are expressed by r(x,y=0,t) at the aperture element array positions.

At first, as expressed by eq. (M2), the received signals are 2D Fourier's transformed regarding the time t and the lateral direction x (2D FFT can be used).

$$R(k_x, y=0, k) = \iint r(x, y=0, t) \exp\{-i(k_x x + \omega t)\} dx dt \tag{M2}$$

Here, k=ω/c, the wavenumber k and the angular frequency ω are related using the proportional coefficient 1/c (one-to-one correspondence) and then, ω can be used instead of k to express the equations and to perform the calculations.

As mentioned above, special 2D FFT method can also be used and however, as a general (popular) method, at step 31, at first, the spectra of analytic signals are obtained by implementing FFT on the received signals regarding the time t at respective lateral coordinates x at the step S31. Besides, FFT is performed regarding the lateral direction x at the respective frequency coordinates within the bandwidth k (It is faster to calculate 2D spectra than the using eq. (M2) for calculating the respective 2D spectra).

When not performing the steered transmission of a plane wave, the above-mentioned calculations are performed and however, when performing the steering, the trimming is performed at the step S32, the results of the above-mentioned FFT on the time t (R'(x,0,k)) are multiplied with the complex exponential function (M3) (Similarly to the complex exponential function (11) used in the method (1), the multiplication of the FFT results on the time t and the complex exponential function can be performed at once and for such calculations, the exclusive FFT is also useful).

$$\exp\{ikx\sin\theta\} \tag{M3}$$

Besides, at the step S33, FFT is implemented on the received signals in the lateral direction x. Here, the results are expressed as R''($k_x$,0,k). Even if the trimming is programmed to be performed, a non-steered plane wave transmission can be processed (The steering angle can be set to zero degree).

In general, the wavenumber matching (or mapping) is performed next. When the beamforming to be performed is one of the methods (1) to (5) except for the general migration (the method (2) with no steering), similarly to using the modifications (conversions) about the propagation speed c and the coordinate ($x_s$,$y_s$) as likely expressed in eq. (M11) for the plane wave transmission, the respective modifications (conversions) of the propagation speed c and the coordinate system ($x_s$,$y_s$) for the respective beamformings into eqs. (E1) and (E2) are performed.

$$\hat{c} \tag{E1}$$

$$(\hat{x}_s, \hat{y}_s) \tag{E2}$$

On the 2D Fourier's transform R''($k_x$,0,k) calculated for the methods including the method (1), however, except for the general migration (the method (2) with no steering) or the above-mentioned R($k_x$,0,k) calculated for the general migration, approximate interpolations (using the most neighborhood angular spectra at the digital frequency coordinate or bi-linear interpolations etc) are used to perform the wavenumber matchings respectively expressed by eqs. (M4) or (M4').

$$F''(k_x, 0, K(\hat{k}_y)) = R''(k_x, 0, k), \tag{M4}$$
where
$$K(\hat{k}_y) = \hat{c}\,\mathrm{sgn}(\hat{k}_y)\sqrt{k_x^2 + \hat{k}_y^2},$$
$$\hat{k}_y = \sqrt{\hat{k}^2 - k_x^2} = \sqrt{\left(\frac{\omega}{\hat{c}}\right)^2 - k_x^2}$$
or
$$\sqrt{\left(\frac{k}{\alpha}\right)^2 - k_x^2},$$

-continued
$$F(k_x, 0, K(k_y)) = R(k_x, 0, sk), \tag{M4'}$$
where
$$K(k_y) = c\,\mathrm{sgn}(k_y)\sqrt{k_x^2 + k_y^2},$$
$$k_y = \sqrt{(sk)^2 - k_x^2} = \sqrt{\left(s\frac{\omega}{c}\right)^2 - k_x^2},$$

when the received signals are reflected ones, s=2; and when transmission signals, s=1.

When the approximate interpolations are not performed on the wavenumber matchings expressed by eqs. (M4) and (M4'), the wavenumbers in the depth direction respectively expressed in the supplementary explanations of equations are used, whereas when the approximate interpolations are performed, the wavenumbers in the depth direction are respectively ones obtained by dividing the angular frequency ω by the converted propagation speed (E1) and c. These are also below.

The wavenumber matchings are performed in these ways, and the next function (M4'') is calculated.

$$F''(k_x,0,K(\hat{k}_y))\ \text{or}\ F(k_x,0,K(k_y)) \tag{M4''}$$

Besides, using the function (M4''), the next eqs. (M5) and (M5') are calculated.

$$\frac{\hat{c}\hat{k}_y}{\sqrt{k_x^2 + \hat{k}_y^2}}F''(k_x, 0, K(\hat{k}_y)) \tag{M5}$$

$$\frac{ck_y}{\sqrt{k_x^2 + k_y^2}}F(k_x, 0, K(k_y)) \tag{M5'}$$

With respect to the respective eqs. (M5) and (M5'), by implementing 2D inverse Fourier's transforms regarding the wavenumber $k_x$ and the wavenumbers (E3) as expressed by eq. (M6) and (M6'), image signal f(x,y) is generated.

$$\hat{k}_y\ \text{or}\ k_y \tag{E3}$$

$$f(x, y) = \tag{M6}$$
$$\int\int \frac{\hat{c}\hat{k}_y}{\sqrt{k_x^2 + \hat{k}_y^2}} F''(k_x, 0, K(\hat{k}_y))\exp\{i(k_x x + \hat{k}_y y_s)\}d\hat{k}_y\,dk_x$$

$$f(x, y) = \int\int \frac{ck_y}{\sqrt{k_x^2 + k_y^2}} F(k_x, 0, K(k_y))\exp\{i(k_x x + k_y y)\}dk_y dk_x \tag{M6'}$$

The 2D inverse Fourier's transform of eqs. (M6) and (M6') can be performed using 2D IFFT. Special 2D IFFT can also be used and however, as general (popular) methods for calculating eqs. (M6) and (M6'), with respect to the respective wavenumbers of $k_x$ within the bandwidths of signals, IFFT can be performed regarding another respective wavenumbers of (E3) within the bandwidths of signals; and further with respect to the respective spatial coordinates y generated, IFFT can be performed regarding the respective wavenumbers of $k_x$ within the bandwidths of signals (It is faster to calculate 2D image signals than the using eq. (M6) or (M6') for calculating the respective 2D image signals).

In the nonpatent document 12, eq. (M6) using $y_s$ in the equation is not disclosed and instead, it is disclosed that not $y_s$ but y is used for the calculation and after the calculation, correction of the coordinate is performed. For the correction of coordinate, approximate interpolations are performed or no approximation interpolations are performed by performing the multiplications of complex exponential functions (a past invention of the inventor of present invention). Eq. (M6) can also be used when the steering angle is zero degree.

The instrument of present invention performs the wavenumber matchings together with the 2D inverse Fourier's transform or together with the inverse Fourier's transform in the depth direction, with no approximate interpolations. That is, on the 2D Fourier's transform $R''(k_x,0,k)$ calculated for the methods including the method (1), however, except for the general migration (the method (2) with no steering), or the above-mentioned $R(k_x,0,k)$ calculated for the general migration, as expressed by eqs. (M7) or (M7'), the integration regarding k is implemented with respect to the respective wavenumbers of $k_x$ within the bandwidths of signals to simultaneously perform the wavenumber matching on the wavenumber (E3) and the inverse Fourier's transform (IFFT possible) in the depth direction (step S34) and after the integrations, the lateral (x) IFFT is performed.

$$f(x,y) = \iint R''(k_x,0,k)\exp\{i(k_x x + \hat{k}_y y_s)\} dk dk_x \quad (M7)$$

$$f(x,y) = \iint R(k_x,0,k)\exp\{i(k_x x + k_y y)\} dk dk_x \quad (M7')$$

In nonpatent document 12, eq. (M7) using $y_s$ in the equation is not disclosed. Eq. (M7) can also be used when the steering angle is zero degree. Similarly to the methods (1) to (6), after summing the spectral k components, the inverse Fourier's transform (IFFT) can be performed on the lateral wavenumber $k_x$ and then, the inverse Fourier's transform is performed once and the total calculations are high speed.

Moreover, the migrations to be performed being different from the general migration (corresponding to the processing of non-steering of the method (2)), corrections of the lateral positions can be performed during performing the calculations of eq. (M6) or (M7). For instance, when performing the transmission of a steered plane wave of the method (1), at the step S34, at first, the calculation about the wavenumber (E3); at the step S35, the function (M8) calculated as each result is multiplied with complex exponential function (M9) for the position correction; at the step S36, IFFT is implemented on the wavenumber $k_x$ in the lateral direction. Alternatively, instead of the steps S35 and S36, eq. (M9) can also be multiplied together with the complex exponential function used for the inverse Fourier's transform regarding the wavenumber $k_x$ in the lateral direction, or the exclusive IFFT can also be implemented. Eq. (M9) can also be used for the zero steering angle. Thus, at the step S37, image signals f(x,y) are generated.

$$F'''(k_x, y) \quad (M8)$$
or
$$R'''(k_x, y)$$

$$\exp\left(ik_x y \frac{\sin\theta}{2-\cos\theta}\right) \quad (M9)$$

Summarizing, using eq. (M6), (M7) or (M7') yields a new processing for generating, with a high speed, image signal f(x,y) with no errors due to approximate interpolations.

Without performing the multiplication of eq. (M9) and with no approximate interpolations, to obtain the same results, eq. (M6) or (M7) is calculated using the next eq. (N4) instead of eq. (M4).

$$F''(k_x, 0, K(\hat{k}_y)) = R''(k_x, 0, k), \quad (N4)$$

where $$K(\hat{k}_y) = \hat{c}\,\text{sgn}(\hat{k}_y)\sqrt{(k_x - k\sin\theta)^2 + \hat{k}_y^2},$$

$$\hat{k}_y = \sqrt{\hat{k}^2 - (k_x - k\sin\theta)^2} = \sqrt{\left(\frac{\omega}{\hat{c}}\right)^2 - (k_x - k\sin\theta)^2}$$

or $$\sqrt{\left(\frac{k}{\alpha}\right)^2 - (k_x - k\sin\theta)^2}.$$

That is, when the approximate interpolations are not performed on the wavenumber matching, the wavenumber in the depth direction expressed in the supplementary explanation of equation is used, whereas when the approximate interpolations are performed, the wavenumber in the depth direction is one obtained by dividing the angular frequency ω by the converted propagation speed (E1).

The equation of wavenumber in the depth direction in these equations is similar to eq. (13) of the method (1). To generate the same result using the method (1), however, with no use of −k sin θ in kx−k sin θ in eqs. (13) to (15) (i.e., use as zero), as in the method (6) the inverse Fourier's transform being implemented on the multiplication with eq. (M9), eq. (16) can be multiplied with eq. (M9) prior to performing the processings mentioned in the paragraphs 0202 and 0203. However, note that the steering of the plane wave achieved by the above-mentioned method (6) is only realized under the approximate calculations and therefore, using eqs. (N4) and (M7) in the method (6) can perform the beamforming with no approximate interpolations and with a high accuracy, whereas the use of eq. (M9) decreases the accuracy of the method (1). Moreover, implementing the 2D IFFT for the last inverse Fourier's transform (as mentioned later, 3D IFFT in a 3D case) increases the calculation speed for the method (6), however, decreases the speed for the method (1) (The processing mentioned in the paragraph 0203 is high speed).

On the respective modified methods (1) and (6), when performing approximate interpolations on the wavenumber matchings, to generate the same results using eqs. (M9) and (N4), the equations of approximate interpolations change correspondingly (mentioned later in the respective (A) and (B) in the paragraph 0352).

On the respective modified methods (1) and (6), when performing approximate interpolations on the wavenumber matchings, to generate the same results using eqs. (11) and (M3) (using the steering angle data θ) or not (the steering angle θ is set to zero degree), the equations of approximate interpolations change correspondingly (mentioned later in the respective (A') and (B') in the paragraph 0352).

Beamforming using the plane wave transmission is applied to various beamformings as mentioned before in the present invention document and instead the processings mentioned in this paragraph can also be used. It is cautious that when the reception dynamic focusing is performed using the method (6) on arbitrary transmission beamformings such as the transmission focusing etc, as mentioned later, eq. (M3''), expressed using the wavenumber [eq. (M13)] expressed by the angular frequency ω and the converted propagation speed (E1), is used instead of eq. (M3) and then, for the wavenumber k in −k sin $\theta_t$ in the expression of approximate interpolation, eq. (M13) is required to be used instead.

On the respective methods (1) and (6), the methods mentioned in this paragraph can also be combined and performed. For instance, similarly to J.-y. Ku's method that performs approximate interpolations for the method (1) (paragraph 0195, expressions are described in (C') in the paragraph 0352), all the wavenumber matchings of the method (6) can be performed via approximate interpolations and accordingly, the first 2D Fourier's transform and the last 2D inverse Fourier's transform can be performed using 2D FFT and 2D IFFT, respectively (Described in (D') in the paragraph 0352. As mentioned later, in a 3D case, 3D FFT). In the respective these, eq. (11) can also be used (The steering angle data θ is used) and eq. (M3) can also be used (Described in (C) and (D) in the paragraph 0352). Off course, non-steering can also be used.

As mentioned above, the plane wave transmission on the basis of the methods (1) and (6) can be applied to various beamformings.

Here, mainly explained is the use of the migration method to the method (1), i.e., a high speed beamforming with no approximate interpolations for a steered or non-steered plane wave transmission. All the beamformings described in other methods of the present invention, the method (2) (a monostatic SA method including a steering case), the method (3) (a multistatic SA method including a steering case), the method (4) (a transmission fixed focus with a steering or no steering), the method (5) (beamformings on the polar coordinate system or arbitrary orthogonal curvilinear coordinate systems) can also be performed similarly. On the transmission and the reception, different steering angles can also be processed similarly. Apodizations can also be performed similarly.

The 3D cases can also be processed similarly. When the received signals obtained using 2D aperture element array are expressed as r(x,y,z,t), the reception signals received at the position of aperture element array (y=0) are expressed as r(x,y=0,z,t).

At first, as shown in eq. (M'2), the reception signals are 3D Fourier's transformed with respect to the time t, the lateral direction x and the elevational direction z (3D FFT can be performed).

$$R(k_x,y=0,k_z,k)=\iiint r(x,y=0,z,t)\exp\{-i(k_x x+_k z+t)\}dxdt \quad (M'2)$$

where k=ω/c.

In general, the spectra R(x,0,z,k) of analytic signals are obtained for the reception signals by performing FFT regarding the time t. Besides, for the respective frequency coordinates k within the bandwidth of signals, FFT is implemented regarding the lateral (x) and elevational (z) directions to generate $R(k_x,0,k_z,k)$ (It is faster to calculate 3D spectra than the using eq. (M'2) for calculating the respective 3D spectra).

When not performing the steered transmission of a plane wave, the above-mentioned calculations are performed and however, when performing the steering with the steering angle being an angle between the transmission direction as a plane wave and the axial direction (y) is expressed using zero or non-zero elevation (θ) and azimuth (φ) angles, the trimming is required to be performed, the results of the above-mentioned FFT on the time t (R'(x,0,z,k)) are multiplied with the complex exponential function (M'3) (The multiplication of the FFT results on the time t and the complex exponential function can be performed at once and for such calculations, the exclusive FFT is also useful).

$$\exp\{ik \sin θ(\cos φx+\sin φz)\} \quad (M'3)$$

Besides, FFT is implemented on the received signals in the lateral direction x. Here, the results are expressed as R"($k_x$,0,z,k). Even if the trimming is programmed to be performed, a non-steered plane wave transmission can be processed (The steering angle can be set to zero degree).

Next, the wavenumber matching (or mapping) is performed. When the beamforming to be performed is one of the methods (1) to (5) except for the general migration (the method (2) with no steering), the respective modifications (conversions) of the propagation speed c and the coordinate system ($x_s,y_s,z_s$) for the respective beamformings into eqs. (E'1) and (E'2) are performed.

$$\hat{c} \quad (E'1)$$

$$(\hat{x}_s,\hat{y}_s,\hat{z}_s) \quad (E'2)$$

On the 3D Fourier's transform R"($k_x$,0,z,k) calculated for the methods including the method (1), however, except for the general migration (the method (2) with no steering) or the above-mentioned R($k_x$,0,z,k) calculated for the general migration, approximate interpolations (using the most neighborhood angular spectra at the digital frequency coordinate or bi-linear interpolations etc) are used to perform the wavenumber matchings respectively expressed by eqs. (M'4) or (M'4').

$$F''(k_x, 0, k_z, k(\widehat{k_y})) = \quad (M'4)$$
$$R''(k_x, 0, k_z, k) \text{ where } K(\widehat{k_y}) = \hat{c}\, \text{sgn}(\widehat{k_y})\sqrt{k_x^2 + k_z^2 + \widehat{k_y}^2},$$
$$\widehat{k_y} = \sqrt{\hat{k}^2 - k_x^2 - k_z^2} = \sqrt{\left(\frac{ω}{\hat{c}}\right)^2 - k_x^2 - k_z^2} \text{ or } \sqrt{\left(\frac{k}{α}\right)^2 - k_x^2 - k_z^2},$$

$$F(k_x, 0, k_z, K(k_y)) = \quad (M'4')$$
$$R(k_x, 0, k_z, sk) \text{ where } K(k_y) = c\, \text{sgn}(k_y)\sqrt{k_x^2 + k_z^2 + k_y^2},$$
$$k_y = \sqrt{(sk)^2 - k_x^2 - k_z^2} = \sqrt{\left(s\frac{ω}{c}\right)^2 - k_x^2 - k_z^2},$$

when the received signals are reflected ones, s=2; and when transmission signals, s=1.

When the approximate interpolations are not performed on the wavenumber matchings expressed by eqs. (M'4) and (M'4'), the wavenumbers in the depth direction respectively expressed in the supplementary explanations of equations are used, whereas when the approximate interpolations are performed, the wavenumbers in the depth direction are respectively ones obtained by dividing the angular frequency ω by the converted propagation speed (E'1) and c. These are also below.

The phase matchings are performed in these ways, and the next function (M'4") is calculated.

$$F''(k_x,0,k,K(\hat{k}_y)) \text{ or } F(k_x,0,k_z,K(k_y)) \quad (M'4'')$$

Besides, using the function (M'4"), the next eqs. (M'5) and (M'5') are calculated.

$$\frac{\hat{c}\hat{k}_y}{\sqrt{k_x^2 + k_z^2 + \hat{k}_y^2}} F''(k_x, 0, k_z, K(\hat{k}_y)) \quad (M'5)$$

$$\frac{ck_y}{\sqrt{k_x^2 + k_z^2 + k_y^2}} F(k_x, 0, k_z, K(k_y)) \quad (M'5')$$

With respect to the respective eqs. (M'5) and (M'5'), by implementing 3D inverse Fourier's transforms regarding the wavenumber $k_x$ and $k_z$, and the wavenumbers (E'3) in the 3D case as expressed by eq. (M'6) and (M'6'), image signal f(x,y) is generated.

$$\hat{k}_y \text{ or } k_y \qquad (E'3)$$

$$f(x, y, z) = \iiint \frac{\partial \hat{k}_y}{\sqrt{k_x^2 + k_z^2 + \hat{k}_y^2}} \qquad (M'6)$$

$$F''(k_x, 0, k_z, K(\hat{k}_y))\exp\{i(k_x x + k_z z + \hat{k}_y y_s)\}d\hat{k}_y\, dk_x dk_z$$

$$f(x, y, z) = \iiint \frac{\partial k_y}{\sqrt{k_x^2 + k_z^2 + k_y^2}} \qquad (M'6')$$

$$F(k_x, 0, k_z, K(k_y))\exp\{i(k_x x + k_z z + k_y y)\}dk_y dk_x dk_z$$

The 3D inverse Fourier's transform of eqs. (M'6) and (M'6') can be performed using 3D IFFT. Special 3D IFFT can also be used and however, as general (popular) methods for calculating eqs. (M'6) and (M'6'), with respect to the respective wavenumbers of $k_x$ and $k_z$ within the bandwidths of signals, IFFT can be performed regarding another respective wavenumbers of (E'3) within the bandwidths of signals; and further with respect to the respective spatial coordinates y generated, IFFT can be performed regarding the respective wavenumbers of $k_x$ and $k_z$ within the bandwidths of signals (It is faster to calculate 3D image signals than the using eq. (M'6) or (M'6') for calculating the respective 3D image signals).

The instrument of present invention performs the wavenumber matchings together with the 3D inverse Fourier's transform or together with the inverse Fourier's transform in the depth direction, with no approximate interpolations. That is, on the 3D Fourier's transform $R''(k_x,0,k_z,k)$ calculated for the methods including the method (1), however, except for the general migration (the method (2) with no steering), or the above-mentioned $R(k_x,0,k_z,k)$ calculated for the general migration, as expressed by eqs. (M'7) or (M'7'), the integration regarding k is implemented with respect to the respective wavenumbers of $(k_x,k_z)$ within the bandwidths of signals to simultaneously perform the wavenumber matching on the wavenumber (E'3) and the inverse Fourier's transform (IFFT possible) in the depth direction and after the integrations, the lateral (x) and elevation (z) IFFTs are performed.

$$f(x,y,z)=\iiint R''(k_x,0,k_z,k)\exp\{i(k_x x+k_z z+\hat{k}_y y_s)\}dk dk_x dk_z \qquad (M'7)$$

$$f(x,y,z)=\iiint R(k_x,0,k_z,k)\exp\{i(k_x x+k_z z+k_y y)\}dk dk_x dk_z \qquad (M'7')$$

In nonpatent document 12, eqs. (M'6) and (M'7) using $y_s$ in the equation are not disclosed. Both equations can also be used when the steering angle is zero degree. Similarly to the methods (1) to (6), after summing the spectral k components, the inverse Fourier's transforms (IFFTs) can be performed on the lateral ($k_x$) and elevational ($k_z$) wavenumbers and then, the inverse Fourier's transform is performed once and the total calculations are high speed.

Moreover, the migrations to be performed being different from the general migration (corresponding to the processing of non-steering of the method (2)), corrections of the lateral (x) and elevational (z) positions can be performed during performing the calculations of eq. (M'6) or (M'7). For instance, when performing the transmission of a steered plane wave of the method (1), at first, the calculation about the wavenumber (E'3); and next, the function (M'8) calculated as each result is multiplied with complex exponential function for the position correction; and finally, IFFTs are respectively implemented on the wavenumbers $k_x$ and $k_z$ in the lateral and elevational directions.

$$F'''(k_x,y) \text{ or } R'''(k_x,y) \qquad (M'8)$$

Summarizing, using eq. (M'6), (M'6'), (M'7) or (M'7') yields a new processing for generating, with a high speed, image signal f(x,y,z) with no errors due to approximate interpolations.

Without performing the multiplication of the complex exponential function corresponding to eq. (M9) and with no approximate interpolations, to obtain the same results, eq. (M6) or (M7) is calculated using the next eq. (N'4) instead of eq. (M'4).

$$F''(k_x, 0, k_z, K(\hat{k}_y)) = R''(k_x, 0, k_z, k), \qquad (N'4)$$

where $$K(\hat{k}_y) = \hat{c}\,\mathrm{sgn}(\hat{k}_y)\sqrt{(k_x - k\sin\theta\cos\varphi)^2 + (k_z - k\sin\theta\sin\varphi)^2 + \hat{k}_y^2},$$

$$\hat{k}_y = \sqrt{\hat{k}^2 - (k_x - k\sin\theta\cos\varphi)^2 - (k_z - k\sin\theta\sin\varphi)^2}$$

$$= \sqrt{\left(\frac{\omega}{\hat{c}}\right)^2 - (k_x - k\sin\theta\cos\varphi)^2 - (k_z - k\sin\theta\sin\varphi)^2}$$

or $$\sqrt{\left(\frac{k}{\alpha}\right)^2 - (k_x - k\sin\theta\cos\varphi)^2 - (k_z - k\sin\theta\sin\varphi)^2}.$$

That is, when the approximate interpolations are not performed on the wavenumber matching, the wavenumber in the depth direction expressed in the supplementary explanation of equation is used, whereas when the approximate interpolations are performed, the wavenumber in the depth direction is one obtained by dividing the angular frequency ω by the converted propagation speed (E'1).

The equation of wavenumber in the depth direction in these equations is similar to eq. (C22) of the method (1). To generate the same result using the method (1), however, with no use of −k sin θ cos φ and −k sin θ sin φ in respective kx−k sin θ cos φ and kz−k sin θ sin φ in eqs. (C22) and (C23) (i.e., uses as zero), as in the method (6) the inverse Fourier's transform being implemented on the multiplication with the complex exponential function corresponding to eq. (M9) in the 2D case, the multiplication can be performed in the processings described in the paragraph 0205. However, note that the steering of the plane wave achieved by the method (6) is only realized under the approximate calculations and therefore, similarly to in the 2D case, using eqs. (N'4) and (M7) in the method (6) can perform the beamforming with no approximate interpolations and with a high accuracy, whereas the use of the complex exponential function corresponding to eq. (M9) in the 2D case decreases the accuracy of the method (1). Moreover, implementing the 3D IFFT for the last inverse Fourier's transform increases the calculation speed for the method (6) similarly to in the 2D case, however, decreases the speed for the method (1) (The processing mentioned in the paragraph 0203 is high speed).

On the respective modified methods (1) and (6), when performing approximate interpolations on the wavenumber matchings, to generate the same results using the complex exponential function corresponding to eqs. (M9) in the 2D case and (N'4), the equations of approximate interpolations change correspondingly similarly to in the 2D case (mentioned in the respective (A) and (B) in the paragraph 0352).

On the respective modified methods (1) and (6), when performing approximate interpolations on the wavenumber matchings, to generate the same results using eqs. (C21) and (M'3) (using the steering angle data θ and φ) or not (the steering angles θ and φ are set to zero degree), the equations of approximate interpolations change correspondingly similarly to in the 2D case (mentioned in the respective (A') and (B') in the paragraph 0352).

Beamforming using the plane wave transmission is applied to various beamformings as mentioned before in the present invention document and instead the processings mentioned in this paragraph can also be used. Similarly in the 2D case, it is cautious that when the reception dynamic focusing is performed using the method (6) on arbitrary transmission beamformings such as the transmission focusing etc, as mentioned later, eq. (M'3''), expressed using the wavenumber [eq. (M'13)] expressed by the angular frequency ω and the converted propagation speed (E'1), is used instead of eq. (M'3) and then for the wavenumber k in −k sin θ₁(cos φ₁x+sin φ₁z) in the expression of approximate interpolation, eq. (M'13) is required to be used instead.

On the respective methods (1) and (6), the methods mentioned in this paragraph can also be combined and performed. For instance, similarly to J.-y. Ku's method that performs approximate interpolations for the method (1) (paragraph 0195, expressions are described in (C') in the paragraph 0352), all the wavenumber matchings of the method (6) can be performed via approximate interpolations and accordingly, the first 3D Fourier's transform and the last 3D inverse Fourier's transform can be performed using 3D FFT and 3D IFFT, respectively (Described in (D') in the paragraph 0352). In the respective these, eq. (C21) can also be used (The steering angle data θ is used) and eq. (M'3) can also be used (Described in (C') and (D') in the paragraph 0352). Off course, non-steering can also be used.

As mentioned above, the plane wave transmission on the basis of the methods (1) and (6) can be applied to various beamformings.

Also by using the migration method, similarly to the method (2) or (3), the monostatic or multistatic SA can be performed with no approximate interpolations.

In the case of monostatic SA, when the software transmission and reception steering angles are $\theta_t$ and $\theta_r$, instead of eq. (M3), similarly used can be $$\exp\{ixk_0(\sin\theta_t+\sin\theta_r)\} \quad (M3')$$

expressed using the wavenumber, $$k_0=\omega_0/c, \quad (M10)$$

expressed using the ultrasound angular frequency $\omega_0$ and the propagation speed c, and used in eq. (M7'), which does require no approximate interpolations on the wavenumber matching in the general migration processings, is $$k=\sqrt{(sk)^2(k_x-k_0\sin\theta_t-k_0\sin\theta_r)^2}+k_0(-2+\cos\theta_t+\cos\theta_r) \quad (M11)$$

when the received signals are reflected ones, s=2; and when transmission signals, s=1.

In the 3D case, when the steering angles of the transmission and reception beams are respectively (an elevation angle, an azimuth angle)=$(\theta_t,\varphi_t)$ and $(\theta_r,\varphi_r)$, similarly to the method (2), the wavenumber matching is performed, at first, for the spatial (lateral) directions, by multiplying the complex exponential function eq. (D41) expressed using the carrier frequency $\omega_0$ of the ultrasound signals and next for the depth direction y, by multiplying the complex exponential function eq. (D43) together with the complex exponential function eq. (D42) with removed the performed lateral matching processing eq. (D41). That is, eq. (D41) is used instead of eq. (M3') in the 2D case, and the multiplication of eqs. (D42) and (D43) is used instead of eq. (M11).

Thus, migration processings of the present invention, corresponding to the method (2) and the method (3) on the basis of the method (2), are equivalent to the methods (2) and (3), respectively.

Also in these cases, similarly to the general migration processings, the approximate wavenumber matching and the IFFT can be performed, in which not being equivalent to the method (2) and the method (3) on the basis of the method (2), after performing the above-mentioned processings using eq. (M3') etc, instead of eq. (M4') with approximation wavenumber matching, eq. (M4'') expressed by eq. (M4''') on the basis of eq. (M11) is calculated and the 2D inverse Fourier's transform [eq. (M6')] of eq. (M5') expressed using the ky expressed in eq. (M4''') is performed.

$$F(k_x, 0, K(k_y)) = R(k_x, 0, sk), \quad (M4''')$$

where $$K(k_y) = c\,\mathrm{sgn}(k_y)$$
$$\sqrt{(k_x - k_0\sin\theta_t - k_0\sin\theta_r)^2 + \{k_y - k_0(-2+\cos\theta_t+\cos\theta_r)\}^2}$$

$$k_y \equiv \sqrt{(sk)^2 - (k_x - k_0\sin\theta_t - k_0\sin\theta_r)^2} + k_0(-2+\cos\theta_t+\cos\theta_r)$$

$$= \sqrt{\left(s\frac{\omega}{c}\right)^2 - (k_x - k_0\sin\theta_t - k_0\sin\theta_r)^2} + k_0(-2+\cos\theta_t+\cos\theta_r),$$

when the received signals are reflected ones, s=2 and when transmission signals, s=1; and the wavenumber in the depth direction obtained by dividing the angular frequency ω by the propagation speed c is used, whereas when not performing the approximate interpolations, the wavenumber in the depth direction expressed in the supplementary explanation of equation is used and similarly as below.

Alternatively, instead of eq. (M4'), eq. (M4'''), which is used for approximate interpolations, expressed by eq. (M4'''') is calculated and the 2D inverse Fourier's transform [corresponding to eq. (M6')] is performed on the multiplication of eq. (M12) and eq. (M5') expressed using the ky expressed in eq. (M4'''').

$$F(k_x, 0, K(k_y)) = R(k_x, 0, sk) \quad (M4'''')$$

where $$K(k_y) = c\,\mathrm{sgn}(k_y)\sqrt{(k_x - k_0\sin\theta_t - k_0\sin\theta_r)^2 + k_y^2},$$
$$k_y = \sqrt{(sk)^2 - (k_x - k_0\sin\theta_t - k_0\sin\theta_r)^2}$$
$$= \sqrt{\left(s\frac{\omega}{c}\right)^2 - (k_x - k_0\sin\theta_t - k_0\sin\theta_r)^2},$$

when the received signals are reflected ones, s=2 and when transmission signals, s=1; and the wavenumber in the depth direction obtained by dividing the angular frequency ω by the propagation speed c is used, whereas when not performing the approximate interpolations, the wavenumber in the depth direction expressed in the supplementary explanation of equation is used and similarly as below.

$$\exp\{ik_0(-2+\cos\theta_t+\cos\theta_r)y\} \quad (M12)$$

Also in these cases, the multistatic SAs can be performed using, instead of the method (2), the monostatic SAs on the basis of these migration methods, similarly to the case where the method (3) is performed using the method (2).

The 3D cases can also be processed similarly. That is, after performing the processing using eq. (M'3') in the 3D cases, instead of eq. (M'4') with approximation wavenumber matching, eq. (M'4'') expressed by eq. (M'4''') on the basis of the multiplication of eq. (D42) and eq. (D43) [corresponding to eq. (M11) in the 2D cases] is calculated and the 3D inverse Fourier's transform [eq. (M'6')] of eq. (M'5') expressed using the ky expressed in eq. (M'4''') is performed.

$$F(k_x, 0, k_z, K(k_y)) = R(k_x, 0, k_z, sk) \qquad (M'4''')$$

where $$K(k_y) = c\,\mathrm{sgn}(k_y)\sqrt{\begin{aligned}&\{k_x - k_0(\sin\theta_t\cos\varphi_t + \sin\theta_r\cos\varphi_r)\}^2 +\\ &\{k_z - k_0(\sin\theta_t\sin\varphi_t + \sin\theta_r\sin\varphi_r)\}^2 +\\ &\{k_y - k_0(-2 + \cos\theta_t + \cos\theta_r)\}^2\end{aligned}}$$

$$k_y \equiv \sqrt{\begin{aligned}&(sk)^2 - \{k_x - k_0(\sin\theta_t\cos\varphi_t + \sin\theta_r\cos\varphi_r)\}^2 -\\ &\{k_z - k_0(\sin\theta_t\sin\varphi_t + \sin\theta_r\sin\varphi_r)\}^2 +\\ &k_0(-2 + \cos\theta_t + \cos\theta_r)\end{aligned}} =$$

$$\sqrt{\begin{aligned}&\left(s\frac{\omega}{c}\right)^2 - \{k_x - k_0(\sin\theta_t\cos\varphi_t + \sin\theta_r\cos\varphi_r)\}^2 -\\ &\{k_z - k_0(\sin\theta_t\sin\varphi_t + \sin\theta_r\sin\varphi_r)\}^2 +\\ &k_0(-2 + \cos\theta_t + \cos\theta_r)\end{aligned}},$$

when the received signals are reflected ones, s=2 and when transmission signals, s=1; and the wavenumber in the depth direction obtained by dividing the angular frequency ω by the propagation speed c is used, whereas when not performing the approximate interpolations, the wavenumber in the depth direction expressed in the supplementary explanation of equation is used and similarly as below.

Alternatively, instead of eq. (M'4'), eq. (M'4''), which is used for approximate interpolations, expressed by eq. (M'4'''') is calculated and the 3D inverse Fourier's transform [corresponding to eq. (M'6')] is performed on the multiplication of eq. (M'12) and eq. (M'5') expressed using the ky expressed in eq. (M'4'''').

$$F(k_x, 0, k_z, K(k_y)) = R(k_x, 0, k_z, sk) \qquad (M'4'''')$$

where $$K(k_y) = c\,\mathrm{sgn}(k_y)\sqrt{\begin{aligned}&\{k_x - k_0(\sin\theta_t\cos\varphi_t + \sin\theta_r\cos\varphi_r)\}^2 +\\ &\{k_z - k_0(\sin\theta_t\sin\varphi_t + \sin\theta_r\sin\varphi_r)\}^2 +\\ &k_y^2\end{aligned}}$$

$$k_y = \sqrt{\begin{aligned}&(sk)^2 - \{k_x - k_0(\sin\theta_t\cos\varphi_t + \sin\theta_r\cos\varphi_r)\}^2 -\\ &\{k_z - k_0(\sin\theta_t\sin\varphi_t + \sin\theta_r\sin\varphi_r)\}^2\end{aligned}} =$$

$$\sqrt{\begin{aligned}&\left(s\frac{\omega}{c}\right)^2 - \{k_x - k_0(\sin\theta_t\cos\varphi_t + \sin\theta_r\cos\varphi_r)\}^2 -\\ &\{k_z - k_0(\sin\theta_t\sin\varphi_t + \sin\theta_r\sin\varphi_r)\}^2\end{aligned}},$$

when the received signals are reflected ones, s=2 and when transmission signals, s=1; and the wavenumber in the depth direction obtained by dividing the angular frequency ω by the propagation speed c is used, whereas when not performing the approximate interpolations, the wavenumber in the depth direction expressed in the supplementary explanation of equation is used and similarly as below.

$$\exp\{ik_0(-2+\cos\theta_t+\cos\theta_r)y\} \qquad (M'12)$$

Also in these cases, the multistatic SAs can be performed using, instead of the method (2), the monostatic SAs on the basis of these migration methods, similarly to the case where the method (3) is performed using the method (2).

On the basis of these migration methods, all the beamformings mentioned in the methods (2) and (3) can be similarly performed.

Using the migration processing [eq. (M7) etc] for the above-mentioned plane wave transmission corresponding to the method (1) allows performing beamformings for such as arbitrary beam transmissions such as fixed, focused beams etc, arbitrary wave transmissions (including non-beam-formed waves), superposition of transmissions of plural beams or waves and simultaneous transmissions of plural beams or waves. Plural beamformings can also be performed by using the multi-directional synthetic aperture (SA) method and in the cases, similarly the processings can be performed with high speeds. The present inventions are not limited to these. In these cases, similarly to the cases where the method (1) is used, the method (2) can be combined to perform the reception dynamic focusings with respect to arbitrary transmission beamformings.

When the physical transmission steering angle of a focused beam is A, if the respective software transmission and reception steering angles are θ (=θt) and θr, instead of eq. (M3), similarly used is $$\exp\{ix(\hat{k}\sin\theta_t + k_0\sin\theta_r)\}, \qquad (M3'')$$

which is expressed using the wavenumber $$\hat{k}=\omega/\hat{c}, \qquad (M13)$$

where if $\theta=\theta_t=0°$, $\hat{k}=k=\omega/c$,
which is expressed using the angular frequency ω and the modification (conversion) of propagation speed (E1) and when the physical transmission steering angle of a plane wave is A, if the respective software transmission and reception steering angles are θ (=θt) and θr, instead of eq. (M3), similarly used is $$\exp\{ix(k\sin\theta_t + k_0\sin\theta_r)\} \qquad (M3''')$$

and both when the transmissions are performed, the following wavenumber is used in eq. (M7).

$$\hat{k}_y=\sqrt{\hat{k}^2-(k_x-k_0\sin\theta_r)^2}+k_0(-1+\cos\theta_r) \qquad (M11''')$$

The 3D cases can also be processed similarly. When the physical transmission steering angle of a focused beam is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is $$\exp\{i(\hat{k}\sin\theta_1(\cos\varphi_1 x+\sin\varphi_1 z)+i\{k_0\sin\theta_2(\cos\varphi_2 x+\sin\varphi_2 z)\} \qquad (M'3'')$$

which is expressed using the wavenumber $$\hat{k}=\omega/\hat{c}, \qquad (M'13)$$

where if $\theta=\theta_t=0°$, $\hat{k}=k=\omega/c$,
which is expressed using the angular frequency ω and the modification (conversion) of propagation speed (E'1) and when the physical transmission steering angle of a plane wave is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is $$\exp\{i\{k\sin\theta_1(\cos\varphi_1 x+\sin\varphi_1 z)\}+i\{k_0\sin\theta z(\cos\varphi_2 x+\sin\varphi_2 z)\} \quad \text{(M'3''')}$$

and both when the transmissions are performed, the following wavenumber is used in eq. (M'7).

$$\hat{k}_Y= \sqrt{\hat{k}^2-(k_x-k_0\sin\theta_2\cos\varphi_2)^2-(k_z-k_0\sin\theta\sin\varphi_2)^2}+k_0(-1+\cos\theta_2) \quad \text{(M'11''')}$$

Also in these cases, similarly to the general migration processings, the approximate wavenumber matching and the IFFT can be performed, in which instead of eq. (M4) with approximation wavenumber matching, eq. (M4") expressed by eq. (M4'''''') on the basis of eq. (M11''') is calculated and the 2D inverse Fourier's transform [eq. (M6)] of eq. (M5) expressed using the ky expressed in eq. (M4'''''') is performed.

$$F''(k_x, 0, K(\hat{k}_y^-)) = R''(k_x, 0, k), \quad \text{(M4'''''')}$$

where $$K(\hat{k}_y^-) = \hat{c}\operatorname{sgn}(\hat{k}_y^-)\sqrt{(k_x-k_0\sin\theta_r)^2+\{\hat{k}_y^--k_0(-1+\cos\theta_r)\}^2},$$

$$\hat{k}_y^- = \sqrt{\hat{k}^2-(k_x-k_0\sin\theta_r)^2}+k_0(-1+\cos\theta_r)$$

$$= \sqrt{\left(\frac{\omega}{\hat{c}}\right)^2-(k_x-k_0\sin\theta_r)^2}+k_0(-1+\cos\theta_r)$$

or $$\sqrt{\left(\frac{k}{\alpha}\right)^2-(k_x-k_0\sin\theta_r)^2}+k_0(-1+\cos\theta_r),$$

when performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used and similarly as below.

Alternatively, instead of eq. (M4), eq. (M4"), which is used for approximate interpolations, expressed by eq. (M4'''''') is calculated and the 2D inverse Fourier's transform [corresponding to eq. (M6)] is performed on the multiplication of eq. (M13) and eq. (M5) expressed using the ky expressed in eq. (M4'''''').

$$F''(k_x, 0, K(\hat{k}_y^-)) = R''(k_x, 0, k), \quad \text{(M4'''''')}$$

where $$K(\hat{k}_y^-) = \hat{c}\operatorname{sgn}(\hat{k}_y^-)\sqrt{(k_x-k_0\sin\theta_r)^2+\hat{k}_y^{-2}},$$

$$\hat{k}_y^- =$$

$$\sqrt{\hat{k}^2-(k_x-k_0\sin\theta_r)^2} = \sqrt{\left(\frac{\omega}{\hat{c}}\right)^2-(k_x-k_0\sin\theta_r)^2}$$

or $$\sqrt{\left(\frac{k}{\alpha}\right)^2-(k_x-k_0\sin\theta_r)^2},$$

when performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used and similarly as below.

$$\exp\{ik_0(-1+\cos\theta_r)y\} \quad \text{(M13)}$$

In the above-mentioned processings, when the software transmission steering is performed (θt is non-zero degree), exchanging of eqs. (M3") and (M3''') leads to errors that the image formation position gets out of the true position. Also when the software reception steering is performed (θr is non-zero degree), the using of, instead of the wavenumber eq. (M10) corresponding to the ultrasound frequency, the wavenumber expressed using the ultrasound angular frequency $\omega_0$ and the modification (conversion) propagation speed (E1), $$\hat{k}_0 = \omega_0/\hat{c}, \quad \text{(M14)}$$

where if θ=θt=0°, $\hat{k}_0 = k_0 = \omega_0/c$,
leads to errors that the generated steering angle becomes larger than that generated using eq. (M10) (for instance, about 1 or 2 degrees when generating the steering angle 20 degrees), with which image formations can be obtained.

Also the 3D cases can also be processed similarly. That is, after performing the processings using eq. (M'3") in the 3D cases etc, instead of eq. (M'4) with approximation wavenumber matching, eq. (M'4") expressed by eq. (M'4'''''') on the basis of eq. (M'11''') is calculated and the 3D inverse Fourier's transform [eq. (M'6)] of eq. (M'5) expressed using the ky expressed in eq. (M'4'''''') is performed.

$$F''(k_x, 0, k_z, K(\hat{k}_y^-)) = R''(k_x, 0, k_z, k) \quad \text{(M'4'''''')}$$

where $$K(\hat{k}_y^-) = \hat{c}\operatorname{sgn}(\hat{k}_y^-)\sqrt{\begin{array}{l}(k_x-k_0\sin\theta_2\cos\varphi_2)^2+\\(k_z-k_0\sin\theta_2\sin\varphi_2)^2+\\\{\hat{k}_y^--k_0(-1+\cos\theta_2)\}^2\end{array}},$$

$$\hat{k}_y^- = \sqrt{\hat{k}^2-(k_x-k_0\sin\theta_2\cos\varphi_2)^2-(k_z-k_0\sin\theta_2\sin\varphi_2)^2}+k_0(-1+\cos\theta_2)$$

$$= \sqrt{\left(\frac{\omega}{\hat{c}}\right)^2-(k_x-k_0\sin\theta_2\cos\varphi_2)^2-(k_z-k_0\sin\theta_2\sin\varphi_2)^2}+k_0(-1+\cos\theta_2)$$

or $$\sqrt{\left(\frac{k}{\alpha}\right)^2-(k_x-k_0\sin\theta_2\cos\varphi_2)^2-(k_z-k_0\sin\theta_2\sin\varphi_2)^2}+k_0(-1+\cos\theta_2),$$

when performing the approximate interpolations, the wavenumber in the depth direction obtained by dividing the angular frequency ω by the modification (conversion) of propagation speed (E'1) is used, whereas when not performing the approximate interpolations, the wavenumber in the depth direction expressed in the supplementary explanation of equation is used and similarly as below.

Alternatively, instead of eq. (M'4), eq. (M4'''), which is used for approximate interpolations, expressed by eq. (M'4'''''') is calculated and the 3D inverse Fourier's transform [corresponding to eq. (M'6)] is performed on the multiplication of eq. (M'13) and eq. (M'5) expressed using the ky expressed in eq. (M'4'''''').

$$F''(k_x, 0, k_z, K(\hat{k_y})) = R''(k_x, 0, k_z, k) \quad (M'4'''''')$$

where $$K(\hat{k_y}) = \hat{c}\,\text{sgn}(\hat{k_y})$$

$$\sqrt{(k_x - k_0\sin\theta_2\cos\varphi_2)^2 + (k_z - k_0\sin\theta_2\sin\varphi_2)^2 + \hat{k_y}^2},$$

$$\hat{k_y} = \sqrt{\hat{k}^2 - (k_x - k_0\sin\theta_2\cos\varphi_2)^2 - (k_z - k_0\sin\theta_2\sin\varphi_2)^2}$$

$$= \sqrt{\left(\frac{\omega}{\hat{c}}\right)^2 - (k_x - k_0\sin\theta_2\cos\varphi_2)^2 - (k_z - k_0\sin\theta_2\sin\varphi_2)^2}$$

or $$\sqrt{\left(\frac{k}{\alpha}\right)^2 - (k_x - k_0\sin\theta_2\cos\varphi_2)^2 - (k_z - k_0\sin\theta_2\sin\varphi_2)^2},$$

when performing the approximate interpolations, the wavenumber in the depth direction obtained by dividing the angular frequency ω by the modification (conversion) of propagation speed (E'1) is used, whereas when not performing the approximate interpolations, the wavenumber in the depth direction expressed in the supplementary explanation of equation is used and similarly as below.

$$\exp\{ik_0(-1+\cos\theta_2)y\} \quad (M'13)$$

In the above-mentioned processings, when the software transmission steering is performed (the steering angle is non-zero degree), exchanging of eqs. (M'3'') and (M'3''') leads to errors that the image formation position gets out of the true position. Also when the software reception steering is performed (the steering angle is non-zero degree), the using of, instead of the wavenumber eq. (M'10) corresponding to the ultrasound frequency, the wavenumber expressed using the ultrasound angular frequency $\omega_0$ and the modification (conversion) propagation speed (E'1), $$\hat{k}_0 = \omega_0/\hat{c}, \quad (M'14)$$

where if θ=θt=0°, $\hat{k}_0 = k_0 = \omega_0/c$,
leads to errors that the generated steering angle becomes larger than that generated using eq. (M'10), with which image formations can be obtained.

Also when using the migrations on the basis of eq. (N4) mentioned in the paragraph 0314 and when the physical transmission steering angle of a focused beam is A, if the software transmission and reception steering angles are θ (=θt) and $\theta_r$, respectively, instead of eq. (M3), similarly used is eq. (M3'''), which is expressed using the wavenumber (M13), which is expressed using the angular frequency ω and the modification (conversion) of propagation speed (E'1); and when the physical transmission steering angle of a plane wave is A, if the software transmission and reception steering angles are θ (=$\theta_t$) and $\theta_r$, respectively, instead of eq. (M3), similarly used is eq. (M3'''); and both when the transmissions are performed, instead of eq. (N4), the following eq. (N4') is similarly used for eq. (M6) or (M7).

$$F''(k_x, 0, K(\hat{k_y})) = R''(k_x, 0, k), \quad (N4')$$

where $$K(\hat{k_y}) = \hat{c}\,\text{sgn}(\hat{k_y})\sqrt{(k_x - k\sin\theta - k_0\sin\theta_r)^2 + \hat{k_y}^2},$$

$$\hat{k_y} = \sqrt{\hat{k}^2 - (k_x - k\sin\theta - k_0\sin\theta_r)^2}$$

$$= \sqrt{\left(\frac{\omega}{\hat{c}}\right)^2 - (k_x - k\sin\theta - k_0\sin\theta_r)^2}$$

or $$\sqrt{\left(\frac{k}{\alpha}\right)^2 - (k_x - k\sin\theta - k_0\sin\theta_r)^2}$$

when performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used and similarly as below.

Also in the 3D cases when using the migrations on the basis of eq. (N'4) mentioned in the paragraph 0329 and when the physical transmission steering angle of a focused beam is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is eq. (M'3'''), which is expressed using the wavenumber (M'13), which is expressed using the angular frequency ω and the modification (conversion) of propagation speed (E'1); and when the physical transmission steering angle of a plane wave is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is eq. (M'3'''); and both when the transmissions are performed, instead of eq. (N'4), the following eq. (N'4') is similarly used for eq. (M'6) or (M'7).

$$F''(k_x, 0, k_z, K(\hat{k_y})) = R''(k_x, 0, k_z, k) \quad (N'4')$$

where $$K(\hat{k_y}) =$$

$$\hat{c}\,\text{sgn}(\hat{k_y})\sqrt{\begin{array}{c}(k_x - k\sin\theta_1\cos\varphi_1 - k_0\sin\theta_2\cos\varphi_2)^2 + \\ (k_z - k\sin\theta_1\sin\varphi_1 - k_0\sin\theta_2\sin\varphi_2)^2 + \hat{k_y}^2\end{array}},$$

$$\hat{k_y} = \sqrt{\begin{array}{c}\hat{k}^2 - (k_x - k\sin\theta_1\cos\varphi_1 - k_0\sin\theta_2\cos\varphi_2)^2 - \\ (k_z - k\sin\theta_1\sin\varphi_1 - k_0\sin\theta_2\sin\varphi_2)^2\end{array}} =$$

-continued $$\sqrt{\left(\frac{\omega}{c}\right)^2 - (k_x - k\sin\theta_1\cos\varphi_1 - k_0\sin\theta_2\cos\varphi_2)^2 - (k_z - k\sin\theta_1\sin\varphi_1 - k_0\sin\theta_2\sin\varphi_2)^2}$$

or $$\sqrt{\left(\frac{k}{\alpha}\right)^2 - (k_x - k\sin\theta_1\cos\varphi_1 - k_0\sin\theta_2\cos\varphi_2)^2 - (k_z - k\sin\theta_1\sin\varphi_1 - k_0\sin\theta_2\sin\varphi_2)^2},$$

when performing the approximate interpolations, the wavenumber in the depth direction obtained by dividing the angular frequency ω by the modification (conversion) of propagation speed (E'1) is used, whereas when not performing the approximate interpolations, the wavenumber in the depth direction expressed in the supplementary explanation of equation is used and similarly as below.

Thus, similarly to the methods mentioned in the paragraphs 0314 and 0329, the beamformings on the basis of these migration methods can also be performed with approximate interpolations or not on the wavenumber matchings.

The processings, regarding the method (1), mentioned in the paragraphs 0314 and 0329 can also be performed when being combined with the method (2) that performs the reception steered dynamic focusing, similarly to the original method (1) being combined with the method (2) as mentioned in the paragraphs 0233 to 0236. That is, in the 2D cases, to obtain the same results when performing the calculations of eqs. (F42) and (F43) with zero steering angles θ, similarly to the cases where eq. (M9) is multiplied and the inverse Fourier's transform is performed in the method (6), eq. (M9) is multiplied to an equation corresponding to eq. (16) prior to performing the processings mentioned in the paragraphs 0202 and 0203. Also in the 3D cases, to obtain the same results when performing the calculations of eqs. (G22) and (G23) with zero steering angles θ and φ, similarly to the cases where complex exponential function corresponding to eq. (M9) in the 2D cases is multiplied and the inverse Fourier's transform is performed in the method (6), the complex exponential equation is multiplied during the processings mentioned in the paragraph 0205.

These beamformings can also be performed with approximate interpolations or not on the wavenumber matchings as mentioned in the paragraphs 0314 and 0329. Others are also as mentioned in the same paragraphs.

On the basis of these migrations, all the beamformings mentioned in the method (4) can be performed similarly.

As likely mentioned in the method (5), all these migrations can be performed directly on the Cartesian coordinate system even when performing the transmissions and receptions on the orthogonal coordinate systems except for the Cartesian coordinate system such as the polar coordinate system etc. That is, in the same ways, implementing the Jacobi operation onto the eqs. (M6), (M6'), (M7), and (M7') for the above-mentioned beamformings yields the results directly on the Cartesian coordinate system. Also in the 3D cases, the Jacobi operation can be implemented onto the eqs. (M6), (M6'), (M7), and (M7') in the same ways and similarly, the results can be obtained. All other beamformings mentioned in the method (5) can also be performed similarly.

One of purposes of the present inventions is to realize high speed and high accuracy beamformings. However, the above-mentioned methods (1) to (6) with no approximate interpolations can also be modified to methods with approximate interpolations in various fashions and can be used as further higher methods, however, with lower accuracies. The modifications can be performed by performing the approximate wavenumber matchings or the multiplications of complex exponential functions etc at least in one or two directions or all in the three directions in the lateral, elevational and depth directions. Performing the approximations increases the a calculation speed, however, decreases the accuracy. The approximations include ones mentioned in the above-explanations. In the present paragraph, regarding the respective 2D and 3D cases, the 8 cases of (A), (A'), (B), (B'), (C), (C'), (D), (D') mentioned in the paragraphs 0314 and 0329 are explained, and the corresponding equations of approximate interpolations are described.

For instance, similarly the migration methods in the method (6) can also perform the processings for the cases where the steerings are performed, and the calculation speed becomes the fastest of all the migration processings similarly to the performing, on the wavenumber matchings, the approximate interpolations in all directions (corresponding to (D')) and the J.-y. Lu's method (the paragraph 0195, corresponding to (C')) performing the approximate interpolations being able to be used in the method (1). However, the accuracies are the lowest of all. Alternatively, when using the J.-y. Lu's method (the paragraph 0195, corresponding to (C')), for instance, when performing only the lateral wavenumber matching prior to performing the Fourier's transform, the accuracy increase and however, the calculation speed decreases (corresponding to (C)). Others including cases of (A), (A'), (B) and (B'), the approximate processings (equations) in the 2D cases (mentioned in paragraph 0314) are described (The 3D cases (paragraph 0329) can also be similarly expressed and omitted). Regarding (A), (A'), (C) and (C'), the equations are expressed according to eqs. (7) and (8). And, on (B') and (D'), the lateral inverse Fourier's transform is performed not on kx but kx'.

In (A) case, $$F(k'_x, k'_y) = R'(k_x, k),\qquad\qquad\text{(N5)}$$

where $$k = \frac{k'^2_y + k'^2_x}{2k'_y},$$

$$k_x = k'_x,$$

$$k'_y = \frac{\omega}{c}.$$

When performing the approximate interpolations on the wavenumber matching, the wavenumber in the depth direction ky is one obtained by dividing the wavelength w by the propagation speed c, whereas when not performing the approximate interpolations, the wavenumber matching can be performed as mentioned above.

In (A') case, $$F(k'_x, k'_y) = R'(k_x, k),\qquad\qquad\text{(N5')}$$

where $$k = \frac{k'^2_y + k'^2_x}{2k'_y},$$

-continued $$k_x = k'_x - k\sin\theta,$$

$$k'_y = \frac{\omega}{c}.$$

When performing the approximate interpolations on the wavenumber matching, the wavenumber in the depth direction ky is one obtained by dividing the wavelength w by the propagation speed c, whereas when not performing the approximate interpolations, the wavenumber matching can be performed as mentioned above.

In (B) case (the same as eq. (N4)), $$F''(k_x, 0, K(\tilde{k}_y)) = R''(k_x, 0, k), \qquad (N6)$$

where $$K(\tilde{k}_y) = \hat{c}\,\mathrm{sgn}(\tilde{k}_y)\sqrt{(k_x - k\sin\theta)^2 + \tilde{k}_y^2},$$

$$\tilde{k}_y = \sqrt{\hat{k}^2 - (k_x - k\sin\theta)^2} = \sqrt{\left(\frac{\omega}{\hat{c}}\right)^2 - (k_x - k\sin\theta)^2}$$

or $$\sqrt{\left(\frac{k}{\alpha}\right)^2 - (k_x - k\sin\theta)^2}.$$

When performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used.

In (B') case, $$F''(k'_x, 0, K(\tilde{k}_y)) = R''(k_x, 0, k), \qquad (N6')$$

where $$k_x = k'_x - k\sin\theta,$$

$$K(\tilde{k}_y) = \hat{c}\,\mathrm{sgn}(\tilde{k}_y)\sqrt{(k'_x - k\sin\theta)^2 + \tilde{k}_y^2},$$

$$\tilde{k}_y = \sqrt{\hat{k}^2 - (k'_x - k\sin\theta)^2} = \sqrt{\left(\frac{\omega}{\hat{c}}\right)^2 - (k'_x - k\sin\theta)^2}$$

or $$\sqrt{\left(\frac{k}{\alpha}\right)^2 - (k'_x - k\sin\theta)^2}.$$

When performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used In (C) case, $$F(k'_x, k'_y) = R'(k_x, k), \qquad (N7)$$

where $$k = \frac{k'^2_y + k'^2_x}{2k'_y\cos\theta + 2k'_x\sin\theta},$$

$$k_x = k'_x - k\sin\theta,$$

$$k'_y = \frac{\omega}{c},$$

When performing the approximate interpolations on the wavenumber matching, the wavenumber in the depth direction ky is one obtained by dividing the wavelength w by the propagation speed c, whereas when not performing the approximate interpolations, the wavenumber matching can be performed as mentioned above.

In (C') case (J.-y. Lu's method), $$F(k'_x, k'_y) = R'(k_x, k), \qquad (N7')$$

where $$k = \frac{k'^2_y + k'^2_x}{2k'_y\cos\theta + 2k'_x\sin\theta},$$

$$k_x = k'_x - k\sin\theta,$$

$$k'_y = \frac{\omega}{c}.$$

When performing the approximate interpolations on the wavenumber matching, the wavenumber in the depth direction ky is one obtained by dividing the wavelength ω by the propagation speed c, whereas in one of the present inventions, when not performing the approximate interpolations, according to the method (1), the wavenumber matching can be performed as mentioned above.

In (D) case (the method disclosed in the nonpatent document 12), $$F''(k_x, 0, K(\tilde{k}_y)) = R''(k_x, 0, k), \qquad (N8)$$

where $$K(\tilde{k}_y) = \hat{c}\,\mathrm{sgn}(\tilde{k}_y)\sqrt{k_x^2 + \tilde{k}_y^2},$$

$$\tilde{k}_y = \sqrt{\hat{k}^2 - k_x^2} = \sqrt{\left(\frac{\omega}{\hat{c}}\right)^2 - k_x^2}$$

or $$\sqrt{\left(\frac{k}{\alpha}\right)^2 - k_x^2}.$$

When performing the approximate interpolations on the wavenumber matching, the wavenumber in the depth direction ky is one obtained by dividing the wavelength ω by the modification (conversion) propagation speed (E1), whereas in one of the present inventions, when not performing the approximate interpolations, according to the method (6) (one of methods), the wavenumber in the depth direction expressed in the supplementary explanation of equation is used.

In (D') case, $$F''(k'_x, 0, K(\tilde{k}_y)) = R''(k_x, 0, k), \qquad (N8')$$

where $$k_x = k'_x - k\sin\theta,$$

-continued $$K(\hat{k}_y) = \hat{c}\,\text{sgn}(\hat{k}_y)\sqrt{k_x'^2 + \hat{k}_y^2},$$

$$\hat{k}_y = \sqrt{\hat{k}^2 - k_x'^2} = \sqrt{\left(\frac{\omega}{\hat{c}}\right)^2 - k_x'^2}$$

or $$\sqrt{\left(\frac{k}{\alpha}\right)^2 - k_x'^2}\,.$$

When performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used Also in these cases, the method (2) can be used at the reception beamformings.

It is important to perform the multidimensional Fourier's transform at first and the multidimensional inverse Fourier's transform with high speeds and then, various types of fast Fourier's transform (FFT) algorithms can be properly used. Also all other beamformings from ones mentioned in the present patent documentation (those of methods (1) to (6)) can also be performed with no approximate interpolations or with approximate interpolations similarly. To increase the accuracy in cases where approximate interpolations are performed, the sampling frequency can be set to be high and however, being different from in cases where image signals of arbitrary positions can be generated when no approximate interpolations are performed, it is cautious that the numbers of data to be used for the Fourier's transforms increase. However, in the cases where approximate interpolation processings are not performed as well, it is important to realize the conditions that allow processing the signals with an increased SNR via performing proper over-samplings.

In these processings, the above-mentioned beamformings in the methods (1) to (5) (including cases of beamformings performed on the reception signals received at once with respect to the simultaneous transmissions of plural different beams or waves or superposing of received signals with respect to the respective transmissions, or using of virtual sources or receivers etc) can also be performed on the basis of the migration processings (method (6)) with approximate interpolations or not.

Method (7): Others

For the above-mentioned methods (1) to (6), the cases using the 1D array are explained mainly. In the cases using the respective 2D or 3D arrays, as mentioned above, the lateral processings are performed in other one or two directions as well. These can be performed on all orthogonal coordinate systems including orthogonal curvilinear coordinate systems. That is, the above-mentioned methods (1) to (6) are extended to those of higher dimensions simply. When direct currents or low frequency components in lateral or axial directions can be generated during processing the method (1) to (6) and (7) mentioned here. In such cases, zero-padding of spectra is effective to be performed prior to the last inverse Fourier's transform. For performing the digital signal processing, analogue or digital processing can be performed to cut the direct currents off as preprocessings and also the zero-spectra-padding can also be performed with respect to the angular spectra.

For other beamformings, disclosed in nonpatent document 9 etc, using Fourier's transforms, the methods disclosed in the methods (1) to (7) can also be used and the same effects can be obtained.

For instance, in the section 2.4 in the nonpatent document 9, a method is disclosed, i.e., a method using a general solution (Green function) of a wave equation for calculating arbitrary beams or waves. As examples of analytically performed calculations, spherical, cylindrical and plane waves are processed, respectively. As a feature of using the Green functions, signals to be calculated have, in the denominators in frequency domains, $k_y = \sqrt{k^2 - k_x^2}$ for using the 2D Cartesian coordinate system (GR1)

and $k_y = \sqrt{k^2 - k_x^2 - k_z^2}$ for using the 3D Cartesian coordinate system, (GR2)

respectively. Using the method, the calculations can be performed using the Green functions on arbitrary orthogonal coordinate systems such as a cylindrical coordinate system, a spherical coordinate system and among others.

That is, regarding the methods or mathematical expressions (both cases performing no approximate interpolations and performing approximate interpolations) disclosed in the methods (1) to (7), the calculations are performed such that the spectra of target signals have respective eqs. (GR1) and (GR2) in the denominators. The methods and the expressions disclosed in the methods (1) to (7) can also be applied to other various methods and beamformings.

In these cases using the Green functions, since a point source can be considered as a source, using the functions is proper for using a virtual source set in front of or behind a physical aperture (patent document 7 or nonpatent document 8). In the cases, it is important to perform the processings regarding actual radiation patterns of physical apertures (elements) as the next paragraph.

The methods (1) to (7) can also use the operations, disclosed in the section 3.2 in the nonpatent document 9, additionally considering the radiation patterns of apertures (elements), for instance. At the time, signal processings can also be performed via correcting the signal intensities properly using physical or software apodizations. As many mentioned in the present patent document, for instance, ISAR, nonlinear processings, adaptive beamformings (nonpatent document 10) and other various processings can be performed to increase the spatial resolution (particularly, directions orthogonal to the propagation direction) or increase the contrast by decreasing the sidelobes. The coherent factor etc disclosed in the nonpatent document 11 etc can also be used. The processings are not limited to these. Apodizations can also be performed properly (For complex signals, the apodizations can also work as delays). The apodizations can also be changeable in the scanning directions as well as the propagation directions.

The methods (1) to (7) can also be used for various positions of the transmissions and receptions and other various beamformings. For instance, in the nonpatent document 9, various examples are disclosed. For instance, there are examples of the geophysical imaging in the section 7.3 (for instance, tale notice of the expression forms of eqs. (7.9) to (7.12)), the so-called X-ray CT (Computed Tomography) etc. In addition to these, the methods (1) to (7) can also be used for astronomical observations and among others. It is worthy of taking notice of FIG. 7.3 and eqs. (7.5) to (7.9) disclosed for the case of transmission imaging disclosed in the section 7.2 in the nonpatent document 9. For these examples can be processed with no approximate interpolations including for the wavenumber matchings etc (For these, approximate interpolations can also be performed).

These methods (1) to (7) have a feature that image signals can be directly and selectively generated on pre-specified bi-planes or multiple planes, desired planes or fault surfaces with spreading in arbitrary directions etc (not always flat and can be curvilinear) or not surfaces but lines (straight or curvilinear lines). For instance, when images can be displayed on the basis of 3D or 2D image signals, there are cases where the images can be displayed on the basis of the image signals, and the images are displayed solo. The image signals or images can also be displayed via approximate interpolations on the signal processings. Also measurement data such as a displacement or a strain, a temperature etc measured on the basis of the image signals or images can also be displayed solo or as superposed ones on the images.

As mentioned several times in the present patent document, the apodizations can be determined in various ways and can be performed. There are various adaptive beamformings, minimum-variance beamformings, Capon method etc as mentioned in the nonpatent document 10 etc. In these beamformings, when implementing the regularizations on the covariance matrices, the parameter to be used for controlling the degree of the regularization (the regularization parameter) can be properly determined on the basis of the SNR etc of the signal at each position and then the processing can be performed spatially variantly. As modified methods, not an identity matrix (i.e., diagonal matrices) but other positive-definite operators such as the gradient operator or the Laplacian operator etc can also be used for the regularization operator. It is possible to increase spatial resolutions in image signals (particularly, directions orthogonal to the propagation direction) and contrasts as well by decreasing sidelobes. On independent component analysis (independent signal separation), It is also effective to implement the regularization on the covariance matrix similarly. These regularizations have not been disclosed. Alternatively, in the both processings, it can also be performed to stabilize the processings by decreasing the rank via the singular value decomposition or the eigenvalue decomposition. These processings are also effective for other methods on beamformings similarly. As mentioned in other parts, it is also effective to use MIMO (Multiple-input and Multiple-output: a wireless communication technology increasing the bandwidth of transmission and reception signals using combinations of plural antennas at transmission and reception sides) and SIMO (Single-input and Multiple-output: a wireless communication technology increasing the bandwidth of transmission and reception signals using a single antenna at a transmission side and combinations of plural antennas at a reception side). The inventor of the present inventions has been using the absolute detection or the power (exponentiation) detection favorably since before, and the coherent factor is effective as mentioned in the nonpatent document 11 etc. The absolute detection or the power detection is effective for visualizing wave oscillations. Via considering the absolute value or implementing powers on signals, with yielding high frequency components using a high order powers, it is possible to assign brightness or colors to the magnitudes of wave (These can be considered as detections for adding biases to signals). In the nonpatent document 10, other various adaptive beamformings are mentioned, and also in the present patent document, various processings such as MUSIC (Multiple Signal Classification: a wireless communication technology using eigenvalues and eigenvectors of correlation matrix calculated for reception signals) etc are mentioned. Effective processings are not limited to these and there exist various processings. It is also possible to perform various processings such as these processings before, during or after the beamformings, and it is also possible to perform them by the processings at the level of the apodizations. For these processings, it is remarkably effective to perform the processings after temporal (time) and/or spatial (position) matchings on the basis of correlation processings.

In the present inventions, the SNR of signal can also be increased particularly by implementing integration (calculation) processing on acquired signals along the fast time axis (in a distance direction). The integration processing can be performed by analogue processings (using a so-called integrator) or by digital processings (integrator or integration calculation).

In the above-descriptions, for the apodizations, the methods performing the multiplications with weight values are explained, which realizes the small number of calculations and simplicities. The present inventions are not limited to these, and convolution integrations can also be performed on the basis of the relationship of a duality about the multiplication and the convolution integration in a spatial domain and a frequency domain. At the respective depths or at the respective same distances from the aperture elements to be used, proper apodizations can be performed.

Superposing the generated steered beams or waves generated by the instrument of the present embodiment using the methods (1) to (6) can generate the above-mentioned lateral modulation signals (image signals) or laterally, widely banded image signals (with an increased high lateral resolution). Similarly to the cases of single transmission, the physical steering or the software steering, or both the steerings can also be performed respectively, or the same combination of steerings (a non-steering can also be included) can also be performed on the all. Regarding the reception beamformings, it is mainly explained that the reception beamformings are performed in software fashions, if necessary, the reception beamformings using the reception delays or the reception apodizations can also be performed physically solo instead or together. Alternatively, regarding the transmission beamformings, it is mainly explained that the transmission beamformings are performed physically, and for instance, high frame rates can be achieved by transmitting a plane wave, or plural beams or waves etc, while one transmission is performed every one element to perform SA (Multidirectional SA can also be performed by decoding the received signals with respect to the encoded transmission of a plane wave, a cylindrical wave, a spherical wave etc). As mentioned above, it is also possible to consider or perform the transmission and the reception inversely. The plane wave penetrates into a deeper position than the focused beams (With comparison, the echo can also be obtained from a deeper position). However, with comparison, the SNR of the wave or as a beam for the purpose of displacement measurement etc is lower. With comparison, the lateral resolution is also lower originally. Alternatively, superposing the plane waves steered in plural directions can yield almost the same lateral resolution regardless the depth position. In contrast, although using the focused beams steered in plural directions for the superposing at the same focus position is effective, multi-focusing or multi-focusings are required to be performed for generating high spatial resolutions at plural positions. Using the present invention, it is possible to achieve the beamformings with high speeds absolutely with respect to the reception signals received with respect to simultaneous transmissions of plural waves or beams, or superposition of reception signals respectively received with respect to transmissions performed at different times, however, at the same phase of the object. Also using plural waves having different carrier frequencies yields axially widely banded signals (image signals with an increased axial resolution). In these cases, the increasing of bandwidths can also be achieved by overlapping the spectra, by which the increasing of the spatial resolution can also be achieved. These plural beams can also be generated simultaneously in a parallel fashion, and can also at different times, however, at the same phase of the object. The waves of plural directions can also be generated by the above-mentioned multidirectional SA.

When making the steering angles large, the image formation position of a reflector or a strong scatter can get out of the original position. For instance, superposing the received signals with respect to the transmissions of plane waves with respective steering angles, with respect to the direction of a face of aperture element, increasing up to ±45° by changing the steering angle by a small angle (for instance, 1°) can make a quasi-SA in the frontal direction and a lateral bandwidth corresponding to that determined by the steering angles ±45° cannot be obtained (the laterally high frequency signals are canceled out at the superposition). It is straightforwardly possible to understand the results by considering a beamforming in a frontal direction to be decomposed into angular spectra as plane waves. To increase a lateral bandwidth by the superposing of signals in a temporal and/or spatial or frequency domain, regardless the plane wave transmitted or not, any steering beamformings should be performed such that the respectively generated spectra not overlapped in the frequency domain can be superposed. However, it is cautious that the errors in image formation positions (different positions from the original position) generated by the respective steered beams or waves lead to the errors in the finally generated image formations. Thus, when performing the superposition of signals with large steering angles, it can be required to perform the corrections of signal positions at least at one timing of at the transmissions for the beamformings, at the receptions with respect to the received signals before performing the reception beamformings, during the reception beamformings and after beamformings. When performing the superresolutions of these signals such as spectra processings (filtering or weighting etc) and nonlinear processings, because the errors (position errors etc) due to the simultaneous performing of the superposition processings (the affections due to the respective position errors) become more remarkable, the corrections of the respective signal positions become more important. For instance, superposing is performed, of which spectra are processed (filtered or weighted) or which is nonlinearly processed, or pre-processed (filtered or weighted) spectra or pre-nonlinearly processed signals are superposed and among others. In addition, the respective position errors can be caused by the frequency dependencies etc of the modified (conversion) propagation speeds or by superposing different frequency signals and can also be similarly coped with. The corrections of positions are also mentioned in the paragraph 0369 etc. Various signal processing technologies can be used such as those of motion compensation and phase aberration correction. The corrections of signal intensity are also mentioned in the paragraph 0663 etc. Beamforming components of weak scattering signals or speckle components are different from such deterministic signals and can be used for imagings or displacement measurements without performing the corrections of positions as it was previously confirmed on the experiments using virtual sources or virtual receivers that are assumed as scatters etc (a past invention of the present invention's inventor: patent document 7 and nonpatent document 8). For instance, for the displacement measurement, the combination of the plane wave transmission(s) with the Gaussian type apodization(s) is effective and when performing the focusing, the exponentiation type apodization(s) such as the 2nd power is effective. The latter apodization also yields a high spatial resolution even when the single beamforming is performed.

To perform the multi-focusing (not limited to a general multi-focusing that generates plural foci at different positions along the direction of beam propagation and including a new multi-focusing that can generate plural foci at arbitrary different positions also including different lateral positions), plural waves respectively having different focus positions can be generated and the reception beamforming can be performed. With respect to one transmission beams, plural reception beams can also be generated at plural positions or in plural directions. Plural transmission beams with plural different steering angles can also be generated. Such beamformings can be performed at separate positions to be with little interferences between the beams to be generated, or the beamformings can be performed in the respective parts, i.e., divisions of one frame, on the basis of such transmissions and such receptions. Then, parallel beamformings can be performed to perform the beamformings of plural beams in a parallel fashion, and respectively in the parts the beamformed results can be superposed at respective positions in an ROI. The method (4) itself has a feature that when the waves propagate in an ROI, even if the waves have interferences each other, the corresponding reception signals can also be processed; the best use of which is made to realize a high frame rate (The method (4) allows performing reception beamformings with respect to arbitrary transmission beams or waves, or single or plural transmissions). Reception signals can also be implemented by various types of signal separation processings, the beamformings can be performed with respect to the signal components properly. Being dependent on the degree of interferences, the processings can also be performed with no removing processings on the waves that arrive from the outside of ROI or propagated to the outside of ROI.

The respective apertures of transmissions and receptions can be the exclusive ones and the apertures can work for both the transmissions and receptions. Thus, the apertures do not always perform the receiving of the responses with respect to the waves transmitted from the apertures themselves and the apertures can also receive waves generated by other apertures, and then parallel processings can be performed and the beamformed results can be superposed. Summarizing, the above-mentioned superposing can be performed with respect to the objects (communication media), in which the waves propagate, or the objects to be observed having the same time, the same or almost the same condition (same phase), at different times or at different phases, via performing one of at least one beamforming, one transmission and one reception at each aperture or using one combination of transmission and reception apertures. Similarly, the respective combinations of plural apertures can also perform one of at least one beamforming, one transmission and one reception. When performing such processings, the superposing the obtained plural, beamformed, transmitted or received results can be performed to yield new data.

Since the processings of superposing are linear processings, in the calculation processes of the above-mentioned methods (1) to (6), plural complex spectral signals having same frequencies can also be superposed in a frequency domain. In the case, the superposed spectra can be inverse-Fourier's transformed at once; achieving a higher speed for completing the superposed beamforming than the above-mentioned superposing, in a spatial domain, of the plural respectively beamformed waves that requires to perform the same number of Fourier's transforms as that of waves to be superposed. Such as arriving waves, however, not limited to this, of which angular spectra are superposed, can also be processed in a direction or in plural directions, for instance. For the processings, plural waves superposed in a spatial domain are Fourier's transformed, and then the superposed angular spectra can be used (The effect can be yielded on performing the Fourier's transform only one time). It can become to confirm the position of object etc.

As mentioned above, when performing the transmissions of plural beamformed waves using the methods including the methods (1) to (6) except for the SAs of the methods (2) and (3) (predetermined transmission delays can be implemented at least and transmission apodizations can also be implemented), specifically for physically performed simultaneous transmissions (the aperture elements to be excited at first in effective apertures for generating the respective waves are simultaneously excited etc), the corresponding reception signals are stored into the memories or storage devices (storage media) in the condition of superposed. And then, using the respective methods, the processings for generating image signals for one frame can be performed (The parallel processing can also be performed on the respective processings to be performed in parts of one frame).

Alternatively, in the above-mentioned other cases in which the plural beamformings are performed at different times, since the instrument of the present invention can confirm the timings of performing transmissions at the aperture elements at first in the effective aperture arrays, the digital signal processing unit can similarly perform the processings via properly superposing the plural reception signals of the respective channels on the reception aperture elements such that the same reception signals can be obtained as those obtained by performing the simultaneous transmissions of the plural waves (The parallel processing can also be performed on the respective processings to be performed in parts of one frame). In these cases, in practical, Fourier's transform to be performed at first can be one time (Note that the proceedings can also be performed at respective divisional parts).

In these active cases, the beamformings except for the SAs (methods (2) and (3)) can be achieved with higher speeds. However, note that if required, the transmission beamformings (predetermined transmission delays can be implemented at least and transmission apodizations can also be implemented) are implemented on the SA reception signals that are generally used for the methods (2) and (3), after which the processings are performed on superposed signals and similarly processed. Incidentally, when the reception signals obtained with no transmission delays are superposed, the reception signals with respect to the plane wave transmission with no steering can be generated. For SA processings, the calculation speeds can also be increased by performing the division(s) and parallel processing. Particularly, when performing the multidirectional SA (a past invention of the present invention's inventor), plural beams can be generated in different directions from same reception signals acquired at one phase of the object and when performing the processings using the instruments or the methods of the present invention, calculations are performed on the same angular spectra obtained by implementing the Fourier's transform on the reception signals once and finally, image signals are generated with a high speed not via performing the inverse Fourier's transforms plural times on the angular spectra obtained for the respective steering angles but via performing the inverse Fourier's transform once on the superposed angular spectra (The proceedings can also be performed at respective divisional parts). However, whenever passive processings are performed using the SAs, reception fixed focusing or other beamformings, as mentioned above, it is effective to perform the processings in a direction or in plural different directions on the superposed reception signals (i.e., one set of angular spectra).

In these processings, in which the superposition of plural waves can be obtained, for instance, if the propagation directions or frequencies, or bandwidths are different, it is effective to perform the processsings after separating the spectra. The superposed signals can also be separated in the digital signal processing unit by using coding, MIMO, SIMO, MUSIC, independent signal separation (independent component analysis), principle component analysis, coding or parametric methods etc. Incidentally, the superposing processing can also be effective for other processings (For instance, using the plural signals obtained at the same phase of the object increases the SNRs of signals etc).

The independent signal separation (independent component analysis) is, for instance, effective for separating the specular reflection signals and scattering signals, i.e., if the frames larger than two including the same specular reflection signals have independent scattering signals or states that includes mixed, independent scattering signals, the processing can separate the commonly included specular reflection signals effectively. Such processing is effective for automatically detecting and/or separating (removing) high intensity signals from blood vessels when performing the measurements of tissue displacements such as blood flow etc, or specifying (detecting) the region of blood flow. Otherwise, it is effective for detecting or extracting the boundaries of organs or tumors etc and similarly, it is possible to detect, separate (or remove) the specular reflections (tissues) and also to specify (or detect) the region with properties or features. It is also possible to simultaneously separate the mixed independent scattering signals. The capability in detection of the specular reflection signals and that in separation of mixed signals of the independent component analysis (independent component separation) are higher than the detections of the signals using the sum (additional average) and the difference of frames, respectively. The detections (envelope detection, squared detection and absolute detection etc) can be performed as preprocessings to increase the capabilities. This can also be confirmed with quantitative evaluations in a deterministically or stochastically as well as visually. Corrections of signal positions can be performed to match the signal positions among the frames by performing the motion compensations regarding the translation, rotation and deformation etc via performing the measurements of a displacement or a strain, and the processing increases the capabilities (For instance, in simulations using a 3 MHz ultrasound pulse, the cross-correlation-based displacement measurement allows the motion compensation for the standard deviation (SD) of the scattering signals being 1.0 and the specular reflection coefficient distribution ranging from 0.1 to 0.5, even if the scattering signals with almost the same intensity are mixed). The processings having a spatial resolution are required to be performed. Performing the displacement measurement etc prior to the detections can yield a higher accuracy and however, after performing the detections, the measurement can also be performed. When performing the high accuracy displacement measurements using various types of measurement methods prior to the detections, the motion compensation using block matching (coarse phase matching) performed in a temporal and/or spatial domain via performing the over-samplings or up-samplings, or phase matching performed by implementing the phase rotation in a frequency domain is effective. When using a medical ultrasound transducer, the independent signals can be obtained by slanting the transducer and receiving from other angles the specular reflection signal generated at the same position or by receiving signals using other subapertures on the basis of the steering processing. Otherwise, it is also effective to get out of the position of the scanning plane and receive the signal including the same specular reflection signal generated at the source of the same specular reflection signal (continua of the same structure or composition). This is an operational technique using a hand. It is also possible to positively use the object motions (when the scanning plane moves out, signals from other tissues are mixed) or the object deformations (can be considered that noises are included) when acquiring signals including the specular reflection signals. When using other waves from the medical ultrasound, such as an ultrasound for a sonar etc or an electromagnetic wave, reflection or transmission waves can be acquired and processed similarly, in which used are motions of a sensor, a signal source and a detector (the shakes of them or the disturbances of their holders etc), the steerings of waves or beams, the target motions or deformations etc. Mixing of noises generated in circuits and the signals can also have similar effects and then, such noises can also be used by positively generating and mixing in analogue or digital fashions (including in a software fashion, where programs can also be used). These processings can also be used for obtaining the same effects on the common and mixed signals existing in signals as well as the separation of specular reflection signals and the scattering signals; and the applications are not limited to these. The differences in a time and/or in a space are not always caused by the displacement or strain, and inhomogeneities of propagation speeds of media themselves or changes in the propagation speeds due to disturbances of media or changes in conditions (for instance, change in a pressure or a temperature etc) etc can also cause the differences, which can be processed using the signal analysis purely. Although the applications are mentioned on the frame signals, beamformed signals (including ones obtained by SAs), reception signals before performing the reception beamformings or reception signals with no beamformed signals (transmission and reception signals for SAs) can also be processed similarly and besides beamformings can be performed. That is, the processings can be performed at least before, during or after the beamformings. On the respective cases, the superresolution can also be performed. The above-mentioned motion compensation processings can effectively correct the temporal and spatial differences etc in addition to, for instance, the differences etc in signals with respect to the transmissions of focusing beams or plane waves, which are referred to with comparison (for instance, for performing the superresolutions). The above-mentioned motion compensation processings performed before or during the beamformings can also work as delay processings in DAS processings. The detections (absolute detection, square detection, envelope detection etc) or increasing a spatial resolution via linear or nonlinear processings mentioned later can also be implemented similarly on beamformed signals (including ones obtained by SAs), reception signals before performing the reception beamformings or reception signals with no beamformed signals (transmission and reception signals for SAs) and besides beamformings can be performed. That is, the processings can be performed at least before, during or after the beamformings. To increase the bandwidths during the processings, if required, over-samplings or up-samplings can be performed in a time and/or in a space, or zero spectra padding can also be performed in a frequency domain (implementing the inverse Fourier's transform on the spectra can yield the results of the over-samplings or up-samplings).

The signal separation can also be performed in a frequency domain with a high accuracy after performing the increasing frequencies and bandwidths using the exponentiation calculations (when the orders larger than 1) or the decreasing frequencies and bandwidths (when the orders smaller than 1). The restorations of the separated signals can be simply performed using the exponentiation calculations with the reciprocals of the used orders.

Alternatively, in the methods (1) to (6), spectral division(s) is implemented on the reception signals stored in memories or storage devices (storage media), generally used for generating image signals for one frame, to yield plural waves with divisions, in a frequency domain, of spectra on which the wavenumber matchings are completed. The states of angular spectra can also be divided and the respective divisions can also be processed. In both cases, the limited bandwidths of signal components can be processed. When plural waves are superposed, the spectral frequency division(s) can also be similarly performed. Correspondingly, these spectral frequency divisions can yield physically quasi-waves having new wave parameters such as frequencies, bandwidths, propagation directions etc). The divided spectra can also be processed in a parallel fashion. The superposing processings are also used for yielding new wave parameters; and to be performed in a spatial domain (corresponding to performing the superposing of angular spectra in a frequency domain) or spectra are superposed in a frequency domain before performing the inverse Fourier's transform. If required, angular spectra obtained by Fourier's transform can also be superposed, or signals obtained by inverse Fourier's transform can also be superposed.

The digital signal unit uses the plural waves generated using these processings to measure, with a high accuracy, a displacement vector expressing the object's displacement in an arbitrary direction (the multidimensional autocorrelation method or the multidimensional Doppler method etc for solving simultaneous equations on unknown displacement vector components (past inventions of the present invention's inventor, nonpatent document 13)) or a general one-directional displacement (high accuracy measurements can also be obtained by performing the least squares solution, the averaging of plural measurements obtainable or the increasing frequencies and bandwidths of signals owing to superposition of spectra on over-determined systems with the larger number of derived equations as that of unknown displacement components, patent document 5). From each generated wave, an equation is derived. The general Doppler method can also be implemented on a wave. The respective waves can also be superposed ones, the spectral-frequency-divided ones and the spectral processed ones. The respective waves are desired to be high frequencies and then, can also be the low-frequency-spectra disregarded ones; and besides when a high spatial resolution is also required, the waves are desired to be large bandwidths (nonpatent document 14). For the divisions and processings on spectra, windows allowing weighting the spectra can also be used. From the measured displacement (vector), a strain (tensor), a strain rate (tensor), a velocity (vector), an acceleration (vector) can be obtained by implementing partial derivative processings using spatial and/or temporal differential filters. These can also be used for calculating the (visco) shear modulus or viscosities, the mean normal pressure, the density etc. As other displacement (vector) measurement methods such as the multidimensional cross-spectrum phase gradient method (one of block matching methods, patent document 6 or nonpatent document 15 etc) or the digital demodulation method (patent document 7) can also be used for the measurements of a strain etc similarly. Using these methods, measurements of wave propagations such as a shear wave or low frequency vibrations can also be performed. The (visco) shear modulus, the shear wave propagation speed and/or direction, the displacement of a shear wave, the frequencies, the phase, the vibration amplitude, the vibration velocity and the vibration acceleration etc can be measured. These can also be calculated as distributions.

To increase the accuracies of the displacement measurements, previously the inventor of the present invention developed the implementing of the regularization. To determine the regularization parameters of penalty terms, for instance, the standard deviation (SD) of displacement (vector) measurements is estimated under the (local) stationary process and used a posteriori (patent document 6) or Ziv-Zakai Lower Bound (ZZLB: for instance, the lower bound of standard deviation (SD) shown in the nonpatent document 16) is estimated using the properties of the wave or beam etc and used a priori (for instance, nonpatent documents 17 and 18).

In the present invention, these standard deviations (SDs) or ZZLB can be used for weighting the above-mentioned, derived Doppler equations to control the confidences of the respective equations when holding the simultaneous equations (A high confidence equation is weighted heavily and a low confidence equations is weighted lightly). That is, the weight values are calculated with respect to the above-mentioned respective waves or beams at respective position in an ROI and the equations, derived from the respective waves or beams at the positions, are correspondingly weighted using the weighted values and are solved. Using the least squares solutions, the weighted least squares solution (WLSQS) can be calculated a posteriori or a priori.

The simultaneous equations of the above-mentioned, derived Doppler equations are expressed as follows.

$$Au=b, \quad (A1)$$

where u is an unknown displacement vector of a position of interest or a local region including the position of interest, or the distribution; b is a change in a phase, generated between frames, of the point of interest or the local region including the position of interest, or the distribution; A is a matrix lexicographically comprising of frequencies of the point of interest or the local region including the position of interest, or the distribution. The components of A and b can be moving-averaged in a temporal or spatial direction. When the demodulations are performed at least in one direction, the equations are derived for Doppler equations about unknown displacement components in one or two directions with carrier frequencies.

The matrix W expressing the distribution of the reciprocals of SDs or ZZLBs, themselves, or the exponentiations or the distribution is used for weighting eq. (A1) and the following simultaneous equations are solved.

$$WAu=Wb \quad (A2)$$

Specifically, let's focus on one position of interest or one local region. With respect to one Doppler equation (or plural equations, i.e., simultaneous equations, derived using the cross-spectrum phase gradient method, comprising of equations hold regarding phase spectra in signal bandwidths calculated from the cross-spectra estimated for the local region or simultaneous equations, derived when performing the block matching using the multidimensional autocorrelation method or the multidimensional Doppler method, comprising of equations hold at respective positions in the local region) derived from one of waves or beams p (=1 to N), since the reciprocal of SD or ZZLB Wp calculated at the position or at the local region is that about the displacement in the beam direction, when the unknown displacement is a 3D vector $u=(Ux,Uy,Uz)^T$, the following equations hold.

$$Wp(AxpUx+AypUy+AzpUz)=Wpbp \quad (A3)$$

where Axp, Ayp and Azp (p=1 to N) are the frequencies in the x, y and z directions and they are components of the matrix A in eqs. (A1) and (A2); bp (p=1 to N) is the change in phase between the frames and it is components of the vector b; Wp is diagonal components of W in eq. (A2). When using the cross-spectrum phase gradient method (one of block matching methods) or the multidimensional autocorrelation method or the multidimensional Doppler method as block matching methods, all the simultaneous equations hold with respect to the local region are multiplied with Wp (i.e., with respect to one p, plural equations simultaneously hold and all the equations are multiplied with Wp).

For instance, according to the ZZLB mentioned in the nonpatent document 16, when the Cramer-Rao Lower Bound (CRLB) holds, the variance that is the square of CRLB is expressed as follows.

$$\sigma^2_{CRLB} = \frac{3}{2\pi^2 T(B_b^3 + 12B_b f_{0b}^2)} \left\{ \left(1 + \frac{1}{SNR_c}\right)^2 - 1 \right\} \quad (A4)$$

where T is, for the multidimensional autocorrelation method or the multidimensional Doppler method, a moving-average width used for calculating the frequency or the change in phase, and for the block matching methods such as the multidimensional cross-spectrum phase gradient method, the multidimensional autocorrelation method or the multidimensional Doppler method, a length of local region used for the measurement; $f_{ob}$ is an ultrasound frequency in the beam direction; $B_b$ is a rectangular bandwidth in the beam direction; SNRc is a combined SNR by expressed using an echo SNR, SNRe, and a correlation SNR, SNRρ (a signal-to-noise ratio regarding the noise components generated by a decrease in echo correlation due to the distortion of signal wave caused by object's displacement or deformation itself):

$$SNR_\rho = \frac{\rho}{1-\rho}, \quad (A5)$$

where ρ is correlation estimated at calculating a local cross-spectra between the frames or the local correlation estimated using the moving-average width, i.e., $$SNR_c = \frac{SNR_\rho SNR_e}{1+SNR_\rho + SNR_e}. \quad (A6)$$

Thus, the SD can be estimated, for instance, as mentioned in the patent document 17, by using T, $f_{Ob}$, $B_b$, SNRc, SNRe, SNRρ, ρ (including measured or estimated ones). $f_{Ob}$ is, as mentioned in the nonpatent document 19, an instantaneous frequency or the 1st order moment (i.e., weighted mean) that can be estimated, and $B_b$ is the square root of the 2nd order center moment that can be estimated.

$$f_{Ob} = \int f_b S(f_b) df_b \tag{S1}$$

and $$B_b = \sqrt{\int (f_b - f_{Ob})^2 S(f_b) df_b}, \tag{S2}$$

where $f_b$ is a frequency in the beam direction, $S(f_b)$ is a spectrum of the frequency $f_b$.

In the cases of the multidimensional signals, the calculations can also be performed using the two axes (i.e., 3D) or one axis (i.e., 2D) orthogonal to the beam direction as well and for instance, in the cases of 3D, $$f_{Ob} = \int f_b(f_x, f_y, f_z) S(f_x, f_y, f_z) df_x df_y df_z \tag{S1'}$$

and $$B_b = \sqrt{\int (f_b(f_x, f_y, f_z) - f_{Ob})^2 S(f_x, f_y, f_z) df_x df_y df_z}, \tag{S2'}$$

where $f_b(f_x, f_y, f_z)$ is a frequency in the beam direction at frequencies $(f_x, f_y, f_z)$ and $S(f_x, f_y, f_z)$ is a spectrum of the frequencies $(f_x, f_y, f_z)$; and in the cases of 2D, using a spectrum $S(f_x, f_y)$ of frequencies $(f_x, f_y)$ and in the cases of 1D, using a spectrum $S(f_x)$ of a frequency $(f_x)$, similarly the calculations can be performed.

The echo SNRs, SNRe, can be statistically estimated by sampling echo data at the respective positions of interest iteratively from the object or calibration phantoms. On the basis of the object or the conditions, or experiences on the measurements, it is also possible to determine SNRe using typical values a priori. Alternatively, the correlation SNRs, SNRρ, can be estimated using the correlations ρ estimated locally at the respective positions of interest. How to calculate these is not limited to these. If some values cannot be used and then the SDs cannot be estimated absolutely, typical values can be used for the unknown values. When setting the regularization parameters, by judging whether the results obtained with changing an unknown constant to be multiplied to the SDs, ones calculated using available data, are good or not, the best constant can also be determined (regarding the regularizations, for instance, patent document 6 and nonpatent documents 17 and 18).

Here, when the 1st order moment or the 2nd order center moment in the beam direction is not directly estimated and instead, those in the respective directions are estimated (for instance, in the 3D cases of signals, the 1st order moment $f_{Ox}$ and the 2nd order center moment $B_x$ are $$f_{Ox} = \int f_x(f_x, f_y, f_z) S(f_x, f_y, f_z) df_x df_y df_z \tag{S1''}$$

and $$B_x = \sqrt{\int (f_x(f_x, f_y, f_z) - f_{Ox})^2 S(f_x, f_y, f_z) df_x df_y df_z}, \tag{S2''}$$

where $f_x(f_x, f_y, f_z)$ is a frequency in x-axis direction of frequencies $(f_x, f_y, f_z)$, and $S(f_x, f_y, f_z)$ is a spectrum; in the 2D cases, using the spectrum $S(f_x, f_y)$ at frequencies $(f_x, f_y)$ and in the 1D cases, using the spectrum $S(f_x)$ at a frequency $(f_x)$, the calculation can be performed similarly; and also in y- and z-axis directions, the calculations can be performed similarly), or other methods from the ZZLB are used and SD of the displacement in the beam direction is not directly estimated and instead, SDs of the displacement vector components in the respective directions are estimated, the following estimations can be performed. That is, under the assumption that the stochastic processes of the displacement component measurements are independent each other, the propagations of the respective measurement errors to the estimation error of the displacement in the beam direction are considered. For instance, when the respective means and SDs of 3D displacement vector components are estimated as (mx,σx), (my,σy) and (mz,σz), the mean $m_{beam}$ and SD $\sigma_{beam}$ of the displacement in the beam direction can be respectively estimated as follows.

$$m_{beam} = \sqrt{m_x^2 + m_y^2 + m_z^2} \tag{A7}$$

$$\sigma_{beam} = \sqrt{\frac{m_x^2 \sigma_x^2 + m_y^2 \sigma_y^2 + m_z^2 \sigma_z^2}{m_x^2 + m_y^2 + m_z^2}} \tag{A8}$$

Using the mean $m_{beam}$ and SD $\alpha_{beam}$, the SD of the displacement in the beam direction $\sigma_{CRLB}$ can be estimated.

When the parameters (T, $f_{Ob}$, $B_b$, SNRc, SNRe, SNRρ) described in eqs. (A4) to (A6) are provided in the respective directions; and then the means of the displacements $f_{Ox}$, $f_{Oy}$ and $f_{Oz}$ in the respective directions and the SDs of the displacements $\sigma_{CRLBx}$, $\sigma_{CRLBy}$ and $\sigma_{CRLBz}$ in the respective directions can be estimated, the SD of the displacement $\sigma_{CRLB}$ in the beam direction can be estimated using eq. (A8) as follows.

$$\sigma_{CRLB} = \sqrt{\frac{f_{0x}^2 \sigma_{CRLBx}^2 + f_{0y}^2 \sigma_{CRLBy}^2 + f_{0z}^2 \sigma_{CRLBz}^2}{f_{0x}^2 + f_{0y}^2 + f_{0z}^2}} \tag{A9}$$

When the unknown displacement at a position of interest is a 2D vector $u=(Ux,Uy)^T$, similarly the SD of the displacement in the beam direction can be calculated (When the unknown displacement is only a component and is a displacement U in an arbitrary direction or in a beam direction, the estimate of SD itself is used).

$$m_{beam} = \sqrt{m_x^2 + m_y^2} \tag{A7'}$$

$$\sigma_{beam} = \sqrt{\frac{m_x^2 \sigma_x^2 + m_y^2 \sigma_y^2}{m_x^2 + m_y^2}} \tag{A8'}$$

$$\sigma_{CRLB} = \sqrt{\frac{f_{0x}^2 \sigma_{CRLBx}^2 + f_{0y}^2 \sigma_{CRLBy}^2}{f_{0x}^2 + f_{0y}^2}} \tag{A9'}$$

When calculating the displacement at the respective positions of interest or at the respective local regions regarding the positions of interest, the simultaneous equations (A2) of the weighted Doppler equation (A3) [p=1 to N] holding at the positions of interest are solved. The number of waves or beams (i.e., the number of equations) N is required to be larger than the number of unknown displacement components. However, note that when performing the above-mentioned block matching, as mentioned above, plural equations of eq. (A3) holds on one wave or one beam p. Thus, compared with other displacement measurement methods, a fewer waves or beams can also be used for the measurements.

When performing the regularizations simultaneously, eq. (A2) of which unknown vector u is the displacement component distributions is obtained by simultaneously deriving all eqs. (A3) holding at the plural positions of interest or at the plural local regions set on the positions of interest in an ROI, and the regularized weighted least squares solution (RWLSQS) can be calculated. To set the regularization parameters, the SDs or the ZZLB can be used (values being proportional to the SDs or the exponentiations etc). Regarding the regularizations, for instance, see the patent document 6. The above-mentioned SDs of the displacements in the respective wave propagation directions or beam directions can also be used for setting the regularization parameters of the displacement components in all directions, and the SDs of the displacements in the respective wave propagation directions or beam directions can also be used for setting the regularization parameters of the displacement components in the respective directions. For instance, regarding the distribution of an unknown 3D displacement vector $(U_x, U_y, U_z)^T$, when calculating the unknown vector $U=(U_x, U_y, U_z)^T$ comprising of the partial unknown vector $U_x$, $U_y$ and $U_z$ being the distributions of the respective displacement components $U_x$, $U_y$ and $U_z$ in the x, y and z directions, the error energy, expressed using the matrix W comprising of the SDs $W_p$ (p=1 to N) of the displacements in the respective beam directions at respective positions as diagonal components or using the matrices $W_x$, $W_y$ and $W_z$ respectively comprising of the SDs $W_{px}$, $W_{py}$ and $W_{pz}$ (p=1 to N) of the respective displacement components at respective positions as diagonal components, to be least-squares-minimized E(u) and the solution u are expressed as follows.

$$E(u) = \|b - Au\|^2 + \alpha_0 \|u\|_W^2 + \alpha_1 \|Du\|_W^2 + \alpha_2 \|D^T Du\|_W^2 \quad (A10)$$
$$= (b - Au)^T(b - Au) + \alpha_0 u^T W^T W u +$$
$$\alpha_1 u^T D^T W^T W D u + \alpha_2 u^T D^T D W^T W D^T D u,$$

and then,
$$(A^T A + \alpha_0 W^T W + \alpha_1 D^T W^T W D + \alpha_2 D^T D W^T W D^T D) u = A^T b$$

or
$$E(u) = \|b - Au\|^2 + \alpha_{0x}\|u_x\|_{W_x}^2 + \alpha_{0y}\|u_y\|_{W_y}^2 +$$
$$\alpha_{0z}\|u_z\|_{W_z}^2 + \alpha_{1x}\|Du_x\|_{W_x}^2 + \alpha_{1y}\|Du_y\|_{W_y}^2 + \alpha_{1z}\|Du_z\|_{W_z}^2 +$$
$$\alpha_{2x}\|D^T Du_x\|_{W_x}^2 + \alpha_{2y}\|D^T Du_y\|_{W_y}^2 + \alpha_{2z}\|D^T Du_z\|_{W_z}^2,$$

and then, $$\left( A^T A + \begin{pmatrix} \alpha_{0x} W_x^T W_x & 0 & 0 \\ 0 & \alpha_{0y} W_y^T W_y & 0 \\ 0 & 0 & \alpha_{0z} W_z^T W_z \end{pmatrix} + \right. \quad (A10')$$
$$\begin{pmatrix} \alpha_{1x} D^T W_x^T W_x D & 0 & 0 \\ 0 & \alpha_{1y} D^T W_y^T W_y D & 0 \\ 0 & 0 & \alpha_{1z} D^T W_z^T W_z D \end{pmatrix} +$$
$$\left. \begin{pmatrix} \alpha_{2x} D^T D W_x^T W_x D^T D & 0 & 0 \\ 0 & \alpha_{2y} D^T D W_y^T W_y D^T D & 0 \\ 0 & 0 & \alpha_{2z} D^T D W_z^T W_z D^T D \end{pmatrix} \right)$$
$$\begin{pmatrix} U_x \\ U_y \\ U_z \end{pmatrix} = A^T b,$$

in the respective equations where $\alpha_0$, $\alpha_1$, $\alpha_2$, $\alpha_{0x}$, $\alpha_{0y}$, $\alpha_{0z}$, $\alpha_{1x}$, $\alpha_{1y}$, $\alpha_{1z}$, $\alpha_{2x}$, $\alpha_{2y}$, and $\alpha_{2z}$ are regularization parameters; D is the gradient operator; $D^T D$ is the Laplacian operator.

The SDs or the ZZLB can also be used as the weights at respective positions for performing weighted averaging of measurement results of displacement components to be calculated by simultaneously holding selected Doppler equations. Using the reciprocal of SD $W_p$ (p=1 to N) of the displacement in the beam direction or the reciprocals of SDs ($W_{px}, W_{py}, W_{pz}$) [p=1 to N] of the displacement components in the respective directions, the weighted averaging of displacements can be calculated at the respective positions as follows.

$$(U_x, U_y, U_z)^T = \frac{\sum_{p=1}^{N} W_p \times (U_{px}, U_{py}, U_{pz})^T}{\sum_{p=1}^{N} W_p} \quad (A11)$$

or $$(U_x, U_y, U_z)^T = \quad (A11')$$
$$\left( \frac{\sum_{p=1}^{N} W_{px} \times U_{px}}{\sum_{p=1}^{N} W_{px}}, \frac{\sum_{p=1}^{N} W_{py} \times U_{py}}{\sum_{p=1}^{N} W_{py}}, \frac{\sum_{p=1}^{N} W_{pz} \times U_{pz}}{\sum_{p=1}^{N} W_{pz}} \right)^T.$$

SD can also be calculated not using the stationary processes or the ZZLB but using ensemble averaging under nonstationary processes. Specifically, calibration phantoms or the measurement object can also be used for estimating the SD. Thus, as mentioned above, the regularization parameters or the weight matrices can be determined. Otherwise, on the basis of the object or the conditions, experiences of measurements, they can also be determined using typical values a priori and not limited to these.

Thus, the weights or the regularization parameters can be set with a spatial resolution and with a high accuracy and however, when the deformation of the object being small or the calculation amounts being decreased, SDs are estimated over a larger region than the local region (for instance, over an ROI) and for the respective waves or beams, SDs can also be estimated globally and are used. The phase matching method (a past invention of the present invention's inventor) is required to be used for making them possible to perform the measurements and to increase the measurement accuracy (patent document 6 and nonpatent document 15). The stretching method etc mentioned in other literatures is also effective for increasing the measurement accuracy.

As Wp, the Wiener filter can also be used. The imaging of signals or the displacement measurements can be performed after weighting the signals directly in a temporal and/or spatial domain. The signals are r(x,y,z) before or after detections.

$$W_p(x, y, z) = \left( \frac{|r(x, y, z)|}{|r(x, y, z)| + \left|\frac{n(x, y, z)}{r(x, y, z)}\right|} \right)^q \quad (A12)$$

or $$W_p(x, y, z) = \left( \frac{|r(x, y, z)|^2}{|r(x, y, z)|^2 + \frac{|n(x, y, z)|^2}{|r(x, y, z)|^2}} \right)^q \quad (A13)$$

where n(x,y,z) is noise signals and q is an arbitrary positive value.

The noise signals n(x,y,z) can be statically estimated by iteratively acquiring echo data with respect to the object or the calibration phantoms. For instance, a standard deviation (SD) can be used and under the assumption of a stationary process, the SD can be estimated by performing summation averaging locally and also by performing ensemble averaging. The SD can also be set, on the basis of the object or the conditions, experiences of the measurements, using typical values a priori and not limited to these. For imaging the signals r(x,y,z) are detected by the envelope detection, the square detection, the absolute detection and at the moment, eqs. (A12) or (A13) can also be multiplied to signals at respective positions. When calculating the autocorrelation function via calculating power spectra by implementing the conjugate of analytic signal to the analytic signal, the weighting can be performed. As pre-processing, the weighting can be performed, i.e., on the signal used for the autocorrelation method or the Doppler method that uses the analytic signal, and the cross-spectrum phase gradient method or the cross-correlation method (that can be sued for others from the analytic signal) etc.

When the signals are 2D or 1D as well, instead of r(x,y,z) and n(x,y,z) in eqs. (A12) or (A13), r(x,y) and n(x,y), and r(x) and n(x) can be respectively used for performing the same processing. Eqs. (A12) or (A13) can also be calculated globally and used for the respective beams or an ROI scanned by the respective beams. Similarly, instead of eq. (A12) or (A13), eqs. (A4) to (A6) can also be used for directly weighting the echo data.

Particularly when using the multidimensional cross-spectrum phase gradient method (patent document 6 and nonpatent document 15), the Wiener filter can be used in a frequency domain as well as in a temporal and/or spatial domain. As mentioned above, on the respective waves or beams, to estimate, using the weighted least squares solution, the gradient of phase spectra $\theta(\omega x, \omega y, \omega z)$ [i.e., unknown 3D displacement vector] in a frequency domain $(\omega x, \omega y, \omega z)$ of the cross-spectra $Hp(\omega x, \omega y, \omega z)$ [p=1 to N], estimated for the signals acquired at pre- and post-displacements or deformations under the same condition, the following weightings can be performed.

$$W_p(\omega_x, \omega_y, \omega_z) = \quad (A12')$$
$$\|H_p(\omega_x, \omega_y, \omega_z)\|^2 \left( \frac{\|H_p(\omega_x, \omega_y, \omega_z)\|}{\|H_p(\omega_x, \omega_y, \omega_z)\| + \sqrt{\frac{PW_{pn}(\omega_x, \omega_y, \omega_z)}{PW_{ps}(\omega_x, \omega_y, \omega_z)}}} \right)^q$$

or $$W_p(\omega_x, \omega_y, \omega_z) = \quad (A13')$$
$$\|H_p(\omega_x, \omega_y, \omega_z)\|^2 \left( \frac{\|H_p(\omega_x, \omega_y, \omega_z)\|^2}{\|H_p(\omega_x, \omega_y, \omega_z)\|^2 + \frac{PW_{pn(\omega x, \omega y, \omega z)}}{PW_{ps}(\omega_x, \omega_y, \omega_z)}} \right)^q$$

or where $PWpn(\omega x, \omega y, \omega z)$ and $PWps(\omega x, \omega y, \omega z)$ are respectively power spectra of noises and signals and for $PWps(\omega x, \omega y, \omega z)$, the squared magnitudes of the cross-spectra ($\|Hp(x, \omega y, \omega z)\|^2$) can be used instead. q is an arbitrary positive value.

For instance, for eqs. (1) to (14') of the patent document 6, the squared magnitudes of cross-spectra ($\|Hp(\omega x, \omega y, \omega z)\|^2$) themselves are used for the weightings and instead, $Wp(\omega x, \omega y, \omega z)$ can be used for the weightings (For Wp, as mentioned above, the SDs of the displacements in the beam direction or the ZZLB can also be used). The weights are evaluated on the respective waves or beams (p=1 to N) at the respective positions and the weighted least squares minimization is performed once at the positions.

The power spectra $PWpn(\omega x, \omega y, \omega z)$ of noises can be statically estimated by iteratively acquiring echo data with respect to the object or the calibration phantoms. The $PWpn(\omega x, y, \omega z)$ can also be set, on the basis of the object or the conditions, experiences of the measurements, using typical values a priori and not limited to these.

Otherwise, n(x,y,z)/r(x,y,z) expressed in eq. (A12) or (A13), or $PWpn(\omega x, \omega y, \omega z)/PWps(\omega x, \omega y, \omega z)$ expressed in eq. (A12') or (A13') can be set on the basis of the reciprocal of the above-mentioned echo SNR (SNRe) or that of the combined SNR (SNRc expressed using the SNRe and the correlation SNRρ). Eq. (A12') or (A13') is calculated with a spatial resolution or globally estimated on the respective beams or on the ROI scanned by the respective beams and similarly to eq. (A12), (A13), (A4) to (A6), and Eq. (A12') or (A13') is used for weighting echo data directly (for imaging or displacement measurement). When performing the detections (envelope detection, square detection, absolute detection etc) of signals r(x,y,z) for performing imaging, eq. (A12) or (A13) can be used, and in the cases, L2-norms of the first spectra $Hp(\omega x, \omega y, \omega z)$ [spectra of local signals or signals over the ROI] in the equations cannot be used. This is also when performing the calculation of the autocorrelation function signal via calculating the power spectra by multiplying the conjugate of the local spectra $Hp(\omega x, \omega y, \omega z)$ to the spectra $Hp(\omega x, \omega y, \omega z)$ When the unknown displacement is a 2D vector u=(Ux, Uy)$^T$ or one displacement in the beam direction, in eqs.

(A12') and (A13'), for the cross-spectra H(ωx,ωy) or H(ωx) estimated for signals acquired at pre- and post-displacements or deformations instead of H(ωx,ωy,ωz), similarly the respective Wiener filters are used to obtain weights and the weights are used Moreover, when implementing the regularizations, according to eq. (1) or (10'), the above-mentioned SDs etc can be used to set the regularization parameters similarly.

When using the cross-spectrum phase gradient method or other block matching methods, a single wave or beam can also be used for calculating a displacement vector at least having two directional components and even which using the single wave or beam, over-determined system can be realized.

All in the above-mentioned displacement measurements, the measurements can also be performed without making over-determined systems and also in the cases, the above-mentioned weighting or regularizations can be performed.

Various techniques such as a detection of object motion and the imaging on the basis of observed waves can be used and for instance, in the field of a medical ultrasounds, on the basis of a mean velocity and variance etc, displayed regarding blood flow, or tissue displacement or deformation, are information about the velocity, moving or not, the complexity etc. An agent (micro bubbles) can be positively used for performing measurement imaging with increased intensity of waves from bloods in vessels or hearts. Such an agent is effective for a functional measurement as well as a geometrical observation. A typical example of a self-emanating type agent is a radioisotope used for PET (Positron Emission Tomography) and the observation is performed on the basis of counting the generation of positron. This is a type to be dealt with as a passive instrument of the 2nd embodiment. For instance, magnetic substances (that can have an affinity with a target such as cancerous diseases etc) are injected into a vein and mechanical vibrations can be applied to generate magnetic fields. In this case, mechanical stimuli are applied using the transmission transducer and as the responses, electromagnetic waves are observed by the reception transducer. The above-mentioned examples of photoacoustics etc can also be performed.

The waves can be separated before performing the last inverse Fourier's transform and then the separated waves can be detected (square detection or envelope detection), the waves separated after performing the last inverse Fourier's transform can be detected, or originally separated waves can be detected before or after performing the Fourier's transform (nonpatent document 1). The imaging of the distributions of the respective wave intensities are imaged or incoherent signals obtained by the detections are superposed to enhance the deterministic signals (for instance, reflection signals or specular signals) and decrease the stochastic signals (for instance, scattering signals or speckle signals), by which the spatial variations of structures of an object or media are imaged effectively (a past invention of the present invention's inventor).

Coherent signals corresponding to superposed waves are detected and the distribution of intensities can also be imaged. Also non-detected, coherent signals can be imaged to display the wave vibrations themselves, images of signal phase distributions can be displayed together with those of the signal intensities (magnitudes). A single wave can also be displayed similarly.

The way to display is generally and popularly on the basis of a gray or color image and if the quantitativeness is required, the numeric data displayed in a gray or color format can also be displayed with a bar. Otherwise, displaying using bird's-eye-views etc can also be performed, and CG can also be used. The images can be display as static or dynamic images, and the dynamic images can also be displayed in a frozen condition, both images can also be displayed in a real-time or via off-line processings. Wave data or image data can also be read out from the storage devices (or storage media) to display the data. Temporal changes in arbitrary numeric data can also be displayed in graph formats.

Otherwise, for instance, using the bandwidths of microwaves or infrared rays, or terahertzes allows measuring the temperature distributions of measurement objects. The transmitted waves are demodulated by the radiations from the objects and the modulations are detected (Using passive-type instruments related to the 2nd embodiment allow the measurements of temperature distributions of objects by using the radiated waves themselves). Similarly to other waves, not using continuous waves but using pulse waves or burst waves and beamformings generate a spatial resolution. The infrared-ray can be used to observe the temperature distributions of the surfaces of objects mainly (it can also be considered that the measurements are limited to object surfaces), whereas using the microwaves or terahertzes allows the measurements of internal temperature distributions. On the basis of the observed physical or chemical quantities, high order processings such as approaches of an inverse problem etc can be performed to calculate (visco) elastic moduli or elastic moduli, viscosities, thermal properties, electric properties (a conductivity or a permittivity (dielectric constant)), a permeability, wave propagation speeds (a light speed or a sound speed), an attenuation, a scattering (forward or backward scatterings etc), a transmission, a reflection, a refraction, wave sources etc with their variances. In the medical applications, when using the ultrasound or MRI etc, for cancerous diseases, the diseases during treatments using warming and heating, and inflammation parts after the thermal treatments or surgeries, observations or monitorings of visco-elastic moduli as well as the temperatures or thermal properties can also be performed. Also the body temperature observations (including in morning, at noon and at night, with a metabolism, growth, aging, before or after meat, before or after smoking, when adding loads to peripheral systems, electrophysiological nervous control etc) or physical loads on various organs etc can be performed similarly. The observings and monitorings are not limited to such medical applications, other organic substances or non-organic substances, mixed substances can also be object to be observed and on the diagnoses, restorations and applications, various observations or monitorings can be performed in conjunction with.

The measured physical quantities such as displacements or temperatures etc can be displayed similarly, the measurements can also be displayed with superposed on the geometrical images simultaneously obtained. When displaying these distributions, the quantitativeness is often required and then, the numeric data corresponding to the displayed brightness or color can also be displayed using bars. Otherwise, displaying using bird's-eye-views etc can also be performed, and CG can also be used. The images can be display as static or dynamic images, and the dynamic images can also be displayed in a frozen condition, and both images can also be displayed in a real-time or via off-line processings. Wave data or image data can also be read out from the storage devices (or storage media) to display the data. Temporal changes in arbitrary numeric data can also be displayed in graph formats.

From other devices, additional information about the object to be observed can be provided via the input devices, or other observed data such as physical or chemical quantities can also be provided. In the cases, the digital signal processing unit can perform, in addition to the above-mentioned processings, high order processings such as data mining, independent signal separation (independent component analysis), signal separations using principle component analysis, coding, multidimensional spectrum analysis, MIMO, SIMO, MUSIC and identification of the object using parametric methods, or superresolutions that can use these methods together or ISAR (Inverse synthetic aperture) etc.

The passive-type instruments related to the 2nd embodiment performs these processings and then, the cases are mentioned there in detail. Being different from the passive-type instruments, since the active-type instruments related to the present embodiment performs the transmissions of waves and the scanning, the position of interest can be specified on the received reception signals. And, when performing the transmission focusing or multi-focusings, the conditions or the functions of focused positions can be understood and if there exists wave sources at the focus positions, the wave sources can be understood by demodulating the waves with high spatial resolutions and with modulated by the information of the wave sources. By using waves that can be categorized in the same types of plane waves (flat array), cylindrical waves (ring-type array) or spherical waves (spherical kernel array), it is possible to perform the understanding speedy, i.e., with high frame rates.

On the applications on communications, the positions to be communicated can be targeted (focused on) and the, the energy saving can be enhanced as well as the security can be increased. When composing the measurement system to perform the observation, the degree of free is high. By using the processings on the basis of the system theory, it is possible to identify the point spread functions (PSFs) to be generated or according to the purposes, it is simple to control the PSFs. It is also possible to use plural transmission transducers and/or plural reception transducers (that can also work as the transmission transducers). The waves to be transmitted or received can be a same kind or not and occasionally, plural instrument bodies exclusive for the plural transducer to be driven synchronizedly can also be used, and the passive-type instrument related to the 2nd embodiment can also be used together. These can also be connected with other instruments (including the instruments that control these) via exclusive or general networks and the instrument body can also have a control function of the networks.

On the basis of the various types of observation data, in conjunction with, other instruments can also work such as manufacturing machines of materials or structures, instruments for performing the treatments or restorations, machines that uses the data such as robots etc. And the instruments are not limited to these. These measurements and the high order processings using the waves can also be performed by other instruments by using the wave data etc stored in the detachable storage devices (storage media), or the data are stored into the common (same) type storage devices (storage media) and can also be used by other instruments.

When the received reception signals stored in the memories or storage devices (storage media) include harmonic waves components generated by an object or in media, prior to performing beamformings, the signals can be separated into a fundamental wave and harmonic waves (only the 2nd harmonic wave or when the higher order harmonic waves are not ignored, plural harmonic waves) and the beamformings (general phasing and summing) can be implemented on the respective separated signals, or after implementing the beamforming on the stored reception signals, the separations can be performed. The separations can be implemented on the spectra of reception signals in a frequency domain and however, there exists the cases where the bandwidths of the spectra corresponding to the plural waves can overlap. Then, in the field of medical ultrasound, the so-called pulse inversion method is performed, i.e., at the same phase of the object, the wave of a polarity being inverted to that of the original wave is generated and the respective reception signals with respect to the wave transmissions are superposed before or after the beamforming, the 2nd harmonic wave component as well as the fundamental wave (separated waves) can be obtained at each stage.

Alternatively, the separation method using a polynomial expression is also known. The instrument of the present embodiment can perform the 1D processings in the wave propagation direction or multidimensional processings for the cases where the lateral modulation is performed or with strictly considering the changing of the wave propagation directions at respective positions, and the proceeding can be performed before or after the beamformings. However, note that when performing the beamformings after separating the reception waves, since the beamformings are implemented on the respective fundamental wave and harmonic waves, the total calculation time can increase and then, the parallel processing is to be performed. Basically, the separation after performing the beamforming requires a short time.

Alternatively, when the waves transmitted from the respective transmission apertures are encoded, prior to performing the beamforming, the reception signals received by the respective reception aperture elements are separated, by performing the signal detections on the basis of the matched filtering, into the wave components to be generated with respect to the transmissions with the respective transmission aperture elements; and in the cases where dynamic focusing can be performed on the transmission as well as the reception, which is well known. The method is also effective for the high speed transmission(s) using the plane wave(s) and in the cases where focused beams and steerings are generated as well.

Also when plural waves or beams are simultaneously transmitted, for instance, the respective waves etc with above-mentioned plural different frequencies or plural different steering angles can be encoded and transmitted. In the cases, the receptions signals are similarly decoded, by which the receptions are separated into the reception signals generated with respect to the respective transmission waves or beams. Thus, the ability for separating the signals can be increased. This is effective, for instance, when the bandwidths of the respective waves overlap or the propagation directions of the waves become same due to the refraction, reflection, transmission, scattering etc. These are on the basis of the idea that the waves to be separated are encoded using independent codes. Under using the same physical parameters, the coding can also be simply performed.

In these processings, although simultaneous equations can also be solved, the matched filtering has its effect and rather the processing can be achieved with a high speed. Codes proper to the object or media are also developed. However, the number of elements to be used increases, the required lengths of codes must be longer and although the signal energy can be increased (the effect can also be effectively used and important), in a contrary, for instance, when the object or media deforms, the accuracy decreases and becomes not proper. The similar problems also occur when the charp signal compression is performed.

In communications, the waves transmitted from the respective aperture elements are encoded using the codes correspondingly to the information to be conveyed, and transmitted (As beamformings, for instance, a plane wave, a cylindrical wave or a spherical wave is used to send the information widely, or by performing focusings, which can be performed at plural positions, the accuracy of information is ensured at the positions, the security is ensured regarding the local communications or the communications with specific objects, or the energy saving is performed), and beamformings are performed with respect to the reception signals and the results are decoded. The applications of the coding using the instrument of the present embodiment are not limited to these (The digital signal processing unit, which can include memories, using the memories or the storage devices (storage media) perform these processings).

Always or occasionally, or with determined temporal intervals, beamforming parameters can be optimized such as a transmission intensity, transmission and reception apodizations, transmission and reception delays, steering angles, transmission and reception time intervals (scan rates), a frame rate, scanning lines, the number of, the geometries, the areas and the directions of the faces of effective apertures, the geometries, the areas and the directions of the faces of aperture elements, the direction of the face of a physical aperture or polarization modes etc) on the basis of the physical quantities (a magnitude or a direction of a displacement, a velocity, an acceleration, a strain, a strain rate etc or a temperature etc) or chemical quantities, additional information, observed by the instrument of the present embodiment or provided by others, or visco elastic moduli, elastic moduli, viscosities, thermal properties, electric properties (a conductivity or a permittivity), a permeability, a wave propagation velocity (light velocity or sound velocity etc), an attenuation, a scattering, a transmission, a reflection, a refraction, wave sources, materials, structures or their variances, related to waves and obtained by the above-mentioned high order processings such as approaches of an inverse problem. Thus, optimized beamformings can be performed such that spatially uniform qualities (a spatial resolution, a contrast, a scanning rate) can be generated; high qualities (a spatial resolution, a contrast, a scanning rate) can be generated at the positions where some targets are detected (using the geometries, materials, structures, properties of motions, temperature, moisture etc) or at the related positions; scattering waves (forward or backward scattering waves), transmission waves, reflection waves or refraction waves can be properly evaluated according to the object motion, the compositions and structures; observing can be performed with respect to rather wide directions mostly.

The wave propagation speeds are determined by the physical properties of media, of which physical properties depend on the environment conditions such as a pressure, a temperature and a moisture etc. Moreover, the physical properties are inhomogeneous in the media and then, the propagation speeds are also inhomogeneous. The propagation speeds can also be measured in a real-time or on the basis of the calibration data regarding the environment conditions, the propagation speeds can also be calculated. The instrument related to the present embodiment is further equipped with the phase aberration correction unit for correcting the inhomogeneity in propagation speed; and in practical, the above-mentioned transmission delays of the respective channels themselves can also be used at the transmissions for performing the phase aberration corrections as well by adjusting the amounts of correction delays as well. In addition, after performing the receptions, to correct the inhomogeneity in propagation speed on the propagation path between the transmission and reception positions, the above-mentioned digital signal processing unit can perform the corrections by multiplying complex exponential function in a frequency domain. Alternatively, the corrections can also be implemented at the calculations of the above-mentioned Fourier's transform or inverse Fourier's transform directly. The confidence of the measured propagation speeds can be confirmed, with respect to the measurement object or the reference existing or set in the neighborhood of the object, by generating image signals, of which image formation conditions, spatial resolutions, signal intensities, contrasts etc can be used as indices. Moreover, using these, the corrections can be further performed. In the 2nd embodiment disclosed later, after performing the receptions, the phase aberration corrections can be performed for transmission and/or reception.

Waves diverges during the propagations with effected by an attenuation, a scattering, a transmission, a reflection, a refraction etc and then, basically the wave intensities become small as the waves propagate. Thus, the instrument of the present embodiment is equipped with the function for performing the corrections with respect to the effects of an attenuation, on the basis of the Lambert's law, with respect to the signals before or after the beamforming. Otherwise, equipped with can be also the function that an operator can adjust the corrections for the attenuations at the respective positions or the respective distances by using the input device. Similarly, as mentioned above, equipped with can be also the function for performing optimized corrections before or after the beamforming according to the object. In these processings, not the digital processings but analogue processings using analogue devices or circuits can also be performed to make much of the speedy of the processings although the degree of freedom is lower.

In the above-mentioned processings, the superposing and the spectral frequency division are linear processings, whereas at or after performing the generations of waves using the above-mentioned methods (1) to (6), nonlinear processings can be implemented to generate new signals with other wave parameters. In the process of the beamforming, when the reception signals are analogue, analogue signal processings can be performed using the analogue circuits (diodes or transistors, amplifiers, exclusive nonlinear circuits etc), whereas when the reception signals are digital, as the digital signal processing to be performed using the digital signal processing unit, exponentiation or multiplication and other nonlinear processings can be implemented on the reception signals. In a frequency domain, nonlinear processing can also be performed with respect to spectra.

Alternatively, as a modifications of DAS, DAM (Delay and Multiplication) processing, that is an invention of the present invention's inventor, can also be performed in a frequency domain using the instrument of the present inventions. The multiplications using the exponentiations or multiplications in a spatial domain can be calculated using the convolution integrals in a frequency domain. It is possible to increase the frequencies or bandwidths, generating quasi-signals of the above-mentioned harmonic waves generated during the wave propagations etc. Regarding the steered waves, signals that are detected at least in one direction or to all directions can be generated, for instance, as the results, imagings of the waves generated can be performed, and a displacement vector can also be performed using a general one-directional displacement measurement method.

In addition, using virtual source, image signals can also be generated. As far, reported were the virtual sources that set behind physical apertures or at transmission-focused positions. Previously, the inventor of the present inventions reported virtual receivers as well as virtual sources that can be set at arbitrary positions, and also physical wave sources or detectors that can be set at arbitrary positions of proper scatters or diffraction gratings etc (patent document 7, nonpatanet document 8). The present inventions can be performed using the virtual sources or the virtual receivers as mentioned above. It is also possible to increase a spatial resolution or make the field of vision (FOV) large. In addition, when performing beamformings of transmissions or receptions, or both the transmissions and receptions on reception signals obtained with respect to the transmissions using at least one aperture element (cases where the beamformings are performed or not, i.e., SA transmissions and receptions), by using at least one different parameter within the plural parameters of waves, those of beamformings and those of transducers (a shape and a size of element, a configuration, a number, an effective aperture width, an element material etc), plural beams or waves with different properties or features can be generated (including the cases where plural results are generated from same reception signal) and the over-determined systems can also be generated. Similarly, the over-determined systems can also be generated using the virtual sources or the virtual receivers, of which positions or distributions (geometries or sizes etc) are changed. Also in the cases, from same reception signals, plural beams or waves with different properties or features can also be generated. As the features of over-determined systems, increasing SNRs and spatial resolutions can be achieved by performing the coherent superposing as well as reducing speckles can be achieved by superposing of coherent signals obtained via the detections etc; these have effects in performing imagings. In addition, the effects for increasing accuracies of various measurements such as displacement measurements, temperature measurements etc can also be obtained. In addition to the virtual sources and the virtual receivers, at least one parameter within the plural wave parameters, plural beamforming parameters and plural transducer parameters can also be set different (for instance, steering angles etc can be changes physically on the basis of electric and electrical engineering or mechanics or in a software fashion).

According to arbitrary wave sources, the transmission waves can be generated on coordinate systems expressed by rotating, using an arbitrary position as the center, the coordinate system determined by a reception aperture element array or spatially shifting (for instance, a coordinate determined by axial and lateral axes of the transmission aperture and then the generated coordinate system is different from that determined by those of the reception aperture). In the cases, after the correction of a coordinate system is implemented on the reception signals, the beamformings can be performed. For instance, when image signals are to be generated directly on the coordinate system, that is expressed by rotating, using the origin as a center, the above-mentioned 2D Cartesian coordinate system (x,y) by an angle θ, eq. (29) can be multiplied to the analytic signals expressed by the first temporal Fourier's transform. The processings can yield image signals without losing the high speedness inherently achievable by the present inventions, i.e., with higher speeds than the calculations using the rotating the wavenumber vector $(k_x, \sqrt{(k^2-kx^2)})$ and the coordinate system (x,y) together with the Jacobi calculation.

$$\exp(isk \tan \theta x) \qquad (29)$$

Note that s=2 for reflection waves, and s=1 for transmission waves. In practical, only for the correction about the transmission, s=1 is used. The spatial shifting (parallel translation) can also be performed in a frequency domain by performing complex exponential function. The above-mentioned method using the rotations of the wavenumber vector $(k_x,\sqrt{(k^2-kx^2)})$ and the coordinate (x,y) together with the Jacobi calculation can perform transmission beamforming with converted to the coordinate system determined by the reception aperture element array (s=1), after which the reception beamforming (s=1) can be performed, i.e., yielding a low speed.

In the active-type instruments related to the present embodiment, similarly to the passive-type instruments related to the 2nd embodiment, other analogue devices can also be used such as lens, reflectors (mirrors), scatters, deflectors, polariscopes, polarizers, absorbent bodies (attenuators), multipliers, conjugators, phase delay devices, adders, differentiators, integrators, matchers, filters (spatial or temporal, frequencies), diffraction gratings, spectroscopes, collimators, splitters, directional couplers, nonlinear media, special devices such as amplifiers of waves etc. Particularly when using lights, in addition, used can be polarizing filters, ND filters, blockers, optical waveguides, optical fibres, optical Kerr effect devices, nonlinear optical fibres, mixing optical fibres, modulation optical fibres, optical trapping (or confinement) devices, optical memories, dispersion shift optical fibres, band-pass filters, temporal inverters, encoders using optical masks etc and for controlling (conversions of wavelengths, switchings, routings) such devices, optical node technologies, optical cross connects (OXC), optical add-drop multiplexers (OADM), optical multiplexers or separators, optical switching devices and also as devices, optical transmission networks or optical networks themselves, and not limited to these. These can be incorporated into the transducers or instrument bodies etc. On the beamformings, all these can be optimally controlled together with the instruments artificially or naturally with the above-mentioned various mechanisms. In a frequency domain, nonlinear processings can also be implemented on.

Under such various combinations, the instrument of the present inventions can also be used in general instruments using waves. In medical instruments, for instance, such instruments are ultrasound diagnosis instruments (reflection or echo methods and transmission-types etc), X-ray CT (agents increasing the attenuation effects can also be used), X-ray roentgens, angiographies, mammographies, MRI (Magnetic Resonance Imaging, agents can also be used), OCT (optical Coherent Tomography), PET (Positron Emission Tomography, corresponding to the 2nd embodiment), SPECT (Single Photon Emission Computed Tomography), endoscopes (including capsule types), laparoscopes, catheters equipped with various types of sensing functions, terahertz instruments, various types of microscopies, various types of radiotherapy instruments (chemotherapies can also be performed together to increase the treatment effects), SQUID meters, electroencephalographs, electrocardiograms and HIFUs (High Intensity Focus Ultrasounds) etc. Particularly, MRI is an originally digital instrument and including the capability, the application range is very large. For instance, using electromagnetic observations and inverse problems etc which the inventor of the present inventions has been conducting allow the applications on all the reconstructions (measurements) of electric current distributions and electric property distributions, observing of displacements or mechanical wave propagations, reconstructions (measurements) of mechanical properties, observing of temperature distributions or thermal waves and reconstructions (measurements) of thermal properties. For the applications, in addition to the MRI, an ultrasound can also be used. As other works, for instance, using OCT, on the basis of the infrared spectroscopy, allows the measurements of absorption spectra and for instance, imagings of an oxygen concentration or a glucose concentration of a skin's basal cell carcinoma or blood can be performed. It is also possible to apply the OCT to general Near Infrared (NIR) and the distribution evaluations can be performed with higher spatial resolutions than the general NIR-based reconstructions. Also on them, instruments of ultrasound sensor (including microscope-types) can be equipped with the OCT or laser instruments, by which photoacoustics can also be performed, and not limited to these. Alternatively, using the laser or OCT instruments will allow detecting and imaging tissue fluctuations with high sensitivities with no mechanical stimuli. Alternatively, responses with respect to every possible (mechanical) stimuli including due to laser lights etc can also be made target of imagings (including the uses of lights for observing the dynamics generated by the lights themselves etc). For other imagings, chemical sensors etc can also be used. Combinations of waves are not limited these. In addition to physical sensors, chemical sensors etc can also be used together. The instruments related to the present inventions can also be used for various types of radars, sonars and optical system devices etc. For waves, continuous waves as well as pulse waves or burst waves can also be used. Such digital processings with a high degree of freedom can also be realized using analogue circuits with a high operation speeds, and vice versa. These exists various types of instruments in respective fields such as resource explorations, non-destructive examinations, communications. On them, the instruments related to the present inventions can also be used. The instruments of the present inventions can be used as instruments (or devices) in general instruments (or devices) regarding the operation modes (for instance, imaging modes, Doppler modes, measurement modes, communication modes etc), and not limited the modes or other above-mentioned modes).

When arbitrary plural beams or waves such as above-mentioned fixed focusing beams, multi-focusing beams, plane waves and others are physically transmitted simultaneously, if a large region can be integrated over an ROI, a high frame rate can be achieved. The simultaneous transmissions in plural directions can also be performed using a same effective aperture, and the simultaneous transmissions in a same direction or in different directions can also be performed using different effective apertures. On the beamformings, in addition to such same or different steering angles or focus positions etc, beamforming parameters such as ultrasound frequencies or bandwidths (those of a beam direction or a propagation direction, directions orthogonal to them), a pulse shape, a wavenumber, an aperture geometry or apodizations etc that determine a beam shape etc and transducer parameters such as an element geometry or an element size, array element configurations etc being same or different can also be used simultaneously. When physically performing the plural transmissions, if the used parameters are different, the followings can be considered as representative cases.

(A1) Performing same software steering on the all.
(A2) Performing plural different software steerings (For instance, the same steering is performed in a software fashion every different physical steering angle).

Also, when physically performing the plural transmissions, if the used parameters are same, the followings can be considered as representative cases.

(B1) Performing a software steering.
(B2) Performing plural software steerings.

However, note that some combinations of them can also be performed. Being dependent on the existences of obstacles or effects of scatterings or attenuations (those can be dependent on a frequency) during the wave propagation process, so-called adaptive beamformings can also be performed. In these cases, when the combinations of the software transmission and reception steerings or apodizations are same, superposed reception signals can be processed at once. When the different combinations are used, every same combination, superposed reception signals can be processed at once and next, the calculated spectra are superposed prior to performing the final inverse Fourier's transform.

In cases (A1) and (B1), reception echo signals received as the superposition of the echo signals with respect to the respective transmission ultrasounds are software-processed once.

In case (A2), the reception echo signals received as the superposition of the echo signals with respect to the respective transmission ultrasounds are separated to be superpositions to be same software-processed; and the respective superpositions are software-processed once and next, the calculated spectra are superposed prior to performing the final inverse Fourier's transform. The signal separation can be performed using the above-mentioned various type methods, and not limited to them.

In case (B2), plural different software processings are performed on angular spectra of all superposed reception signals and next, the calculated spectra are superposed prior to performing the final inverse Fourier's transform.

Alternatively, when such plural beams or waves are not physically transmitted simultaneously, if the plural transmissions and receptions are performed under the condition or the assumption that the phase of the object is same, the same processing as those of the above-mentioned simultaneous transmissions can be performed. In these cases, when the combinations of the software transmission and reception steerings or apodizations are same, superposed reception signals can be processed at once. When the different combinations are used, every same combination, superposed reception signals can be processed at once and next, the calculated spectra are superposed prior to performing the final inverse Fourier's transform. The reception signals received with respect to the simultaneous transmissions or transmissions with different times can also be processed similarly under the same condition or under the same assumption. The parameters used for the physical transmissions can be known in advance; or can also be calculated to be used by analyzing the beams or waves. These are also in the cases of passive-types mentioned later.

By performing the plural transmissions of beams or waves simultaneously or at different times, high frame rates, or a same focusing or plural foci can be generated. In addition, the same processings including the superposing processings allows yielding beams or waves with new parameters (for instance, increasing bandwidths and improving spatial resolution etc). Using together the spectral frequency division method also allows yielding beams or waves with new parameters. By separating the generated beams or waves into those with same parameters, of respective which can also be used (For instance, displacements in directions of generated beams or waves can be measured as well as a displacement vector measurement). Nonlinear processings or increasing bandwidths via nonlinear processings mentioned later can also be performed on the superposed signals, signals of which spectra are divided ones, or separated signals. The superposed signals, signals of which spectra are divided ones, separated signals or such signals on which the nonlinear processings are implemented etc can be used for the displacement measurement etc. The respective signals can also be detected for performing the imagings, the detected signals can also be superposed for imagings (For instance, speckle reduction can be performed). The applications are not limited to these and as mentioned above, various and not limited.

<Simulation Results>

Below, when the waves to be processed are ultrasounds and mainly, the representative results obtained for the above-mentioned beamforming methods (1) to (7) in simulations, performed to confirm the feasibilities, are shown (image signal generations using plane wave transmission, steered monostatic SA, multistatic SA, fixed focusing; and those on the Cartesian coordinate system for transmission and reception performed on the polar coordinate system; and migration).

Figure 16:
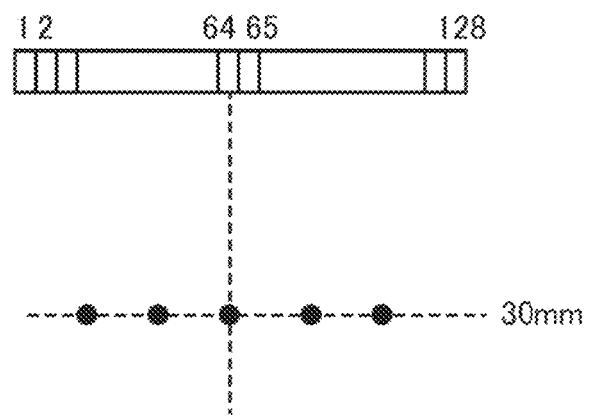
FIG. 16 shows a schematic of a numerical phantom used in simulations.

FIG. 16 shows a schematic of a numerical phantom used in simulations. The numerical phantom have 5 point scatters at a 30 mm depth with a lateral interval, 2.5 mm, in anechoic and non-attenuate media. To generate the echo signals, Field II (nonpatent document 20) is used. Here, the depth and lateral directions are expressed using the z and x axes, respectively.

Figure 17:
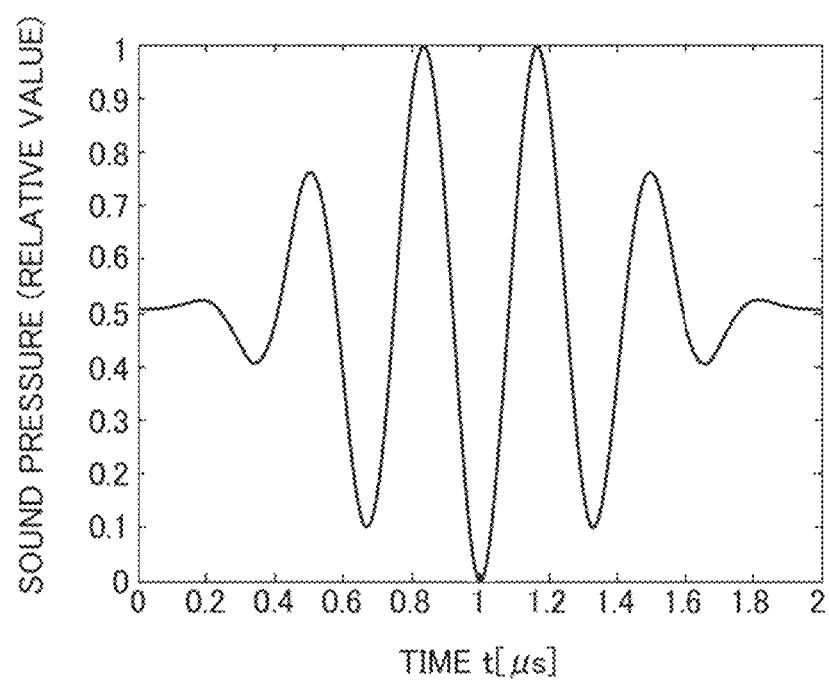
FIG. 17 shows a schematic of a shape of an acoustic pressure pulse wave used in simulations.

For the plane wave transmission and the migration method, and the monostatic SA, a 1D linear-type array transducer (128 elements; an element width, 0.1 mm; kerf, 0.025 mm; an elevational width, 5 mm) is used, whereas for the fixed focusing and the multistatic SA, a 1D linear-type array transducer (256 elements; an element width, 0.1 mm; kerf, 0.025 mm; an elevational width, 5 mm; an effective aperture width, 33 to 129 elements) is used. For the transmission and reception on the polar coordinate system, a convex-type transducer (128 elements; an element width, 0.1 mm; kerf, 0.025 mm; an elevational width, 5 mm; a curvature radius, 30 mm) is used. The center frequency of the transmitted ultrasound pulses is 3 MHz, and the pressure shape is shown in FIG. 17. The steering angle is defined with respect to the depth direction (the direction of the face of aperture) and expressed as θ below.

(1) Transmission of Plane Wave

FIGS. 18A(a) to 18A(d) respectively show the simulation results obtained using the method (1) for steered plane wave transmissions with steering angles θ=0,5,10,15°. Moreover, FIG. 18B show the results obtained, when θ=0°, by performing approximate interpolations on the wavenumber matching. These results are obtained using the same reception steering angles as those of the transmission steering angles. The horizontal and vertical axes of FIGS. 18A and 18B respectively express the lateral (x) and depth (z) positions ([mm]), respectively. As shown in FIG. 18A, it can be confirmed that the echo images with image formations are obtained and the steerings can also be performed. All the images are obtained via down-sampling from 100 MHz to 10 MHz (paragraph 0206 and 0207) and the imaging data are obtained with a spatial interval in the depth direction corresponding to the sampling frequency 25 MHz (also for other image data).

Alternatively regarding the results obtained, when θ=0°, via performing the approximate interpolations on the wavenumber matchings, FIG. 18B(e) shows for the sampling frequencies 100 (left) and 25 MHz (right), the results obtained by using neighborhood spectra for the wavenumber matching, whereas FIG. 18B(f) shows for the sampling frequencies 100 (left) and 25 MHz (right), those obtained by performing linear approximate interpolations for the wavenumber matching. Although the higher sampling frequency and performing not the replacing of spectra but the linear approximations yield the images with higher stability, the results does not reach the stability of the no approximate result [FIG. 18A(a)]. Performing non-zero steering yields less stability when performing the approximate wavenumber matchings.

Figures 19, 20:
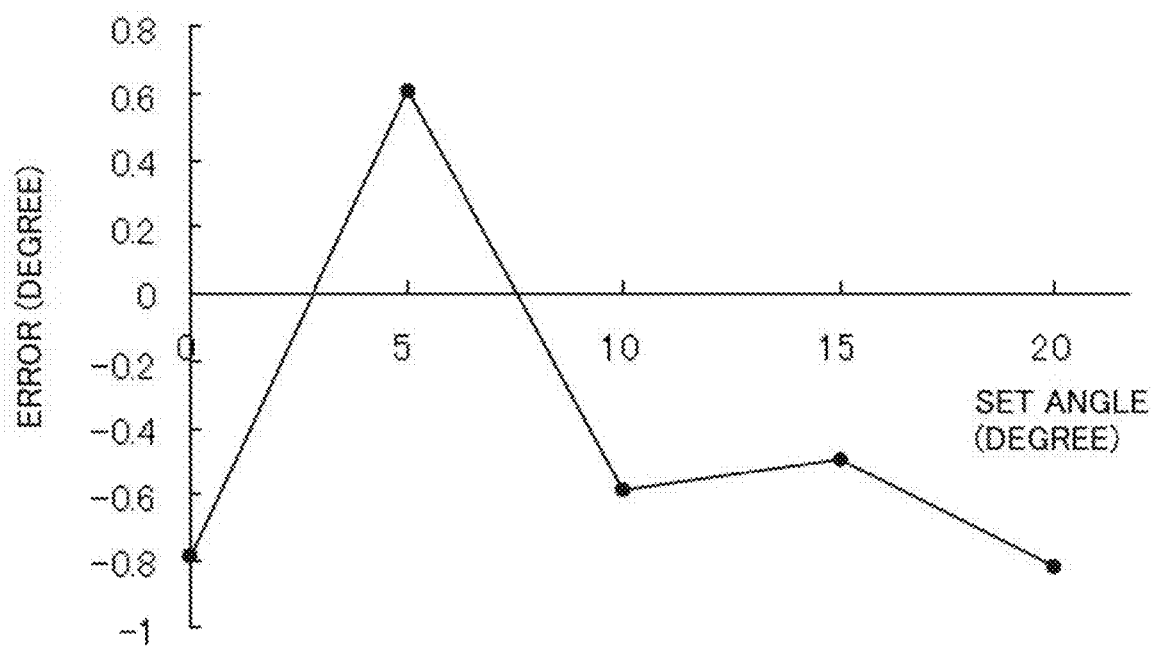
FIG. 19 shows a table summarizing for the steered plane wave transmissions with method (1), the obtained steering angles and the errors with respect to the set steering angles.
FIG. 20 shows a figure exhibiting errors of steering angles obtained for steered plane wave transmissions with method (1)

FIGS. 19 and 20 show the results calculated for the generated steering angles, ones estimated from the spectra of the generated image signals. To perform the estimation with a stability, the scatters in the numerical phantom is increased by positioning 300 scatters randomly in the depth range, 0 to 40 mm. The reflection coefficient of the respective scatters are set to −1 to 1. Regardless the steering angles, the errors ranging from 0.5 to 0.8 are confirmed. The errors depend on the positions of the scatters with respect to the generated waves. Increasing the number of scatters improves the accuracy of estimation (omitted).

Figure 22:
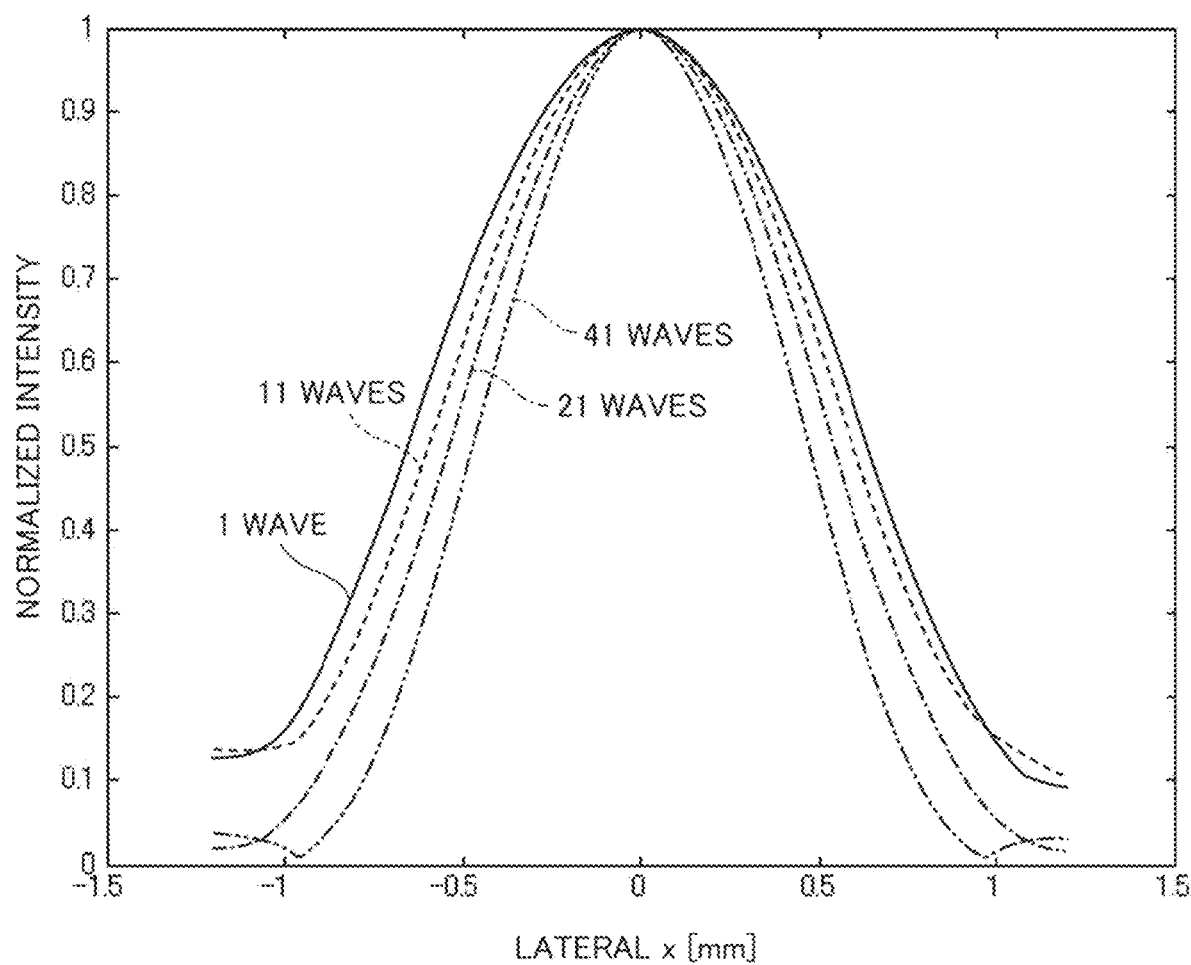
FIG. 22 shows point spread functions (PSFs) generated for steered plane wave transmissions and method (1)

FIG. 21 shows images obtained by superposing the image signals generated for the respective steering angles. The steering angles are increased with respect to the 0° (one wave) by the interval of 1°; and the results are obtained for 11 waves (−5° to 5°), 21 waves (−10° to 10°), 41 waves (−20° to 20°). FIG. 22 shows the lateral profiles of the point spread functions (PSFs) estimated from the generated image signals, of which the horizontal axis expresses the lateral (x) position ([mm]) and the vertical axis expresses the relative brightness. As shown in FIG. 22, increasing the number of superposing improves the lateral resolution.

Migration Method [Method (6) Applied to the Same Plane Wave Transmissions]

FIG. 23 shows the images obtained by using the migration method for the same steered plane wave transmissions as those of FIG. 18A. The steering angles are θ=0,5,10,15°. Unstable results obtained for cases with approximate wavenumber matchings are omitted.

(2) Monostatic SA

FIG. 24 shows the simulation results obtained by performing the steered monostatic SA. Similarly to FIG. 18A, performed steering angles are θ=0,5,10,15°. As shown in FIG. 24, the image formations are obtained and the performed steerings can also be confirmed.

(3) Multistatic SA

FIG. 25 shows the simulation results obtained by performing the steered multistatic SA. Similarly to FIG. 18A, performed steering angles are θ=0,5,10,15°. FIG. 25(a) shows the low resolution image generated using the received signals using the same elements for the receptions as those for the transmissions only (i.e., one set). That is, it is the same result as that of monostatic SA. FIG. 25(b) shows the results obtained by using the monostatic data together with 16 elements of the respective left and right sides with respect to the transmission element for the reception, i.e., superposing of the results of 33 sets. FIGS. 25(c) and 25(d) are respectively the results obtained using the superposing of 65 sets (monostatic data and those of left and right 32 elements with respect to the transmission element) and 129 sets (monostatic data and those of left and right 64 elements with respect to the transmission element). As shown in FIG. 25, the successful image formations can be confirmed.

Figure 26:
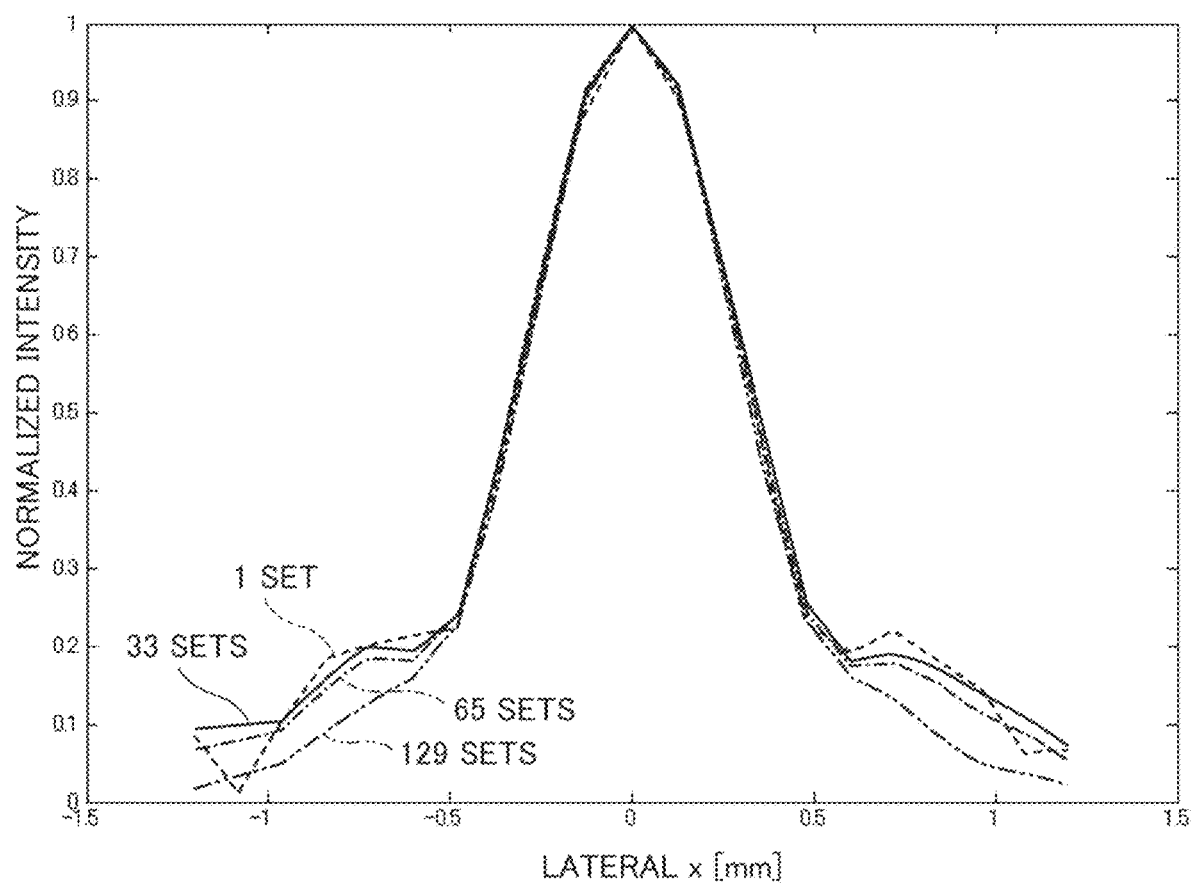
FIG. 26 shows point spread functions (PSFs) generated using method (3), i.e., multistatic SA.

FIG. 26 shows the lateral profiles of the PSFs. As shown in FIGS. 25 and 26, increasing the number of superposing suppresses the sidelobes and improves the lateral resolution.

(4) Fixed Focusing

FIG. 27 shows the results obtained for the focusing transmissions. Here, the method (1) is used. FIG. 27(a) shows the result obtained by implementing the method (1) once onto the superposing of the echo signals received on the respective transmission effective apertures as the respective reception effective apertures (method 4-1); FIG. 27(b) shows the result obtained by superposing the results of low resolution image signals generated on the respective effective apertures (method 4-2); FIG. 27(c) shows the result obtained by superposing the results generated on the respective sets comprising of echo data of the same relationships about the positions between the transmission and reception elements similarly to the multistatic SA (method 4-3). As shown in FIG. 27, all methods successfully yield the image formations and there exists no particular differences. The method used for obtaining the result of FIG. 27(a) [method (4-1)] yields a higher speed calculation than other two methods and then effective. The result also shows that reception beamformings can also be performed on the reception signals received with respect to plural beams or all beams to be transmitted simultaneously ideally (Reception signals generated by transmitted beams with interferences can also be processed to yield a high frame rate). The processing can also be implemented on plural transmissions of all kinds of waves (including combinations of different type waves) as well as the fixed focusing transmissions. That is, the plural waves can also include ones generated by different transmission beamformings, by beamformed and not beamformed, different kinds of waves (electromagnetic waves or mechanical waves, thermal waves etc), nonlinear processings or detections, superresolutions or adaptive-beamformings, minimum variance processings, separations, processings such as filtering, weighting or dividing of spectra etc. During the beamformings, the processings can also be performed. Off course, reception signals with respect to the respective transmissions can also be superposed to be processed. However, also in these wavenumber matchings, approximate interpolation processings can be performed.

(5) Image Signal Generation on Cartesian Coordinate System with Respect to Transmission and Reception on the Polar Coordinate System (5-1) Cylindrical Wave Transmission FIG. 28(a) shows the result obtained by performing the signal processings on reception signals in a frequency domain with respect to a cylindrical wave transmission performed by exciting all the convex-type array elements simultaneously. In fact, as mentioned in the method (5-1'), at the transmission and the reception, a plane wave or a virtual linear array is generated at the depth, 30 mm. As shown in FIG. 28(a), the image formations can be obtained on the scatters.

(5-1') Cylindrical Wave Transmission Using Linear-Type Array

Next, shown is the results of echo signals generated with respect to a cylindrical wave transmitted using a linear-type array and a virtual source (FIG. 8A(a)) set behind the array. FIG. 28(b) shows the result obtained using a virtual source behind the array at a distance, 30 mm, and the method (1) disclosed in the method (5-1'); FIG. 28(c) shows the result obtained using a virtual source behind the array at a distance, 60 mm, and the method (2) disclosed in the method (5-1'). The image formations can be obtained on the scatters.

On the using the linear-type array transducer and the method (1) disclosed in the method (5-1'), the case where a cylindrical wave is generated using a virtual source behind the array at a distance, 30 mm, is applied to generate a plane wave or a virtual linear-type array transducer with an extended lateral width (FIG. 8B(g)) at the distance, 30 mm. The result is shown in FIG. 28(d).

(5-2) Foxed Focusing

Using a convex-type array, fixed focusing is performed at a distance, 30 mm, from the respective elements (FIG. 14(a)). The results obtained by processing the reception signals are shown in FIGS. 29(a) and 29(b): FIG. 29(a) shows the result obtained by performing the echo signal generation processing once on the superposition of received signals of the respective effective apertures; and FIG. 29(b) shows the result obtained by superposing the low-resolution image signals generated with respect to the respective transmissions. Although omitted to show is the result obtained by superposing echo data generated with respect to the respective sets comprising of reception signals acquired at the same distances between the transmission and reception elements (similarly to the multistatic SA), these three calculation results are almost same similarly to in using the method (4). Alternatively, FIG. 29(c) shows the result obtained for the fixed focusing at a depth, 30 mm (FIG. 14(b)), by performing the echo signal generation processing once on the reception signals. The image formations can be obtained on the scatters.

These results are obtained similarly to the method (4). The result also shows that reception beamformings can also be performed on the reception signals received with respect to plural beams or all beams to be transmitted simultaneously ideally (Reception signals generated by transmitted beams with interferences can also be processed to yield a high frame rate). The processing can also be implemented on plural transmissions of all kinds of waves (including combinations of different type waves) as well as the fixed focusing transmissions. That is, the plural waves can also include ones generated by different transmission beamformings, by beamformed and not beamformed, different kinds of waves (electromagnetic waves or mechanical waves, thermal waves etc), nonlinear processings or detections, superresolutions or adaptive-beamformings, minimum variance processings, separations, processings such as filtering, weighting or dividing of spectra etc. During the beamformings, the processings can also be performed. Off course, reception signals with respect to the respective transmissions can also be superposed to be processed. However, also in these wavenumber matchings, approximate interpolation processings can be performed.

It is demonstrated that the beamformings performed via above simulations according to the present invention, using the digital Fourier's transform, allows performing arbitrary beamforming processings on arbitrary orthogonal coordinate systems, with no approximate interpolations and with high accuracies, on the basis of the proper using the complex exponential functions and Jacobi calculations. Although all the beamformings achieved by the present invention can also be performed using DAS (Delay and Summation) method, owing to the differences in the lateral wavenumber matchings and the lateral Fourier's transforms, all the beamformings achieved by the present invention achieves high speeds in calculations. For instance, when using the 1D array and a general PC, the calculations to be performed are at least 100 times as fast as the DAS methods. When the aperture elements distribute in a 2D or 3D space or comprise a 2D or 3D multidimensional array, the above methods can be multidimensional simply and the present invention efficiently solve the problem that it takes more processing times in the multidimensional processings than in the 1D processings, i.e., the increasing the speediness of beamforming becomes more efficient. Cases where superposing of plane wave transmissions with different steerings etc becomes effective are also demonstrated. High contrasts owing to suppressions of sidelobes as well as high spatial resolutions can be achieved with high speeds.

On the above examples, it is confirmed that arbitrary focusings (including no focusing) and steerings can be performed using arbitrary array-type aperture geometries and further, it is confirmed that arbitrary beamforming processings can be performed on arbitrary orthogonal coordinate systems with no approximate interpolations and high accuracies as well as with high speeds. The time can be shorten, required for obtaining the high order measurement results such as a displacement measurement etc on the basis of using the image signals generated and further, the measurement accuracy also become high. However, on the present invention, as disclosed in the methods (1) to (7), arbitrary beamformings can also be performed via implementing approximate interpolations on the wavenumber matchings; and then much higher processings can be achieved. To increase the accuracies of the approximate wavenumber matchings, proper over-samplings of reception signals are required in return an increased calculation amount. In the cases, being different from in the cases where image signals of arbitrary positions can be generated when no approximate interpolations are performed, it is cautious that the number of data to be used for the Fourier's transforms increases.

At first, explained are examples of the 1st embodiment of the present invention using the representative transducers, the reception sensors, the transmission unit and the reception unit, the control unit, the output unit and the external storage devices etc. The confirmed feasibilities of the method (1) to (7) demonstrate that arbitrary beamformings that are on the basis of the focusing and the steering can be performed on arbitrary orthogonal coordinate systems, and beamformings and the applications achieved by the instruments of the present invention are not limited these including other beamformings and applications mentioned above.

2nd Embodiment

Next, the compositions of the measurement and imaging instrument or the communication instrument related to the second embodiment of the present invention are explained. FIG. 1 shows a schematic representation (block map) of compositions for the active-type of instrument related to the first embodiment of the present invention; and FIG. 2 shows the specific schematic representation (block map) of compositions of a body of instrument shown in FIG. 1. In the second embodiment of the present invention, passive-type of instruments are used. Thus, at least the instruments related to the second embodiment are equipped with no transmission transducers and neither wire lines nor wireless lines for transferring drive signals from the control unit to the transmission transducers.

Regarding the active-type instrument related to the first embodiment, referring to FIGS. 1 and 2 showing a schematic representation (block map) of compositions of instrument, the compositions of the units and the devices are specifically explained. Absolutely active-type instruments use transmission and reception transducer array devices with arbitrary aperture geometries (including a case where a transducer can be used for both transmission and reception at least), whereas passive-type instruments do not use the transmission transducer array devices on them.

That is, the basic compositions of instrument related to the second embodiment are the reception transducers (or reception sensors) 20, the body of instrument 30, the input devices 40, the output devices (or display devices) 50, the external storage devices 60. The body of instrument 30 is equipped with the reception unit 32, the digital signal processing unit 33, the control unit 34 and not shown storage unit (memories, storage devices or storage media) mainly. The body of instrument 30 can also be equipped with the transmission unit 31. The explanations about the compositions performed on the first embodiment can also be adopted to the second embodiment.

Similarly to the first embodiment, the respective devices or the respective units in the body of instrument can also be set at different positions. The body of instrument 30 is conventionally referred to one comprised of such plural units. Similarly to the first embodiment, the reception transducer 20 can also be mechanical scanned to perform the receiving signals. No array-type transducer generally referred to as can also be used to perform almost same processings as those of array-type transducer.

However, being different from the instruments related to the first embodiment, the instruments related to the second embodiment has the functions for sensing the timings of wave generations as explain in detail below. It is possible to generate a timing signal by receiving the wave, that arrives at from an arbitrary wave source, to be observed. Otherwise, a timing signal is generated via other process and the timing signal is sensed by the control unit via a wire or wireless line. The timing signals are used as trigger signals for the reception unit to start the acquisition of data (AD converters and writing into memories of the respective reception channels).

A way how to sense the timing signals that informed the control unit of the generations of waves is, when the waves arrive at from the wave sources themselves are used as the timing signals, to use the reception signals received by the reception aperture elements 20a of the reception transducers (or reception sensors) related to the present embodiment themselves or to use the timing signals received by the exclusive receiving devices that can be equipped with the body of instrument 30.

In this case, the signals received by the reception aperture elements 20a (that can be all elements, elements existing at an edge or a center etc, or sparsely used) or the exclusive receiving devices (the reception channels can be plural at least) are temporally, continuously detected and for instance, information about reception signals such as a signal intensity, a frequency, a bandwidth or codes etc are set on the control unit 34 itself (internal memories) or the analogue judging circuit (in this case, can be non-variable in a software or hardware fashion and can also be fixed in a hardware fashion) via above-mentioned various types of input means. Otherwise, the sensing of the timings of wave generations can also be performed on the basis of by collating the received signals by the reception aperture elements 20a or the exclusive receiving devices with the judging data such as thresholds or values, or databases about features of waves to be observed etc recorded by the memories or storage devices (storage media).

When judging the received signals in an analogue fashion, exclusive analogue circuits equipped with can be used and only when the received signals are judged as signals to be observed, the trigger signals are generated for starting the data acquisitions, i.e., the reception signals are AD converted and stored into memories or storage devices (storage media); and beamforming processings can be performed.

When judging the received signals in a digital fashion, the received signals are temporally, continuously AD converted and stored into the memories or storage devices (storage media) and always or occasionally (when the command is given via the input means etc) or at the specified temporal intervals (can be set via the input means etc), the stored signals are read out by the digital signal processing unit 33 and further judged on the basis of by collating with the judging data. Only when the signals are judged as the signals to be observed, beamformings can be performed.

Since the storage capacity of the memories or storage devices (storage media) is finite, when the digital judging is performed, if the signals to be observed are not detected within a specified time (that can be set via the input means etc), the memory address can be initialized. Although it is not effective for energy saving, occasionally the beamformings are performed to yield image signals with high accuracies and on the basis of using the generated image signals for collating with the judging data, the wave signals can be judged. Also when the waves of general communication purposes are observed, the processings can be performed similarly.

The exclusive receiving devices can be set at different positions from other devices or units, for instance, positions in the neighborhoods of wave sources to be observed, positions where the reception environments with respect to the timing signals are favorable, etc. Waves (to be the timing signals) that propagate with higher speeds than the reception signals received by the reception apertures can be used, the timing signals can be transferred to the control unit in the body of instrument via the exclusive receiving devices. Exclusive lines (wire or wireless) that can use repeaters can also be used. In this case, the timing signals are used as the trigger signals for performing the acquisitions of reception signals (AD converting, storing into the memories or storage devices, storage media) and beamformings.

After the waves to be observed are received by the instruments of the present invention, the timing signals of the wave generations can arrive at. That is, the propagation speed is slow, or such a mechanism is employed. Such a case also occurs consequently. To cope with such cases, the acquisitions of reception signals are always, continuously performed to make it possible to retroactively reading out the corresponding reception signals stored into the memories or storage devices (storage media), and beamformings can be performed. In the cases, information about the waves obtained by other observers or observing instruments can be added onto the timing signals as additional information at repeaters etc; and the timing signals with the additional information are transferred; and information including the additional information are read out by the exclusive receiving devices; and the information read out can be used by other instruments as well as the instruments of the present invention. The lines to be used are not limited to exclusive lines and general networks can also be used. Also when the waves of general communication purposes are observed, the similar timing signals can also be used. The additional information can also be transferred using other waves or signals from the timing signals.

Together with the generations of waves to be observed, waves being different from the timing signals with higher or lower propagation speeds than the waves received at the reception aperture elements are generated before, at or after the generations of the waves to be observed; and the exclusive receiving devices or lines can be similarly set and used. In the cases, information about the waves to be observed can also be added to timing signals; and at repeaters etc, information about the waves obtained by other observers or observing instruments can also be added to the timing signals as additional information and the timing signals with the additional information are transferred; and information including the additional information are read out by the exclusive receiving devices; and the information read out can be used by other instruments as well as the instruments of the present invention. The lines to be used are not limited to exclusive lines and general networks can also be used. Also when the waves of general communication purposes are observed, the similar timing signals can also be used. The additional information can also be transferred using other waves or signals from the timing signals.

As these exclusive receiving devices, exclusive sensing devices are used such that the timing signals can be sensed or the additional information can be read out. Arbitrary observers or arbitrary observing instruments (arbitrary active- or passive-types of observing devices or the similar observing devices etc and others such as arbitrary active- or passive-types of observing devices or the similar observing devices etc related to other phenomena or waves that can be the presages of the target wave generations, other phenomena or waves simultaneously generated related to the target waves, or other phenomena or waves generated after the target wave generations etc) can also be used. Irregularly, the exclusive receiving devices can perform only the reception of timing signals, reading out the additional information can also be performed by the digital signal processing unit using the control unit in exclusive devices or the body of instrument.

In the cases where the active- or passive-types of instruments themselves can also be used as the sensing devices for the timing signals, similarly, the additional information can be read out by the digital signal processing unit 33. The timing signals can also be generated by the sensing devices equipped with. When the time or the place, or both the time and the place the waves are generated are unknown, the generations of timing signals are important for increasing the efficiencies about the data acquisition operations and beamforming processings, saving the electric power, saving the memories or storage devices (storage media). On the basis of the clock signals of the control unit 34, the data acquisitions and the beamformings are performed. When the wave sources are temporally digital, the synchronizing should be performed with respect to the clocks of the control unit. On the basis of the digital receptions of waves to be observed, the instruments can work with high clock frequencies and high sampling frequencies. When the timing signals are digital, the synchronizing is performed in the body of instrument and this is also when the timing signals are analogue.

The objects to be observed are waves generated by self-emanating type wave sources themselves, the features of wave sources (magnitudes, types of sources etc), the positions where or the times when the sources work etc. Similarly to when the instruments are active-type, temperatures (distributions) of objects can also be calculated from the spectra of waves, or distributions such as of a displacement, a velocity, an acceleration, a strain, a strain rate etc can also be measured. Also, the properties of media in which the waves propagate (a propagation speed, physical properties related to waves, an attenuation, a scattering, a transmission, a reflection, a refraction etc or their frequency variances etc) can be observed; and further the structures or compositions of the objects can also be clarified. For instance, radioactive substances (isotopes used for PET etc), substances with nonzero thermodynamic temperature, earthquake sources, nervous activities, celestial astronomical observations, weathers, arriving bodies, moving bodies, communication instruments including mobile communication instruments, reactors with respect to physical or chemical stimuli, electric sources, magnetic sources, radioactive sources, or various types of energy sources etc can also be observed and the observation objects are not limited to these.

Via multiphysics and multichemistries using reception transducers or reception sensors with respect to plural different types of waves, the fusion of measurement results or the data mining can also be performed. With respect to multi-functions or a function on the basis of physical or chemical properties, or ones that effect the surrounding in other states etc, by observing the behaviors of a systemic of object (for a human, a whole body) or of a local is performed in a multi-faceted fashion, newly or specifically the behaviors of the systemic of object (for a human, a whole body) or the local can also be understood. For instance, on living things, various nervous controls (body temperatures, blood flows, metabolisms etc) performed for a short or long time, effects (radiation exposures, nutrient intakes) etc performed for a short or long time can be observed to be used for developing artificial organs or cultured tissues that contribute to a longevity or lengthening-life, the hybrids, medicines or supplements etc and for monitoring their actions or operations. These include the cases equipped with replacements or complementaries of various sensors equipped with living tissues, or new sensors. When the objects are living tissues, a small size and wearable, and geometries and materials to be familiar to the living tissues can also be demanded. The contents of proceedings to be performed are also various, for instance, when plural mechanical waves such as compressible waves or shear waves arrive at simultaneously, similarly to in the first embodiment, the waves can be separated on the basis of the modes, frequencies, bandwidths, codes, propagation directions etc using analogue exclusive devices or the digital signal processing unit; and beamformings can be performed. When there exist plural electromagnetic wave sources, plural electromagnetic waves with different features can be being superposed, the separations can be performed similarly. Otherwise, even if plural waves arriving at, high accuracy image signals can be generated owing to the effects of the phasings and summings in beamformings (for instance, the media include scatters).

Off course, after performing the beamformings, signals can also be separated on the basis of the same processings. To obtain the effects of phasings and summings, the arrival directions of waves or the positions of wave sources are required to be calculated; and the beamformings can be performed with steering in the calculate directions and with focusing at the calculated positions. On performing the reception beamformings, the fixed focusings as well as the dynamic focusing are useful. To calculate the data, the first moments of the multidimensional spectra or the instantaneous frequencies of waves received at the reception aperture element array, the bandwidths, the so-called MIMO, SIMO or MUSIC, the independent components analysis, encoding, or various types of parametric methods etc can also be used. After performing the beamformings, the same processings can also be performed. Particularly, after performing the beamformings at plural positions, waves can also be observed using geometrical information. The processing methods are not limited to these, for instance, methods are performed under the approaches of inverse problems etc.

For instance, the propagation directions of arriving waves can be calculated on the basis of the analysis of multidimensional spectra (a past patent of the patent invention's inventor). Furthermore, using the instruments of the present invention, even when the information of propagation times cannot be obtained using plural transducers or reception effective apertures set at different positions (generally, using the times when the waves are observed at plural positions are used to calculate the position of the wave source and the distance to the source), it is possible to calculate the position and the distance geometrically. If the wave is not a pulse wave nor a burst wave but a continuous wave, the wave source can be observed. When the arrival direction of the wave is confirmed using an arbitrary processing, by performing the reception steering and the reception focusing in the direction where the wave source exists (monostatic or multistatic SA), the wave source can also be observed in detail. If necessary, using the active-type instruments of the first embodiment, the transmission beamformings can also be performed. In these processings, by interrogating the directions with high possibilities of the existence of wave source mainly by performing the reception beamformings with changing the steering angle, the direction of the wave source can also be specified via observing the obtained images or image formations, spatial resolutions, contrasts, signal intensities etc or performing the multidimensional spectra analyses. The steering can also be automatically controlled.

Performing superesolutions, the spatial resolutions of image signals can be increased. The descriptions about the processings are also performed in the paragraphs 0009 and 0404. As the effects of the superresolutions, it becomes simple to measure the wave sources, or the sizes, intensities, positions etc of scatters or reflectors in measurement objects or in media. Although the bandwidths of targets are absolutely limited by the physically generated wave fields, the representative superresolution implements the inverse filtering onto the bandlimited data to increase the bandwidths and restore the original wave sources or signals. Generally, the waves are suffered from the frequency-dependent attenuations, out of focusings, motion artifacts (when the wave sources can be moving), disturbances possible in media existing between the transducers and the objects. To compensate these effects, such a superresolution can also be performed.

Also, when the measurement object etc moves during performing the transmission and/or reception to generate an image signal, the motion compensation is required to be performed. There is often that the PSF is unknown and in the cases, blind convolution can be performed including the cases where the above-mentioned signal separation processing (particularly, blind separation) is performed together, The methods etc mentioned in the paragraph 0404 are well known. The PSF is estimated using some ways and ideally, the PSF is desired to be coherent. However, including the cases where a spectra distribution geometry or a bandwidth is estimated with respect to incoherent signals, inverse filtering can be performed.

If the PSF cannot be estimated when the PSF is required to be observed, for instance, data-base prepared in advance, comprising the data on the PSF estimated when the estimation can be achieved, should be used. One of the effective methods performing inverse filterings is to weight the spectra of the observed signals such that the amplitude spectra (strictly, effective values) distribution becomes the same as those of the desired PSF or the desired echo distribution. The amplitude spectra distribution of the desired PSF or the desired echo distribution can also be set analytically; using simulations; or via optimization etc; or by performing the beamforming using desirable parameters with respect to the measurement object and specifically, by performing the estimation once with performing the beamforming once or by calculating an ensemble mean with performing the beamforming plural times; by similarly performing the estimations with respect to calibration phantoms. For instance, the spatial resolution of low resolution signals generated by performing a plane wave transmission that allows high speed receptions with a Gaussian-type apodization (nonpatent document 15) can be increased by using a desired, high spatial resolution PSF or echo distribution generated using a fixed focusing or a dynamic focusing with an exponentiation-type apodization (nonpatent document 15). The using a plane wave transmission is proper for achieving a high accuracy measurement of a rapid object motion or a shear wave propagation and then, the simultaneous using the beamforming and the superesolution realizes the high spatial ultrasound imaging as well as the measurement. Otherwise, the spectra of the signals themselves can be used for performing the inversion. The processing can be performed onto the angular spectra obtained before the wavenumber matching or the spectra obtained after the wavenumber matching. That is, using the angular spectra or the spectra of a signal distribution such as a desired PSF or echo distribution etc to those of the reception signal can yield the spatial resolution. On the weighting processing, it is cautious that various type noises filled in the reception signals should not be amplified, i.e., not by dividing the object spectra with zero or small spectra, and as mentioned above, the regularization (suppressing the extra amplifications of high frequency components) or the Wiener filter (suppressing the amplifications of low SNR frequency components), singular-value-decomposition (small singular values and spectra are disregarded and the corresponding frequency signal components are not used) etc are effective to cope with the problem.

Also on the processes of the above-mentioned digital wave signal processings in the methods (1) to (7), the inverse filtering can be performed. The spatial resolution of the correspondingly obtained image signals can be increased; and regarding the quantitativeness (numeric data), the same effects can also be obtained and then, when the numeric data are display as images, the same effects can also be obtained. Effects such that blurred images can be restored or focusings are yielded can be obtained. The inverse filtering can also be implemented on incoherent signals. However, it is effective to implement it on the coherent signals and particularly, the effects can be confirmed on the understanding of the spatial distributions of physical properties. The superresolution can also be implemented on superposed image signals or spectral frequency divisions; and the applications of the superresolutions are not limited to these.

In the present invention, it is also possible to perform new superresolutions. One is on the basis of the nonlinear processings disclosed later, whereas another is the instantaneous phase imaging.

The signal, obtained using a single wave or beam with the propagation direction t (coordinate axis), at the position coordinate t=s is expressed as follows.

$$r(s)=A(s)\cos\{\int_{t=0}^{t=s}\omega(t)dt+\theta(s)\}, \quad (30\text{-}1)$$

where $$\theta(s)=\int_{t=0}^{t=s}\delta\theta(t)dt, \quad (30\text{-}2)$$

and t=0 is the reference position of the t-axis direction, i.e., the position of the wave source and $\delta\theta(t)$ expresses the change in phase generated at the position coordinate t due to the reflection or scattering.

On the basis of the signal model, the instantaneous angular frequency $\omega(t)$ and the instantaneous phase $\theta(s)$ etc along the propagation direction t are calculated and imaged. The propagation direction t directs in the facial direction when not performing a steering, whereas the direction t has a steering angle (nonzero) when performing a steering. The ROI can also be 3D, 2D or 1D. As disclosed in nonpatent document 19, the propagation direction of the wave or beam can be measured with a spatial resolution (the 1st moments or the instantaneous frequencies can be used) together with the frequency in the propagation direction. Thus, the frequency in the direction of an integration path (tangential direction) set on the spatial integration processing of a frequency disclosed later can be calculated with a high accuracy. For instance, the integration path can be set as a straight line using the steering direction (expressed by an angle) set at performing the transmission or using the global estimate of a steering direction (an angle) of the generated wave or beam similarly. To simplify the processings, the nominal frequency or simultaneously obtained global frequency estimate in the globally estimated direction can also be used. It is not impossible to perform the integration in the propagation direction estimated with a spatial resolution, however, since the interpolation processing is required, it is not practical.

Here, A(s), being an amplitude, expresses the reflection intensity or the scattering intensity at the position coordinate t=s and for instance, can be calculated by performing the envelope detection (square root of summing of squared IQ signal components) via the quadrature detection of eq. (30-1). Otherwise, the quadrature signal component $$r'(s)=A(s)\sin\{\int_{t=0}^{t=s}\omega(t)dt+\theta(s)\} \quad (31)$$

is generated by Hilbert's transform using Fourier's transform; and using the in-quadrature signal component eq. (30-1) together, A(s) can be calculated (patent document 7 or nonpatent document 14). The latter calculation method is proper to the digital signal processing particularly.

Using eqs. (30) and (31), the complex analytic signal can be expressed as follows (patent document 6 or nonpatent document 7).

$$r(s)=A(s)\exp[i\{\int_{t=0}^{t=s}\omega(t)dt+\theta(s)\}] \quad (32)$$

To calculate the instantaneous phase $\theta(s)$, at first, the instantaneous angular frequency is calculated. As the usual practice, using the methods disclosed in the patent document 6 and the nonpatent document 7, assuming is performed that the instantaneous frequency at the position coordinate t=s equals to that at the next sampling position coordinate t=s+Δs, however, the instantaneous phase at the position coordinate t=s does not equal to that at the next sampling position coordinate t=s+Δs ($\delta\theta(t)$ is a random change in phase determined by the random scattering intensity or reflection and with respect to t, the change can be large).

$$\omega(s) \approx \omega(s+\Delta s) \quad (33)$$

$$\Delta\theta(s)=\theta(s+\Delta s)-\theta(s)=\int_{t=s}^{t=s+\Delta s}\delta\theta(t)dt \text{ (random and the value can be small)} \quad (34)$$

Under the assumptions, the signal at the position coordinate $t=s+\Delta s$ is expressed as $$r(s+\Delta s)=A(s+\Delta s)\exp[i\{\int_{t=s}^{t=s+\Delta s}\omega(t)dt+\theta(s+\Delta s)\}], \quad (35)$$

and under the assumptions of eqs. (33) and (34), the conjugate multiplication of eqs. (32) and (35) is expressed as follows.

$$R(s) = r(s+\Delta s)r^*(s) \quad (36)$$
$$\approx A(s+\Delta s)A(s)\exp[i\{\omega(s)\Delta s + \Delta\theta(s)\}]$$

Thus, the instantaneous frequency at the position coordinate $t=s$ can be estimated as follows.

$$\omega(s) \approx \tan^{-1}\frac{Imag\{R(s)\}}{Real\{R(s)\}} \Big/ \Delta s \quad (37)$$

As disclosed in the patent document 6 or the nonpatent document 7, in practice, since noises are filled in the signal $r(s)$ and assuming eqs. (33) and (34), the moving-average processing is performed in the s-axis direction or including the orthogonal two or one direction to increase the accuracy of estimate. This moving-average processing can also be performed on eq. (36) and the estimate is calculated according to eq. (37):

$$\overline{\omega}(s) \approx \tan^{-1}\frac{Imag\{\overline{R(s)}\}}{Real\{\overline{R(s)}\}} \Big/ \Delta s, \quad (38\text{-}1)$$

or the moving-average processing is also performed on eq. (37) itself:

$$\overline{\omega}(s) \approx \overline{\tan^{-1}\frac{Imag\{R(s)\}}{Real\{R(s)\}}}/\Delta s. \quad (38\text{-}2)$$

It was previously confirmed that for a displacement (vector) measurement, eq. (38-1) yields a higher accuracy than eq. (38-2).

Using these moving-averaged instantaneous frequencies, detection can be performed on the instantaneous frequency at the respective position coordinate. Since the estimate of the instantaneous frequency is unbias, in the digital signal processing cases, the following equation $$demf(s)=\exp[-i\{\int_{t=t'}^{t=s}\overline{\omega}(t)dt\}] \quad (39)$$

is multiplied to eq. (32) and under the assumption that the instantaneous phase $\theta(s)$ is the integral of a random change in phase determined by the random scattering intensity or reflection (i.e., random), the estimate can be obtained.

$$\theta'(s) = \tan^{-1}\left[\frac{Imag\{r(s)demf(s)\}}{Real\{r(s)demf(s)\}}\right] \quad (40)$$

Instead the moving-averaged instantaneous frequencies calculated by eqs. (38-1) and (38-2), the 1st moment of spectra (i.e., a weighted mean) (×2π) can also be used. The expression is given as eq. (S1).

The t in the expression of the above-mentioned observed signal being 0 (t=0) expresses the reference position of the t-axis direction, i.e., the position of the wave source. With respect to this, the reference position t=t' in eq. (39) can also be set to 0 (i.e., t'=0, the position of the wave source) and in the cases where the θ'(s) calculated as a distribution regarding the position coordinate t=s is the estimate of the instantaneous phase [eq. (30-2)] itself, expressed as the integration of the change in phase due to the reflection and scattering. The averaged instantaneous frequency is used and then, the calculated θ'(s) is an estimate obtained under the condition.

When due to the effects of window lengths used for the moving-average processings or calculations of spectra, the instantaneous frequencies cannot be estimated from the position of the wave source (t=0) to t=s' (not zero and not equal to s as well), using t'=0 and an angular frequency $\omega_0$ that is a nominal frequency or a measurement/estimate obtained in advance, $$\overline{\omega}(t)=\omega_0 \quad 0 \le t \le s' \quad (41)$$

in eq. (39), which is calculated. Otherwise, using t'=s' (not zero, but not equal to s as well) in eq. (39) is possible and however, in the cases the following bias error is generated in the estimate θ'(s).

$$\theta_{bias}=\int_{t=0}^{t=s}\overline{\omega}(t)dt \quad (42)$$

However, when the change in the instantaneous phase Δθ(s) between at the position coordinate t=s and the next sampling position coordinate t=s+Δs (i.e., sampling interval is Δs) is estimated on the basis of eqs. (30-2) and (34), the bias becomes no problem. The estimate result can be obtained as follows.

$$\Delta\theta'(s) = \tan^{-1}\left[\frac{Imag[\{r(s+\Delta s)demf(s+\Delta s)\}\{r(s)demf(s)\}^*]}{Real[\{r(s+\Delta s)demf(s+\Delta s)\}\{r(s)demf(s)\}^*]}\right] \quad (43)$$

In the above eqs. (34), (36) (43) etc, the subtraction of phase is calculated using the forward difference and instead, the backward subtraction can also be performed. And, in eqs. (37), (38-1), (38-2), the calculation of differentiation of phase is approximated by dividing the above-mentioned phase difference by the sampling interval and instead, a differential filter with a high cutoff frequency can also be used for the differential processing. And, for the integration of the estimate of an instantaneous frequency in eq. (39), known various integration operations such as a trapezoidal method can be performed.

The estimate of the instantaneous phase [eq. (30-2)] including no phase rotation, expressed by eq. (40), can also be obtained using an alternative method: at first, arctan (i.e., inverse of tangent) is implemented on imaginary part/real part of the analytic signal expressed by eq. (32) to calculate the kernel of the cosine expressed by eq. (30-1) (i.e., instantaneous phase including the phase rotation), which is directly subtracted by the phase rotation calculated by the integration eq. (42) with s'=s on the moving-averaged instantaneous frequency or on the 1st moment of spectra. Note that since the arctan's direct calculation results are ranging −π to π, the calculate results are required to be unwrapped prior to perform the subtraction. Since the instantaneous phase including the phase rotation monotonically increases, if the arctan's result changes to be negative, the unwrapping can be performed by adding 2πm, where m is a positive natural number expresses the number of times to be counted when the arctan's result becomes negative in the propagation direction of the beam or wave. Similarly to the above-mentioned calculations, eq. (41) can also be used, and there exists the cases where the bias error expressed by the eq. (42) is generated. When estimating the change in the instantaneous phase $\Delta\theta(s)$ between at the position coordinate $t=s$ and the next sampling position coordinate $t=s+\Delta s$ (i.e., sampling interval is $\Delta s$), that is with no bias error, instead of eq. (43), the difference of the estimates of instantaneous phases including no phase rotations at the neighboring two position coordinates can be directly calculated by the subtraction.

Images regarding the phase expressed by Eq. (40) or Eq. (43) has an increased bandwidths, this is a kind of the superresolution. Also note that regarding the analytic signal of which phase is expressed by eq. (40), the square root of the summing of squared real and imaginary parts is equivalent to the envelope detection. Thus, squared detection, absolute detection, raw signals ideally with no broken wave oscillations (sign of signal values, phase) should be imaged (as a gray or color image). Mainly, the images exhibit the phase or change in phase together with the signal amplitude that determined by the reflection or scattering. Alternatively, the calculated instantaneous frequency can also be imaged to display the effect of attenuations (as a gray or color image)

When the observed signals are also multidimensional, i.e., the carrier frequencies exist in plural coordinate axes (lateral modulation etc), the instantaneous frequencies can be estimated similarly. As disclosed in the nonpatent document 19, the propagation direction of the wave or beam can be measured with a spatial resolution (using the 1st moments or the instantaneous frequencies) and simultaneously, the frequency in the direction can also be measured. Thus, the frequency in the direction of an integration path (tangential direction) set on the spatial integration processing of a frequency can be calculated with a high accuracy. For instance, on the above 1D signal case, the integration path can be set as a straight line using the steering direction (expressed by an angle) set at performing the transmission or using the global estimate of a steering direction (an angle) of the generated wave or beam similarly and in this multidimensional signal case, the integration path can be arbitrarily set in the multidimensional space theoretically. However, in practice, important is that the integration calculation is performed using integration paths properly set on the coordinate system used for performing the beamforming and for instance, straight lines, arcs or the connections are often used. To simplify the processings, the nominal frequency or simultaneously obtained global frequency estimate can also be used (to be projected onto the integration path). It is not impossible to perform the integration in the propagation direction estimated with a spatial resolution, however, since the interpolation processing is required, it is not practical. Now, the signal in an ROI is expressed by $$r(s_1,s_2,s_3)=A(s_1,s_2,s_3)\cos\{\int_c[\omega_1(t_1,t_2,t_3),\omega_2(t_1,t_2,t_3),\omega_3(t_1,t_2,t_3)]\cdot(dt_1,dt_2,dt_3)^T+\theta(s_1,s_2,s_3)\} \quad (30\text{'-}1)$$

where $$\theta(s_1,s_2,s_3)=\int_c\delta\theta(t_1,t_2,t_3)(dt_1,dt_2,dt_3)^T \quad (30\text{'-}2)$$

and $\delta\theta(t)$ expresses the change in phase generated at the position coordinate $(t_1,t_2,t_3)$ due to the reflection or scattering and the integration path c denotes an arbitrary path from the starting position 0, i.e., the reference position expressing the position with a zero instantaneous phase, to the position of interest $(s_1,s_2,s_3)$. If there exists plural positions with zero instantaneous phases in an ROI (for instance, respective positions of aperture elements in an array possible), they have the same mean. Thus, imaging is performed via calculating the instantaneous angular frequencies $[\omega_1(t_1,t_2,t_3), \omega_2(t_1,t_2,t_3), \omega_3(t_1,t_2,t_3)]$ and the instantaneous phase $\theta(t_1,t_2,t_3)$ etc. When the ROI is 2D, $$r(s_1,s_2)=A(s_1,s_2)\cos\{\int_c[\omega_1(t_1,t_2),\omega_2(t_1,t_2),\omega_3(t_1,t_2)]\cdot(dt_1,dt_2)^T+\theta(s_1,s_2)\}, \quad (30\text{'''-}1)$$

where $$\theta(s_1,s_2)=\int_c\delta\theta(t_1,t_2)(dt_1,dt_2)^T \quad (30\text{''-}2)$$

and the integration path c denotes an arbitrary path from the starting position 0, i.e., the reference position expressing the position with a zero instantaneous phase, to the position of interest $(s_1,s_2)$ similarly to in eqs. (30'-1) and (30'-2). Below, the processings are performed similarly to in the 3D case.

Here, $A(s_1,s_2,s_3)$, being an amplitude, expresses the reflection intensity or the scattering intensity at the position coordinate $(s_1,s_2,s_3)$ and for instance, can be calculated by performing the envelope detection (square root of summing of squared IQ signal components) via the quadrature detection of eq. (30'-1). Otherwise, the quadrature signal component $$r'(s_1,s_2,s_3)=A(s_1,s_2,s_3)\sin\{\int_c[\omega_1(t_1,t_2,t_3),\omega_2(t_1,t_2,t_3),\omega_3(t_1,t_2,t_3)]\cdot(dt_1,dt_2,dt_3)^T+\theta(s_1,s_2,s_3)\} \quad (31')$$

is generated by Hilbert's transform using Fourier's transform; and using the in-quadrature signal component eq. (30'-1) together, $A(s_1,s_2,s_3)$ can be calculated (patent document 7 or nonpatent document 14). The latter calculation method is proper to the digital signal processing particularly.

Using eqs. (30') and (31'), the complex analytic signal can be expressed as follows (patent document 6 or nonpatent document 7).

$$r(s_1,s_2,s_3)=A(s_1,s_2,s_3)\exp[i\{\int_c[\omega_1(t_1,t_2,t_3),\omega_2(t_1,t_2,t_3),\omega_3(t_1,t_2,t_3)]\cdot(dt_1,dt_2,dt_3)^T+\theta(s_1,s_2,s_3)\}] \quad (32')$$

To calculate the instantaneous phase $\theta(s_1,s_2,s_3)$, at first, the instantaneous angular frequencies are calculated. As the usual practice, using the methods disclosed in the patent document 6 and the nonpatent document 7, assuming is performed that the instantaneous frequency in the $t_j$ direction at the position coordinate $(s_1,s_2,s_3)$ equals to that at the next sampling position coordinate in the $t_1$ direction, $(s+\Delta s_1,s_2,s_3)$, however, the instantaneous phase at the position coordinate $(s_1,s_2,s_3)$ does not equal to that at the next sampling position coordinate $(s_1+\Delta s_1,s_2,s_3)$ ($\delta\theta(t_1, t_2, t_3)$ is a random change in phase determined by the random scattering intensity or reflection and with respect to $(t_1,t,t_3)$, the change can be large).

$$\omega_1(s_1, s_2, s_3) \approx \omega_1(s_1 + \Delta s_1, s_2, s_3) \quad (33')$$

$$\Delta\theta_1(s_1, s_2, s_3) = \theta(s_1 + \Delta s_1, s_2, s_3) - \theta(s_1, s_2, s_3)$$
$$= \int_{t_1=s_1}^{t_1=s_1+\Delta s_1} \delta\theta(t_1, s_2, s_3)dt_1$$

(random and the value can be small) (34')

Under the assumptions, the signal at the position coordinate $(s_1+\Delta s_1,s_2,s_3)$ is expressed as $$r(s_1+\Delta s_1,s_2,s_3)=A(s_1+\Delta s_1,s_2,s_3)\exp[i\{t[\omega_1(t_1,t_2,t_3),\omega_2(t_1,t_2,t_3),\omega_3(t_1,t_2,t_3)]\cdot(dt_1,dt_2,dt_3)^T+\theta(s_1+\Delta s_1,s_2,s_3)\}] \quad (35')$$

where the integration path c, is an arbitrary path from the starting position 0, i.e., the reference position expressing the position with a zero instantaneous phase in eq. (32'), via an arbitrary path to the position of interest $(s_1,s_2,s_3)$ (on the processings, conventionally the same path as that of eq. (32') can also be used) and further from the position of interest $(s_1,s_2,s_3)$ to the neighboring sampling position in the $s_1$ direction by the sampling interval $\Delta s_1$, i.e., $(s_1+\Delta s_1,s_2,s_3)$.

And, under the assumptions of eqs. (33') and (34'), the conjugate multiplication of eqs. (32') and (35') is expressed as follows.

$$R_1(s_1, s_2, s_3) = r(s_1 + \Delta s_1, s_2, s_3)r^*(s_1, s_2, s_3) \quad (36')$$

$$\approx A(s_1 + \Delta s_1, s_2, s_3)A(s_1, s_2, s_3)\exp[i\{\omega_1(s_1, s_2, s_3)$$

$$\Delta s_1 + \Delta \theta_1(s_1, s_2, s_3)\}]$$

Thus, the instantaneous frequency $\omega_1(s_1,s_2,s_3)$ in the $s_1$ direction at the position coordinate $(s_1,s_2,s_3)$ can be estimated as follows.

$$\omega_1(s_1, s_2, s_3) \approx \tan^{-1} \frac{Imag\{R_1(s_1, s_2, s_3)\}}{Real\{R_1(s_1, s_2, s_3)\}} / \Delta s_1 \quad (37')$$

As disclosed in the patent document 6 or the nonpatent document 7, in practice, since noises are filled in the signal $r(s_1,s_2,s_3)$ and assuming eqs. (33') and (34'), the moving-average processing is performed in the $s_1$-axis direction or including the orthogonal two or one direction to increase the accuracy of estimate. This moving-average processing can also be performed on eq. (36') and the estimate is calculated according to eq. (37'):

$$\overline{\omega_1}(s_1, s_2, s_3) \approx \tan^{-1} \frac{Imag\{\overline{R_1(s_1, s_2, s_3)}\}}{Real\{\overline{R_1(s_1, s_2, s_3)}\}} / \Delta s_1 \quad (38'\text{-}1)$$

or the moving-average processing is also performed on eq. (37') itself:

$$\overline{\omega_1}(s_1, s_2, s_3) \approx \overline{\tan^{-1} \frac{Imag\{R_1(s_1, s_2, s_3)\}}{Real\{R_1(s_1, s_2, s_3)\}}} / \Delta s_1 \quad (38'\text{-}2)$$

It was previously confirmed that for a displacement (vector) measurement, eq. (38'-1) yields a higher accuracy than eq. (38'-2). Similarly, the instantaneous frequencies in the $s_1$ and $s_3$ directions can also be calculated via calculating $R_2(s_1,s_2,s_3)$ and $R_3(s_1,s_2,s_3)$, respectively.

Using these moving-averaged instantaneous frequencies, detection can be performed on the instantaneous frequencies at the respective position coordinate. Since the estimates of the instantaneous frequencies are unbias, in the digital signal processing cases, the following equation $$demf(s_1,s_2,s_3)=\exp[-i\{\int_{c'}[\overline{\omega_1}(t_1,t_2,t_3),\overline{\omega_2}(t_1,t_2,t_3), \overline{\omega_3}(t_1,t_2,t_3)]\cdot(dt_1,dt_2,dt_3)^T\}]$$

where the integration path c' is an arbitrary path from the starting position, which can be set at an arbitrary position except for the position of interest $(s_1,s_2,s_3)$ in an ROI possibly including a reference position 0 with a zero instantaneous phase, to the position of interest $(s_1,s_2,s_3)$, which is regardless the integration path c in eq. (32'), however, on the processings, the same path as that of eq. (32') or the part can also be used conventionally. If there exists plural positions with zero instantaneous phases in an ROI (for instance, array element positions), since they have the same mean, the position of distance to the respective positions of interest $(s_1,s_2,s_3)$ being short can be used as the stating position 0. The integration path can also be set along the coordinate axes, which does not require interpolations of instantaneous frequencies. That is, the axes of integration directions can be changed at the positions of the sampling positions, (39') is multiplied to eq. (32') and under the assumption that the instantaneous phase $\theta(s_1,s_2,s_3)$ is the integral of a random change in phase determined by the random scattering intensity or reflection (i.e., random), the estimate can be obtained.

$$\theta'(s_1, s_2, s_3) = \tan^{-1}\left[\frac{Imag\{r(s_1, s_2, s_3)demf(s_1, s_2, s_3)\}}{Real\{r(s_1, s_2, s_3)demf(s_1, s_2, s_3)\}}\right] \quad (40')$$

Instead the moving-averaged instantaneous frequencies calculated by eqs. (38'-1) and (38'-2), the 1st moments of spectra (i.e., weighted means) ($\times 2\pi$) can also be used. The expression of moment in the x-axis, one axis of 3D orthogonal coordinate system, is given as eq. (S1''). Moments in other axes can also be calculated similarly, and also in the 2D case.

The integration path c, expressed in the equation of the above-mentioned observed signal, denotes an arbitrary path from the starting position 0, i.e., the reference position expressing the position with a zero instantaneous phase, to the position of interest $(s_1,s_2,s_3)$. The 0 expresses the position of the wave source. With respect to this, the stating position of the integration path c' in eq. (39') can also be set to 0 (the wave source position) and in the cases where the $\theta'(s_1,s_2,s_3)$ calculated as a distribution regarding the position coordinate $(t_1,t_2,t_3)=(s_1, s_2,s_3)$ is the estimate of the instantaneous phase [eq. (30'-2)] itself, expressed as the integration of the change in phase due to the reflection and scattering. The averaged instantaneous frequencies are used and then, the calculated $\theta'(s_1,s_2,s_3)$ is an estimate obtained under the condition.

When due to the effects of window lengths used for the moving-average processings or calculations of spectra, the instantaneous frequencies cannot be estimated from the position of the wave source 0 to $(t_1,t_2,t_3)=(s_1,s_2',s_3')$ (not the wave source position and not equal to $(s_1,s_2,s_3)$ as well), using the 0 as the starting position of the integration path c' and angular frequencies $(\omega_{0x},\omega_{0y},\omega_{0z})$ that are nominal frequencies or measurements/estimates obtained in advance, $$(\overline{\omega}_1(t1,t2,t3),\overline{\omega}_2(t1,t2,t3),\overline{\omega}_3(t1,t2,t3))\equiv(\omega_{01},\omega_{02},\omega_{03})$$
$$(t1,t2,t3)\in c' \text{ (interval from the wave source}$$
$$\text{position 0 to } (t_1,t_2,t_3)=(s_1',s_2',s_3')) \quad (41')$$

in eq. (39'), which is calculated. Otherwise, using $(t_1,t_2,t_3)=(s_1',s_2',s_3')$ as the starting position of the integration path c' (not the wave source position and not equal to $(s_1,s_2,s_3)$ as well) in eq. (39') is possible and however, in the cases the following bias error is generated in the estimate $\theta'(s_1,s_2,s_3)$.

$$\theta_{bias}=\int_{c''}[\overline{\omega}_1(t_1,t_2,t_3),\overline{\omega}_2(t_1,t_2,t_3),$$
$$\overline{\omega}_3(t_1,t_2,t_3)]\cdot(dt_1,dt_2,dt_3)^T, \text{ where } c'' \text{ denotes an}$$
$$\text{arbitrary integration path from the wave source}$$
$$\text{position 0 to } (t_1,t_2,t_3)=(s_1',s_2',s_3'). \quad (42')$$

However, when the change in the instantaneous phase $\Delta\theta_1'(s_1,s_2,s_3)$ between at the position coordinate $(s_1,s_2,s_3)$ and the next sampling position coordinate $(s_1+\Delta_{s1},s_2,s_3)$ (i.e., sampling interval is $\Delta s_1$) is estimated on the basis of eqs. (30'-2) and (34'), the bias becomes no problem. The estimate result can be obtained as follows.

$$\Delta\theta'_1(s_1, s_2, s_3) = \tan^{-1}\left[\frac{\text{Imag}[\{r(s_1+\Delta s_1, s_2, s_3)demf(s_1+\Delta s_1, s_2, s_3)\}\{r(s_1, s_2, s_3)demf(s_1, s_2, s_3)\}^*]}{\text{Real}[\{r(s_1+\Delta s_1, s_2, s_3)demf(s_1+\Delta s_1, s_2, s_3)\}\{r(s_1, s_2, s_3)demf(s_1, s_2, s_3)\}^*]}\right] \quad (43')$$

The changes in the instantaneous phases in the respective $t_2$ and $t_3$ directions, $\Delta\theta_2'(s_1,s_2,s_3)$ and $\Delta\theta_3'(s_1,s,s_3)$, between at the position coordinate $(s_1,s_2,s_3)$ and the next sampling position coordinates $(s_1,s_2+\Delta s_2,s_3)$ and $(s_1,s_2,s_3+\Delta s_3)$ (i.e., the respective sampling intervals are $\Delta s_z$ and $\Delta s_3$), can also be estimated similarly. In the above eqs. (34'), (36') (43') etc, the subtraction of phase is calculated using the forward difference and instead, the backward subtraction can also be performed. And, in eqs. (37'), (38'-1), (38'-2), the calculation of differentiation of phase is approximated by dividing the above-mentioned phase difference by the sampling interval and instead, a differential filter with a high cutoff frequency can also be used for the differential processing. And, for the integration of the estimates of instantaneous frequencies in eq. (39'), known various integration operations such as a trapezoidal method can be performed.

The estimate of the instantaneous phase [eq. (30'-2)] including no phase rotation, expressed by eq. (40'), can also be obtained using an alternative method: at first, arctan (i.e., inverse of tangent) is implemented on imaginary part/real part of the analytic signal expressed by eq. (32') to calculate the kernel of the cosine expressed by eq. (30'-1) (i.e., instantaneous phase including the phase rotation), which is directly subtracted by the phase rotation calculated by the integration eq. (42') with $(s_1',s_2',s_3')=(s_1,s_2,s_3)$ on the moving-averaged instantaneous frequencies or on the 1st moments of spectra. Note that since the arctan's direct calculation results are ranging $-\pi$ to $\pi$, the calculate results are required to be unwrapped prior to perform the subtraction. Since the instantaneous phase including the phase rotation monotonically increases, if the arctan's result changes to be negative, the unwrapping can be performed by adding $2\pi m$, where m is a positive natural number expresses the number of times to be counted when the arctan's result becomes negative in the propagation direction of the beam or wave. Similarly to the above-mentioned calculations, eq. (41') can also be used, and there exists the cases where the bias error expressed by the eq. (42') is generated. When estimating the change in the instantaneous phase $\Delta\theta_1'(s_1,s_2,s_3)$ between at the position coordinate $(s_1,s_2,s_3)$ and the next sampling position coordinate $(s_1+\Delta s_1,s_2,s_3)$ (i.e., sampling interval is $\Delta s_1$), that is with no bias error, instead of eq. (43'), the difference of the estimates of instantaneous phases including no phase rotations at the neighboring two position coordinates can be directly calculated by the subtraction. The changes in the instantaneous phases in the respective $t_2$ and $t_3$ directions, $\Delta\theta_2 d(s_1,s_2,s_3)$ and $\Delta\theta_3'(s_1,s_2,s_3)$, between at the position coordinate $(s_1, s_2,s_3)$ and the next sampling position coordinates $(s_1,s_2+\Delta s_2,s_3)$ and $(s_1,s_2,s_3+\Delta s_3)$, can also be estimated similarly.

Images regarding the phase expressed by Eq. (40') or Eq. (43') has an increased bandwidths, this is a kind of the superresolution. Also note that regarding the analytic signal of which phase is expressed by eq. (40'), the square root of the summing of squared real and imaginary parts is equivalent to the envelope detection. Thus, squared detection, absolute detection, raw signals ideally with no broken wave oscillations (sign of signal values, phase) should be imaged (as a gray or color image). Mainly, the images exhibit the phase or change in phase together with the signal amplitude that determined by the reflection or scattering. Alternatively, the calculated instantaneous frequency can also be imaged to display the effect of attenuations (as a gray or color image). The existence of the above-mentioned instantaneous phase decreases the measurement accuracies of the above-mentioned displacement measurement methods on the basis of the Doppler method or classical measurement methods when using the methods solo even if the target displacement (vector) is infinitesimal. The inventor of the present invention previously solve the problem by developing the phase matching method to be performed on the successive frames (for instance, nonpatent document 15). Also another method for stretching or compressing the signals expressing a tissue deformation can be also effective, when rather high intensity and random signals are used, for instance, on the tissue displacement or strain measurement etc, the phase matching method should be used absolutely. Generally, blood flow is measured using narrowband signals and however, the present invention open up new high spatial resolution measurement and viscoelastic measurements etc. The multidimensional vector and tensor can also be measured.

The above-mentioned envelope detection methods is usual practice for being implemented on the generated image signals and however, it is also effective to implement processing using the conjugate multiplication on the angular spectra or spectra and further on the respective wavenumber (frequency) components prior to the summing processing (one of nonlinear processings related to the present inventions). Also for the amplitude detection, in addition to the above-mentioned method, square detection or absolute detection etc can be implemented. Also in the present invention, implementing multidimensional Fourier's transform on the image signals generated by beamforming (i.e., focusing or steering realized by implementing delays or apodizations) generates spectra and further when implementing beamforming on the beamformed, image signals, implementing multidimensional Fourier's transform on the image signals generated angular spectra. That is, after generating image signals, further some beamforming can be performed on the generated image signals. The results obtained by the beamforming processing as well as other processing (weighting spectra (processing on spectra), non-linear processing, inverse filtering etc, others) including superresolutioned images can also be used for the above-mentioned coherent superposition (compounding) as well as incoherent superposition (compounding). The targets to be superposed are different or same signals (obtained at before or after beamformings), signals implemented by other processings, or their raw signals etc. The coherent superposition is proper for increasing the bandwidths (spatial resolutions) or the SNRs, whereas the incoherent superposition is for reducing the speckles as well as increasing the SNRs. For the reduction of speckles, often the decreasing in spatial resolution also occurs. However, the processings including the superesolutions can allow for coping with the problem and yielding high spatial resolution results. The incoherent superposition is performed on positive values converted to from wave signals by some detections (including exponentiation detections). The above-mentioned detections except for the envelope detection yields detected signals, however, with remaining coherencies (At least, the oscillations of waves can be confirmed). Although the envelope detection is useful, the detections being able to leave the coherencies in detected signals are also useful not to lose a spatial resolution. In comparison, the envelope detection allows the decreasing the spatial resolutions simply.

The operation modes can be set by the commands (signals) inputted into the instrument. When additional information is provided regarded the waves to be observed (kinds, features, properties, intensities, frequencies, bandwidths or codes etc) or objects or media in which waves propagate (propagation velocities, physical properties related to waves, attenuations, scatterings, transmissions, reflections, refractions etc or their frequency variances etc) are given, the instrument can also perform analogue or digital processings properly. The properties or features of generated image signals (intensities, frequencies, bandwidths or codes etc) can also be analyzed. The data acquired by the instruments related to the present embodiment can also be used by other instruments. The instruments related to the present embodiment can also be used as one of network devices and then, can also be controlled by the control instruments (devices). Otherwise, the instruments can also work as the control instruments (devices) for controlling networks. Local networks can also be controlled by the instruments.

When using the passive-type instrument related to the present embodiment as the active-type instrument, the transmission transducer (or applicator) 10 is connected to the transmission unit 31 equipped with in the instrument body 30. One of the following formations can be realized: when the transmitter 31a is an analogue type and has an input terminal for a trigger signal, the trigger signal generated by the control unit 34 is inputted; when the transmitter 31a is a digital type and has a mode for working according to external clock signals, clock signals generated by some unit or the control unit 34 are provided; or whole the instrument body works according to the clocks of the transmitter 31a. When the transmitter 31a is a digital type, on the either formation, clocks of the transmission and the reception are synchronized. This is significant on the generation of an image signal on the basis of plural transmissions. If the synchronizing cannot be performed, the errors can be decreased by increasing the clock frequency and the sampling frequency.

Thus, arbitrary beamformings can be performed by digital processings such as FFT with no approximate interpolations. In practical, arbitrary focusings and arbitrary steerings can be performed using arbitrary aperture geometries. However, in the present invention, as mentioned in the method (1) to (7), approximate interpolations can also be performed in the wavenumber matchings of arbitrary beamformings and then, the faster beamforming can also be achieved. For performing approximate wavenumber matchings with high accuracies, reception signals must be over-sampled properly and in return, the calculation amounts increase. In the cases, being different from in cases where image signals of arbitrary positions can be generated when no approximate interpolations are performed, it is cautious that the number of data to be used for the Fourier's transforms increases. The 2nd embodiment can also be performed using general instruments regarding the instrument and the operation mode (for instance, imaging mode, Doppler mode, measurement mode, communication mode etc) and not limited to these or above-mentioned ones.

On the above 1st and 2nd embodiments, waves such as electromagnetic wave, vibration waves (mechanical waves) including acoustic waves (compressible waves), shear waves, ballistic waves, surface waves etc, thermal waves etc are used to perform arbitrary beamformings with high speeds and with no approximate interpolations on the basis of digital processings, i.e., and with high accuracies such as the transmission and the reception focusings, the transmission and the reception steerings, the transmission and the reception apodizations including performing or not, those when the coordinate systems of transmissions and/or receptions are different from those where beamformed signals are obtained. Increasing of the frame rate for imaging the beamformed signals as well as increasing the image qualities such as a spatial resolution and a contrast can be achieved. Furthermore, using the beamformed signals increases the measurement accuracies such as of a displacement, a deformation, a temperature etc. However, in the present invention, as mentioned in the method (1) to (7), approximate interpolations can also be performed in the wavenumber matchings of arbitrary beamformings and then, the faster beamforming can also be achieved. For performing approximate wavenumber matchings with high accuracies, reception signals must be over-sampled properly and in return, the calculation amounts increase. In the cases, being different from in cases where image signals of arbitrary positions can be generated when no approximate interpolations are performed, it is cautious that the number of data to be used for the Fourier's transforms increases. The high speed beamformings performed on the superposing and/or spectral frequency division on the waves or beams generated by the high speed beamformings, or the superposing and/or spectral frequency division on the reception signals prior to the reception beamformings yield various applications and the present invention is not limited to these. The high speed processings provides a great effects on the use of a multidimensional array for multidimensional imaging. The Fourier's transforms and the inverse Fourier's transforms performed on the above-mentioned calculation algorithms are desired to be FFTs and IFFTs including the exclusive ones. The present invention is not limited to the above embodiments and much transformation is possible in technical thought of the present invention by a person having normal knowledge in the technical area concerned.

The measurement objects are various such as organic and inorganic substances or matters, solids, liquids, gases, rheology matters, living things, celestial objects, an earth, environments etc, the application range is prominently widespread. The present invention contributes to nondestructive evaluations, diagnoses, resource explorations, growth and manufacturing of substances and structures, monitoring of physical and chemical restorations and treatments, applications of clarified functions and physical properties etc, where a high measurement accuracy can be achieved without generating turbulences under the conditions of a noninvasiveness, a low invasiveness, no observable blood etc. Ideally, the measurement objects can be observed at their original positions in situ. Measurement objects can also be treated or restored owing to the actions of the waves themselves. Simultaneously, the processes can also be observed by performing the beamforming using the responses from the objects. The Beamformings can also be performed on satellite communications, radars, sonars etc to achieve accurate communications under saving energies by realizing informationally safe environments. In ad hoc communication instruments and mobile instruments, the present invention is effective. The present invention can also be used for sensor networking. When the objects are dynamic and real time characteristics is demanded, the present invention also make it possible to perform digital beamformings with high speeds, i.e., in short times as well as with high accuracies.

3rd Embodiment

Being dependent on a frequency, a bandwidth, an intensity or a mode etc, the waves such as electromagnetic waves, lights, mechanical vibrations, acoustic waves or thermal waves exhibit different behaviors. As far, many transducers for various type waves are developed and the waves' transmission waves, reflection waves or scattering waves are used for imaging. For instance, it is well known that on nondestructive examinations, medicines or sonars, ultrasounds, i.e., acoustic waves with higher frequencies, are used. Also on radars, electromagnetic waves with proper frequencies with respect to observation objects are used such as microwaves, terahertz waves, infrared rays, visible waves or radioactive rays such as an X-ray etc. These are also for other waves.

On the imagings using such waves, amplitude data obtained via the quadrature detection, the envelope detection or the square detection are displayed in a gray or color scale in a 1D, 2D or 3D. Alternatively, on the Doppler measurements using such waves, raw coherent signals are processed (ultrasound Doppler, radar Doppler, Laser Doppler etc). Moreover, it is well known that in the fields of image measurements, object motions are observed using incoherent signals obtained via the detections (cross-correlation processing or optical flow etc). On the medical ultrasounds or sonars, the imagings are also carried out using harmonic waves, and chord and different tone waves generated physically.

In such fields, for instance, the present inventor develops ultrasonic imaging techniques for a differential diagnosis of lesions such as cancerous diseases, sclerosis etc of human tissues. The present inventor increases a spatial resolution in echo imaging and an accuracy in measurement and imaging of a tissue displacement; and the present inventor also increases a spatial resolution and an efficiency of HIFU (High Intensity Focus Ultrasound) treatment; and the present inventor also promotes those imagings based on the reception of the echo with respect to the HIFU radiation. Those imagings are based on performing appropriate beamformings and also, proper detection methods or displacement measurement methods are demanded etc.

For instance, the inventor of the present invention developed as the beamforming methods, the lateral modulation method using crossed beams, the spectral frequency division method, one using many crossed beams and over-determined systems etc; and as the detection methods, the quadrature detection, the envelope detection and the square method etc; and as the displacement vector measurement methods, the multidimensional autocorrelation method, the multidimensional Doppler method, the multidimensional cross-spectrum phase gradient method and the phase matching method etc. In addition, the inventor of the present invention reported the techniques for reconstructing a (visco) shear modulus distribution or a thermal property distribution on the basis of the measurements of a displacement or a strain (nonpatent documents 13 and 29). In practice, several methods and techniques in the developments are used clinically. Many recent reports by the inventor of the present invention are performed at ITECs (International Tissue Elasticity Conferences), IEEE Trans. on UFFC, IEICE ultrasound meetings, ASJ acoustical imaging meetings etc.

Related to these, the inventor of the present invention focuses on nonlinear imaging. Today on the medical ultrasounds, so-called harmonic imaging is performed, i.e., nonlinear imagings on the basis of the results of physical actions during the ultrasound propagations. Below, mentioned are applications of nonlinear ultrasounds to the diagnosis and the treatment, particularly.

The harmonic imaging is to image the harmonic wave components generated during the wave propagations due to the fact that the wave propagation speeds of high intensity sound pressures are large (generally, it is explained that a bulk modulus is large with respect to a high intensity sound pressure). For this harmonic imaging, the contrast media (ultrasound agents) can also be used to increase nonlinear effects generated during the ultrasound propagation.

Long time has passed since the effectiveness was recognized in clinics, such as a capability for imaging a blood flow in capillary etc (nonpatent document 21). The Doppler measurement using the nonlinear components (harmonic components) is also possible and then, the results obtained using the multidimensional vector measurements in such a case will be presented in the near future. In the nonpatent document 22, the so-called pulse inversion method is used to separate harmonic waves from a fundamental wave signal.

Alternatively, the tissue imaging was performed in advance to the blood flow imaging historically. At the initial applications, the harmonic components are separated by filterings (nonpatent document 23) and in the historical present, the above-mentioned pulse inversion method is used to separate them. When the transmission signal is wideband, the bandwidths of the fundamental wave and the harmonic waves filled in the generated wave are to be overlapped, the use of the filtering is limited. Otherwise, there is a report that the fundamental wave and the harmonic waves are separated in a least squares sense by expressing the observed wave using a polynomial expression comprised of the respective exponentiation terms corresponding to the waves to be separated (nonpatent document 24).

Recently, on the ultrasound microscope (nonpatent document 25) or the radiation force imaging (nonpatent document 26), the applications of the harmonic components or chords are also reported. There exists deep relationships between the nonlinear propagations and the thermal absorptions and in the applications of HIFU, high intensity ultrasounds are focused on the focus position and including the cases where cavitations are generated (nonpatent document 27). When an ultrasound is converted into the energy of a shear wave (or the wave mode is converted to other energy), the generated high frequency shear wave is well absorbed in the neighboring tissues during the propagation (Girke). For instance, shear phenomena are caused by a scattering or an ultrasound to be a slanted incident wave into a boundary such as between a soft tissue and a bone.

The contrast media to be used for increasing the nonlinear effects on the HIFU treatment can also be considered to be effective on these points (nonpatent document 28 etc). On the treatment of cancerous diseases, the inventor of the present invention referred to, 17 years ago, the effects of blocking the feeding artery by coagulating the blood at the position and the inventor of the present invention considers that such effects can also be acquired using the contrast media. Recently, it becomes possible to cheaply introduce applicators having the same bandwidths as those of diagnostic transducers and then, the inventor of the present invention considers that the exclusive contrast media should be developed. The inventor of the present invention considers that both destructive and nondestructive properties are attractive and then, the diagnostic contrast media with both the properties or some mixed several type contrast media can be used proximately.

A wave is effected by attenuations during the propagation and then, the wave energy becomes smaller with the propagation distance. A diverging wave are also effected by the diverging. In the cases, since the transmission wave, the reflection wave or the scattering wave reflects a change in impedance, the or existence of a reflector or a scatter, the waves are used for imaging them or the Doppler measurements. On the imagings, the signal is desired to have high frequency components and to be wideband whenever possible and on the Doppler measurements they are also similar.

However, generally, the high frequency signal components are effected by attenuations, the energies are lost with the propagation distance; causing the signal to be low frequency and narrow band. That is, the imaging at far position from a wave source become to have a low signal-to-noise ratio (SNR) and a low spatial resolution. Accordingly, the accuracy of Doppler measurement decreases. To decrease the effects due to the attenuations is of extreme importance in an engineering sense.

It also becomes possible to perform higher spatial resolution imaging and higher accuracy Doppler measurement if a high frequency signal being not able to be generated by a single wave source can be generated. It is acceptable that a high frequency signal is generated simply. Generally, the attenuations is intense on the high frequency components and then, for instance, the microscope being well suffered from the attenuations is desired to allow observing positions as deeply as possible using the high frequency. Also it is useful if low frequency imagings or measurements using low frequency signals can be performed. It is also useful if a low frequency signal being not able to be generated by a single wave source can be generated. For instance, it is possible to deform at a deep position with a low frequency. On the applications of medical ultrasounds, MRIs, OCTs and lasers, deeply situated tissues are deformed in a low frequency using plural signal sources (Tissue Elasticity).

For instance, vibrations are applied to in plural directions to generate lower frequency vibrating waves than the respective applied vibrations; or plural ultrasound beams are crossed at their same focus position etc to yield a low frequency mechanical source for generating low frequency vibrating waves. The generated vibrating waves may be ultrasounds (longitudinal waves). Otherwise, the generated vibrating waves are shear waves (transverse waves), which can be observed using ultrasounds. It is useful if the propagation directions of the generated waves can be controlled. If these signals can be generated theoretically or on the basis of calculations, the generated waves can be controlled, which is useful. Moreover, detection methods, which allows simply performing detections in short times instead of a general quadrature detection and a general enveloped detection, or the square detection, are also important.

Then, in consideration of the above-mentioned points, the 2nd purpose of the present invention is to provide imaging instrument that allows increasing the spatial resolution and the measurement accuracy by increasing or newly generating high frequency components with the generally relatively small intensities or lost on arbitrary waves propagating from an inside of measurement object. The imaging instrument can be used for increasing or imitating the nonlinear effects in the measurement object, or for newly generating nonlinear effects when there exists no nonlinear effects in the measurement object, or virtually realizing and imaging nonlinear effects. And the 3rd purpose of the present invention is to allow generations of high frequency signals, which cannot be generated by using a single wave source. And the 4th purpose of the present invention is to realize detection methods, which can be performed simply in short times.

To solve the above-mentioned problems, the imaging instrument related to the one of viewpoints of the present invention is equipped with a nonlinear reception processing unit that performs at least one of the three processings with respect to arbitrary waves propagating form the inside of measurement object, i.e., (i) after implementing nonlinear processings at arbitrary positions on the propagation path, generating reception signals is performed by receiving using a transducer; (ii) generating analogue reception signals is performed by receiving using a transducer, after which analogue nonlinear processings are implemented; (iii) generating analogue reception signals is performed by receiving using a transducer, after which digital nonlinear processings are implemented onto the digital reception signals obtained by performing digital sampling with respect to the generated analogue reception signals; and further equipped with image signal generation unit that generates image signals exhibiting the image of the measurement object.

According to one of viewpoints of the present invention, implementing nonlinear processings, on arbitrary waves arriving from the inside of measurement object, with respect to signals having frequencies that do not lead to serious problems regarding attenuations makes it possible to increase or newly generate high frequency components with the generally relatively small intensities or lost on arbitrary waves propagating from an inside of measurement object and further to improve the spatial resolution and the measurement accuracy. With respect to arbitrary coherent signals generated by detecting, by a transducer, waves arriving from signal sources of arbitrary waves such as electromagnetic waves, lights, mechanical vibrations, acoustic sounds or thermal waves etc or the transmission waves, the reflection waves or the scattering waves with respect to the waves generated from the signal sources, implementing effects of multiplications or exponentiations during the wave propagations or performing processings including their analogue or digital calculations allows increasing nonlinear effects in the measurement object. Otherwise, the similar effects can also be imitated or newly generated or virtually realized.

For instance, on the imagings or the Doppler measurements using the coherent signals, compared with imagings using the raw signals, high spatial resolution imagings can be realized utilizing widebanded signals including the high frequency components and compared with Doppler measurements using the raw signals, high accuracy measurements of a displacement, a velocity, an acceleration, a strain or a strain rate can be realized. With respect to incoherent signals, the similar processings can be performed on the similar problems. For the hardwares, general devices can be used. Off course, analogue processings (circuits) is faster than digital processings (circuits). For performing calculations including high order calculations and at the point of a large degree of freedom, used can be calculators or devices having calculation functions such as FPGA and DSP etc.

Particularly, it is robust to the effects of attenuations during the wave propagations and it is also possible to generate high frequency components that cannot be generated using a single signal source; yielding high spatial resolution imagings and high accuracy Doppler measurements. For instance, using plural 100 MHz ultrasound transducers, physically the same times as the number of used transducers as high frequency ultrasounds as that of the single transducer used can be generated, i.e., high frequencies being not able to be generated by a general transducer can be generated. It is also useful for generating a high frequency simply. The present invention can also generate high frequencies by performing calculations. Thus, it is also possible to generate high frequency waves or signals that cannot be generated physically. Similarly, low frequency imagings or measurements using low frequency signals can also be performed similarly. Also, it is possible to generate low frequency signals that cannot be generated by a single signal source physically. The generated waves can also be controlled by realizing these signals theoretically or on the basis of calculations.

For instance, on the ultrasonic microscope, ultrasounds with a higher frequency than the frequency determined by the ultrasound sources can be generated using high frequency ultrasounds (signals) with several hundred MHz and since the generated ultrasounds are robust to the attenuations, a special ultrasonic microscope allowing high spatial resolutions imagings and high accuracy Doppler measurements can be realized. Also, low frequency imagings or measurements using low frequency signals can also be performed. Also, when performing the measurements of tissue deformation, for instance, deeply situated tissues can be deformed in low frequencies. On the applications of medical ultrasounds, MRIs, OCTs, lasers etc, deeply situated tissues can be deformed using plural signal sources. These are also for other imaging instruments or other Doppler instruments. Otherwise, it is also possible to increase the spatial resolutions for performing warming, heating, cooling, freezing, welding, thermal treatment, washing or restorations. The same effects can be obtained on incoherent signals obtained by various type detections.

On the technical aspects of signal processings, it is also possible to perform the quadrature detection and envelope detection simply. For instance, when the present invention is applied to the steered beams or waves, the IQ signals, i.e., results of quadrature detections performed on all coordinate axes, can be obtained and the envelope detection becomes simple. Moreover, when applying the present invention to the crossed beams, the IQ signals, i.e., results of quadrature detections performed on the respective coordinate axes, can be obtained and then, only implementing the Doppler signal processings on the respective directions makes it possible to measure a displacement vector, a velocity vector, an acceleration vector, a strain tensor or a strain rate tensor. Off course, on the imagings, the square detection can also be performed.

On the radars, sonars, non-destructive examinations or diagnose, imagings and Doppler measurements using arbitrary coherent signals generated by detecting, by a transducer, waves arriving from signal sources of arbitrary waves such as electromagnetic waves, lights, mechanical vibrations, acoustic sounds or thermal waves etc or the transmission waves, the reflection waves or the scattering waves with respect to the waves generated from the signal sources, are widely used for respective various media with proper frequencies. Waves generated from signal sources are also applied to the heating, the cooling, the freezing, the welding, the thermal treatment, the washing or the restorations. The same effects can be obtained on incoherent signals obtained by various type detections. Moreover, recently, the image measurements using incoherent signals are performed such as motions etc, and various imagings or measurements are performed on the basis of the image processings and signal processings. The present invention brought effects on these all, and the usability and the market potential of the present invention are prominently high.

Figure 30:
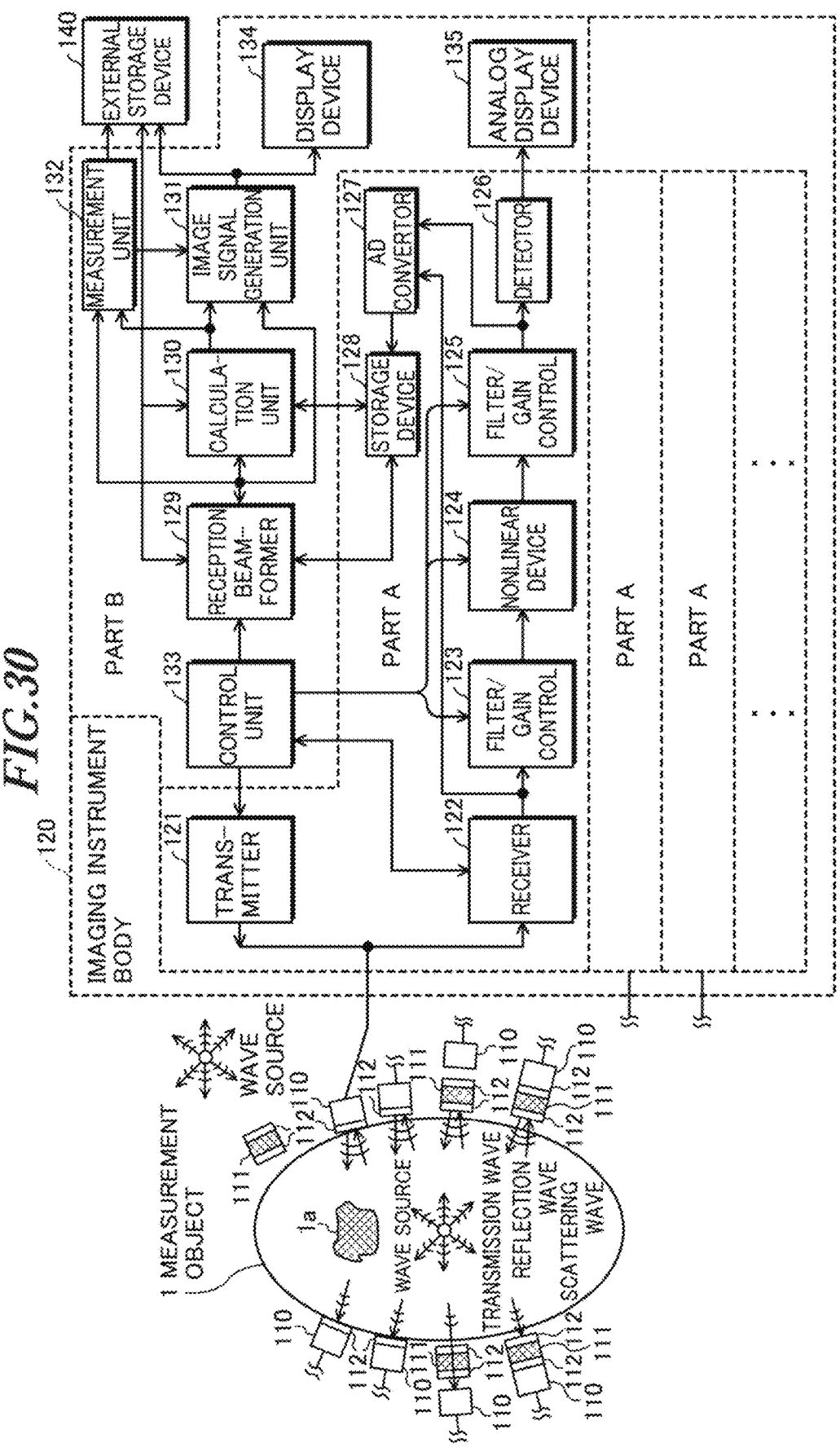
FIG. 30 shows schematic representation (block map) of compositions of imaging instrument related to the third embodiment of the present invention and the modification.

FIG. 30 shows schematic representation (block map) of the compositions of imaging instrument related to the third embodiment of the present invention. This imaging instrument performs imagings of measurement objects or measuring of physical quantities such as displacements in measurement objects nondestructively on the basis of arbitrary waves such as electromagnetic waves, lights, mechanical vibrations, acoustic sounds or thermal waves etc arriving from the measurement objects.

As shown in FIG. 30, the imaging instrument includes at least one transducer 110 and the imaging instrument body 120. The transducer 110 can be able to generate or receive arbitrary waves such as electromagnetic waves, lights, mechanical vibrations, acoustic waves or thermal waves etc. In the cases, the transducer 110 can be used for transmitting arbitrary waves to the measurement object 1 and for receiving reflected waves or scattered waves generated in the measurement object 1. For instance, when arbitrary waves are ultrasounds, ultrasound transducers can be used to perform the transmissions of ultrasounds according to the drive signals and the receptions of ultrasounds for generating reception signals. It is well known that according to the applications, ultrasound elements (PZT, PVDF etc) are different as well as the structures of the transducers.

In the medical applications, for blood flow measurement, a narrowband ultrasound is used historically. First in the world, the inventor of present invention has been realizing to use a wideband echo imaging transducer for measurements of soft tissues' displacement or strain (including static cases), shear wave propagation (speed) etc. Also for HIFU treatment, although a continuous wave can be used, in order to realize a high spatial resolution treatment, the inventor of the present patent has been developing new applicators using devices in a wideband type. As one of applications of a high intensity ultrasound, as mentioned above, tissues are stimulated by generating mechanical sources in the measurement object 1 with no thermal effects, for which echo imaging transducer can also be used. In addition to the thermal treatments and generations of mechanical sources, echo imagings can also be performed simultaneously. This is also for using of other wave sources and transducers. There exists for the transducers, contact and noncontact types, which are used by properly performing the respective wave impedance matchings.

Otherwise, as the transducers 110, transmission transducer used for generating arbitrary waves and reception transducer (sensor) used for receiving arbitrary waves can be able to be used. In the cases, the transmission transducers can transmit arbitrary waves to the measurement object 1 and the sensor can receive reflected waves, scattered waves or transmission waves etc generated in the measurement object.

For instance, when the arbitrary waves are thermal waves, thermal sources being not intentionally generated such as a sunlight, an illumination or a metabolism in vivo in a body can be used, whereas a stationary thermal source such as an infrared warmer or a heater etc, an ultrasound transducer that transmits ultrasounds for heatings, often driven by a drive signal (that can be able to generate a mechanical source in the measurement object 1), an electromagnetic transducer or a laser etc can also be used. An infrared sensor generating reception signals by receiving thermal waves, a pyroelectric sensor, detectors of microwaves or terahertz waves, a temperature sensor such as using optical fibres etc, an ultrasound transducer (that detects a change in temperature using the dependencies of changes in a sound speed or a volume on the temperature) or a nuclear magnetic resonance signal detector (that uses a chemical shift of nuclear magnetic resonance signal) can be used. A proper reception transducer can be used.

The transducer 110 can also be used positively for generating waves including harmonic waves according to drive signals. For instance, the transducer 110 generate the waves according to the wave sources and the nonlinearities of the circuit of transmitter 121 that drive the transducer 110. The transducer 110 can have a transmission aperture or a reception aperture, or plural transmission or reception apertures. The transmission aperture of transducer 110 also can be equipped with a nonlinear device 111 that implements nonlinear processings on the generated arbitrary waves. The reception aperture of transducer 110 can also be equipped with a nonlinear device 111 that implements nonlinear processings on arbitrary waves arriving from an inside of the measurement object 1. The nonlinear device 111 are not always to be contacted on the transmission apertures or the reception apertures of transducer 110, the device 111 can also be set at arbitrary positions on the propagation paths of arbitrary waves.

Between the measurement object 1 and the transmission or reception apertures of transducer 110, operation devices 112 such as filters (spectroscopes etc), blockers, amplifiers or attenuators etc can also be set. When using a nonlinear device 111, the operation devices 112 can also be set in front of, behind or both sides of the nonlinear device 111. The transducer 110, the nonlinear device 111 and the operation device 112 can be separated or incorporated in into a body.

FIG. 30 also shows the case where a wave source(s) exist in the measurement object 1, and the direct control of the wave source(s) by the controller 133 can be possible. By using the lens etc, the focusing can be performed on the waves generated by the transducer 110 or by using plural transducers 110, focused transmissions can be performed etc, which can generate a wave source(s) (including sources of mechanical waves or thermal sources, new generations of electromagnetic waves, for instance, with respect to magnetic substances etc that can be contrast media, or controlling of the wave intensity or the wave propagation direction by physical actions between waves or stimuli on physical properties etc).

Off course, a wave source(s) can exist in the measurement object originally (for instance, an electric current source(s) expresses the electric activities of brain or cardiac and the cardiac can also work as a mechanical source). There exists the cases where the wave source(s) can be controlled or not, the measurement object 1 is observed in situ, or such wave sources can be an imaging or measurement object themselves. Otherwise, such a wave source(s) can exist outside the measurement object 1 and similarly dealt with, which can also be a measurement object(s). Between the wave source(s) and the measurement object 1, the nonlinear device 111 or the operation device 112 can also be set properly.

Moreover, to obtain nonlinear effects in the measurement object 1 or to increase nonlinear effects in the measurement object positively, contrast media such as microbubbles (increasing nonlinearities) 1a etc can be injected at least into a part of the measurement object 1. The contrast media 1a can have affinities for diseases or fluids, which are targets, etc in the measurement object 1. Thus, to the transducer that receives a wave, waves generated by plural wave sources can be arrived at.

The transducer 110 is provided with a drive signal from the imaging instrument body 120 via wire lines or wireless and/or the transducer 110 outputs received signals into the imaging instrument body 120. When wireless is used, the transducer 110 is equipped with a wireless receiver and/or a wireless transmitter; and wireless transmitter and receiver are set in the imaging instrument body 120.

The imaging instrument body 120 can include, in the part A, a transmitter 121, a receiver 122, a filter/gain control unit 123, a nonlinear element 124, a filter/gain control unit 125, a detector 126, an AD (Analogue-to-digital) convertor 127 and a storage device 128. Also, the imaging instrument 120 can include, in the part B, a reception beamformer 129, a calculation unit 130, an image signal generation unit 131, a measurement unit 132, a control unit 133, a display device 134, an analogue display device 135. The control unit 133 controls the respective units or devices in the imaging instrument body 120.

When using the plural transducers 110, the same number of part A as that of the transducers 110 (the number of channels) can be set. Below, also explained is the case where an array is comprised of the plural transducers. As shown in FIG. 30, when plural numbers (channels) of part A are set, reception signals outputted from storage devices 128 of the respective parts A can be provided to the reception beamformer 129 of the part B. Otherwise, parts B can also be connected with respect to the respective parts A in a cascade fashion and the received signals can be processed independently. In the case, the received signals outputted from the storage devices of the respective parts A are provided to the reception beamformers 129 of the parts B of the respective channels. The plural transducers 110 can include ones for other different type waves and in the cases, nonlinear effects of different type waves can also be observed simultaneously, and not nonlinear effects of the same type waves but those generated between different type waves can also be observed.

On the part A, the transmitter 121 to the detector 126 can also be comprised of analogue circuits and at least partially it can also be comprised of digital circuits. On the part B, the reception beamformer 129 to the control unit 133 can also be comprised of digital circuits, or the CPU (central processing unit) and the storage media in which softwares for making the CPU to perform respective type processings are recorded. As the storage media, a hard disk, a flexible disk, an MO, an MT, a CD-ROM or a DVD-ROM etc can be used. At least partially the reception beamformer 129 to the control unit 133 can be comprised of analogue circuits.

The transmitter 121 includes a signal generator such as a pulser that generates a drive signal according to a trigger signal provided by the control unit 133 etc. The control unit 133 can control the frequency or the carrier frequency, the bandwidth, the transmission signal intensity (apodization), the wave shape or the geometry of a pulse wave or a burst wave etc. The control unit 133 can set timings of trigger signals or the delay times on the respective channels. Otherwise, the transmitter 121 can also include delay devices for adding delays to the respective trigger signals (channels) according to the delay times set by the control unit 133 and for all the channels, the timings of trigger signals outputted from the control unit 133 is set at a constant, The transmitter 121 provides a generated drive signal to the transducer 110 and makes the transducer 110 to generate an arbitrary wave. For instance, the transmitter 121 can include an amplifier for working on the drive signal (and being able to work as an apodization) to control the wave intensity to be transmitted or the harmonic wave intensities to be generated and furthermore, the transmitter 121 can also include a delay device of which delay time is set by the control unit 133. A drive signal including harmonic waves can also be generated and can be used. Not a resonance but an apodization can be performed, or in the cases where forcedly vibrating is performed, various waves including a charp wave etc can be generated and can be used. When drive signals generated by a transmitter 121 with plural channels are provided to plural transducers 110, according to the delay times set by the control unit 133, the beam transmission with a focusing or a steering and the plane wave transmission can be performed (Since the plane wave transmission yields a narrow band in the direction orthogonal to the propagation direction and it is also effective to be wide banded in the direction).

Furthermore, the transmitter 121 can also include nonlinear devices to which nonlinear effects are similarly set (analogue devices such as a transistor, a diode or a nonlinear circuit etc or digital devices such as a nonlinear calculators (processors) etc). Frequencies or carrier frequencies, bandwidths, apodizations, delays and nonlinear effects to be used are prepared in advance, which can also be controlled via the control unit 133 by an operator. Otherwise, they can also be determined adaptively by the calculation unit 130 according to the observed states and can be controlled.

When driving the plural transducers 110, the frequencies or the carrier frequencies, the bandwidths, the apodizations, the delay devices and nonlinear devices of the transmitters of respective channels can be controlled and specifically, the prepared patterns of them in advance can also be used, the pattern can also be controlled via the control unit 133 by an operator, or the pattern can also be determined adaptively according to the observed states by the calculation unit 130 and can be set.

The receiver 122 can include, for instance, an amplifier for amplifying or an attenuator for attenuating reception signals (that can be possible in working as an apodization or a filter) and furthermore, the receiver 122 can also include a delay device of which delay time is set by the control unit 133. Furthermore, the receiver 122 can also include a nonlinear device to which nonlinear effects are similarly set (analogue devices such as a transistor, a diode or a nonlinear circuit etc or digital devices such as a nonlinear calculators (processors) etc). In cases where waves are received by plural transducers 110, they can be set similarly to those of the transmitter 121. The receiver 122 amplifies the reception signals generated from arbitrary waves received by the transducer 110, and the amplified reception signals can be outputted to the filter/gain control unit 123 and the AD convertor 127.

The filter/gain control unit 123 is a filter to limit the bandwidth of reception signals, or includes an amplifier or an attenuator for controlling the gain of reception signals. The filter/gain control unit 123 can control the bandwidth or the gain of reception signals and can output the reception signals to the nonlinear element 124.

The nonlinear element 124 can include, for instance, analogue devices such as a transistor, a diode or a nonlinear circuit etc and implements analogue nonlinear processings on the reception signals. The nonlinear processings can be an exponentiation calculation at least on one frequency component signals included in the reception signals or a multiplication calculation on plural frequency component signals included in the reception signals (A Hall effect device etc can be used).

The filter/gain control unit 125 is a filter to limit the bandwidth of reception signals, or includes an amplifier or an attenuator for controlling the gain of reception signals. The filter/gain control unit 125 can control the bandwidth or the gain of reception signals and can output the reception signals to the detector 126 and the AD convertor 127.

The above-mentioned filter/gain control units 123 and 125 and the nonlinear element 124 can also be set on the prepared ones in advance, they can also be controlled via the control unit 133 by an operator, or they can also be determined adaptively according to the observed states by the calculation unit 130 and can be set. When driving the plural transducers 110, their respective channels can be controlled independently, the prepared patterns in advance can also be used, the pattern can also be controlled via the control unit 133 by an operator, or the pattern can also be determined adaptively according to the observed states by the calculation unit 130 and can be set.

For instance, when not performing the reception beamformings, the detector 126 generates analogue signals by implementing the envelope detection or the square detection etc. Otherwise, the displacement measurement can also be performed via the quadrature detection. On the basis of the image signals or the measurements generated by the detector 126, the analogue display device 135 displays the images of the measurement object 1 or the wave sources.

The AD convertor 127 selects the reception signals outputted by the filter/gain control unit 125 and by the receiver 122 when the analogue nonlinear processings are implemented onto the reception signals and not, respectively. The AD convertor 127 can convert the analogue signals into the digital signals by digital samplings. The digital reception signals generated the AD convertor 127 are outputted to the storage device 128. The storage device 128 are comprised of memories such as RAM for instance, and the reception signals are stored.

The reception signals stored by the storage device 128 are provided to the reception beamformer 129. While the signal processings are performed by the reception beamformer 129, the signals under being processed are be stored in the storage device 128 or the external storage device 140 temporally and if required, the stored signals are read out. When using a single or plural transducers 110, the reception beamformer 129 can perform the pulse inversion method or the separation of harmonic waves etc using the polynomial fitting method etc (The calculation unit 130 can also be possible to perform the same processings).

When using the plural transducers 110, the reception beamformer 129 performs the reception beamformings with respect to the reception signals provided by the storage devices 128 of plural channels. For instance, after the reception beamformer 129 performs the delays via implementing the delays onto the reception signals of plural channels according to the delay times set by the control unit 133, the reception beamformer 129 synthesizes the receptions signals to generate new reception signals with focusing by implementing the summing or the multiplication.

Otherwise, when the respective receivers 122 of plural channels include the delay devices, the receivers 122 can implement delays onto the respective reception signals according to the delay times set by the control unit 133. The reception beamformer 129 synthesizes the reception signals by implementing the summing and the multiplications onto the reception signals of plural channels. On the reception beamforming, the reception beamformer 129 can also perform the apodizations.

Otherwise, by the (multidimensional) fast Fourier's transformer being equipped with the imaging instrument body 120, the spectra of the reception signals are obtained and on the basis of the spectral analysis, the properties of filterings, or beams or waves can be controlled such as a frequency or a carrier frequency, a bandwidth, a frequency or a carrier frequency of at least one of directions, a bandwidth of at least one of directions, a shape, a beam geometry, a steering direction or a propagation direction etc. By performing the spectral frequency division (nonpatent document 29), plural reception signals can be obtained from a single reception signal etc (corresponding to plural quasi-beamformings) and furthermore, the nonlinear processings can also be implemented on these signals. With respect to the signals to which the nonlinear processings are implemented on, these processings can also be performed.

On this imaging instrument, the above-mentioned plural wave signals generated by the single or plural transducers (nonlinear processed or not processed) are stored into the storage device 128 or the external storage device 140. The reception beamformer 129 or the calculation unit 130 reads out the results and performs the summation (superposing, linear processing) or the multiplication (nonlinear processing), which can be used for the imaging or various measurements. In the cases, the phasings are properly performed.

The calculation unit 130 can perform, mainly, digital nonlinear processings onto the digital reception signals outputted by the reception beamformer 129. The nonlinear processings can be an exponentiation calculation at least on one frequency component signals included in the reception signals or a multiplication calculation on plural frequency component signals included in the reception signals. The calculation unit 130 can also work as the beamformer 129 as mentioned above. Including the case, while the signals are processed, the signals under being processed can be stored into the storage device 128 or the external storage device 140 temporally and if required, the signals are read out.

Here, the transducer 110 to the operation device 112 and the receiver 122 to the calculation unit 130 composes the nonlinear reception processing unit that implements the nonlinear processings onto arbitrary waves arriving from the inside of measurement object 1 or the reception signals obtained by receiving the arbitrary waves. On the nonlinear reception processing unit, at least one of the nonlinear device 111, the nonlinear element 124 and the calculation unit 130 implements the nonlinear processings onto the arbitrary waves arriving from the inside of measurement object 1 or the reception signals obtained by receiving the arbitrary waves. There are also other ways to obtain such nonlinear effects as mentioned above.

That is, the nonlinear reception processing unit performs at least one of the three processings with respect to arbitrary waves propagating form the inside of measurement object 1, i.e., (i) after implementing nonlinear processings using the nonlinear devices 111 at arbitrary positions on the propagation path, generating reception signals is performed by receiving using a transducer 110; (ii) generating analogue reception signals is performed by receiving using a transducer 110, after which analogue nonlinear processings are implemented using the analogue nonlinear elements 124; (iii) generating analogue reception signals is performed by receiving using a transducer, after which digital nonlinear processings are implemented using the digital nonlinear devices 130 onto the digital reception signals obtained by performing digital sampling with respect to the generated analogue reception signals; and further equipped with image signal generation unit that generates image signals exhibiting the image of the measurement object. As mentioned above, there also exists other ways to obtain nonlinear effects.

The image signal generation unit 131 and the measurement unit 132 select the reception signals outputted by the calculation unit 130 and by the reception beamformer 129 when the digital nonlinear processings are implemented onto the reception signals and not, respectively.

The image signal generation unit 131 generates the image signals expressing the measurement object 1 on the basis of the reception signals generated by the nonlinear reception processing unit. Otherwise, the image signal generation unit 131 can generate image signals on the basis of the reception signals obtained by the nonlinear processings and not together. The image signal generation unit 131 can also select the reception signals obtained in the cases of no implementation of the nonlinear processings and can generate the image signals expressing the measurement object 1. For instance, the image signal generation unit 131 generates image signals by implementing the envelope detection processing or the square detection processing etc. The display device 134 generates the image signals expressing the measurement object 1 on the basis of the image signals generated by the image signal generation unit 131.

The measurement unit 132 can perform the measurement of a displacement etc in the measurement object 1 using at least one of the plural signals obtained by the nonlinear processings. For instance, on the observing the propagations of mechanical or electromagnetic waves, the measurement unit 132 measures a particle displacement and a particle velocity generated by arbitrary wave propagations of the wave itself or other waves on the basis of the measured displacement. In the cases, the image signal generation unit 131 generates image signals expressing the wave propagations on the basis of the particle displacement or the particle velocity measured by the measurement unit 132. When plural waves arrive at, the waves can also be separated in advance, or the measurements can also be performed via separating processing on the waves by analogue or digital processings after the receiving the waves.

Otherwise, on the measurements of thermal wave propagations, the measurement unit 132 uses, as the transducer 110, an infrared sensor or a pyroelectric sensor, detectors of microwaves or terahertz waves, a temperature sensor such as using optical fibres etc, an ultrasound transducer (that detects a change in temperature using the dependencies of changes in a sound speed or a volume on the temperature) or a nuclear magnetic resonance signal detector (that uses a chemical shift of nuclear magnetic resonance signal) for measuring the thermal waves. In the cases, the image signal generation unit 131 generates image signals expressing the thermal wave propagations on the basis of the thermal waves measured by the measurement unit 132. The image signals generated by the image signal generation unit 131 and the measurement data obtained by the measurement unit 132 can be stored in the external storage device 140.

The above-mentioned nonlinear reception processing unit can obtain the results of exponentiation calculations by the nonlinear processings with respect to the arbitrary waves arriving from the inside of the measurement object 1, or when the nonlinear processings are the exponentiation calculations, with respect to the arbitrary waves, as the results of the chord and different tone waves and harmonic tone waves, reception signals with an increased or decreased frequency can be obtained compared to the corresponding signals obtained when the nonlinear processings are not implemented on. The nonlinear processings can also be multiplication calculations. The nonlinear processings can also be high order nonlinear processings and as the effects, mainly the results of the exponentiation calculations and the multiplication calculations can also be obtained.

Thus, when the arbitrary waves have plural different frequency components, the nonlinear processings generate wideband reception signals compared to the corresponding signals obtained when the nonlinear processings are not implemented on. The reception signals generated with the increased frequency are harmonic wave signals with an increased frequency, an increased spatial resolution, a decreased sidelobes or an increased contrast compared to the corresponding signals obtained when the nonlinear processings are not implemented on. In addition, the reception signals generated with the decreased frequency are the signals with the direct currents approximately obtained by implementing the quadrature detections on the generated harmonic wave signals. The image signal generation unit 131 generates image signals on the basis of at least one of signals obtained by the nonlinear processings.

Also, when plural arbitrary waves arriving from the inside of the measurement object 1 have at least one different value about the propagation direction, the steering angle, the frequency, the carrier frequency, the pulse shape, the beam geometry, the frequency or the carrier frequency in one of three directions or the bandwidth in one of three directions from others in the measurement object 1, with respect to the superposed plural arbitrary waves arriving at, the nonlinear reception processing unit can perform at least one processing of the above-mentioned (i) to (iii). The image signal generation unit 131 generates image signals on the basis of the reception signals obtained by the nonlinear reception processing unit.

Prior to the reception of plural arbitrary waves, the nonlinear reception processing unit let the plural arbitrary waves to pass at least through the analogue delay device or the analogue storage device as the operation device 112 such that the plural arbitrary waves can be superposed at respective positions in the measurement object 1. This is the so-called phase aberration correction.

The nonlinear reception processing unit can obtain the results of exponentiation calculations by the nonlinear processings with respect to the superposition of arbitrary waves arriving from the inside of the measurement object 1, or when the nonlinear processings are the exponentiation calculations, with respect to the superposition of arbitrary waves, as the results of the chord and different tone waves and harmonic tone waves, reception signals with an increased or decreased frequency can be obtained compared to the corresponding signals obtained when the nonlinear processings are not implemented on. By this, the above-mentioned similar effects can be obtained. The image signal generation unit 131 generates image signals on the basis of at least one of signals obtained by the nonlinear processings.

Also, when plural arbitrary waves arriving from the inside of the measurement object 1 have at least one different value about the propagation direction, the steering angle, the frequency, the carrier frequency, the pulse shape, the beam geometry, the frequency or the carrier frequency in one of three directions or the bandwidth in one of three directions from others in the measurement object 1, with respect to the superposed plural arbitrary waves arriving at, the nonlinear reception processing unit can not only perform at least one processing of the above-mentioned (i) to (iii) but also perform, at arbitrary timing after receiving the plural arbitrary waves, the separating the reception signals into plural signals on the basis of the analogue or digital signal processings using the analogue or digital device. The image signal generation unit 131 generates image signals expressing the image of above-mentioned measurement object on the basis of one of the separated plural signals obtained by the nonlinear reception processing unit. By performing the nonlinear calculations (processings), the effects of multiplication calculation can be obtained. Also, after performing the analogue or digital phase aberration correction and the signals are superposed again, the effects of exponentiation calculation can also be obtained.

Also, when plural arbitrary waves arriving from the inside of the measurement object 1 have at least one different value about the propagation direction, the steering angle, the frequency, the carrier frequency, the pulse shape, the beam geometry, the frequency or the carrier frequency in one of three directions or the bandwidth in one of three directions from others in the measurement object 1, with respect to at least one of the not superposed plural arbitrary waves arriving at, the waves not superposed by blocking using the operation device 112, and waves separated by using the device (analogue or digital) or the analogue or digital signal processing, the nonlinear reception processing unit can perform at least one processing of the above-mentioned (i) to (iii). The image signal generation unit 131 generates image signals on the basis of the reception signals obtained by the nonlinear reception processing unit.

Prior to the reception of plural arbitrary waves, the nonlinear reception processing unit lets the plural arbitrary waves at least to pass through the analogue delay device or the analogue storage device as the operation device 112 such that the plural arbitrary waves can be superposed at respective positions in the measurement object 1. This is the so-called phase aberration correction.

Also, the nonlinear reception processing unit lets the analogue reception signals at least to pass through the analogue delay device and the analogue storage device, or implements delays on the digital reception signals by digital processings, or lets the digital reception signals to pass through the digital storage device, such that the plural arbitrary waves can be superposed at respective positions in the measurement object 1.

Also, the nonlinear reception processing unit can obtain the results of exponentiation calculations by the nonlinear processings with respect to the respective arbitrary waves arriving from the inside of the measurement object 1, or when the nonlinear processings are the exponentiation calculations, with respect to the respective arbitrary waves, as the results of the chord and different tone waves and harmonic tone waves, reception signals with an increased or decreased frequency can be obtained compared to the corresponding signals obtained when the nonlinear processings are not implemented on. By this, the above-mentioned similar effects can be obtained. The image signal generation unit 131 generates image signals on the basis of at least one signals obtained by the nonlinear reception processing unit.

Also, the nonlinear reception processing unit can obtain the results of multiplication calculations by the nonlinear processings with respect to the respective arbitrary waves arriving from the inside of the measurement object 1, or when the nonlinear processings are the multiplication calculations, with respect to the respective arbitrary waves, as the results of the chord and different tone waves and harmonic tone waves, reception signals with an increased or decreased frequency can be obtained compared to the corresponding signals obtained when the nonlinear processings are not implemented on.

Thus, when the arbitrary waves have plural different frequency components, the nonlinear processings generate wideband reception signals compared to the corresponding signals obtained when the nonlinear processings are not implemented on. Also, the reception signals generated with the increased or decreased frequency are signals, having direct currents due to (approximate) quadrature detections at least in one direction as well as having bandwidths of harmonic waves at least in other one direction, with an increased spatial resolution, a decreased sidelobes or an increased contrast compared to the corresponding signals obtained when the nonlinear processings are not implemented on. The image signal generation unit 131 generates image signals on the basis of at least one of signals obtained by the nonlinear processings.

To generate image signals, the image signal generation unit 131 can also implement an arbitrary detection processings onto at least one of the plural signals generated by the nonlinear processings, or implement onto the superposed plural signals or implement onto the plural signals and the implemented signals are superposed.

4th Embodiment

Figure 31:
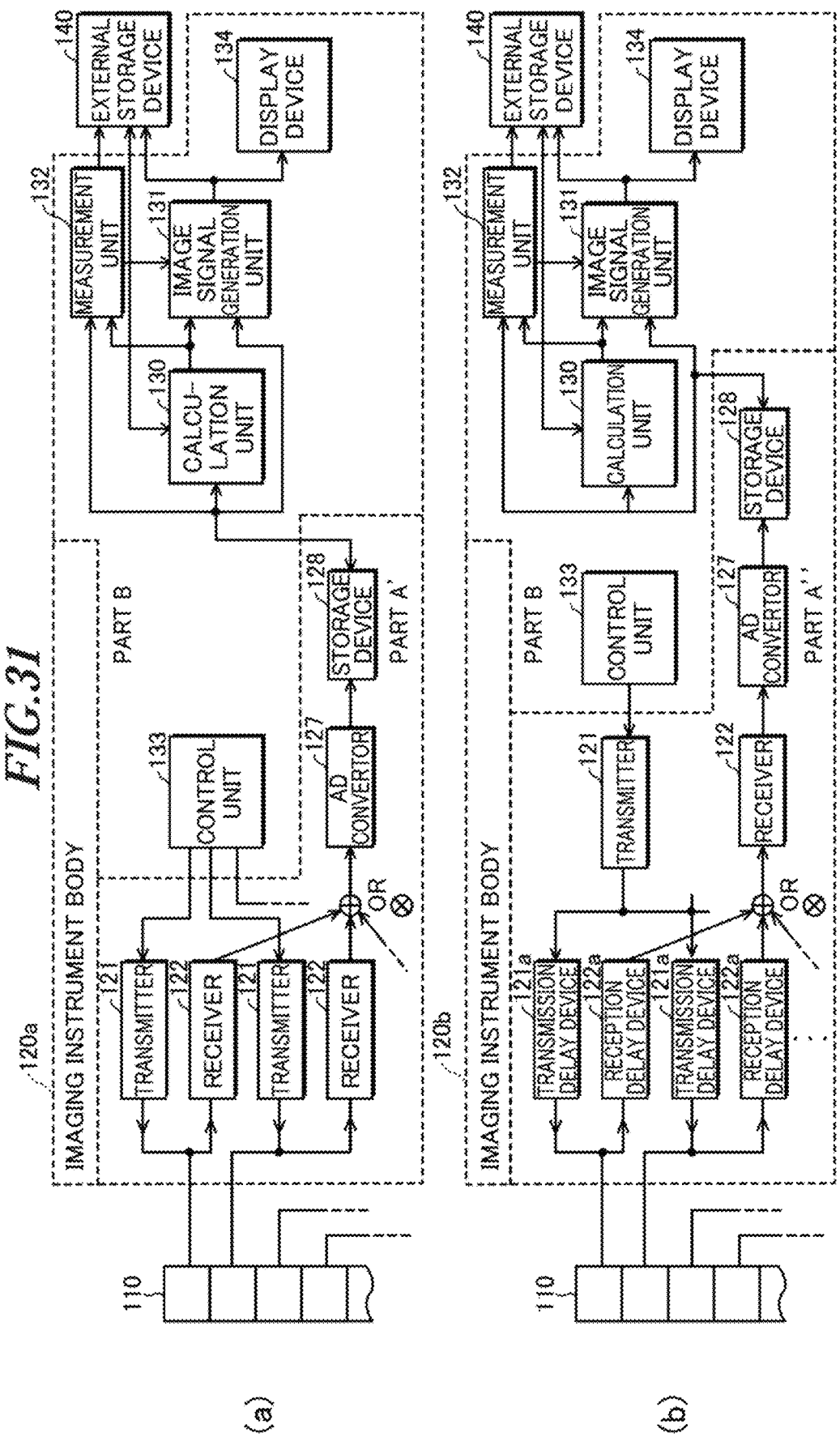
FIG. 31 shows schematic representation (block map) of compositions of imaging instrument related to the fourth embodiment of the present invention and the modification.

Next, explained is the 4th embodiment of the present invention. FIG. 31 shows schematic representation (block map) of compositions of imaging instrument related to the fourth embodiment of the present invention and the modifications. The imaging instruments related to the 4th embodiment and the modifications are instruments that generate waves by driving plural transducers 110 or a transducer array or receive waves for performing imagings (FIG. 31 shows a transducer array). As composition elements, the same capabilities as the compositions of the 3rd embodiment can be used.

On the imaging instrument related to the 4th embodiment and shown in FIG. 31(a), the plural transducers 110 or the transducer array elements are respectively connected to the plural transmitters 121 and receivers 122 similarly to the cases where the imaging instrument related to the 3rd embodiment uses plural transducers 110 or a transducer array. On the imaging instrument body 120a, plural transmitters 121 or receivers 122 are set in a part A'.

Analogue reception signals from the plural transducers 110 or the transducer array are phased by using the delay devices in the receiver 122, or analogue reception signals not phased, are summed (linear analogue processing) by the sum processing unit or multiplied (nonlinear analogue processing, Hall effect devices etc can be used) by the multiplication processing unit. Thus, the reception beamforming is performed and on the part B, the reception beamformer 129 (FIG. 30) is not required.

Moreover, the reception digital signals obtained via the AD convertor 127 are stored in the storage device 128. The part B of the imaging instrument body 120a performs the imaging or the measurement imaging, similarly to the 3rd embodiment, by making the control unit 133 to control the respective units or devices to obtain all the nonlinear effects that are obtainable by the 3rd conduct on the basis of the reception signals. In FIG. 31, wires connections from the control unit 133 to the receiver 122 etc are omitted.

Also on the 4th embodiment, similarly to the transmitters and receivers of the 3rd embodiment, delays can be added onto the drive signals for the respective transducers or the reception signals and then, the transmission or the reception focusing or steering etc can also be performed. Compared with the 3rd embodiment that requires the same number of AD convertors 128 and storage devices 128 as the channel number, on the 4th embodiment, one AD convertor 127 and one storage device 128 are required and then the instrument can be simpler.

Alternatively, on the imaging instrument related to a modification of the 4th embodiment, shown in FIG. 31(b), in the part A" in the imaging instrument body 120b, the transmission delay devices 121a and the reception delay devices 122a are set outside the transmitter 121 and the receiver 122. Being different from in the imaging instrument shown in FIG. 31(a), in the imaging instrument shown in FIG. 31(b), the phasing is performed on the analogue reception signals by the reception delay devices 122a or the phasing is not performed on, and the sum processing unit performs the summing (linear analogue processing) or the multiplication processing unit performs the multiplication (nonlinear analogue processing) and the receiver 122 received the results. Thus, one transmitter 121 and one receiver 122 are required and then, the instrument can be prominently simpler and however, the same nonlinear effects as those of the 3rd embodiment can also be obtained.

The imaging instrument related to the 3rd embodiment shown in FIG. 30, the imaging instrument related to the 4th embodiment shown in FIG. 31(a), the imaging instrument related to the modification of the 4th embodiment shown in FIG. 31(b), other type imaging instruments and their composition elements can also be used simultaneously. For instance, the respective coherent or incoherent image signals, or measurement results obtained by using plural type instruments can also be displayed, or simultaneously they can also be displayed in parallel, or their superpositions or the multiplications can also be displayed. Basically, reception signals of the same time or the same phase can be processed. On one imaging instrument, when plural image signals or measurement results can be obtained using reception signals received at the same time or the same phase, the same processings can also be performed. The signals to be processed is analogue or digital signals after the phasing is performed, the summings and the multiplications are performed by analogue (Hall effect elements etc can be used) or digital (calculators or computing units) processing.

The imaging instrument of the 1st or 4th embodiment of the present invention basically implements the nonlinear processings on the signals using analogue calculators of various type devices, digital calculators, computers or devices like these (FPGA or DSP etc). As mentioned later in detail, the nonlinear processings are mainly to obtain the effects of exponentiation or multiplication, and the calculations themselves are not limited to these and the calculations can also be high order calculations including other nonlinear properties. Through the polynomial fitting, the spectral analysis, the pulse inversion method, the numerical calculations, or signal processings etc, such effects can also be extracted or separated. The nonlinear processing can be implemented on not only the signals but also the waves and prior to performing the reception, a wave can also be extracted or separated using wave devices (filters on a time or a space, or their frequencies or spectroscopy etc). Exclusive devices can also be used.

As mentioned above, the imaging instrument is equipped with the nonlinear device 111, the nonlinear element 124 or the calculation unit 130 together with the transducer 110 for an arbitrary wave, the transmitter 121 and the receiver 122. If necessary, a data storage device (a memory, a hard disk, a photograph, a CD-RW or other storage media) or a display device etc can also be equipped with. The imaging instrument can also be comprised of the respective general devices, which can be realized by building up them. To existing instruments without the nonlinear devices 111, the nonlinear elements 124, the calculation unit 130 or other nonlinear devices, the devices performing the nonlinear processings of the present invention can also be added to perform the nonlinear processings.

The waves transmitted from the transmitter 121 (wave source) or the transducer 110 are a pulse wave, a burst wave or a coded wave (phase-modulated etc) and then imaging or measurement can be performed with spatial resolutions. However, if the spatial resolution is not required on the measurement, the waves are not limited to these and a continuous wave can also be used.

The generated waves are determined by the transducer properties of the electric signals (drive signals) to the waves on the transducer 110 and then the device and the drive signals properly designed can be used. For instance, for lights, various light sources (coherent or incoherent, light emitting diode (LED), mixed LED, laser (variable wavelength) or optical oscillator etc) can be used and for acoustic waves, an electroacoustic transducer or an vibrator etc can be used. For the oscillatory waves, an actuator-based oscillation source can be used and for thermal waves, a thermal source etc can be used. Thus, on the present embodiment, transducers 110 that generated various type waves can be used.

For the transducer 110 to be used for processing the above-mentioned respective type waves, representative transducers can be used and also special transducers having nonlinear properties that are not used generally can be used positively. In general, if high voltages are applied to the ultrasound elements, ultrasounds including harmonic waves are generated by the nonlinear phenomena and however, mainly the so-called harmonic imaging using the extractions of nonlinear components generated during the wave propagations in the media is performed. And then, only the fundamental wave can also be performed by filtering out the harmonic wave components.

On the present conduction, such nonlinear waves positively generated can be used. That is, when nonlinear properties can be obtained at the transmissions, the nonlinear properties can be effectively used on the present invention. Alternatively, by generating with no nonlinear components, nonlinear phenomena occurring in the measurement object can also be explored.

When the waves including the nonlinear components, such harmonic waves can also be effected by nonlinear phenomena. When transmitted waves have harmonic waves originally or crossed plural waves (or other wave parameters except for the propagation direction or the steering angle are different such as a frequency or a carrier frequency, a pulse shape, a beam geometry, or frequencies, carrier frequencies or bandwidths in respective directions), as mentioned later, analogue processings such as the pulse inversion method, the temporal or spatial filtering, the spectral filtering, or the polynomial fitting or digital processings such as those corresponding the analogue processings or signal processings etc are used to separate the waves and the present invention can also be performed, or the present invention can also be performed under the waves are not separated. Also, using blockers such as obstacles, filter devices or spectroscopies (on a time or a space, or their frequencies) or physical stimuli for changing the refraction of media (optical switch etc) etc during the wave propagation, the receptions of the respective waves separated in advance can also be performed. When it is possible to control the respective wave sources, the respective waves can also be generated independently and the respective observations can be performed.

Also, after generating the waves using the transducer 110, prior to the propagations of waves propagating in the measurement object, by using the devices for directly generating nonlinear phenomena on the waves, waves including the nonlinear components can be propagated into the measurement object. Also, during or after the wave propagations in the measurement object, it is possible to use devices for generating the nonlinear phenomena. By coupling waves or signals or mixing them etc can also performed to yield multiplication effects.

For instance, on lights, used can be (i) nonlinear optical elements (for instance, optical harmonic generation device used for the wavelength conversion of laser light to the short wavelength region), (ii) optical mixing devices, (iii) devices for generating optical parametric effects such as optical parametric generation, stimulated Raman scattering, coherent Raman scattering, stimulated Brillouin scattering, stimulated Compton scattering or four wave mixing etc, (iv) devices for generating multiphoton transitions such as general Raman scattering (spontaneous emission) etc, (v) devices for generating nonlinear refraction index change and (vi) devices for generating electric field dependence refractive index change, etc. Couplers or optical fibres etc can also be effectively used. Observations of plural positions (multichannels) can also be performed and are suited to performing the signal processings.

When using lights, there exists deep relationships with wide areas such as optical electronics, nonlinear optical effects or laser engineering etc on the generation, the control or the measurement of lights. The optical devices to be used generally can also be used as the operation devices 112 or nonlinear devices 111, and exclusively developed devices can also be used. For these, an optical amplifier (a photon multitube etc), an absorber (an attenuator), a reflector, a mirror, a scatter, a collimator (variable focus), a lens, a deflector, a polariscope, a polarizing filter, an ND filter, a polarized beam splitter (a separator), a blocker, an optical waveguide (using photonics crystal etc), an optical fibre, an optical Kerr effect device, a nonlinear optical fibre, a mixing optical fibre, a modulation optical fibre, an optical trapping (or confinement) device, an optical memory, a coupler, a directional coupler, a distributor, a mixed distributor, a spectrometer, a dispersion shift optical fibre, a band-pass filter, a phase conjugator (using degenerate four-wave mixing or photorefractive effects etc), a switch using optical control of ferroelectric semiconductors, a phase delay device, a phase correction device, a temporal invertor, an optical switch or an encoder using optical masks etc, etc can be used solo or together, and not limited to these. Under optical controls (wavelength conversion, switching, routing), an optical node technology, an optical cross connect (OXC), an optical add-drop multiplexer (OADM), an optical multiplexer or separator or an optical switching element are used as well as an optical transmission network or an optical network itself as a device, and optical signal processings can also be performed.

For detectors, a CCD camera, a photodiode, a mixed-type photodiode or a virtual source (as a wave source as well) disclosed in the present invention can also be used. For optical signal processings, a temporal or spatial filter, a correlation calculation, a matched filtering processing, an extracting of signal, a heterodyne or superheterodyne (obtained low frequency signals can be AD converted and can also be demodulated) and homodyne etc can be used. Also, electromagnetic wave detectors can also be used.

Particularly for nonlinear media, for instance, there are a great variety of media such as a carbon bisulfide, a sodium vapor, a semiconductor on the basis of silicone, gallium arsenide etc, a quantum well and an organic dye such as a fluorescein, an erythrosine etc. On crystals such as a barium titanate, self-pumped four wave mixing can also be used without an externally provided pumped wave.

On visible lights, infrared rays, microwaves or terahertz waves and other waves such as radioactive rays etc, the respective general devices can also be used and also the exclusive devices can also be used. Not only SAW but also other devices that have relationships between oscillation systems and electromagnetic systems are also useful. Also, nonlinear devices can be used. On thermal transfers, non-linearities are variously exhibited such as by a synthesis between alumina and zirconium, a solder and a layered cobalt oxide. A heat acts on optical devices and can yield nonlinearities, the applications can also be considered.

For a transducer 110, there are contact and contactless types with respect to the measurement object. It is possible to be required to use impedance matching devices on the respective waves. It is also between the devices in an instrument or an electric circuit as well as in a measurement space. When observing living tissues using ultrasounds, a gel or water etc is used as a matching material. On the ultrasonic microscopes, in general, the specimens are observed on the stage and however, an array-type or a mechanical type (an element or an element array is mechanically moved to perform the scan in housing filled with a matching material such as water etc) can also be realized and used and then, the setting is simpler with respect to the specimens (the observation direction can be determined freely etc), or the developing a handy type can make it possible to be used for performing direct observing of the measurement object in situ or in vivo without cutting and carrying the specimens off (in vitro). Almost the ultrasound microscopes have fixed focusing determined by the used lens and then, particularly such elements or the element array can be used favorably. Thus, the mechanical scanning can be performed in the wave propagation direction as well as the lateral and elevational directions. With respect to the RF waves, antennas are used. And for observing the potential of magnetic field of living tissues, electrolyte gels and electrodes, or SQUID meters can be used. According to the size of measurement object, miniaturized devices can be used (microscopes etc). The weak signals can have no nonlinearity and in the cases, quasi-nonlinearities can be generated, or nonlinearities can be generated virtually. When nonlinear signals are so weak to be observed, the nonlinearities can also be increased.

The nonlinear devices and the transmitter 121 or the transducer 110 can also be installed into one body. Also, the nonlinear devices can be build up respectively and used. Thus, the nonlinear devices can increase the frequency and the bandwidth, and can also implement nonlinear processings (calculations) onto the waves themselves by using the nonlinear devices at arbitrary positions as well as onto the reception signals.

Also, when observing waves passively including the cases where the wave sources cannot be controlled, the present invention can be used. The present invention can also be used after obtaining a signal source position or an arrival direction, a signal intensity, a size of wave source or the source distribution using various methods or devices, or the present invention can also be used for obtaining a signal source position or an arrival direction, a signal intensity, a size of wave source or the source distribution. In the cases, a signal source position or an arrival direction, a signal intensity, a size of wave source or the source distribution can be obtained on separated waves or signals; or after obtaining a signal source position or an arrival direction etc, the waves or signals can also be separated; or both can be performed simultaneously. Obtaining the wave source or the arrival direction increases the accuracy of beamforming. Onto the signals, signal processings such as the analogue or digital processings etc can be implemented; and onto the waves, temporal or spatial filters, the frequency filters or spectrometer etc can be used.

On using a transducer for receiving waves that propagated in media including the measurement object, the transducer used for the wave transmission can also be used for the reception (The reflection signals are observed). Alternatively, the reception transducer can also be different from a transmission transducer. In the cases, the transmission transducer and the reception transducer can have neighboring positions (for instance, a case where reflected waves are observed) or different (far) positions (for instance, transmission or refraction waves etc are observed).

The transducer 110 can have a single aperture; or the plural transducers 110 can be used in an array fashion (1D, 2D or 3D array) with densely and adjacently positioned, in a sparse array fashion or in a far positioned fashion simultaneously. The geometries of the apertures are various (a circular, a rectangular, a flat, a concave and a convex) and accordingly, the directivities of the apertures are also various. Every element can also have plural apertures facing different directions in a body and then at every position, the plural directivities can be obtained. Not only scalar measurements such as potentials or pressures, or temperatures etc but also vector measurements such as magnetic waves or electric waves can also be performed. Polarization can also be performed. Off course, element materials or structures are various with respect to one wave. Also, the configurations using them are also various and for instance, there exists one having plural apertures facing to different directions etc.

FIG. 32 shows illustrations of configurations of plural transducers. FIG. 32(a1) shows plural transducers 110 arrayed densely in a 1D array state; FIG. 32(b1) shows plural transducers 110 arrayed sparsely in a 1D array state; FIG. 32(a2) shows plural transducers 110 arrayed densely in a 2D array state; FIG. 32(b2) shows plural transducers 110 arrayed sparsely in a 2D array state; FIG. 32(a3) shows plural transducers 110 arrayed densely in a 3D array state; FIG. 32(b3) shows plural transducers 110 arrayed sparsely in a 3D array state.

By using lens etc at the part of the transducer aperture, a beam can be generated or controlled in an analogue fashion. Using the drive signals mentioned above can also control beams. Also, the imaging instrument related to the present embodiment can be equipped with a mechanical scanning device having 6 freedoms at a maximum (rigid motions in three directions and rotations in three directions) and then, the mechanical scanning device mechanically can also move at least one transducer 110 or at least one transducer array at least in one direction to perform the scanning, controlling the focus positions or steerings with respect to the measurement object 1.

Alternatively, when using plural transducers 110, the same number of channels of transmitters 121 as that of the transducers 110 are equipped with to generate the same number of drive signals as that of the transducer 110 to be driven. Otherwise, using delay elements, plural drive signals can also be generated from a limited number of generated signals to perform desired beamformings (with a desired focus position or a desired steering direction).

Also, general analogue or digital beamformer can also be used. By performing the above-mentioned beamformings (including only reception beamformings) in a parallel fashion, the real-time processings of the scanning the measurement object can also be improved.

Also, by driving the plural transducers 110 at the same time, the plural beamformings can also be performed simultaneously. Otherwise, there are cases where the transmitters 121 are switched and used and within the time allowed to receive the signals of the same phase of the measurement object, using different transducers 110 at different times can also be used for performing plural beamformings. Using the same transducer to be used for mechanical scanning can also make it possible to perform the plural beamformings.

On the respective beamformings including the cases where the mechanical scan is performed, the classical SA can also be performed, in which a general delay-and-summation (DAS) processing or the delay-and-multiplication (DAM) processing on the basis of the present invention can be performed (both processing can be realized in monostatic and multistatic types). For the transmissions, with no fucusings, plane waves can also be generated. In the cases, a large region can also be observed at once in a short time. At the times, the plane waves can also be steered. Waves can also be received as plane waves and also dynamic focused (When performing transmission focusing, the receptions should also perform the steerings). The respective plane waves are narrow band in the directions orthogonal to the propagation direction and then, increasing the bandwidths is effective.

FIG. 33 shows figures that explain various wave formations obtained using 1D transducer array. On FIG. 33, (a) shows a focusing of wave and at respective transmission and reception, a wave beam with a focus position determined by delay times are formed; (b) shows a steering of wave and the respective transmission and reception, a steered wave beam with a steering direction determined by delay times are formed; (c) shows a transmission or reception of plane wave and the plane wave steered to the direction determined by delay times are formed. The plane wave is narrow band in the direction orthogonal to the propagation direction and then, increasing the bandwidths is effective.

Prior to performing the reception by the transducer 110, by letting the plural waves pass through at least one of the analogue delay device and the analogue storage device such that the plural waves can be superposed at respective positions in the measurement object 1. Also, after performing the reception by the transducer 110, by letting the plural waves pass through at least one of the analogue delay device and the analogue storage device, or after performing digital sampling of the received signals, by implementing digital delays onto the sampled digital signals via digital processings or by passing the digital signals into the digital storage device such that the plural waves can be superposed at respective positions in the measurement object 1. The so-called phase aberration correction can be performed in the above-mentioned fashion or in conjunction with the phasing in the above-mentioned beamformings as well. There are various devices, for instance for lights, an optical fibre can also become a delay line; and an optical trapping (or confinement) device can also become a delay device or a storage device.

Alternatively, with respect to the measurement object, as the results of the waves propagating in the measurement object, the signals effected by nonlinear effects can also be observed or inversely, nonlinear components cannot be obtained. In general, when the intensity of a wave is strong, the nonlinear phenomena can be observed well whereas when the intensity is weak, the nonlinear phenomena cannot be observed well. For both cases, the present invention can be performed. The reception signals can also be processed by the present invention after separating the signals via proper signal processings etc.

For the signal separations, analogue devices of various type waves (temporal or spatial filter, their frequency filters, or spectroscopies) can also be used or on the basis of the signal processings, the analogue or digital processings can also be performed (the above-mentioned decoding processing with respect to the coding processing, calculations of the 1st moments of spectra via spectral analysis, calculations of the instantaneous frequencies using calculated analytic signals, MIMO, SIMO, MUSIC or independent signal separation processing etc). In the passive cases, the present invention can also be used after obtaining a signal source position or an arrival direction, a signal intensity, a size of wave source or the source distribution using various methods or devices, or after using the present invention, a signal source position or an arrival direction can also be obtained. Otherwise, simultaneously with the beamformings, a signal source position or an arrival direction, a signal intensity, a size of wave source or the source distribution can also be obtained. As mentioned later, after expressing the target waves with harmonic waves etc via nonlinear processings, the signal separations can also be accurately performed. Concretely, By performing the exponentiation calculations, after increasing frequencies and bandwidths (when the orders are larger than 1) and decreasing frequencies and bandwidths (when the orders are smaller than 1), the processing can be performed in a frequency domain with a high accuracy. The restorations of the separated signals can be simply performed using the exponentiation calculations with the reciprocals of the used orders.

FIG. 34 shows illustrations of a beam direction, an angle of a direction of arriving wave (arrival direction) and the first moments of spectra in spatial and frequency domains in a 2D measurement case. In FIG. 34, (a) shows for a position of interest (x,y) in a spatial domain, the direction angles of beams 1 and 2 are expressed by $\theta_1$ and $\theta_2$. (b) shows in a frequency domain, the 1st moments of spectra of beams 1 and 2, and the instantaneous frequencies (fx,fy).

Basically, beamformings are performed on waves in an analogue fashion or when using plural transducers 110, beamformings (focusing or steering) are performed. As mentioned above, after performing the signal separations, the beamformings can be performed and also after performing the beamformings, the signal separations can also be performed.

Also, when performing the SA, from the same reception signal set, plural focused signals with plural different focus positions or plural steered signals with plural different steering angles can be generated (Delay-and-summation or the delay-and-multiplications on the basis of the present invention). The present invention can also be implemented on the generated signals. The transmitter 121 and the receiver 122 can be installed into a body or not (a separated type).

As the nonlinear elements 124, there are various elements. For the electric analogue signals after receiving by the transducer 110, a diode or a resistor can be used. Any nonlinear elements used in circuits, leading nonlinear phenomena to signals including applications of superconducting phenomena etc, can also be used. Also, nonlinear elements for distributed parameter system can also be used. According to the frequencies of waves (signals), proper elements are used. Using various type amplifiers, the gains of waves or signals can also be controlled properly.

Prior to performing the receiving using the transducer 110, nonlinear processings (calculations) can also be performed by using the nonlinear devices for directly generating nonlinear phenomena on the waves. For instance, on lights, used can be (i) nonlinear optical elements, (ii) optical mixing devices, (iii) optical parametric effects, (iv) multiphoton transitions such as general Raman scattering (spontaneous emission Raman scattering) etc, (v) nonlinear refraction index change and (vi) electric field dependence refractive index change, etc. The nonlinear devices and the transducer 110 can also be installed into a body and also the nonlinear devices can be build up respectively and used. Also, nonlinear phenomena occurring at the conversion from a wave to electric signal by the transducer 110 (i.e., at the reception of the wave) can also be used.

In all the above cases, the analogue nonlinear processing can be performed onto the waves themselves or signals after receptions, whereas after AD conversions of signals, nonlinear processings can also be performed on signals using the digital processings or calculators, or devices like these (FPGA or DSP etc).

Regarding the imaging instrument related to an embodiment of the present invention, when calling the instrument as an analogue type, the processings are performed by analogue processings as mentioned above. And then, for instance, analogue signals effected by the nonlinear phenomena can be displayed using display devices such as a Braun tube display or an oscilloscope (an analogue or digital one) etc. If required, the signals are recorded by storage media such as a photograph (an analogue or digital one) or a holography etc. Otherwise, the signals are digitized via AD conversions and if required, the signals can be recorded by digital data storage media such as a memory, a hard disk or a CD-RW etc and can also be displayed using display devices.

Alternatively, when calling the instrument as a digital type, the analogue signals are AD converted after proper analogue processings (gain control or filtering) and there also exists the cases where the digitized signals are stored into storage media such as a memory or a hard disk etc, and the digital nonlinear calculation processings are performed on the digital signals. And if required, the data are stored into data storage devices (the above-mentioned photograph or digital storage media etc) and displayed on display devices.

On the above-mentioned compositions, in the cases where the effects of nonlinear phenomena occurred in the measurement object are included in the reception signals, the above-mentioned analogue or digital instrument can also be used for increasing the nonlinear effects, whereas in the cases where the effects are not included in the reception signals, the instrument can newly generate, imitate or virtually realize nonlinear effects. Also, separations of the nonlinear effects (harmonic wave components) occurred in the measurement object, the nonlinear components generated by signal sources (harmonic wave components) and effects of nonlinear processings can also be performed. Exceptionally, including the cases where the nonlinear processings are not performed, the above-mentioned devices or signal processings can be used to separate the preceding two nonlinear effects (nonlinear components).

On the above explanations about the imaging instrument, the cases where transducers for waves to be observed are used are mentioned. However, for instance, the propagations of vibration waves can also be observed optically on the basis of the laser Doppler or the optical image processings and also the propagation of a shear wave that is a dominant low frequency vibration wave in human tissues can be observed using a same vibration, i.e., the ultrasound Doppler effect The propagations of the audible sound or the ultrasound etc can also be captured optically. The optical processing means the processings of generally called electromagnetic waves and then, radioactive rays such as an X-ray are also included. Regarding thermal waves, an infrared camera on the basis of a radiation, a microwave, a terahertz wave, an ultrasound using changes in a sound speed or a volume, a nuclear magnetic resonance using a chemical shift or an optical fibre etc can be used to achieve the observations. The observations are enabled by the coherent signal processings or by the incoherent processings such as image processings etc. The case examples about the observations of waves of interest using other waves are not limited to these, and the measurement results are analogue or digital signals in any case. Thus, the present invention can also be implemented onto the observed waves (signals). In addition to the Doppler effects, it can be grasped that the physical properties of media are modulated by the target waves and then, the waves to be used for sensing the target waves are modulated. On these, the detection processings for waves to be effected by the Doppler effects or the modulations are effective. Particularly, on the uses of electromagnetic waves, the polarization can be used to simply observe waves propagating in various directions and also to simply capture the structures with various directions. Alternatively, as mentioned in the document of the present invention, acoustic waves can also allow various measurements on the basis of the divergence. The radiation measurement is also important. Using the microwaves, in addition to the temperature distribution measurement, various remote sensing can be performed, for instance, measuring scatterings or attenuations allows the measurements of distributions of raindrops or moistures, atmospheric pressures etc. In this situation, performing the beamformings mentioned in the document of the present invention and other various processings are effective for generating high spatial resolutions and particularly for observing the desired positions with high speeds. The effects such as a directness and a high speediness in observing arbitrary surfaces or regions and spaces regardless the image processings after generating images.

On the above explanations about the imaging instrument, mentioned are nonlinear processing devices of electromagnetic waves, vibrations including acoustic waves, thermal waves or the corresponding signals. However, it is also possible to increase, imitate and virtually realize nonlinear effects between different kind (type) physical energies (i.e., in addition to cases where nonlinear effects are generated physically, chemically, or biologically, cases where nonlinear effects cannot be generated are included) and in the cases, the present invention can also be performed by that devices regarding the plural kind (type) waves to be processed are simultaneously used to receive the waves or at the same phase of the measurement object, the waves can be received at different times. That is, it is possible for the present invention to process the cases where plural kind (type) waves are generated simultaneously as well as the cases single kind (type) waves are generated solo.

On the respective electromagnetic waves, vibrations including acoustic waves and thermal waves, the waves with different frequencies exhibit different dominant behaviors being dependent on the respective measurement objects (media) and then, the names are different. In this situation, the waves can also be considered to be different types. For instance, on the electromagnetic waves, there are a microwave, a terahertz wave, a radioactive ray such as an X-ray etc and on the vibration waves, for instance, in human soft tissues, a shear wave cannot propagate as a wave in a Mega Hertz bandwidth and an ultrasound is dominant, whereas a property of an incompressibility is intense and a shear wave is dominant in a low frequency range such as 100 Hz etc.

The present invention increases, imitates and virtually realizes nonlinear effects between such waves that exhibit different behaviors. In the cases, the present invention can also be performed by that devices regarding the plural kind (type) waves to be processed are simultaneously used to receive the waves or at the same phase of the measurement object, the waves can be received at different times. Off course, since the phenomena such as attenuations, scatterings or reflections etc have variances, there is a limitation that the waves must be properly used with considerations about the SNRs of reception signals. However, since high frequency components, which cannot be physically generated or captured, can be generated, the application range of the present invention is prominently broad.

Investigating the nonlinear effects occurring in the measurement object can also be performed by switching the uses of cases where the observation of the nonlinear effects occurring in the measurement object is positively performed and the implementing of the present invention is performed; or by using both cases simultaneously and by using the nonlinear processing or calculations positively.

Next, using the above-mentioned compositions of the imaging instrument, one embodiment that the present invention is applied to ultrasound echo signals is explained. The generation of harmonic waves during the ultrasound propagations can be expressed by the multiplication or the exponentiation. Particularly, the chord and different tone waves are expressed by the multiplications between the waves with different propagation directions or frequencies (nonpatent document 26), whereas in general, the harmonic tone waves are expressed by the exponentiations of the same frequency waves (nonpatent document 24). As physical phenomena, when the wave intensity is large, the phenomena occur well. Also, there are effects that for high intensity wave components, the wave components' distortions become larger with increasing the propagation distance and however, being more suffered from the attenuations than the fundamental waves during the propagations. Alternatively, when the waves' intensities are not so large, as an interference of the waves, only the superpositions (summations and subtractions) can be observed well. The application of the interference is the lateral modulation previously developed by the inventor of the present invention (nonpatent documents 13 and 29 etc).

Figure 35:
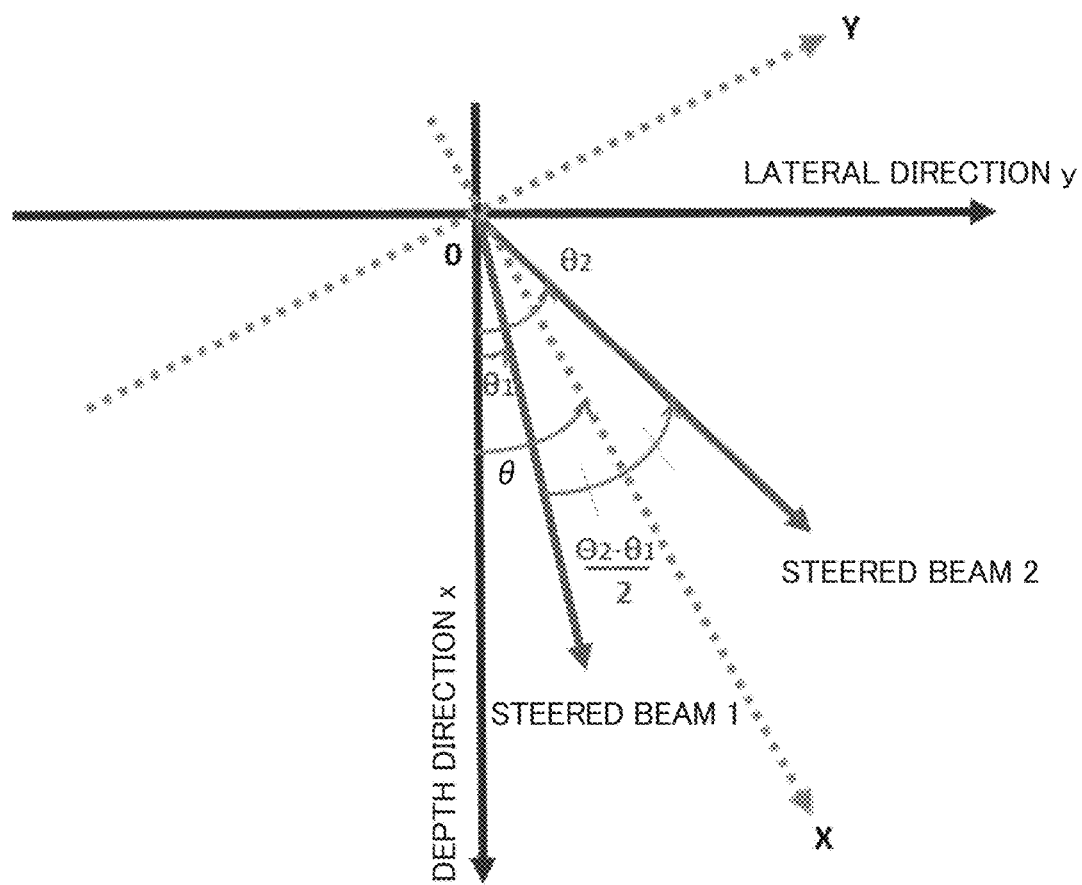
FIG. 35 shows an illustration for the lateral modulation, of two steered beams in a 2D spatial domain.

FIG. 35 shows an illustration for the lateral modulation, of two steered beams in a 2D spatial domain. In FIG. 35, the horizontal and vertical axes respectively show the lateral and axial positions y and x. Here, as representative examples, in two cases where the beamforming is performed in an arbitrary direction (the direction of angle θ in the figure) and the lateral modulation is performed with respect to an arbitrary direction as an axis (X-axis), respectively, the effects of nonlinear processings performed after the reception beamformings are confirmed. The calculations can be extended to a 3D case simply and also it is possible to confirm that the same effects can be obtained in a 3D space. Below, λ is a wavelength corresponding to the 1st moment of an ultrasound. The distances in the depth and lateral directions x and y respectively express the distances between the origin, where the ultrasound is transmitted, and an arbitrary position, where the ultrasound is reflected, i.e., if the time t is required for the round trip, the distance of the ultrasound propagation generated during the time t/2.

<0> Lateral modulation: Superposition of two beams or waves (plane waves etc) with steering angles $\theta_1$ and $\theta_2$ (simultaneous transmissions and receptions or superposition of the respective transmissions and receptions).

The superposition of two RF echo signals (addition, i.e., summation) is expressed as the next equation.

$$A(x,y)\cos[2\pi(2/\lambda)(x\cos\theta_1+y\sin\theta_1)]+A'(x,y)\cos[2\pi(2/\lambda)(x\cos\theta_2+y\sin\theta_2)] \quad (0')$$

Here, assuming $A(x,y)=A'(x,y)$ (i.e., the reflections and scatterings of two waves are equal), the superposition of the two RF echoes can be expressed by the next equation on the coordinate system (X,Y), of which X-axis expresses the central direction between the propagation directions of the two waves and Y-axis expresses the direction orthogonal to X-axis.

$$A(x,y)\cos\{2\pi(2/\lambda)\cos[(½)(\theta_2-\theta_1)]X\}\times\cos\{2\pi(2/\lambda)\sin[(½)(\theta_2-\theta_1)]Y\} \quad (0)$$

Thus, on the coordinate (X,Y), the lateral modulation is realized. The two waves can also have different frequencies. For instance, in below <2> and <3>, nonlinear processing is implemented onto the lateral modulation. In a 3D space, there are two directions to be laterally modulated and then, at least three crossed beams are required to be generated (nonpatent documents 13 and 29).

<1> Exponentiation Calculation of One Beam or One Wave Steered in One Direction (Steering Angle, θ)

The RF echo signal is expressed as the next equation.

$$A(x,y)\cos[2\pi(2/\lambda)(x\cos\theta+y\sin\theta)]$$

In this case, for instance, the 2nd order exponentiation (2nd power) of the RF echo can be expressed as the next equation (51).

$$(½)A^2(x,y)\times\{1+\cos[2\pi(2\cdot2/\lambda)(x\cos\theta+y\sin\theta)]\} \quad (51)$$

Thus, the 2nd harmonic wave component can be simultaneously generated with the direct current component and therefore, a base-banded signal can also be obtained simultaneously (The envelope signal can also be directly obtained). The calculated squared echo signal has spectra with a wider bandwidth than the basic signal owing to the multiplication effects between the signals with different frequencies within the basic signal bandwidth; yielding high spatial resolutions both in the wave propagation direction and the direction orthogonal to the propagation direction by generating a shorter pulse length and a narrower beam width.

As a simpler example, for instance, when an RF echo signal has two frequency $f_1$ and $f_2$ components at a depth position x, the squared signal obtained by the square calculation can be expressed as the next equation.

$$e_I(x;f_1,f_2)^2=e_{II}(x;0,2f_1,2f_2,f_1+f_2,f_1-f_2)$$

Thus, the squared signal had a direct current (frequency zero) and frequency $2f_1$, $2f_2$, $f_1+f_2$ and $f_1-f_2$ components.

That is, if the wave has different frequency signal components, the signals generated by the exponentiation calculations (processings) have wider bandwidths in the directions, in which the wave has the different frequency components, than the reception wave to be received when the nonlinear processings are not implemented; and a generated harmonic wave obtains at least one of effects such as increasing in frequencies, increasing in spatial resolutions, decreasing in sidelobes, increasing in contrasts with respect to the reception wave to be received when the nonlinear processings are not implemented; and a signal generated in a bandwidth including a direct current (a base-banded signal) is a signal obtained by implementing approximate quadrature detection onto the generated harmonic wave; and at least on the basis of one of signals generated by the nonlinear processing, the corresponding wave can be imaged.

Performing the higher order exponentiation calculations (processings), for instance, n-order (n>2), yields the n-fold high frequency signal components and the higher spatial resolutions. Also, strictly, the generated base-banded signal is different from the results of quadrature detection of the 2nd harmonic wave (the general base-band signal) since the generated base-banded signal has a generated pure direct current. Then, if the detection processing is not implemented on the 2nd harmonic signal, a higher spatial resolution image can also be obtained than the original echo image. The direct current generated by the nonlinear processing can be calculated by the intensities of high frequency wave, low frequency wave or harmonic wave etc generated simultaneously and basically, the direct current components to be filled in the base-banded signal are removed. Occasionally, when omitting the calculations, all the direct current components can also be removed. By performing the processings, without performing the brightness control to be dependent on the depth, the imaging can be performed with respect to the deeper position than the imaging including the direct current components.

The harmonic wave signals or low frequency signals are expressed in various fashions (four arithmetic operations about sine wave or cosine wave etc) on the basis of the double angle or the arcminute theorem, if required, the calculations can be performed via the digital Hilbert's transform (nonpatent document 13). The actual measured harmonic waves can also be processed. These are calculated nonlinear signals at respective positions with respect to arbitrary intensity waves and differs from the nonlinear components physically accumulated and effected by the attenuations during the propagations, which realizes new harmonic wave or low frequency imagings.

<2> Exponentiation Calculation of Lateral Modulation Echo Signal

For instance, the square of eq. (0) is expressed by the next eq. (52).

$$A(x,y)^2 \times \cos^2\{2\pi(2/\lambda)\cos[(1/2)(\theta_2-\theta_1)]X\} \times \cos^2\{2\pi(2/\lambda)\sin[(1/2)(\theta_2-\theta_1)]Y\} = A(x,y)^2 \times [1+\cos\{2\pi(2\cdot2/\lambda)\cos[(1/2)(\theta_2-\theta_1)]X\} + \cos\{2\pi(2\cdot2/\lambda)\sin[(1/2)(\theta_2-\theta_1)]Y\} + \cos\{2\pi(2\cdot2/\lambda)\cos[(1/2)(\theta_2-\theta_1)]X\} \times \cos\{2\pi(2\cdot2/\lambda)\sin[(1/2)(\theta_2-\theta_1)]Y\}] \quad (52)$$

Thus, obtained can be a direct current (corresponding to the above-mentioned base-banded signal), the two signals of the 2nd harmonic waves detected in different one direction, and the signal of the 2nd harmonic waves' lateral modulation. Similarly to <1>, increasing in a spatial resolution is also performed. The base-banded signal or other high order harmonic wave signals can also be calculated similarly to <1>.

As a simpler example, for instance, when crossed echo signals at a position (x,y) are respectively expressed as $e_1((x,y);(f_1,f_1))$ and $e_2((x,y);(f_0,f_2))$ and are symmetric in the y direction, the squared signal of the superposition can be expressed as the next equation.

$$[e_1((x, y); (f_0, f_1)) + e_2((x, y); (f_0, f_2))]^2 =$$

$$e_1((x, y); (f_0, f_1))^2 + 2e_1((x, y); (f_0, f_1))e_2((x, y); (f_0, f_2)) +$$

-continued $$e_2((x, y); (f_0, f_2))^2 = e'_1((x, y); (0, 0), (2f_0, 2f_1)) +$$

$$e'_{12}((x, y); (2f_0, 0), (0, 2f_1), (0, 2f_2)) + e'_2((x, y); (0, 0), (2f_0, 2f_2))$$

Thus, it can be grasped that the squared signal of the superposition has frequency (0,0), ($2f_0,2f_1$), ($2f_0,2f_2$), ($2f_0$, 0), ($0,2f_1$) and ($0,2f_2$) components.

That is, the signals generated by the exponentiation calculation are the harmonic wave signals of the respective signals to be linearly superposed (corresponding to the crossed waves) and base-banded signals (having bandwidths at least including direct currents in one direction), and if the wave has different frequency signal components, the signals generated by the exponentiation calculations (processings) have wider bandwidths in the directions, in which the wave has the different frequency components, than the reception wave to be received when the nonlinear processings are not implemented; and the generated harmonic waves obtain at least one of effects such as increasing in frequencies, increasing in spatial resolutions, decreasing in sidelobes, increasing in contrasts with respect to the corresponding waves to be received when the nonlinear processings are not implemented; the and base-banded signals are signals obtained by implementing the quadrature detection or approximate quadrature detection onto the generated harmonic waves in the respective directions or plural directions; and at least on the basis of one of signals generated by the nonlinear processing, the corresponding wave can be imaged. When the crossed waves or beams have different frequencies or are not symmetric with respect to the axis, the exponentiation processings yield the chord and different tone waves in a multidimensional space and similarly, the generated signals can be used for the imaging or measurements. When other parameters are different on plural waves used, they can also act on the nonlinear processing results.

As mentioned above, in a 3D space, the lateral modulation requires the generations of three crossed beams at least and in the cases, the obtained base-banded signals are a signal of the approximately quadrature-detected harmonic waves of the respective beams (a signal having a direct current) and signals of the harmonic waves quadrature-detected in arbitrary one or two directions. That is, since with respect to an axis set with respect to the two beams such that the two beams become symmetric, the polarities of the frequencies in the symmetric direction is inverse, the addition is zero. All the waves or beams can also be generated symmetrically with respect to the coordinate axes and however, not limited to the case. The frequencies or other parameters can also be different on the plural beams or waves.

<3> Multiplication Calculation of Lateral Modulation Echo Signals

For instance, since the two waves expressed in eq. (0') can be used separately and on the consideration about the multiplication, to hold a simplified equation, let the propagation directions equal two directions symmetric with respect to the x axis, i.e., $\theta_1 = -\theta_2$. In the case, the multiplication (production) of the two RF echo signals can be expressed by the next eq. (53).

$$A(x,y)\cos[2\pi(2/\lambda)(x\cos\theta_1+y\sin\theta_1)] \times A'(x,y)\cos[2\pi(2/\lambda)(x\cos\theta_1-y\sin\theta_1)] = A(x,y)A'(x,y) \times \{\cos[2\pi(2\cdot2/\lambda)\cos\theta_1 x] + \cos[2\pi(2\cdot2/\lambda)\sin\theta_1 y]\} \quad (53)$$

Thus, the two signals of the 2nd harmonic waves detected in different one direction can be obtained. These signals are the same signal components as those obtained in eq. (52).

As a simpler example, when crossed echo signals at a position (x,y) are respectively expressed as $e_1((x,y);(f_0,f_1))$ and $e_2((x,y);(f_0, f_2))$ and are symmetric in the y direction, the multiplication of the signals can be expressed as the next equation.

$$e_1((x,y);(f_0,f_1)) \times e_2((x,y);(f_0,f_2)) = e_{12}'((x,y);(2f_0,0),(0,2f_1),(0,2f_2))$$

Thus, it can be grasped that the multiplication of the signals have frequency $(2f_0,0)$, $(0,2f_1)$ and $(0, 2f_2)$ components.

That is, the signals generated by the multiplication calculation are base-banded signals (having bandwidths at least including direct currents in one direction) correspondingly obtained from the respective signals to be linearly superposed (corresponding to the crossed waves), and if the wave has different frequency signal components, the signals generated by the multiplication calculations (processings) have wider bandwidths in the directions, in which the wave has the different frequency components, than the reception wave to be received when the nonlinear processings are not implemented; and the base-banded signals are signals obtained by implementing the quadrature detection onto the harmonic waves in the respective directions or plural directions, of which harmonic waves will obtain at least one of effects such as increasing in frequencies, increasing in spatial resolutions, decreasing in sidelobes, increasing in contrasts with respect to the respective waves to be received when the nonlinear processings are not implemented; and at least on the basis of one of signals generated by the nonlinear processing, the corresponding wave can be imaged. When the crossed waves or beams have different frequencies or are not symmetric with respect to the axis, the exponentiation processings yield the chord and different tone waves in a multidimensional space and similarly, the generated signals can be used for the imaging or measurements. When other parameters are different on plural waves used, they can also act on the nonlinear processing results.

As mentioned above, in a 3D space, the lateral modulation requires the generations of three crossed beams at least and in the cases, the obtained base-banded signals are signals of the harmonic waves quadrature-detected in arbitrary one or two directions. That is, since with respect to an axis set with respect to the two beams such that the two beams become symmetric, the polarities of the frequencies in the symmetric direction is inverse, the addition is zero. All the waves or beams can also be generated symmetrically with respect to the coordinate axes and however, not limited to the case. The frequencies or other parameters can also be different on the plural beams or waves.

Similarly to the above-mentioned crossed beams, in addition to the propagation directions or the steering angles of the respective beams or waves, other parameters can be different, for instance, the frequency or the carrier frequency, the pulse geometry, the beam geometry, the frequencies, the carrier frequencies or the bandwidths in the respective directions. Also, being different from the cases where for performing the lateral modulations, two and four (can be three) crossed waves or beams are respectively generated in 2D and 3D cases, more waves or beams can be used in the respective dimensions. Particularly, performing the transmissions of plane waves, cylindrical waves or spherical waves allows high speed transmissions and receptions and then, such using of plural waves can achieve beamformings with higher speeds than the general imaging. Also, since when using focusing beams, the superposed reception signals can also be processed by the high speed beamformings using the FFT, particularly included when performing the simultaneous transmissions of plural beams, the high speed processing can be performed similarly (as mentioned above, on the wavenumber matching, approximate interpolations can also be performed). For stabilizing the nonlinear processings, it is also effective to superpose (additional averaging) the plural transmissions and receptions performed under using the same parameters. The above-mentioned same processings can also be implemented on the reception signals obtained when performing the so-called pulse inversion transmissions, specifically, the same processings can be implemented onto the harmonic wave obtained by superposing the reception signals received by the pulse transmissions with different polarities; or the same processings can be implemented onto the respective reception signals prior to performing the superposition. These superpositions (i.e., additions) yield harmonic waves with a frequency being even number times of the frequency of the fundamental wave and instead of the additions, performing the subtractions yield harmonic waves with a frequency being odd number times of the frequency of the fundamental wave. It is also important to use these harmonic waves for imagings (Even the simple subtraction on the reception signals with the pulse inversion transmissions yields the 3rd harmonic wave mainly). When superposition of harmonic wave signals are obtained using the present invention with respect to the reception signals band-limited by the transducer's bandwidth or by implementing an analogue or digital filter onto, the harmonic waves can be separated by using filterings (analogue or digital), or by performing signal processings (analogue or digital) using various superpositions or the basic signal. Also, not using a pulse inversion method, signals with phase differences except for 180 degree can be transmitted and in such cases, these processings can be performed. Summarizing, on beams or waves with at least one different parameter, when the beams or waves are being superposed, being separated or being not superposed etc, the same nonlinear effects can also obtained and can also be used effectively. It can be grasped that waves or beams to be generated by the nonlinear effects as well as the linear effects can be designed (parameters of beams or waves such as a propagation direction etc) via theories and calculations and can also be controlled.

The harmonic wave signals, the chord or different tone waves, or harmonic tone waves etc generated by these nonlinear processings (calculations) improve the qualities of echo imagings owing to their above-mentioned properties. There is no effects due to the attenuations, which causes effects on the general harmonic imagings. The present invention is also effective for generating nonlinear components at the respective positions virtually or interpreting the nonlinear signals physically generated. Also, the present invention is effective for non-observable cases due to the weak intensities of the waves. Furthermore, on a displacement measurement, the increasing frequency is received enthusiastically because the phase rotation speed increases and the displacement measurement accuracy will become high. However, in the below shown phantom experiment, although the spatial resolution improved, only the high spatial resolution measurement tends to increase the measurement noises.

In this situation, the regularization (for instance, non-patent document 18) or the above-mentioned weighted least squares solution method or weighted averaging processing via statistical evaluations becomes effective. For instance, using the general one-directional displacement measurement methods onto the two signals of the 2nd harmonic waves detected in different one direction obtained in processings <2> and <3> allows the measurements of the displacement components in the respective directions. Specifically, for measuring a displacement or a displacement vector generated during the different temporal phases of the measurement object, on the signals with a carrier frequencies in arbitrary one direction, at each position of interest, the instantaneous phase change generated during the temporal phases is divided by the instantaneous frequency, the 1st moment frequency or a nominal frequency etc to measure the displacement in the direction; and furthermore on the basis of the measurements of different directions, a displacement vector can be synthesized. At past, it requires more calculations than the autocorrelation method (nonpatent document 13) and however, to make a displacement vector measurement using the general one-directional displacement measurement methods possible, a digital demodulation method for a lateral modulation echo signal is disclosed (calculating the product and conjugate product on analytic signals: nonpatent document 29 etc). According to the present invention, the lateral modulation echo signal can be demodulated using remarkedly fewer memories and calculations and moreover, the obtained signals are harmonic wave signals. For decreasing noises, it is effective when the same waves can be acquired plural times under the same conditions, additional averaging can also be performed on the raw reception signals or the nonlinear-processing-implemented signals after the reception of the raw signals and otherwise, integration processing etc can also be performed on them. Also, instead of the exponentiation or the multiplication, it is also possible to calculate a squared norm or an inner product and in the cases, the spatial resolution is determined by the signal length to be used for the calculations. These methods can also be effective for imagings etc except for of the displacement measurements.

The inventor of the present invention developed the digital demodulation method disclosed in the nonpatent document 29, concretely in which the phases determined by the displacement components in the respective directions are derived to calculate the respective displacement components and as below, for instance, when performing the measurement of a 2D displacement vector (dx,dy), since the instantaneous phase difference between the two different temporal phase of an arbitrary position in a 2D ROI is expressed as the phases of analytic autocorrelation signals expj(fxdx+fydy) and expj(fxdx−fydy), that can also be expressed as independent two single quadrant spectra generated by the respective two crossed beams or waves, by calculating the production or the conjugate production of them, expj(2fxdx) and expj(2fydy) are obtained and then, by dividing the instantaneous phases differences 2fxdx and 2fydy in the respective directions using the instantaneous frequencies fx and fy in the respective directions, the unknown displacement vector (dx, dy) can be obtained. When performing the 3D displacement vector (dx,dy,dz) measurement, four or at least three analytic autocorrelation signals expj(fxdx+fydy+fzdz), expj(fxdx+fydy−fzdz), expj(fxdx−fydy+fzdz), expj(fxdx-fydy-fzdz), which are calculated using four or at least three crossed beams or waves, are used and similarly the displacement vector can also be calculated. With respect to arbitrary waves crossed in arbitrary directions, since these digital demodulations or nonlinear processings <2> or <3> yields waves with carrier frequencies in the respective directions of the symmetric axis and the axis orthogonal to the symmetric axis (waves with detected in one or two directions), by making the waves to avoid passing to an obstacle or a blocker etc related to the waves and by crossing the waves behind the obstacle or a blocker etc in such a fashion, waves with carrier frequencies in arbitrary directions can be generated behind the obstacle or blocker etc. Such waves cannot be directly generated through the obstacle or blocker etc. Thus, such configurations allow the imaging or the displacement measurement behind an obstacle or a blocker etc, which is difficult in general. For instance, cases where such waves with carrier frequencies in the depth and lateral directions are generated behind an obstacle or a blocker etc are equivalent to cases where the obstacle or blocker is looked through from the frontal direction and also the object motion in an arbitrary direction behind the obstacle and blocker can be measured. The imaging and the displacement measurement can also be performed on from an arbitrary direction, and not limited to from the frontal direction of the obstacle or blocker etc. On the digital demodulation method, or the nonlinear processings <2> or <3>, since the frequencies of the two-fold instantaneous frequencies of the respective directions are generated, the beamformings are to be performed in advance with a sufficiently wide bandwidth on the basis of the Nyquist theorem, the number of beams are to be interpolated in a space, or the bandwidth is to be increased in a frequency domain by padding zero spectra (interpolation of data). These processings also fall in a variety of signal separations.

As far, several examples are presented, where the present invention is applied to the ultrasonic imagings or the ultrasonic measurements. When the bandwidth of the signal components generated (calculated) using the present invention overlaps that of other signal, it is impossible to separate them in a frequency domain. In the cases, the pulse inversion method or the separation using polynomial terms can be used. Alternatively, the inventor of the present invention processes the superposed spectra and for instance, the spectra can also be divided (nonpatent document 29). On the present invention, included cases where spectra overlaps, the way how to separate the waves with a high accuracy is to obtain an effect that the overlapped spectra can be distinguished well in a frequency domain by performing the exponentiation processings (calculations) as the nonlinear processings onto the superposed waves, and the waves shown as the harmonic waves are to be separated in a frequency domain. The separation can also be performed with a high accuracy in a frequency domain after performing decreasing the frequencies and the bandwidths (the order less than 1) as well as the increasing the frequencies and the bandwidths (the order larger than 1) using the exponentiation processings (calculations). The propagation direction can be calculated using the estimates of the 1st moments of spectra of the harmonic wave generated (local direction, i.e., with a spatial resolution, or macro direction with low or no spatial resolution) or the instantaneous frequencies (having a spatial resolution) estimated from the analytic signals. Otherwise, using the exponentiation order implemented can allow the inverse calculations about the wave parameters such as frequencies or bandwidths etc of the original waves, and the restoration can also be allowed to be performed in a separated state (It is simple to restore the waves after separating the harmonic waves, i.e., by implementing the exponentiation processings (calculations) using the reciprocals of the order used). In such situations, it is also possible to measure the signal source positions or the signal arrival directions, the signal source intensities, the sizes of single sources or the distributions. When generating higher frequency signals than the original signal, in advance to the processings (calculations), it is required to increase the bandwidth such that the processings can be achieved. For that, the spectral zero padding is effective with no approximations (nonpatent document 29), whereas the sampling intervals can also be shorter directly on the basis of the temporal or spatial approximate interpolations.

Recently, it becomes possible to perform simulations on the nonlinear propagations with low costs. Therefore, the nonlinear calculations of the present invention or such simulation technologies can also be implemented onto not beamformed signals (plane wave etc) or SA echo signals (data set) to generate nonlinear signals. Also, on the basis of these, the nonlinear signals measured in practical can also be analyzed using an inverse problem approach (inverse analyses) and can be used for the tissue diagnoses.

For instance, when using ultrasounds for living tissues, for performing the tissue characterization, estimations about the acoustic propagation speed, the bulk modulus, the acoustic impedance, the reflection, the Rayleigh scattering, the back scattering, the multiple scattering or the attenuation can be performed and can be used for diagnoses. Also on other waves, it becomes possible to perform the inverse analyses about the phenomena or physical properties related to (On lights, Mie scattering, scatterings on radioactive rays or Compton scattering etc).

On the treatments using heating or warming, it is required to be clarified the object's reception properties of heat (for instance, properties with respect to the pressure of a high intensity ultrasound, or effects of agents or contrast media etc) and the characteristics of increase in a temperature, which is required to understand generally or at clinical sites. In such situations, the calculations including the nonlinear calculations become effective. Also on the treatment, it is effective that the effects are evaluated and used on the basis of the imagings of nonlinear effects using the present invention. Otherwise, it is also possible to perform echo imagings or tissue displacement measurements using the present invention on the reception signals physically effected by the nonlinearities or the separated base-banded signals and plural harmonic waves.

The present invention relates to imaging instruments that increases the frequencies, the bandwidths and contrasts of signals by implementing nonlinear processings such as the multiplications or the exponentiations onto coherent signals of arbitrary waves such as electromagnetic waves, lights, radioactive rays, mechanical vibrations, acoustic waves except for the ultrasounds, and thermal waves etc in addition to the ultrasounds. Using the present invention, increasing, imitating, newly generating the harmonic waves can be performed. Furthermore, the harmonic waves can be virtually realized.

Also, with fewer calculations than the general detection processings, a signal of a base-band and detected signals, in an arbitrary direction, of the harmonic wave signals can also be simultaneously obtained. As the results, for instance, increasing the frequencies and bandwidths, and contrasts or suppressing the sidelobes can be achieved and also high SNR nonlinear imagings become possible. Also, using the general one-directional displacement measurement methods, the measurement of a displacement vector become possible to be performed simply with fewer calculations. From the viewpoint of the generating the chord or different tone waves, or the harmonic tone waves, high or low frequency signals can be obtained including the cases where the frequencies or carrier frequencies, the steering directions or the propagation directions etc are different and then, these can also be effectively used for imagings or measurements. The waves or beams to be generated by the nonlinear effects as well as the linear effects can be designed (parameters of beams or waves such as a propagation direction etc) via theories and calculations and can also be controlled.

Alternatively, in the area of an image measurement, it is well known that observations of motions are performed by using incoherent signals (the results are displayed using images) generated by implementing various type detections (including simply absolute values being evaluated on signals etc) on coherent signals. Methods equivalent to the cross-correlation method, the optical flow or the SAD (Sum and Difference) method etc can be used. Also, implementing the present invention onto incoherent signals increases the bandwidths (spatial resolution). Also, used can be the above-mentioned high spatial resolution detection signals obtained using the present invention. High density data via increasing the bandwidths are proper to the processings and then, the measurement accuracies of the motions also increase. The above-mentioned method can also be used for the coherent signals and also in the cases, the increasing the bandwidths is effective for increasing the measurement accuracy. That is, the present invention can be used both for arbitrary coherent signals and arbitrary incoherent signals.

Otherwise, on the warming, the heating, the cooling, the freezing, the welding, the restoration, the thermal treatment of cancerous diseases (thermal therapy) or the cryotherapy or the washing such as of arbitrary objects (glasses etc) performed using waves (laser, ultrasound or high intensity focus ultrasound), the present invention can increase the effects and the spatial resolution via the nonlinear phenomena or the prediction about the effects (for instance, the exponentiation effects by the thermal treatment using the high intensity focus ultrasound, the increases the effects using the crossed beams, i.e., the increasing the frequencies and the spatial resolutions by the multiplication as well as the increasing the spatial resolutions by the addition etc).

On the thermal treatment etc using the high intensity focus ultrasound, since the harmonic waves are generated owing to the tissue nonlinear effects and the harmonic waves are high frequencies, the absorption effects as a thermal energy are strong. Thus, it is simple to understand the heat build up in tissues and it is also possible to predict it. Form the same viewpoint, for the treatment, it is effective to transmit a high frequency signal, a wideband signal or a harmonic wave, or to generate superposed beams or crossed beams and also, the understanding and the prediction becomes simply possible. Concretely, a sound pressure geometry or a PSF (point spread function) can be estimated on the basis of the simulation on the sound field or the estimation of autocorrelation function on a system allowable to receive reception signals and then, it is effective that the harmonic wave signals are evaluated directly or the nonlinear processings (calculations) are also implemented onto the fundamental wave signal. This is similar for other waves.

Also, the present invention is also effective in obtaining nonlinear effects even under the physical conditions that physically the nonlinear effects cannot be obtained (For instance, the wave intensity cannot be increased with respect to the measurement object or due to a high frequency of the wave, a high intensity of the wave cannot be obtained etc). In contrary, for instance, for the ultrasound echo imaging, the displacement measurement or the treatment, it is possible to perform the present invention under the condition that the nonlinear effects are enhanced by using contrast agents such as microbubbles etc. The tissues with the agents diffused through can also be processed and the agents are also proper to the measurements or imagings on bloods in the vessels or in a heart. That is, the present invention can increase, imitate, newly generate the nonlinear effects. Furthermore, the present invention can also virtually realize the nonlinear effects. As mentioned above, it is possible to perform the evaluations of the nonlinear effects. The contrast agents can also be used for increasing the effects of the thermal treatments. These are similar for other waves.

Also, when high frequency signals are generated, which cannot be realized by using a single signal source, it becomes to possible to perform higher spatial resolution imagings and higher accuracy Doppler measurements. In general, the effects of attenuations are intense on high frequency components and for instance, it is desired that on microscopes that is suffered from the attenuations, the deep region can be observed using high frequency waves. For instance, when using plural 100 MHz ultrasound transducers, physically the same times as the number of used transducers as high frequency ultrasounds as that of the single transducer used can be generated, i.e., high frequencies being not able to be generated by a general transducer can be generated. It is also useful for generating a high frequency single (a chord tone wave) simply. By using the present invention, such high frequency waves can also be generated through processings or calculations. Thus, the present invention can also generate high frequency waves or signals that cannot be generated physically. Similarly, it is also possible to perform the low frequency imagings or measurements using the low frequency signals (for instance, a different tone wave). Also, it is possible to generate low frequency signals that cannot be generated by a single signal source. The generated waves can also be controlled by realizing these signals theoretically or on the basis of calculations.

Below, to demonstrate the effects of the present invention, explanation is performed about experimental data, simulation results and material data such as photographs etc. These are ultrasonic simulations and agar phantom experiments used for demonstrating the effectiveness of the present invention on the ultrasonic echo imagings and measurement imagings. The present invention can also be used for arbitrary signals except for the ultrasonic echo method (familiar signals by lasers, light waves, OCT signals, electric signals, magnetic signals, radioactive rays such as an X-ray and thermal waves etc) and can also be used between different type signals. These can be used for raw coherent signals or incoherent signals obtained after signal processings.

With respect to the echo signals obtained by performing the frontal beamforming and lateral modulation beamforming (a lateral modulation frequency, 3.5 MHz) using the SA echo data (a linear-type array transducer, 7.5 MHz) obtained from an agar phantom disclosed in the nonpatent document 29, the above-mentioned processings <1> to <3> are performed.

Figure 36:
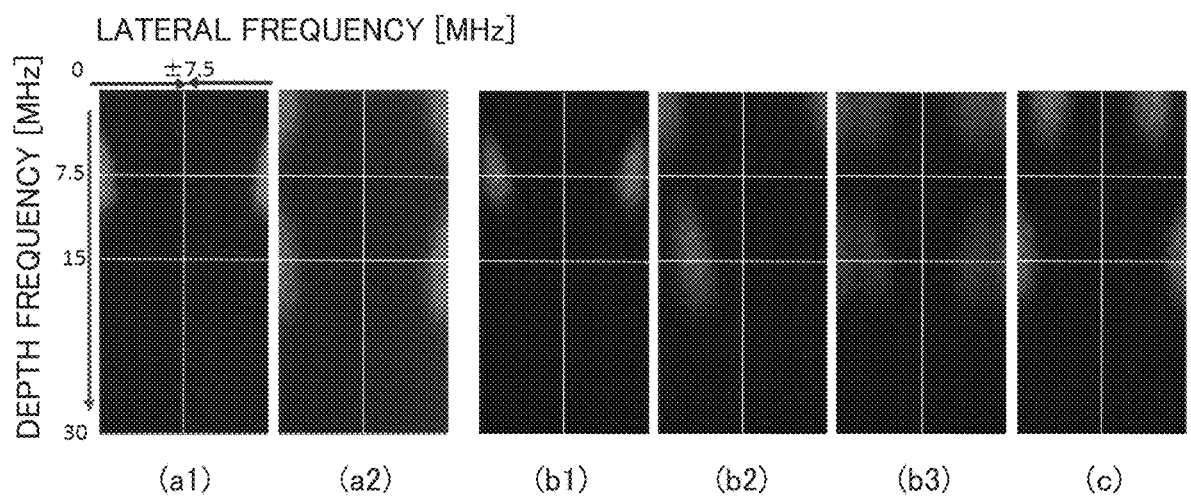
FIG. 36 shows varieties of spectra of echo signals obtained via an embodiment of the present invention.

FIG. 36 shows varieties of spectra of echo signals obtained via an embodiment of the present invention. In FIG. 36, the horizontal and vertical axes respectively express the lateral frequency [MHz] and the depth frequency [MHz]. In FIG. 36, (a1) and (a2) respectively show for the no steering case, spectra of the original echo signals and squared echo signals. (b1), (b2) and (b3) respectively show for the lateral modulation, spectra of the original echo signals, squared echo signals steered only in one direction and squared lateral modulation echo signals. (c) shows the spectra obtained by the multiplication of echo signals of the crossed, steered beams. From FIG. 36, the spectra derived in the above-mentioned theory for the respective signals can be confirmed. For all the echo signals, as the results of the square or the multiplication, the spectra of the 2nd harmonic waves are generated of which bandwidths become wider than the original spectra.

Figure 37A:
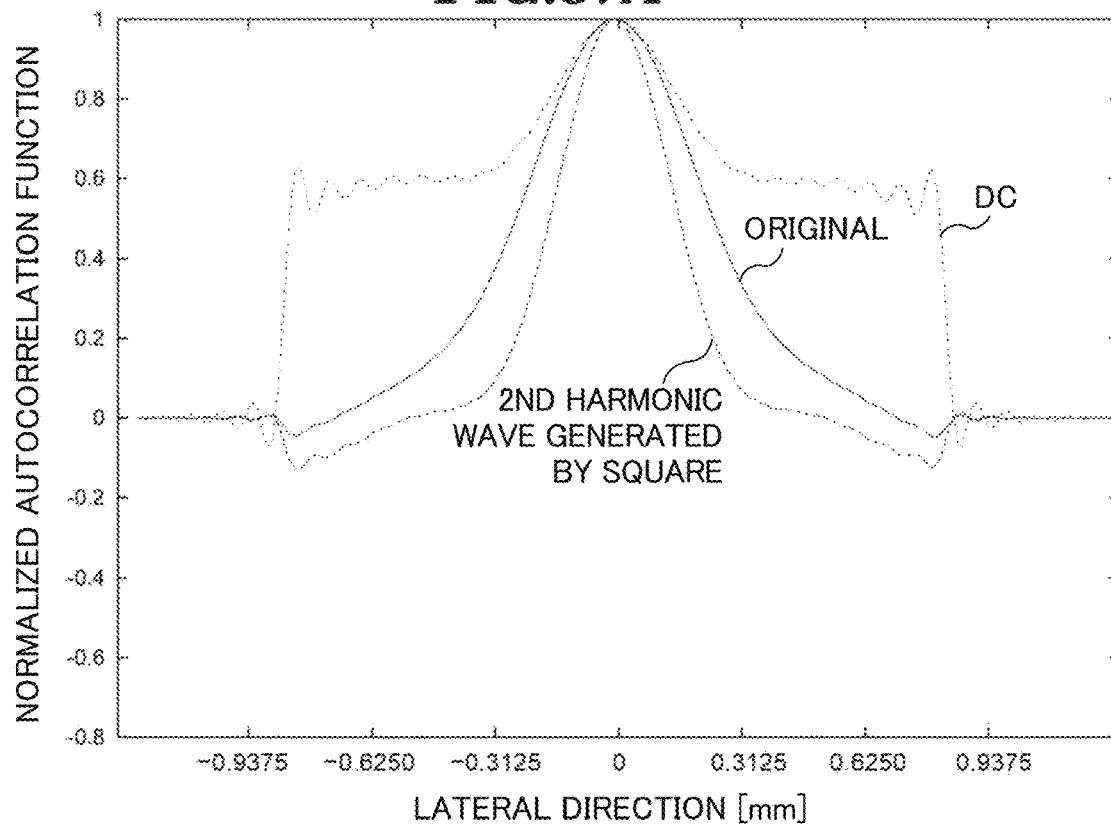
FIGS. 37A to 37C show varieties of autocorrelation functions of echo signals obtained via an embodiment of the present invention.
Figure 37B:
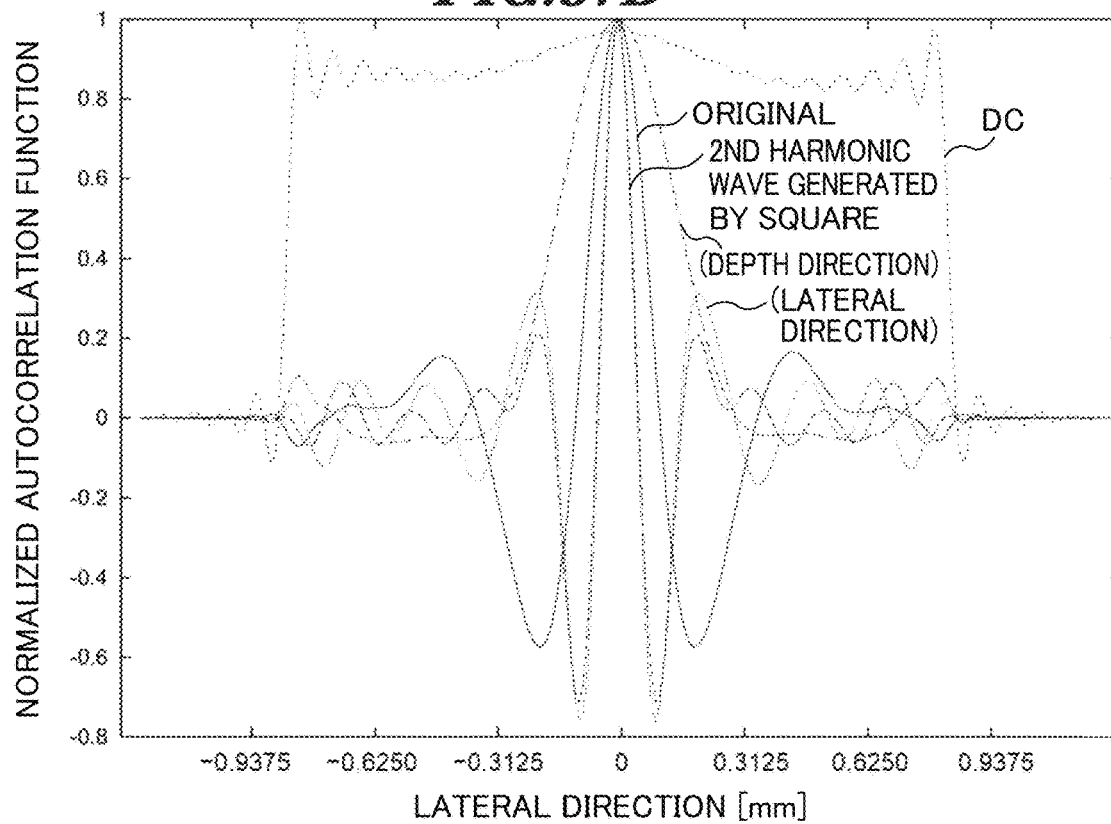
Figure 37C:
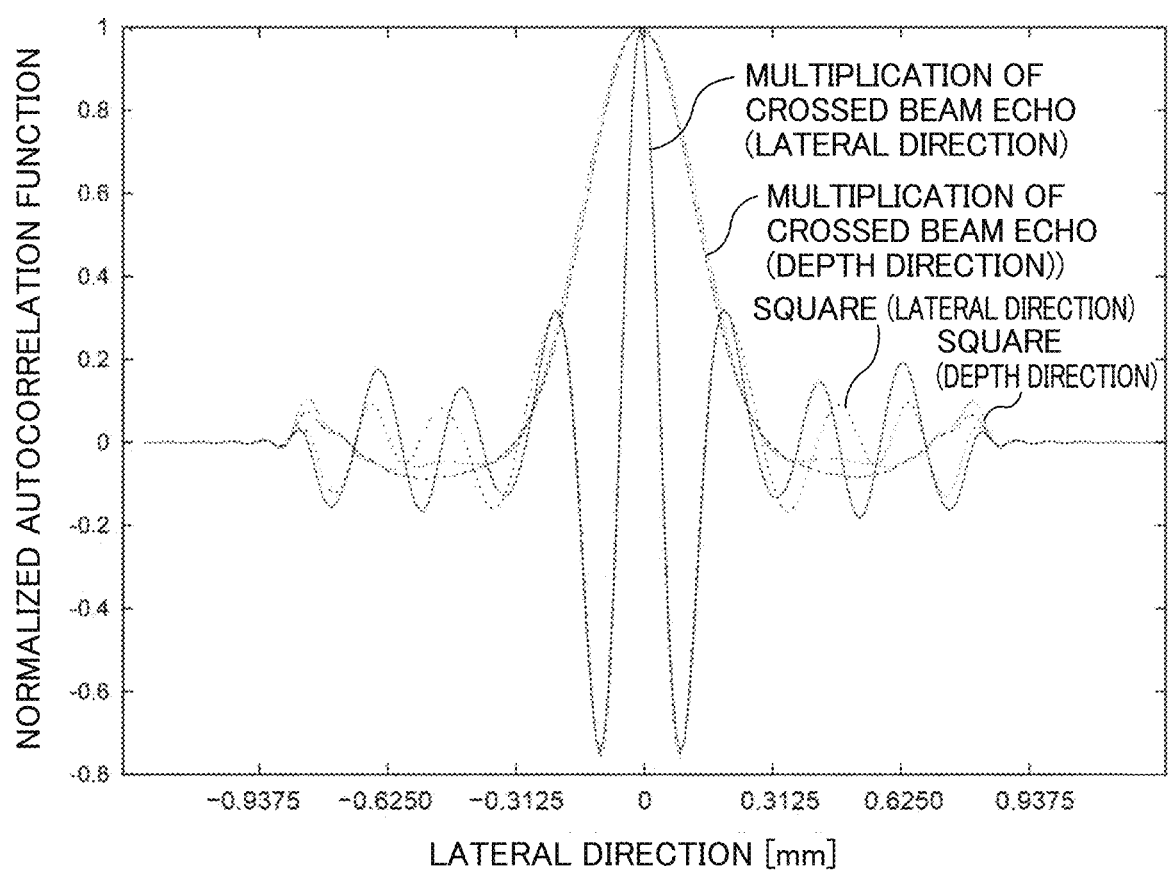

FIGS. 37A to 37C show varieties of autocorrelation functions of echo signals obtained via an embodiment of the present invention. Here, the lateral and vertical axes respectively show the lateral position [mm] and the normalized autocorrelation function. FIG. 37A shows for the no steering case, comparison about the normalized autocorrelation functions between the original echo signal and the 2nd harmonic wave obtained from the squared echo signal. FIG. 37B shows for the lateral modulation case, comparison about the normalized autocorrelation functions between the original lateral modulation echo signal and the 2nd harmonic waves obtained from the squared lateral modulation echo signal. FIG. 37C shows for the multiplication of crossed beam echo signals and the squared lateral modulation echo signal, the normalized autocorrelation functions of the lateral components and depth components. On the basis of the autocorrelation functions, the lateral profile of the sound pressure or the point spread function (PSF) can be evaluated (in the case of depth, 19.1 mm, i.e., at a centered depth in the ROI). Although omitted here, with respect to the 2D echo signals, calculation of the 2D autocorrelation function allows the evaluation of a 2D distribution of the sound pressure or the PSF, whereas with respect to a 3D echo signals, a 3D autocorrelation function can be used.

FIG. 38 to FIG. 40 show varieties of B-mode echo images obtained via an embodiment of the present invention. The depth of these echo images ranges from the depth, 10.0 to 28.1 mm, and the lateral width is 20.7 mm. In the agar phantom, a cylindrical inclusion (dia.=10 mm) is centered on the ROI (depth, 19 mm) of which shear modulus is 3.29 times as large as that of the surrounding.

In FIGS. 38 to 40, (a1), (a2) and (a3) respectively show for the no steering case, echo images obtained on the basis of the original echo signal, the base-banded signal, the 2nd harmonic wave obtained from the squared echo signals. In the cases where there exists two images at the left and right sides, the left and right images respectively show the results obtained on the basis of the envelope and squared detections.

(b1), (b2), (b3), (b4) and (b5) respectively show for the lateral modulation case, echo images obtained on the basis of the original lateral modulation echo signal, the base-banded signal, the 2nd harmonic wave obtained from the squared lateral modulation echo signal, the lateral component of the 2nd harmonic wave obtained from the squared lateral modulation echo signal and the depth component of the 2nd harmonic wave obtained from the squared lateral modulation echo signal.

Also, (c1) and (c2) respectively show for the 2nd harmonic waves obtained by the multiplication of the crossed beam echo signals, echo images obtained on the basis of the lateral components and the depth components. When there exists plural waves, the inventor of the present inventor also disclosed the detection to be implemented on a superposition of coherent signals at past and however, the results of a superposition of the respective detection signals are shown here.

It can be confirmed that corresponding to the increasing in bandwidths as the spectra shown in FIG. 36, the spatial resolutions increase as shown in FIGS. 37A to 37C and FIGS. 38 to 40. Here, the direct current in the base-banded data is not cut off. The direct current or if required, the remarkedly low frequency spectra in the depth and lateral directions are cut off by filtering etc, the lines running in the vertical direction with the high and low brightness (vertical stripes) can be removed completely (the results omitted). From FIGS. 37A to 37C, it can be confirmed that the sidelobes are suppressed. Corresponding to these, From FIGS. 38 to 40, the increasing in a contrast can also be confirmed (It is worthy of note the strong scatter etc). Since the attenuations are not corrected on the original echo signals, due to the increasing in a contrast under the no correction, the images obtained from the signals after implementing the nonlinear processing onto have much lower signal intensities at the deep region than the shallow region compared to the original signal images.

On the imagings using the original signals, the so-called attenuation correction with respect to the wave propagation is implemented onto the coherent signals or the incoherent signals obtained by the detection, whereas on the present instrument, the nonlinear processings can also be implemented onto the coherent signals obtained by implementing the attenuation correction onto the original coherent signals in advance, or the coherent or incoherent signals obtained by implementing the nonlinear processings onto are corrected. Similarly to the general correction processing, on the present invention, the correction processing itself can also be implemented mainly on the basis of the signal intensities before or after performing the reception beamformings or after generating the images. According to the Lambert's law, the correction can also be performed.

In the cases, a mean attenuation coefficient can also be used simply, whereas for performing accurate corrections, the attenuation coefficients of respective positions on the waves or beams propagation paths can also be calculated by the calculation unit 130 via signal processings or in an inverse problem approach and can be used. That is, the correction can be adaptively or automatically performed. Otherwise, the operator can adjust the intensities at the respective depths within the specified range via the control unit 133 with referring to the generated images. According to the measurement object, patterns to be selected can also be prepared.

The gain control can be performed by the receiver 122, the amplifier or the attenuator installed into the filter/gain control unit 123 or 125, the amplifier, the attenuator installed into or the digital processings performed by the reception beamformer 129, or the analogue or digital processings performed by the calculation unit 130. On the transmitter 121, the intensities of beams or waves to be transmitted can also be adjusted. Also, as the operation device 112, an amplifier or an attenuator can be used and then, the wave intensities themselves can also be adjusted. It is cautious that the use of the contrast agent 1a has prominent effects on the determinations.

On the square calculation on the lateral modulation echo signal (processing <2>) of the above-mentioned experiments, since the laterally detected spectra (one of two spectra that can also be obtained by detecting the 2nd harmonic waves in different one direction) overlaps with those of the simultaneously generated 2nd harmonic waves, the inventor of the present invention divided them by the visual estimation. Although the results are compared with those of the multiplication of the two waves of the lateral modulation echo signals (processing <3>) on the estimated autocorrelation functions (FIG. 37C), there is no difference except for that the harmonic frequency becomes lower slightly.

In addition to these experiments, using the multidimensional autocorrelation method, a displacement vector measurement, a strain tensor measurement and a shear modulus reconstruction are performed. In the results obtained, here shown in FIG. 41 are the results obtained using the processing <3>, i.e., the two signals of the 2nd harmonic waves detected in different one direction, for the measurements of displacement components in respective two directions.

Figure 41:
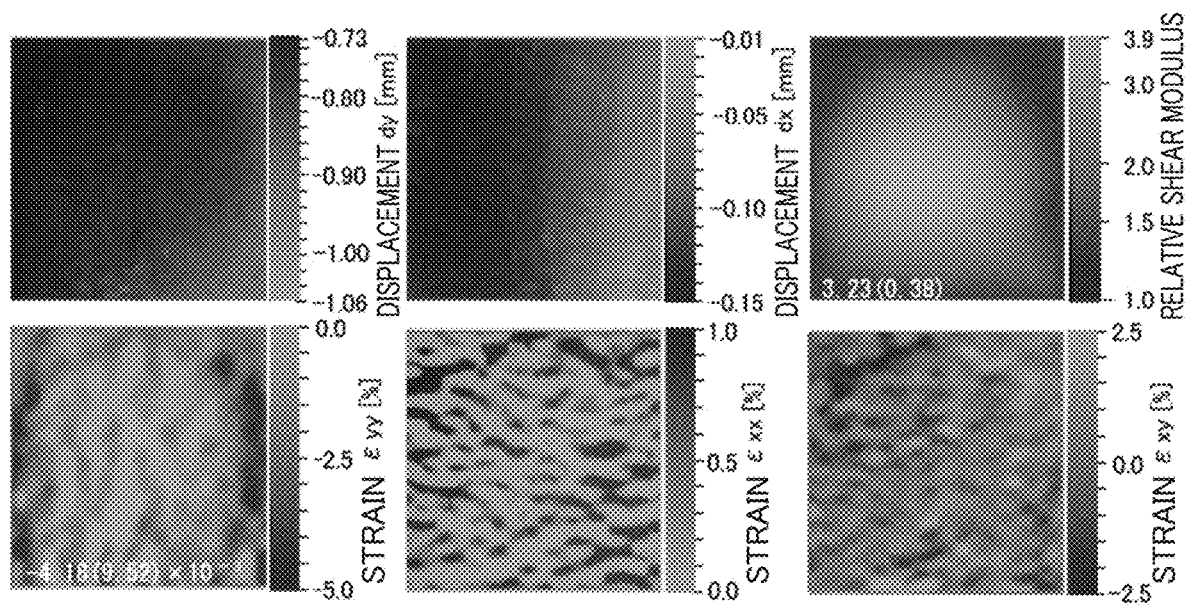
FIG. 41 shows images of a displacement vector, a strain tensor and a relative shear modulus measured on an agar phantom via an embodiment of the present invention.

FIG. 41 shows images of a displacement vector, a strain tensor and a relative shear modulus measured on an agar phantom via an embodiment of the present invention. The parts of FIG. 41 also show the means and the standard deviations (SDs) estimated on the center of the inclusion in the parentheses. Compared with the results obtained by performing the digital demodulation onto the same lateral modulation echo data, the noise intends to increase (SD of the lateral (y) strain increased from $3.08 \times 10^{-3}$ to $9.52 \times 10^{-3}$) and however, the spatial resolution becomes the two-fold and on the shear modulus reconstruction, the accuracy is also improved with performing the regularization (the means changes from 3.37 to 3.23).

Here, although the results are omitted, as mentioned in the paragraph 0629, with respect the generated plural beams or waves, the nonlinear processings can also be implemented onto the superposition, or after the nonlinear processings are implemented onto the respective beams or waves, the superposition can also be performed on them. As mentioned at others, the nonlinear processings can also be implemented onto raw reception signals (no reception-beamformed signals: only transmission beamforming or SA cases). Although plural waves or beams generated under using same wave or beamforming parameters can also be processed, those obtained under using different parameters can also be processed.

To increase the spatial resolution, the superesolution on the above-mentioned linear model is effective and then, such a superesolution can also be used for these plural waves or beams. That is, the superresolutions can also be implemented onto the superposition, or after the superresolutions are implemented onto the respective beams or waves, the superposition can also be performed on them. Both can be mixed and can also be processed. Superposition performed under the same parameters (additional averaging) with the noises to be reduced can also be processed. With respect to the original signals (including the cases where the signals are harmonic waves), prominently high spatial resolutions can be realized. Various type superresolutions are mentioned. For instance, as mentioned in the paragraph 0361, when the inverse filtering is performed using a desired PSF or spectra of a desired signal distribution such as a desired echo distribution etc as a target, similarly to as mentioned together with the displacement measurement in the paragraph 0373 to 0397, the Wiener filter can be used as the weights for the imagings of signals themselves. Particularly, for instance, when the weights on the basis of the Wiener filter used for eq. (A12') or eq. (A13') (the first squared norms of signal spectra are respectively removed) are used, the weighted norm of the inverse filter $$\frac{G_p(\omega_x, \omega_y, \omega_z)}{H_p(\omega_x, \omega_y, \omega_z)}, \quad \text{(AA1)}$$

where the respective $H_p(\omega_x,\omega_y,\omega_z)$ and $G(\omega_x,\omega_y,\omega_z)$ are the spectra of the signal to be processed and the target, being $$W_p(\omega_x, \omega_y, \omega_z) = \left\|\frac{G_p(\omega_x, \omega_y, \omega_z)}{H_p(\omega_x, \omega_y, \omega_z)}\right\| \quad \text{(AA2)}$$

$$\left(\frac{\|H_p(\omega_x, \omega_y, \omega_z)\|}{\|H_p(\omega_x, \omega_y, \omega_z)\| + \sqrt{\frac{PW_{pn}(\omega_x, \omega_y, \omega_z)}{PW_{ps}(\omega_x, \omega_y, \omega_z)}}}\right)^q \quad \text{or}$$

$$W_p(\omega_x, \omega_y, \omega_z) = \left\|\frac{G_p(\omega_x, \omega_y, \omega_z)}{H_p(\omega_x, \omega_y, \omega_z)}\right\| \quad \text{(AA3)}$$

$$\left(\frac{\|H_p(\omega_x, \omega_y, \omega_z)\|^2}{\|H_p(\omega_x, \omega_y, \omega_z)\|^2 + \sqrt{\frac{PW_{pn}(\omega_x, \omega_y, \omega_z)}{PW_{ps}(\omega_x, \omega_y, \omega_z)}}}\right)^q,$$

where PWpn ($\omega_x, \omega_y, \omega_z$) and PWps ($\omega_x, \omega_y, \omega_z$) are respectively the power spectra of the noise and the signal. q is an arbitrary positive value.

can be used for the processings. Also for other superresolutions on the linear model mentioned above, the Wiener filter can be used to decrease the amplification of noise. When, with no the Wiener filter, the norm of eq. (AA1) itself is implemented, only the frequency spectra having an $\epsilon$-fold ($\epsilon<1$) norm of the signal spectra Hp($\omega_x, \omega_y, \omega_z$) can also be processed (Results of other frequency spectra are set to zero). On these, anomalistically, not the norm of eq. (AA1) but eq. (AA1) itself can also be used and the phase can also be matched. In the case, Gp($\omega_x, \omega_y, \omega_z$) can often have phase information about the measurement object.

Otherwise, these weighting processes can also be performed on the blind convolution. When performing the whitening by implementing the inverse filtering using an another calculated PSF or system transfer function, when multiplying the conjugate of such PSFs, the system transfer functions or eq. (AA1) or when they are performed onto the pre- or post-beamformed signals (the state of only the transmission beamforming performed or reception signals acquired for SA), these weightings are useful. Particularly, on the inverse filterings, the regularizations can also be implemented.

With respect to the signals obtained by implementing the superresolution using these linear models, above-mentioned nonlinear processings can also be implemented. The spatial resolutions increase further and the contrasts increase further. As the results of the superresolutions using these linear models, the followings can be used, i.e, the superresolution-implemented original signal (that can also be a harmonic wave and also below), the superposition of the plural super-resolution-implemented signals, the superresolution-implemented, superposed plural original signals, their mixed and processed etc. Also, when there exists plural original signals, the superresolutions are implemented onto the respective signals under the linear models and subsequently, the nonlinear processings are implemented onto the respective results and superposed. They can also be mixed and processed.

Also, as mentioned above, with respect to the nonlinear processing-implemented signals, the superresolutions using the linear models can also be used. Although the spatial resolution can increase and however, the contrast can decrease. As the results of the superresolutions using the nonlinear processings, the followings can be used, i.e, the nonlinear-processings-implemented original signal (that can also be a harmonic wave and also below), the superposition of the plural nonlinear-processings-implemented signals, the nonlinear-processings-implemented, superposed plural original signals, their mixed and processed etc.

Also, when there exists plural original signals, the nonlinear processings are implemented onto the respective signals and subsequently, the superresolutions using the linear models are implemented onto the respective results and superposed. They can also be mixed and processed.

When implementing these nonlinear processings onto the plural signals (expressing beams or waves and not limited to a fundamental wave and can be harmonic waves) at a position of interest, if the intensities of original signals before being processed are different due to the effects by the directivities of apertures, or the scatterings or attenuations in the object (including a case where they depend on the frequency), the differences can be increased and particularly when high order harmonic waves are generated, the differences becomes prominent. The differences can be positively imaged or can also be quantitatively confirmed on the spectral images (The frequency characteristics can be increased and confirmed) Alternatively, to decrease the differences for imagings, before or after implementing the nonlinear processings, the energies of signals or specific frequency spectra can also be weighted and can be used for the imagings. The plural signals superposed can also be imaged. The signal spectra or energies can also be estimated at a local region including a position of interest or over the ROI. Off course, regardless implementing the nonlinear processings or not, the weighting can also be performed similarly at performing the linear superposition.

Also, due to the effects of attenuations or reflections/scatterings during the propagations, the signal intensities becomes weak in a propagation direction and however, for instance, the degree of attenuation of a plane wave is weaker than that of a focused beam. Particularly for a higher order, the implementation of the nonlinear processings increases the effects. Thus, as mentioned above, before or after performing the nonlinear processings, the signal intensities can also be corrected (Also when not performing the nonlinear processings, the correction can also be performed). The processings can also be performed before or after performing the detections.

There also exists other various superresolutions, one of which can be used together on the same or a different signal for performing the coherent addition to be used. Instead, inherent addition can also be performed to reduce speckles. Often the incoherent addition via the superresolutions does not make the spatial resolutions low as mentioned above.

Also, being dependent on the single intensities or SNRs, or the spatial resolutions on the respective processings of the superresolutions, spatially nonuniform addition can also be performed. That is, being dependent on them at the respective positions, the parameters of the respective methods can be variable. The cases where the spectra are processed are as above-mentioned and for instance, in the cases of the nonlinear processings, the parameters are the order of the exponentiation or the number of multiplications etc. And when performing the additions of the coherent signals or the incoherent signals. The parameters are the number of additions or the weight values etc. Off course, spatially uniform processes can also be performed.

As the effects of increasing contrasts by the nonlinear processings, scatters or reflectors can also be visualized particularly well. Increasing the order of exponentiation or the number of multiplications can also generate an effect that the difference in signal intensity (brightness for a gray image) becomes prominent. For instance, it can also become simple to detect the calcifications after the necroses of living tissues. Otherwise, for instance, being dependent on the signal intensities, coloring can be performed, which can be displayed with the superposing onto the general gray images or Doppler images, power Doppler images, contrast agent images etc. After correcting the intensities of the signal distribution, the processings can also be performed. For instance, after performing the correction on the intensity of a signal (before or after detection) received from the ROI such that the signal intensity become uniform in the ROI, the nonlinear processings can be implemented to visualize the scattering intensity distribution or the scattering intensities of plural scatters, or the reflection intensity distribution or the difference in reflection intensity of reflectors. To count the number of the reflectors or scatters, the processings can also be performed. Except for a focused beam or SA, using a plane wave or a spherical wave, or cylindrical wave yields a low spatial resolution and also in such situations, various superresolutions such as the nonlinear processings are useful and particularly when performing the nonlinear processings, scattered waves or reflected waves can be visualized remarkedly well at the generated positions. For instance, when generating crossed waves, a cross-type wave shape can be enhanced and displayed as a scattered wave at the scatter position.

The PSF is calculated in a simulation for using one or two concave aperture HIFU applicators (simulation: frequency, 5 MHz; an aperture diameter, 12 mm; a focus depth, 30 mm) and also the exponentiation and the multiplication of the PSF. As mentioned above, this type calculation is effective in performing the considerations about the thermal effects. By collecting experimental data, it is possible to formulate the relationship among the sound pressure (PSF), the sound pressures of harmonic waves and reception properties of a heat etc and then, the formulation can be useful for increasing the efficiency of thermal treatment via designing the applicator or a radiated acoustic pressure (ultrasound parameter) etc. These are also for using other waves.

FIG. 42 shows varieties of acoustic pressures obtained using a concave HIFU applicator via an embodiment of the present invention. In FIG. 42, (a1) and (a2) shows for using one aperture the acoustic pressure image obtained from the original signal and the acoustic pressure images obtained from the squared signal (left including a direct current as well; right showing only the generated harmonic wave), respectively. (b1) and (b2) shows for using the two apertures (the crossed angles are ±5° with respect to the lateral direction) the acoustic pressure image obtained from the original signal and the acoustic pressure images obtained from the multiplied signals (left including a direct current as well; right showing only the generated harmonic wave), respectively. The images are obtained by the envelope detection and the image size is 3.8×12.8 mm². It can be confirmed that on the 2nd harmonic wave components respectively obtained by the square and the multiplication, the acoustic pressures concentrate on the desired regions and the contrast increases. Thus, the estimation of the intensity (i.e., power) of a fundamental wave and the acoustic pressure distribution geometry of the generated harmonic wave (with the 2nd order and over) can be performed. Also, the power consumed from the harmonic wave (intensity) can also be estimated. On the harmonics to be observed in practical, the similar estimations can be performed.

As far, regarding the imaging instrument related to an embodiment of the present invention, the nonlinear processing device of mainly the electromagnetic waves, mechanical vibrations including sounds, thermal waves, or the corresponding signals are mentioned. However, it is also possible to increase, imitate and virtually realize nonlinear effects between different kind (type) physical energies (i.e., in addition to cases where nonlinear effects are generated physically, chemically, or biologically, cases where nonlinear effects cannot be generated are included) and in the cases, the present invention can also be performed by that devices regarding the plural kind (type) waves to be processed are simultaneously used to receive the waves or at the same phase of the measurement object, the waves can be received at different times. That is, it is possible for the present invention to process the cases where plural kind (type) waves are generated simultaneously as well as the cases single kind (type) waves are generated solo.

On the respective electromagnetic waves, vibrations or thermal waves, the waves with different frequencies exhibit different dominant behaviors being dependent on the respective measurement objects (media) and then, the names are different. For instance, on the electromagnetic waves, there are a microwave, a terahertz wave, a radioactive ray such as an X-ray etc and on the vibration waves, for instance, in human soft tissues, a shear wave cannot propagate as a wave in a Mega Hertz bandwidth and an ultrasound is dominant, whereas a property of an incompressibility is intense and a shear wave is dominant in a low frequency range such as 100 Hz etc. The present invention increases, imitates and virtually realizes nonlinear effects between such waves that exhibit different behaviors.

In the cases, the present invention can also be performed by that devices regarding the plural kind (type) waves to be processed are simultaneously used to receive the waves or at the same phase of the measurement object, the waves can be received at different times. Off course, since the phenomena such as attenuations, scatterings or reflections etc have variances, there is a limitation that the waves must be properly used with considerations about the SNRs of reception signals. However, since high or low frequency components, which cannot be physically generated or captured, can be generated, the application range of the present invention is prominently broad.

Also mentioned are regarding imagings of the nonlinear processings or the nonlinear effects in the measurement object or applications to other measurements, where harmonic waves can be positively propagated in the measurement object as well as the original fundamental wave can also be positively used together in the situations. Also, over-determined systems can also be generated. The fundamental wave can also be processed similarly to the harmonic waves.

Furthermore, an arbitrary detection processing can be implemented onto at least one of plural signals generated via the nonlinear processings, or superposition can be performed after an arbitrary detection processing is implemented onto the plural signals that can include the basic signal, or an arbitrary detection processing can be implemented onto the superposition of plural signals that can include the basic signal to perform the imagings or measurements such as a displacement etc. Regarding the superposition, the incoherent addition (incoherent compounding) is effective in speckle reduction and if the generated high frequency signals are used, the spatial resolution does not become small. The problem of a low spatial resolution generation often caused by the general speckle reduction does not occur. Using the low frequency signals can also be useful, although the spatial resolution decreases. Alternatively, the coherent addition (coherent compounding) can increase the signal bandwidths, i.e., spatial resolution. Particularly, when a high frequency signal is generated and used, the frequency increases, whereas when a low frequency signal is generated and used, the frequency decreases. Consequently, the spatial resolutions of imagings can also increase as well as the measurement accuracies such as a displacement and others can also increase. As mentioned above, the generated plural beams or waves, and signals obtained by the spectral frequency division can also be processed by these including the nonlinear processings.

The displacement measurements can be used as mentioned above, for instance, for radars, sonars and environmental measurements etc. The application range is not limited. In addition to the displacement, a temperature can also be measured, for instance. Temperature sensors can directly also used for sensing a temperature, whereas the dependency of wave propagation properties on a temperature can also be detected to measure a temperature distribution, for instance, when using an ultrasound, thermal strains generated by the dependency of a sound speed and a volume change on a temperature are measured by the exclusive signal processings. Also, a chemical shift of magnetic resonance frequency can also be detected by using the signal processings. When measuring thermal waves, the nonlinearities can be imaged and can also be used for achieving a high efficiency of thermal treatments.

Investigating the nonlinear effects occurring in the measurement object can also be performed by switching the uses of cases where the observation of the nonlinear effects occurring in the measurement object is positively performed and the implementing of the present invention is performed; or by using both cases simultaneously and by using the nonlinear processing or calculations positively. That is, by skillfully using the nonlinearities of signal sources or contrast media, or the analogue or digital nonlinear processings, the nonlinear effects in the measurement abject can be measured with a high accuracy and can also be imaged.

The above-mentioned imagings and measurements are on the basis of the performing proper beamformings, and proper detection methods and tissue displacement vector measurement methods etc are also important. As past, the present inventor developed particularly as the detection methods for multidimensional signals, the square detection etc in addition to the quadrature detection or the envelope detection; as the beamforming methods, the lateral modulation methods using crossed beams (nonpatent documents 13 and 29), the spectral frequency division method (nonpatent 29), the controlling the wave or beam geometries using spectral filtering, the using plural crossed beams and the over-determined system method etc; as the displacement vector measurement methods, the multidimensional autocorrelation method, the multidimensional Doppler method, the multidimensional cross-spectral phase gradient method and the phase marching method etc (nonpatent documents 13 and 29); and others, on the basis of the displacement or the strain measurement, the (visco) shear modulus distribution or the thermal property distributions can be reconstructed and imaged. With respect to not only the original waves or beams but also the superposition of plural waves or signals, or the waves or signals generated by the nonlinear processings being implemented onto (which can also include imitations), the spectral frequency division can yield quasi-waves or quasi-beams can be generated, and the spectral filtering can control the wave or beam geometries.

With respect to the superposition of plural signals that can include a fundamental wave or at least one of plural signals that can include a fundamental wave, signals obtained by implementing the spectral division or the filtering in a frequency domain (nonpatent document 29), the original signals that not there-processings-performed, or the using them together can also be used for generating the over-determined systems to perform the imagings or the other measurements such as a displacement etc as mentioned above, As mentioned above, the present invention for the coherent signals obtained by the sensors by detecting the transmission waves, the reflection waves or the scattering waves of arbitrary waves, the nonlinear responses with respect to a high intensity of a wave during the propagation or the nonlinear effects (generations of a harmonic wave or a chord tone wave, a different tone wave etc) such as the multiplication or the exponentiation generated on the superposing of waves can be obtained by implementing the analogue processings or the digital processings using the calculator and then, compared to the imagings using the original signals, imaging with a high frequency, a broad band, a high contrast and a high spatial resolution can be achieved. Not imaging with the increased frequency but with the decreased frequency can also be performed. Under the same effects, compared to the Doppler measurements using the original signals, measurements on the displacement, the velocity, the acceleration, the strain or the strain rate can be achieved with high spatial resolutions and with high accuracies.

The superposing of waves mean ones that generated among waves during the physical beamformings, or physically beamformed waves, physically nonbeamformed waves etc. When the wave intensity is weak, mainly the superposition theorem on the basis of the linear principle can be observed, whereas when the wave intensity is strong, signals effected by the nonlinear effects such as the multiplication or the exponentiation (i.e., harmonic waves, chord tone waves, different tone waves) can be observed in addition to the superposition. The present invention focuses on the latter phenomena. The present invention also has one feature that the present invention can be used all these wave components and the superposed waves regardless the intensities. Off course, the present invention can be used for the fundamental wave or the waves including harmonic waves artificially radiated or generated during the wave propagation. As the harmonic waves generated during the wave propagation, for instance, there are ultrasound harmonic signals etc.

With respect to this, for instance, with respect to beams generated by the beamformings (physical apodizations, delay processings or summing, or their calculations), the waves themselves not beamformings-performed (plane waves, reception signal sets for SA etc), or arbitrary waves such as the transmission waves, the reflection waves or the scattered waves etc, the present invention allows the high accuracy measurements or imitations of the nonlinear effects such as the multiplication or the exponentiation etc generated by the nonlinear effects owing to the high intensity of wave or the superposing of plural waves propagating in a same direction or in different directions (the same waves of the same physical quantities and however only with different propagation directions, waves of the same physical quantities with different parameters, waves of different type physical quantities), for instance, by positively using the analogue or digital processing device after the transducer(s) detects the signals for implementing the nonlinear processings onto, i.e., harmonic waves, chord tone waves or different tone waves with increased bandwidths can be obtained. Also, in addition to the cases where nonlinear effects are generated physically, chemically or biologically, the present invention also allows the increasing of the nonlinear effects, or when no nonlinear effects can be observed or no nonlinear effects are not generated, the present invention also allows the generating nonlinear effects. Also, plural detected signals can also be obtained simultaneously. In addition, the using the base-banded signals generated by the physical actions is also included in the present invention (The harmonic waves calculated from reception signals by using the pulse inversion method or the filtering method etc can be removed, or using the estimated signals obtained by the above-mentioned processings or calculations etc).

At past, the inventor of the present invention disclosed the lateral modulation method on the basis of the linear theorem using the crossed waves (plane waves etc) or crossed beams (there exists the carrier frequencies both in the depth and lateral directions) and using the present invention allows yielding the effects of exponentiation can also be obtained on the lateral modulation as well as the effects of multiplication between the crossed waves. Also, although the effects of exponentiation and multiplication can be obtained in general by increasing the wave intensities, the present invention allows yielding the nonlinear effects regardless the wave intensities.

Also, the present invention allows yielding the base-banded signals by using the new detection processing to be performed with fewer calculations instead of the general quadrature detection or the envelope detection; and the effects can be obtained for the echo imagings and the Doppler measurement. However, note that the detected signals are different from a base-band signal refereed to as in general in that the direct current is included. Then, the base-banded signals can be directly used or used after removing the direct current via analogue or digital processings. In addition, the using the base-banded signals obtained by the physical actions is also included in the present invention. The signals generated by the processings to have base-band bandwidths are also referred to as the base-banded signals.

For instance, in the area of medical ultrasounds or sonars, although the so-called harmonic echo imaging is clinically used, where harmonic waves are generated by nonlinear phenomena during the ultrasound propagations in living tissues (for a higher pressure, the acoustic propagation speed is higher since the bulk modulus acts higher and then, the wave shape distorts and the effects are accumulated during the propagation), it is not disclosed to use the physically generated base-banded signals. It is also not disclosed to use base-banded signals physically generated by other nonlinear phenomena. The base-band signals, base-banded signals and incoherent signals obtained using the envelope detection and the square detection etc can also be included in the processing objects of the present invention.

Particularly, on the Doppler measurements, the inventor of the present invention makes it possible to measure a displacement vector, a velocity vector or an acceleration vector in an arbitrary direction, or a strain tensor or a strain rate tensor with high accuracies by using the multidimensional signals being different from the performing of a general Doppler measurement that allows the measurement of a displacement in the wave propagation direction. Being different from the general detections, the present invention can yield signals of the harmonic waves quadrature-detected in arbitrary one direction (bas-banded signals) from the multidimensional signals simultaneously and then, general one-directional displacement measurement methods can be used to simply perform the measurements with fewer calculations and in short times. In this situation, it is also possible to perform the echo imagings using the harmonic waves or above-mentioned base-banded signals simultaneously obtained. In addition, the suppressing the sidelobes and then the increasing the contrast are possible. Also, as mentioned above, the temperature measurements can also be performed.

There exists the base of the present invention in that chord tone waves and different tone waves are generated by performing the multiplication between the sine waves or cosine waves with a different single frequency; implementing the exponentiation calculation on a wave yields the order-fold frequency of the wave (both the double angle and the arcminute theorem can be performed); implementing the nonlinear processings onto a signal having plural frequency components (distortion wave) yields an increased bandwidths. In addition, the effect of the suppressed sidelobes can also be obtained and then, the contrast increases. Although these effects can be often observed as the effects obtainable particularly for high intensity waves during the propagations, regardless the wave intensities, the present invention allows increasing, imitating or newly generating the nonlinear effects by implementing analogue or digital processings onto an arbitrary signals. It is also possible to virtually realize the nonlinear effects. Not limited to the cases where the spatial resolutions exists, similarly with respect to the continuous waves, the harmonic waves or the detected signals can also be generated physically or artificially. If the physically generated base-banded signals can be understood under the present invention, the applications also becomes useful in an engineering sense. For instance, the measurements of a displacement or a displacement vector components can be performed (General one-directional displacement measurement methods can be used). Also, the observed harmonic waves can also be used for performing the measurements of a displacement or a displacement vector (The above mentioned various multidimensional displacement vector measurement methods can be used), and also the over-determined systems can be generated for performing the imagings (high SNRs, high spatial resolutions, speckle reductions etc) and the displacement component measurements (high accuracies) etc similarly to the cases using the nonlinear processings of the present invention. In these cases, the contrast agents can be positively used for effectively increasing the nonlinear effects.

Otherwise, on the warming, the heating, the cooling, the freezing, the welding, the restoration, the thermal treatment of cancerous diseases (thermal therapy) or the cryotherapy or the washing such as of arbitrary objects (glasses etc) performed using waves (laser, ultrasound or high intensity focus ultrasound etc), the present invention can increase the effects and the spatial resolution via the nonlinear phenomena or the prediction about the effects (for instance, the exponentiation effects by the thermal treatment using the high intensity focus ultrasound, the increases the effects using the crossed beams, i.e., the increasing the frequencies and the spatial resolutions by the multiplication as well as the increasing the spatial resolutions by the addition etc). On these, continuous waves can also be used and similar effects can be obtained.

The present invention is also effective in obtaining nonlinear effects even under the physical conditions that physically the nonlinear effects cannot be obtained (For instance, the wave intensity cannot be increased with respect to the measurement object or due to a high frequency of the wave, a high intensity of the wave cannot be obtained etc). In contrary, for instance, for the ultrasound echo imaging, the displacement measurement or the treatment, it is possible to perform the present invention under the condition that the nonlinear effects are enhanced by using contrast agents such as microbubbles etc. That is, the present invention can increase, imitate, newly generate the nonlinear effects. Furthermore, the present invention can also virtually realize the nonlinear effects. Also, the present invention can be used for the purposes of purely increasing the spatial resolutions, the accuracies and the efficiencies on the imagings, displacement measurements and treatments etc.

Similarly to the harmonic imaging, the present invention allows increasing the frequencies, the bandwidths and the contrast, or suppressing the sidelobes and then, high SNR nonlinear imagings can be performed. In addition, required memories and calculations are fewer and the analogue and digital detections can be performed simultaneously.

The effectiveness of the present invention was demonstrated by performing ultrasonic simulations and agar phantom experiments on the ultrasonic echo imagings and measurement imagings. The present invention can also be used for arbitrary signals except for the ultrasonic echo method (familiar signals by lasers, light waves, OCT signals, electric signals, magnetic signals, radioactive rays such as an X-ray and thermal waves etc) and can also be used between different type signals. Signals including incoherent signals obtained by analogue processings (for instance, energy detection on reception signals using a sensor or using nonlinear elements etc) or digital processings can be processed together with the coherent signals.

Alternatively, in the area of an image measurement, it is well known that the observations of motions are performed by using incoherent signals (the results are displayed using images) generated by implementing various type detections (physical phenomena or general signal processings) on coherent signals. Also, implementing the present invention onto incoherent signals increases the bandwidths (spatial resolution). Also, used can be the above-mentioned high spatial resolution detection signals obtained using the present invention. The measurement accuracies of the motions also increase. That is, the present invention can be used both for arbitrary coherent signals and arbitrary incoherent signals.

Long time has passed since the imagings and the measurements of motions etc using the above-mentioned coherent or incoherent signals are to be performed in various areas including the above-mentioned examples etc. In such situations, it is useful and effective to perform the imagings, with high or low frequencies, with broad bandwidths and high spatial resolutions, and with high contrasts as well as to measure a displacement etc with high accuracies using the nonlinear effects obtained by the present invention. It is also effective to perform the multidimensional signal processings themselves and also in an engineering sense. Also, on other applications such as the treatments as mentioned above, it is effective and useful to evaluate and use the treatment effects on the basis of the nonlinear effect imagings.

On the imaging instrument, using the harmonic wave components and base-banded signals (the above-mentioned new detection signals) generated by implementing the multiplication and the exponentiation is useful for generating the image signals and not limited to the multiplication and the exponentiation, implementing high order nonlinear processings can also yield the same effects. In view of the costs, the present invention and the existing technology can be selectively employed, or used together.

The present invention is not limited to the above embodiments and much transformation is possible in technical thought of the present invention by a person having normal knowledge in the technical area concerned.

INDUSTRIAL APPLICABILITY

The present invention can be utilized on beamforming methods that use arbitrary waves arrival from a measurement object for performing the beamformings and on measurement and imaging instruments and communication instrument using such beamforming methods.

These days, the signal generations of a radar or a sonar, other optical type waves or an acoustic wave, a thermal wave etc are usually performed using digital instruments and also for the purposes of the signal applications, the digital instruments are also required to be equipped with a capability of performing the high order processings or calculations at least. The increasing the dimensionality of various instruments will increase the importance of the present invention. The measurement objects are various such as solids, fluids, rheology matters, inorganic and organic substances, living things, environments etc, the measurement range is immeasurable and will be prominently widespread. Henceforth, the down sizings will be carried out on the respective devices in the instruments; and calculators with sufficiently high capabilities, however cheap, will be able to be built up together; and then it can be expected to that many useful, real-time instruments will be realized. Furthermore, not only wave imaging instruments but the applications through the measurements using waves will also be developed enthusiastically and the application range will also be prominently widespread. The more various type instruments will become digital henceforth, in the situations, the demands for performing on the basis of the present invention, the high speed, real-time beamformings with high accuracies will increase. Especially, in addition to that the processings are high speed, it is not required to perform approximate interpolations at all, which was required at past. However, when the higher speediness is more considered, also on the present invention, the approximate interpolations will be able to be performed, although the accuracies decrease. The instruments are also effective for a general communication and a sensor network. The availability and marketability of the digital beamformings related to the present invention on the basis of the digital signal processings are sufficiently high.

The invention claimed is:

1. A beamforming method which is used in a measurement and imaging instrument for generating an image signal with respect to a measurement object when a wave source positioned at an arbitrary direction transmits an arbitrary wave toward said measurement object in an orthogonal coordinate system determined by a reception aperture element array, said beamforming method comprising the steps of:
    (a) receiving a wave arrived from said measurement object by using at least one reception aperture element to generate a reception signal; and
    (b) performing a transmission and/or reception beamforming processing at least by implementing wavenumber matching with Fourier's transform onto said reception signal generated at step (a),
    wherein step (b) includes performing a transmission and/or reception steering with a steering angle direction expressed at least by a zero or non-zero angle of a deflection, an elevation, or an azimuth with respect to a frontal direction of said at least one reception aperture element, and directly generating the image signal in a desirable orthogonal coordinate system based on said wavenumber matching by multiplying complex exponential functions, which are expressed using at least said steering angle direction, onto said reception signal in respective directions of orthogonal spatial coordinate axes with performing Fourier's transform onto said reception signal with respect to said orthogonal spatial coordinate axes so as to match wavenumber coordinates of angular spectra of said reception signal to wavenumber coordinates of spectra corresponding to said image signal without directly implementing interpolation approximations onto said angular spectra.

2. A measurement and imaging instrument for generating an image signal with respect to a measurement object when a wave source positioned at an arbitrary direction transmits an arbitrary wave toward said measurement object in an orthogonal coordinate system determined by a reception aperture element array, said measurement and imaging instrument comprising:

at least one reception aperture element configured to receive a wave arrived from said measurement object to generate a reception signal; and a digital signal processing unit configured to perform a transmission and/or reception beamforming processing at least by implementing wavenumber matching with Fourier's, transform onto said reception signal generated by said reception aperture element, wherein said digital signal processing unit performs a transmission and/or reception steering with a steering angle direction expressed at least by a zero or non-zero angle of a deflection, an elevation, or an azimuth with respect to a frontal direction of said at least one reception aperture element, and directly generates the image signal in a desirable orthogonal coordinate system based on said wavenumber matching by multiplying complex exponential functions, which are expressed using at least said steering angle direction, onto said reception signal in respective directions of orthogonal spatial coordinate axes with performing Fourier's transform onto said reception signal with respect to said orthogonal spatial coordinate axes so as to match wavenumber coordinates of angular spectra of said reception signal to wavenumber coordinates of spectra corresponding to said image signal without directly implementing interpolation approximations onto said angular spectra.

3. The measurement and imaging instrument according to claim 2, wherein said digital signal processing unit directly generates another image signal in a desirable orthogonal coordinate system at least based on one of:

(i) wavenumber matching performed by directly implementing, in at least one direction of orthogonal coordinate axes, interpolation approximations onto the angular spectra in a wavenumber or frequency domain calculated from said reception signal through Fourier's transform; and (ii) delay-and-summation performed on said reception signal.

4. The measurement and imaging instrument according to claim 2, wherein said digital signal processing unit performs at least one transmission and/or reception beamforming processing with one of a non-focused beamforming and a synthetic aperture beamforming.

5. The measurement and imaging instrument according to claim 2, wherein at least one of said at least one reception aperture element and said digital signal processing unit performs an apodization processing based on linearity of the apodization processing.

6. The measurement and imaging instrument according to claim 2, wherein when at least one wave is received in a two-dimensional Cartesian orthogonal coordinate system (x,y) or a three-dimensional Cartesian orthogonal coordinate system (x,y,z) with an axial direction y determined by a frontal direction of a reception aperture element array and a lateral direction x or lateral directions x and z orthogonal to the axial direction y, or a two-dimensional polar coordinate system (x,y) with a radial direction y determined by a frontal direction of a circular reception aperture element array and a deflection direction x, or a three-dimensional polar coordinate system (x,y,z) with the radial direction y and an elevational direction x and an azimuth direction z, or a two-dimensional orthogonal coordinate system (x,y) or a three-dimensional orthogonal coordinate system (x,y,z) with the axial direction y determined by a frontal direction of an arbitrary shape reception aperture element array and a lateral direction x or lateral directions x and z orthogonal to the axial direction y, said digital signal processing unit performs at least one beamforming processing using the orthogonal coordinate system.

7. The measurement and imaging instrument according to claim 6, wherein when at least one wave is received in a two-dimensional Cartesian orthogonal coordinate system (x,y) or a three-dimensional Cartesian orthogonal coordinate system (x,y,z) determined by a frontal direction of a reception aperture element array, or a two-dimensional polar coordinate system (x,y) or a three-dimensional polar coordinate system (x,y,z) determined by a frontal direction of a circular reception aperture element array, or a two-dimensional orthogonal coordinate system (x,y) or a three-dimensional orthogonal coordinate system (x,y,z) determined by a frontal direction of an arbitrary shape reception aperture element array, said digital signal processing unit processes at least one wave as a transmission wave or a reception wave including at least one of a plane wave, a circular wave, a cylindrical wave, a spherical wave, and an arbitrary curved wave which are focused or non-focused.

8. The measurement and imaging instrument according to claim 2, further comprising at least one transmission aperture element configured to transmit at least one wave with a steering angle direction expressed at least by a zero or non-zero angle of a deflection, an elevation, or an azimuth toward said measurement object.

9. The measurement and imaging instrument according to claim 8, wherein said at least one transmission aperture element transmits at least one of a plane wave, a circular wave, a cylindrical wave, a spherical wave, and an arbitrary curved wave which are focused or non-focused.

10. The measurement and imaging instrument according to claim 2, further comprising at least one transmission aperture element configured to transmit plural waves toward said measurement object at a substantially same phase, at the same time or at different times, said plural waves having the same angles of a deflection, an elevation, and an azimuth, or having at least one different angle, and said plural waves having the same wave parameters and beamforming parameters, or having at least one different wave parameter or at least one different beamforming parameter.

11. The measurement and imaging instrument according to claim 2, wherein said digital signal processing unit performs plural transmission and/or reception beamforming processings with respect to the same reception signal generated by said reception aperture element and by using at least one different wave parameter or at least one different beamforming parameter, and yields a new wave parameter or a new beamforming parameter by superposing results of said plural transmission and/or reception beamforming processings in a spatial domain or in the wavenumber or frequency domain.

12. The measurement and imaging instrument according to claim 2, further comprising at least one transmission aperture element configured to perform at least one wave transmission toward said measurement object from every transmission aperture element, wherein in order to perform a multi-static synthetic aperture beamforming for a transmission and/or reception dynamic focusing with a transmission and/or reception steering with a steering angle direction expressed at least by a zero or non-zero angle of a deflection, an elevation, or an azimuth with respect to an axial direction y determined by a reception effective aperture element array for performing a mechanical scan or an electric scan in a lateral direction x or lateral directions x and z in a two-dimensional or three-dimensional orthogonal coordinate system, said reception aperture element performs, at every time when the wave transmission is performed, at least one reception of a wave arrived from said measurement object by using one of plural reception aperture elements having different positions to generate at least one reception signal, and said digital signal processing unit performs a multi-static synthetic aperture beamforming with said steering angle direction at least by implementing a combination of Fourier's transform and wavenumber matching onto said reception signal generated by said reception aperture element, and wherein in order to generate the wave at least by a transmission, a forward scattering, a refraction, a reflection, a backward scattering, or a diffraction within said measurement object, said transmission aperture element performs at least one wave transmission from every transmission element within a transmission effective aperture element array which is partially or completely overlapped or non-overlapped with a reception effective aperture element array and positioned at an origin of y-axis coordinate and arbitrary x-axis coordinate or x-axis and z-axis coordinates or positioned in a transmission effective aperture element array facing said reception effective aperture element array, at an arbitrary constant y-axis coordinate except for the origin of y-axis coordinate and arbitrary x-axis coordinate or x-axis and z-axis coordinates, and said digital signal processing unit generates the image signal without performing interpolation approximations by performing corrections of lateral positions and subsequently superposing in a wavenumber or frequency domain all image signals generated by implementing a mono-static synthetic aperture beamforming based on said transmission and/or reception beamforming processing, onto every reception signal set newly including a reception signal generated by a reception aperture element having the same relative lateral position with respect to every transmission aperture element, in said steering angle direction and with (i) a half total distance from every transmission aperture element to the reception aperture element via a point of interest in the case where the transmission effective aperture element array is positioned at said origin of y-axis coordinate, and (ii) a total distance from every transmission aperture element to the reception aperture element via a point of interest in the case where the transmission effective aperture element array is not positioned at said origin of y-axis coordinate.

13. The measurement and imaging instrument according to claim 12, wherein in order to generate the image signal expressing an unknown wave source or a wave propagation generated by the unknown wave source, said digital signal processing unit performs said transmission and/or reception beamforming processing by assuming that a y-axis coordinate of the unknown wave source is a y-axis coordinate of the transmission effective aperture element array.

14. The measurement and imaging instrument according to claim 2, comprising plural reception effective aperture element arrays each including plural reception aperture elements set at different positions in a physical aperture and configured to generate reception signals, wherein when at least one wave source generates at least one arbitrary wave propagating in an arbitrary direction with a steering angle direction expressed at least by a zero or non-zero angle of a deflection, an elevation, or an azimuth with respect to an axial direction y determined by a reception effective aperture element array and a lateral direction x or lateral directions x and z in a two-dimensional or three dimensional coordinate system, said plural reception effective aperture element arrays perform at least one reception of at least one wave arrived from said measurement object, and said digital signal processing unit performs one of (i) a non-focused beamforming and a dynamic focused beamforming respectively for a transmission beamforming processing and a reception beamforming processing, and (ii) a synthetic aperture beamforming for said transmission and/or reception beamforming processing at least by implementing a combination of Fourier's transform and wavenumber matching onto said reception signals generated by said plural reception effective aperture element arrays, and generates the image signal without performing interpolation approximations by implementing one of processings (a) to (c) onto said reception signals generated by said plural reception effective aperture element arrays:

(a) performing one of beamformings (i) and (ii) once onto one reception signal set generated by superposing plural reception signals generated by said plural reception aperture elements or expressed as a superposition of the plural reception signals generated by said plural reception aperture elements;

(b) superposing a low spatial resolution image signal generated by implementing one of beamformings (i) and (ii) onto each reception signal generated by each reception effective aperture element array at every time when said arbitrary wave is generated by said at least one wave source; and (c) superposing plural image signals generated by implementing one of beamformings (i) and (ii) onto plural reception signal sets each including a reception signal generated by a reception aperture element having the same relative lateral position with respect to every transmission aperture element or a transmission effective aperture element.

15. The measurement and imaging instrument according to claim 2, wherein said digital signal processing unit generates the image signal directly in an orthogonal coordinate system based on a migration method.

16. The measurement and imaging instrument according to claim 2, wherein said digital signal processing unit generates, based on Jacobi operation and without performing interpolation approximations, the image signal directly in a Cartesian orthogonal coordinate system or a curvilinear orthogonal coordinate system which is different from an orthogonal coordinate system in which a wave reception is performed.

17. The measurement and imaging instrument according to claim 2, wherein said digital signal processing unit generates the image signal directly in an orthogonal coordinate system by implementing inverse Fourier's transform in a lateral direction at an arbitrary axial y-axis coordinate or within an arbitrary axial range with an arbitrary axial interval onto a summation of all spectra of respective wavenumbers obtained after wavenumber matching.

18. The measurement and imaging instrument according to claim 17, wherein said digital signal processing unit performs said inverse Fourier's transform in a lateral direction at an arbitrary axial y-axis coordinate or within an arbitrary axial range with an arbitrary axial interval, where the inverse Fourier's transform is performed at an arbitrary lateral coordinate or within an arbitrary lateral range with an arbitrary lateral interval.

19. The measurement and imaging instrument according to claim 2, wherein at least one of a physically generated beam or wave, a transmission beam or wave generated by said digital signal processing unit, and a reception beam or wave generated by said digital signal processing unit has a different steering angle direction from other beams or waves.

20. The measurement and imaging instrument according to claim 2, wherein said at least one reception aperture element includes plural transmission or reception elements.

21. The measurement and imaging instrument according to claim 2, wherein said digital signal processing unit performs a beamforming processing based on information regarding a wave source or a transmission aperture element such as a position, a direction, and a distance with respect to a reception aperture element, a frontal direction of an aperture, a propagation direction of a generated wave, and a generation time of a wave.

22. The measurement and imaging instrument according to claim 2, wherein in the case where said reception signal includes plural signals generated with respect to different wave sources, said digital signal processing unit performs a beamforming processing having a steering angle directed to a propagation direction of a wave of interest.

23. The measurement and imaging instrument according to claim 2, wherein in the case where said reception signal includes plural signals generated with respect to different wave sources, said digital signal processing unit performs a beamforming processing on a separated signal obtained based on 1st order moments of multidimensional spectra or instantaneous frequencies, or bandwidths, or using MIMO (multiple-input and multiple-output), SIMO (single-input and multiple-output), MUSIC (multiple signal classification), independent component analysis, encoding, or parametric methods.

24. The measurement and imaging instrument according to claim 2, wherein in the case where said reception signal includes plural signals generated with respect to different wave sources, said digital signal processing unit performs a separation on an image signal obtained by said transmission and/or reception beamforming processing based on 1st order moments of multidimensional spectra or instantaneous frequencies, or bandwidths, or using MIMO (multiple-input and multiple-output), SIMO (single-input and multiple-output), MUSIC (multiple signal classification), independent component analysis, encoding, or parametric methods.

25. The measurement and imaging instrument according to claim 2, wherein said digital signal processing unit further performs a beamforming processing with controlling a transmission and/or reception steering angle based on a calculation of a direction of a wave source existence or a propagation direction of a wave from 1st order moments of multidimensional spectra or instantaneous frequencies of said reception signal or said image signal obtained by a beamforming processing.

26. The measurement and imaging instrument according to claim 2, wherein said digital signal processing unit further performs a geometrical calculation of a position of a wave source or a direction of a wave source existence by performing geometrical calculations of a position of a wave source or a direction of a wave source existence with respect to plural reception aperture elements or plural reception effective aperture element arrays.

27. The measurement and imaging instrument according to claim 2, wherein said digital signal processing unit implements a superresolution onto angular spectra or spectra of said reception signal obtained before or after performing said wavenumber matching by using angular spectra or spectra of said reception signal and/or a desired point spread function.

28. The measurement and imaging instrument according to claim 2, wherein said wave arrived from said measurement object is one of an arbitrary electromagnetic wave, an arbitrary mechanical wave, and arbitrary thermal wave.

29. The measurement and imaging instrument according to claim 2, wherein said wave arrived from said measurement object is a physically different kind from that of the wave transmitted toward said measurement object.

30. The measurement and imaging instrument according to claim 2, wherein said digital signal processing unit implements a phase aberration correction onto said reception signal in order to compensate an inhomogeneity in propagation speed of a transmission and/or reception wave.

31. The measurement and imaging instrument according to claim 2, wherein said digital signal processing unit performs generations of plural partial image signals in a region of interest in a parallel manner.

32. The measurement and imaging instrument according to claim 2, wherein in the case where the wave is transmitted by an arbitrary wave source in a transmission coordinate system which is different from an orthogonal coordinate system in which said reception signal is processed for a beamforming, (i) said digital signal processing unit implements a conversion on a reception signal expressed in the transmission coordinate system into said reception signal by a signal processing or using a transmission and/or reception delay device prior to performing a beamforming processing, or (ii) the wave source performs a transmission beamforming with the same correction by using a transmission delay device.

33. The measurement and imaging instrument according to claim 2, wherein said digital signal processing unit performs a beamforming processing by using a virtual wave source, a virtual transmission aperture element array, a virtual reception aperture element, or a virtual reception aperture element array, which are different from a physically set wave source, a physically set transmission aperture element array, a physically set reception aperture element, or a physically set reception aperture element array.

34. The measurement and imaging instrument according to claim 2, wherein when plural waves are received at a substantially same phase, at the same time or at different times, said digital signal processing unit performs one of (i) a beamforming processing onto a reception signal expressed as a superposition of said plural waves, (ii) a superposition of said plural waves in a spatial domain prior to performing Fourier's transform, or (iii) a superposition of spectra of said plural waves in a wavenumber or frequency domain prior to performing inverse Fourier's transform.

35. The measurement and imaging instrument according to claim 2, wherein said digital signal processing unit uses only band-limited spectra selected in a wavenumber or frequency domain.

36. The measurement and imaging instrument according to claim 2, wherein said digital signal processing unit performs fast Fourier's transform that allows directly yielding the same result of wavenumber matching as that obtained by implementing a complex exponential function onto temporal Fourier's transform of said reception signal.

37. The measurement and imaging instrument according to claim 2, wherein said digital signal processing unit performs a beamforming processing onto said image signal after generating said image signal instead of a beamforming processing onto said reception signal.

38. The measurement and imaging instrument according to claim 3, wherein in order to decrease degradations or artifacts generated by performing said interpolation approximations, said digital signal processing unit performs an over-sampling of said reception signal or performs an up-sampling.

39. The measurement and imaging instrument according to claim 2, wherein in the case where a coordinate system in which a wave transmission is physically performed is a Cartesian orthogonal coordinate system or a curvilinear orthogonal coordinate system, said digital signal processing unit generates the image signal represented in said coordinate system in which a wave transmission is physically performed and which is different from a coordinate system determined by a reception aperture element array.

40. The measurement and imaging instrument according to claim 2, wherein said digital signal processing unit calculates at least one of a propagation of other waves of interest, and a displacement, a velocity, an acceleration, a strain, a strain rate, a temperature, and a mechanical or thermal property of said measurement object based on one of (i) said image signal directly obtained in a Cartesian orthogonal coordinate system or a curvilinear orthogonal coordinate system by performing a beamforming processing, and (ii) an image signal obtained by an interpolation approximation in other Cartesian orthogonal coordinate system or other curvilinear orthogonal coordinate system from said image signal directly obtained in an orthogonal coordinate system by performing a beamforming processing.

* * * * *